US012396905B2

(12) United States Patent
Grey et al.

(10) Patent No.: US 12,396,905 B2
(45) Date of Patent: Aug. 26, 2025

(54) INTERACTIVE QUERY FLOWS USING PORTABLE MEDICAL TREATMENT AND GUIDANCE APPARATUSES

(71) Applicant: ZOLL Medical Corporation, Chelmsford, MA (US)

(72) Inventors: Matthew J. Grey, Fairport, NY (US); Joseph A. Bart, Elma, NY (US)

(73) Assignee: ZOLL Medical Corporation, Chelmsford, MA (US)

( * ) Notice: Subject to any disclaimer, the term of this patent is extended or adjusted under 35 U.S.C. 154(b) by 820 days.

(21) Appl. No.: 17/708,015

(22) Filed: Mar. 30, 2022

(65) Prior Publication Data
US 2022/0323275 A1 Oct. 13, 2022

Related U.S. Application Data

(60) Provisional application No. 63/168,716, filed on Mar. 31, 2021.

(51) Int. Cl.
A61B 5/00 (2006.01)
A61F 17/00 (2006.01)

(52) U.S. Cl.
CPC .............. A61F 17/00 (2013.01); A61B 5/743 (2013.01); A61B 5/7435 (2013.01);
(Continued)

(58) Field of Classification Search
CPC ....... A61F 17/00; A61B 5/743; A61B 5/7435; A61B 5/7475; A61B 2505/01; A61B 2560/0431
(Continued)

(56) References Cited

U.S. PATENT DOCUMENTS

2003/0114885 A1* 6/2003 Nova .................... A61N 1/0492
607/2
2016/0210439 A1* 7/2016 Hartlaub ............... A61J 7/0084
(Continued)

FOREIGN PATENT DOCUMENTS

WO WO-2021/202292 A1 10/2021

OTHER PUBLICATIONS

Intl. Patent Application No. PCT/US2021/062591, entitled "Inventory Management Of Portable Medical Treatment And Guidance Apparatuses," filed Dec. 9, 2021.
(Continued)

Primary Examiner — Jacob K Ackun
(74) Attorney, Agent, or Firm — Mintz, Levin, Cohn, Ferris, Glovsky and Popeo, P.C.

(57) ABSTRACT

In one aspect, a portable medical treatment and guidance apparatus for assisting a caregiver in evaluating and treating a patient experiencing a medical emergency according to a time sensitive prioritization of the medical emergency is provided. The portable medical treatment and guidance apparatus includes a housing having at least one compartment; a plurality of medical supplies housed within the at least one compartment; a user interface configured to receive input and provide an interactive query flow for assisting the user in providing medical treatment; and at least one processor and memory communicatively coupled to the user interface. The at least one processor and memory is configured to determine instructions for assisting the caregiver in treating the patient and present, via a user interface, the determined instructions to assist the caregiver in treating the medical emergency.

27 Claims, 64 Drawing Sheets

(52) U.S. Cl.
CPC ........ *A61B 5/7475* (2013.01); *A61B 2505/01* (2013.01); *A61B 2560/0431* (2013.01)

(58) Field of Classification Search
USPC ................................................ 206/570, 571
See application file for complete search history.

(56) References Cited

U.S. PATENT DOCUMENTS

| | | | |
|---|---|---|---|
| 2020/0305805 A1* | 10/2020 | Freeman ............ | A61B 5/02055 |
| 2023/0124963 A1* | 4/2023 | Laskin .................. | A45C 5/065 |
| | | | 206/570 |
| 2024/0006057 A1* | 1/2024 | Edgell ..................... | A61F 17/00 |
| 2024/0157074 A1* | 5/2024 | Goldberg .......... | A61M 16/0051 |

OTHER PUBLICATIONS

Intl. Application No. PCT/US2022/013700, entitled "Deployment Stations For Emergency Medical Treatment And Guidance Apparatuses," filed Jan. 25, 2022.

\* cited by examiner

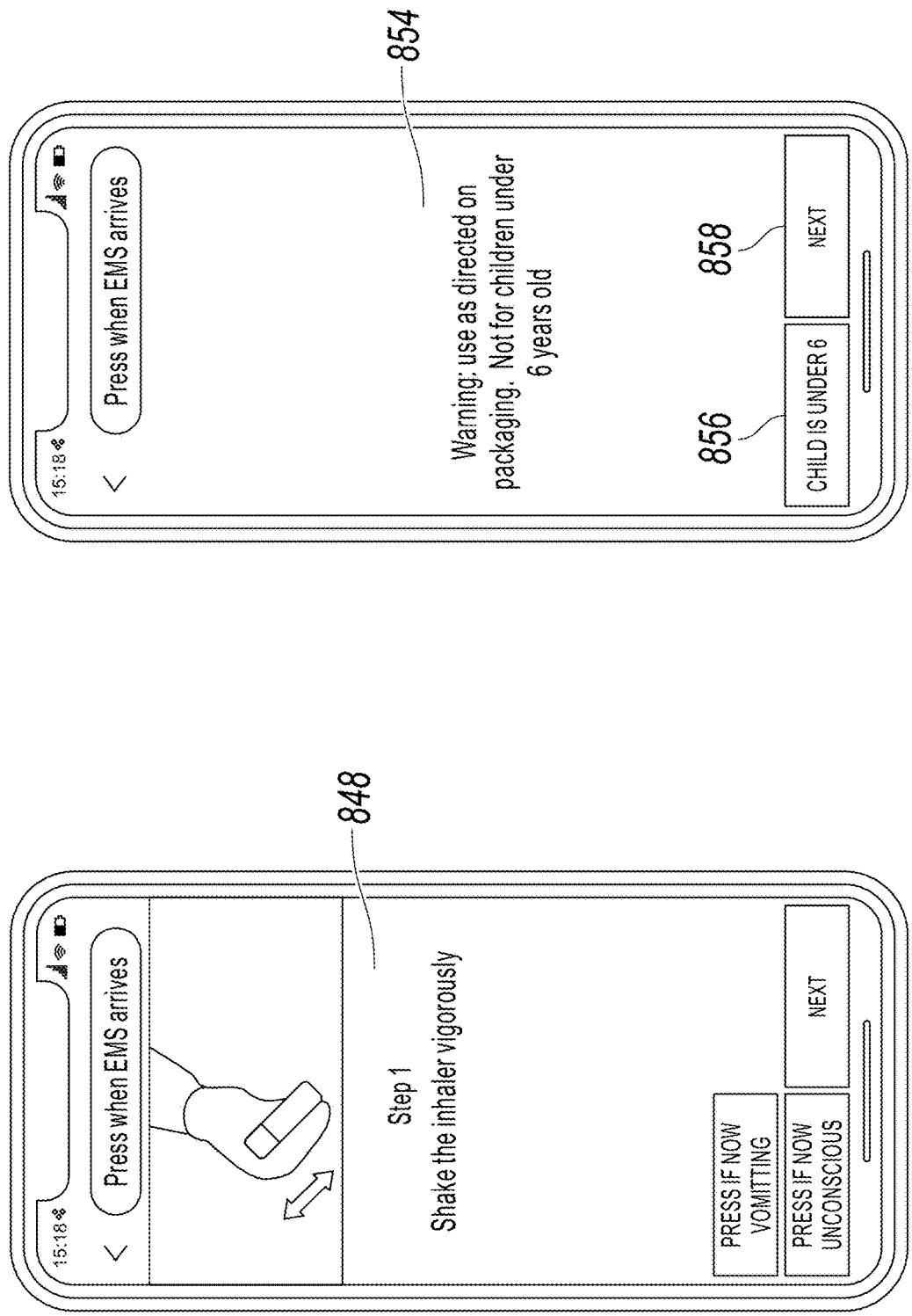

INTERACTIVE QUERY FLOWS USING PORTABLE MEDICAL TREATMENT AND GUIDANCE APPARATUSES

CROSS REFERENCE TO RELATED APPLICATIONS

The present application claims priority to U.S. Provisional Patent Application No. 63/168,716 entitled "Interactive Query Flows Using Portable Medical Treatment And Guidance Apparatuses" filed Mar. 31, 2021, which is hereby incorporated by reference in its entirety.

FIELD

This description relates to interactive query flows using portable medical treatment and guidance apparatuses, and in particular, providing treatment and guidance of medical emergencies based on a priority of the medical emergency, patient characteristics, apparatus types, substitutions of medical supplies, and/or memory of previous responses.

BACKGROUND

Various types of medical first aid kits exist to supply first aid to an injured person. Some such first aid kits also provide written and/or audible instructions for how to treat patients, using the medical supplies contained within the first aid kits. First aid kits may be stored at places where people congregate and therefore medical emergencies are likely to occur (e.g., at workplaces, stores, and schools). In an emergency, a caregiver may locate a portable first aid kit and carry the portable first aid kit to a location of a patient. The caregiver may use the supplies in the portable first aid kit to treat one or more medical emergencies from which the patient may be suffering.

SUMMARY

In one aspect, a portable medical treatment and guidance apparatus for assisting a caregiver in evaluating and treating a patient experiencing a medical emergency according to a time sensitive prioritization of the medical emergency is provided. The apparatus can include a housing having at least one compartment; a plurality of medical supplies housed within the at least one compartment; a user interface configured to receive input and provide an interactive query flow for assisting the caregiver in providing medical treatment; and at least one processor and memory communicatively coupled to the user interface. The at least one processor and memory can be configured to: present, via the user interface, at least one inquiry according to a first priority medical emergency as part of the interactive query flow; receive, via the user interface, at least one user input in response to the at least one inquiry according to the first priority medical emergency; present, via the user interface, at least one inquiry regarding a characteristic of the patient after receiving the at least one user input in response to the at least one inquiry according to the first priority medical emergency; receive, via the user interface, at least one user input in response to the at least one inquiry regarding the characteristic of the patient; determine a patient characteristic based on at least one response from the user interface regarding the characteristic of the patient; present, via the user interface, at least one inquiry according to a second priority medical emergency after receiving the at least one user input in response to the at least one inquiry regarding the characteristic of the patient; receive, via the user interface, at least one user input in response to the at least one inquiry according to the second priority medical emergency; determine instructions for assisting the caregiver in treating the patient based on at least one of: i) the at least one user input according to the first priority medical emergency, ii) the determined patient characteristic, or iii) the at least one user input according to the second priority medical emergency, the instructions including instructions for using at least one medical supply for treating the medical emergency of the patient; and present, via the user interface, the determined instructions to assist the caregiver in treating the medical emergency.

In some implementations, the at least one processor and memory is configured to: present, via the user interface, at least one inquiry regarding an apparatus type of the portable medical treatment and guidance apparatus after receiving the at least one user input in response to the at least one inquiry according to the second priority medical emergency; receive, via the user interface, at least one user input in response to the at least one inquiry regarding the apparatus type; determine an apparatus type of the portable medical treatment and guidance apparatus; present, via the user interface, at least one inquiry according to a third priority medical emergency after receiving the at least one user input in response to the at least one inquiry regarding the apparatus type of the portable medical treatment and guidance apparatus; receive, via the user interface, at least one user input in response to the at least one inquiry according to the third priority medical emergency, wherein determining the instructions for assisting the caregiver in treating the patient are based on the at least one user input according to the third priority medical emergency.

In some implementations, determining the instructions for assisting the caregiver in treating the patient are determined based on the determined patient characteristic and the determined apparatus type. In some implementations, the at least one processor and memory is configured to receive information that a first choice medical supply and a second choice medical supply are available within the portable medical treatment and guidance apparatus represented by the determined apparatus type.

In some implementations, the instructions include instructions for assisting an adult patient experiencing a bleeding head injury and include instructions for using the second choice medical supply after the first choice medical supply is unavailable based on at least one user input. In some implementations, the at least one processor and memory is configured to store information in memory, the information indicating that the first choice medical supply is unavailable to the caregiver based on the at least one user input.

In some implementations, the first priority medical emergency includes an immediate life threat emergency that requires treatment within a first time limit. In some examples, the first time limit is 3 minutes. In some examples, the second priority medical emergency includes a breathing related emergency that requires treatment within a second time limit. In some examples, the second time limit is greater than the first time limit. In some examples, the second time limit is 6 minutes.

In some implementations, the user interface is part of a mobile device. In some implementations, the patient characteristic at least one of an age classification, a type of injury, and a gender of the patient. In some implementations, the patient characteristic is an age classification that identifies whether the patient is an infant, a child, or an adult. In some implementations, the patient characteristic is an age classification and determining the instructions for assisting the caregiver in treating the patient are determined based on the age classification.

In some implementations, the instructions include instructions for treating a choking medical emergency and the instructions are different depending on whether the patient is an infant, a child, or an adult based on the age classification. In some implementations, the instructions for treating the choking medical emergency account for a height of the waist of the patient based on whether the patient is a child or an adult based on the age classification. In some implementations, the instructions for treating the choking medical emergency include (i) instructions for a administering a Heimlich maneuver to adult patients and children patients based on the age classification and (ii) instructions for administering a sequence of chest compressions and back blows for infant patients based on the age classification.

In some implementations, the instructions include instructions for treating chest palpitations and the instructions are different depending on whether the patient is an infant, a child, or an adult based on the age classification. In some implementations, the instructions for treating the chest palpitations include (i) instructions for administering aspirin to adult patients and children over 10 years old based on the age classification and (i) instructions for keeping children under 10 years old and infants comfortable based on the age classification.

In some implementations, the instructions include instructions for treating dull and/or sharp chest pain and the instructions are different depending on whether the patient is an infant, a child, or an adult based on the age classification. In some implementations, the instructions for treating the dull and/or sharp chest pain include (i) instructions for administering aspirin and prescribed nitroglycerin to adult patients based on the age classification and (ii) instructions for keeping child and infant patients comfortable based on the age classification.

In some implementations, the instructions include instructions for treating an allergic reaction and the instructions are different depending on whether the patient is an infant, a child, or an adult based on the age classification. In some implementations, the instructions for treating the allergic reaction include (i) instructions for administering allergy medicine and administering a prescribed rescue inhaler to adult patients based on the age classification and (ii) instructions for administering allergy medicine to children over age 6 and administering a prescribed rescue inhaler to children patients based on the age classification.

In some implementations, the instructions for treating the allergic reaction include one or more warning screens to warn that the prescribed rescue inhaler is a prescribed medication and the instructions include instructions to administer a prescribed number puffs per a rescue inhaler prescription of the patient. In some implementations, the one or more warning screens are based on whether the patient is an adult or a child. In some implementations, the one or more warning screens include text indicating that a legal guardian is authorizing the caregiver to administer the prescribed rescue inhaler to a child patient.

In some implementations, the instructions for treating the allergic reaction include instructions to administer allergy medicine based on a weight and/or size of the patient according to instructions on a packaging of the allergy medicine. In some implementations, the instructions for treating the allergic reaction include instructions that avoid administering allergy medicine to infants.

In some implementations, the instructions include instructions for treating a fracture and the instructions are different depending on whether the patient is an infant or an adult based on the age classification. In some implementations, the instructions for treating the fracture are based on which body part is fractured. In some implementations, the instructions include instructions for using gauze, a splint, elastic wrap, and ice to treat the patient when experiencing a broken ankle injury and instructions for using gauze, a splint, elastic wrap, ice, and a triangular bandage to treat the patient experiencing a broken elbow injury. In some implementations, the instructions for treating the fracture include instructions that avoid manipulation of fractures above an elbow and/or a knee for adults and children.

In some implementations, the instructions for treating the fracture include positioning instructions based on stored information in memory. In some implementations, the stored information in memory relates to whether or not the patient is experiencing a neck injury. In some implementations, the instructions for treating the fracture include instructions to treat a fracture of an infant patient with ice packs and instructions for the caregiver to maintain a comfort of the infant patient.

In some implementations, the instructions include instructions for treating a diabetic problem and the instructions are different depending on whether the patient is an infant or an adult based on the age classification. In some implementations, the instructions for treating the diabetic problem include (i) instructions for administering oral glucose with altered mental status and perceived hypoglycemia to adult patients based on the age classification, (ii) instructions for swallowing the oral glucose in adult patients, and (iii) instructions treating seizures in infant patients based on the age classification.

In some implementations, the instructions include instructions for treating unconsciousness and the instructions are different depending on whether the patient is an infant, a child, or an adult based on the age classification. In some implementations, the instructions for treating unconsciousness in adults include instructions to retrieve a defibrillator first, followed by instructions to administer hands-only cardiopulmonary resuscitation to the patient after the defibrillator has been retrieved. In some implementations, the instructions for treating unconsciousness in children include instructions to begin cardiopulmonary resuscitation first, followed by instructions to locate a defibrillator after the cardiopulmonary resuscitation has begun. In some implementations, the instructions for treating unconsciousness in infants and children include instructions for alternating giving breaths and performing chest compressions.

In some implementations, the instructions for treating unconsciousness include instructions for a second caregiver to assist in administering cardiopulmonary resuscitation to the patient. In some implementations, the instructions for treating unconsciousness in infant patients include instructions for administering cardiopulmonary resuscitation to an infant patient that focus on an airway and repositioning of the airway of the infant patient.

In some implementations, the at least one processor and memory is configured to determine the instructions for using the at least one medical supply based on a type and/or brand of the at least one medical supply. In some implementations, determining the instructions for using the at least one medical supply includes determining a particular type of tourniquet as the at least one medical supply.

In some implementations, the determined instructions relate to communicative diseases and include instructions for applying at least one face mask. In some implementations, the determined instructions are based on at least one response to at least one inquiry related to shortness of breath and/or a patient cough. In some implementations, the least one inquiry related to shortness of breath and/or the patient cough is the at least one inquiry according to the second priority medical emergency.

In another aspect, a computer-implemented method for assisting a caregiver in evaluating and treating a patient experiencing a medical emergency according to a time sensitive prioritization of the medical emergency is provided. The computer-implemented method can include: presenting, via an user interface, at least one inquiry according to a first priority medical emergency as part of an interactive query flow; receiving, via the user interface, at least one user input in response to the at least one inquiry according to the first priority medical emergency; presenting, via the user interface, at least one inquiry regarding a characteristic of the patient after receiving the at least one user input in response to the at least one inquiry according to the first priority medical emergency; receiving, via the user interface, at least one user input in response to the at least one inquiry regarding the characteristic of the patient; determining a patient characteristic based on at least one response from the user interface regarding the characteristic of the patient; presenting, via the user interface, at least one inquiry according to a second priority medical emergency after receiving the at least one user input in response to the at least one inquiry regarding the characteristic of the patient; receiving, via the user interface, at least one user input in response to the at least one inquiry according to the second priority medical emergency; determining instructions for assisting the caregiver in treating the patient based on at least one of: i) the at least one user input according to the first priority medical emergency, ii) the determined patient characteristic, or iii) the at least one user input according to the second priority medical emergency, the instructions including instructions for using at least one medical supply for treating the medical emergency of the patient; and presenting, via the user interface, the determined instructions to assist the caregiver in treating the medical emergency.

In some implementations, the computer-implemented method includes presenting, via the user interface, at least one inquiry regarding an apparatus type of a portable medical treatment and guidance apparatus after receiving the at least one user input in response to the at least one inquiry according to the second priority medical emergency; receiving, via the user interface, at least one user input in response to the at least one inquiry regarding the apparatus type; determining an apparatus type of the portable medical treatment and guidance apparatus; presenting, via the user interface, at least one inquiry according to a third priority medical emergency after receiving the at least one user input in response to the at least one inquiry regarding the apparatus type of the portable medical treatment and guidance apparatus; and receiving, via the user interface, at least one user input in response to the at least one inquiry according to the third priority medical emergency, wherein determining the instructions for assisting the caregiver in treating the patient are based on the at least one user input according to the third priority medical emergency.

In some implementations, determining the instructions for assisting the caregiver in treating the patient are determined based on the determined patient characteristic and the determined apparatus type. In some implementations, the computer-implemented method includes receiving information that a first choice medical supply and a second choice medical supply are available within the portable medical treatment and guidance apparatus represented by the determined apparatus type.

In some implementations, determining the instructions for assisting the caregiver in treating the patient include determining instructions for treating a bleeding head injury and include determining instructions for using the second choice medical supply after the first choice medical supply is unavailable based on at least one user input. In some implementations, the computer-implemented method includes storing information in memory, the information indicating that the first choice medical supply is unavailable to the caregiver based on the at least one user input.

In some implementations, the first priority medical emergency includes an immediate life threat emergency that requires treatment within a first time limit. In some examples, the first time limit is 3 minutes. In some examples, the second priority medical emergency includes a breathing related emergency that requires treatment within a second time limit. In some examples, the second time limit is greater than the first time limit. In some examples, the second time limit is 6 minutes.

In some implementations, the user interface is part of a mobile device.

In some implementations, the patient characteristic at least one of an age classification, a type of injury, and a gender of the patient. In some implementations, the patient characteristic is an age classification that identifies whether the patient is an infant, a child, or an adult. In some implementations, the patient characteristic is an age classification and determining the instructions for assisting the caregiver in treating the patient are determined based on the age classification.

In some implementations, determining the instructions for assisting the caregiver in treating the patient includes determining instructions for treating a choking medical emergency and determining different instructions based on whether the patient is an infant, a child, or an adult based on the age classification. In some implementations, determining the instructions for assisting the caregiver in treating choking medical emergency includes accounting for a height of the waist of the patient in the instructions based on whether the patient is a child or an adult based on the age classification. In some implementations, determining the instructions for assisting the caregiver in treating choking medical emergency include (i) determining instructions for a administering a Heimlich maneuver to adult patients and children patients based on the age classification and (ii) determining instructions for administering a sequence of chest compressions and back blows for infant patients based on the age classification.

In some implementations, determining the instructions for assisting the caregiver include determining instructions for treating chest palpitations and determining different instructions based on whether the patient is an infant, a child, or an adult based on the age classification. In some implementations, determining the instructions for treating the chest palpitations include (i) determining instructions for administering aspirin to adult patients and children over 10 years old based on the age classification and (i) determining instructions for keeping children under 10 years old and infants comfortable based on the age classification.

In some implementations, determining the instructions for assisting the caregiver include determining instructions for treating dull and/or sharp chest pain and determining different instructions based on whether the patient is an infant, a child, or an adult based on the age classification. In some implementations, determining the instructions for treating the dull and/or sharp chest pain include (i) determining instructions for administering aspirin and prescribed nitroglycerin to adult patients based on the age classification and (ii) determining instructions for keeping child and infant patients comfortable based on the age classification.

In some implementations, determining the instructions for assisting the caregiver include determining instructions for treating an allergic reaction and determining different instructions based on whether the patient is an infant, a child, or an adult based on the age classification. In some implementations, determining the instructions for treating the allergic reaction include (i) determining instructions for administering allergy medicine and instructions for administering a prescribed rescue inhaler to adult patients based on the age classification and (ii) determining instructions for administering allergy medicine to children over age 6 and instructions for administering a prescribed rescue inhaler to children patients based on the age classification. In some implementations, determining the instructions include determining instructions to administer a prescribed number puffs per a rescue inhaler prescription of the patient.

In some implementations, determining the instructions include determining one or more warning screens including warning text indicating that a legal guardian is authorizing the caregiver to administer the prescribed rescue inhaler to a child patient. In some implementations, presenting the determined instructions to assist the caregiver in treating the medical emergency include presenting, via the user interface, the one or more warning screens to warn the caregiver that the prescribed rescue inhaler is a prescribed medication. In some implementations, determining the instructions for assisting the caregiver include determining instructions for treating an allergic reaction in accordance with instructions on a packaging of an allergy medicine.

In some implementations, determining the instructions for treating the allergic reaction include determining instructions to administer allergy medicine based on a weight and/or size of the patient according to the instructions on the packaging of the allergy medicine. In some implementations, determining the instructions for treating the allergic reaction include determining instructions that avoid administering allergy medicine to infants.

In some implementations, determining the instructions for assisting the caregiver include determining instructions for treating a fracture and determining different instructions based on whether the patient is an infant or an adult based on the age classification. In some implementations, determining the instructions for treating the fracture include determining the instructions based on which body part is fractured. In some implementations, determining the instructions include determining instructions for using gauze, a splint, elastic wrap, and ice to treat the patient when experiencing a broken ankle injury and determining instructions for using gauze, a splint, elastic wrap, ice, and a triangular bandage to treat the patient experiencing a broken elbow injury. In some implementations, determining the instructions for treating the fracture include determining instructions that avoid manipulation of fractures above an elbow and/or a knee for adults and children.

In some implementations, determining the instructions for treating the fracture include positioning instructions based on stored information in memory. In some implementations, wherein the stored information in memory relates to whether or not the patient is experiencing a neck injury. In some implementations, determining the instructions for treating the fracture include determining instructions to treat a fracture of an infant patient with ice packs and determining instructions for the caregiver to maintain a comfort of the infant patient.

In some implementations, determining the instructions for assisting the caregiver include determining instructions for treating a diabetic problem and include determining different instructions based on whether the patient is an infant or an adult based on the age classification. In some implementations, determining the instructions for treating the diabetic problem include (i) determining instructions for administering oral glucose with altered mental status and perceived hypoglycemia to adult patients based on the age classification, (ii) determining instructions for swallowing the oral glucose in adult patients, and (iii) determining instructions treating seizures in infant patients based on the age classification.

In some implementations, determining the instructions for assisting the caregiver include determining instructions for treating unconsciousness and determining different instructions based on whether the patient is an infant, a child, or an adult based on the age classification. In some implementations, determining the instructions for treating unconsciousness in adults include instructions to retrieve a defibrillator first, followed by instructions to administer hands-only cardiopulmonary resuscitation to the patient after the defibrillator has been retrieved. In some implementations, determining the instructions for treating unconsciousness include determining instructions to begin cardiopulmonary resuscitation first in children, followed by instructions to locate a defibrillator after the cardiopulmonary resuscitation has begun. In some implementations, determining the instructions for treating unconsciousness include determining instructions for alternating giving breaths and performing chest compressions in infants and children.

In some implementations, determining the instructions for treating unconsciousness include determining instructions for a second caregiver to assist in administering cardiopulmonary resuscitation to the patient. In some implementations, determining the instructions for treating unconsciousness in infant patients include determining instructions for administering cardiopulmonary resuscitation to an infant patient that focuses on an airway and a repositioning of the airway of the infant patient.

In some implementations, the computer-implemented method includes determining the instructions for using at least one medical supply based on a type and/or brand of the medical supply. In some implementations, determining the instructions for using the at least one medical supply includes determining a particular type of tourniquet as the at least one medical supply.

In some implementations, determining the instructions include determining instructions to treat communicative diseases and include instructions for applying at least one face mask. In some implementations, determining the instructions includes determining the instructions based on receiving at least one response to at least one inquiry related to shortness of breath and/or a patient cough and associating the at least with response with communicative diseases. In some implementations, receiving the at least one inquiry according to the second priority medical emergency includes receiving the least one inquiry related to shortness of breath and/or the patient cough.

In another aspect, a portable medical treatment and guidance apparatus for assisting a caregiver in evaluating and treating a patient experiencing a medical emergency according to a time sensitive prioritization of the medical emergency is provided. The apparatus can include: a housing having at least one compartment; a plurality of medical supplies housed within the at least one compartment; a user interface configured to receive input and provide an interactive query flow for assisting the caregiver in providing medical treatment; and at least one processor and memory communicatively coupled to the user interface. The at least one processor and memory can be configured to: present, via the user interface, at least one inquiry as part of the interactive query flow; receive, via the user interface, at least one user input in response to the at least one inquiry; determine a patient characteristic based on at least one characteristic type input; determine instructions for assisting the caregiver in treating the patient experiencing the medical emergency based on the determined patient characteristic, the instructions including instructions for using at least one medical supply of the plurality of medical supplies to treat the medical emergency of the patient; and present, via the user interface, the determined instructions to assist the caregiver in treating the medical emergency of the patient using the at least one medical supply.

In some implementations, the at least one processor and memory is configured to determine an apparatus type of the portable medical treatment and guidance apparatus based on at least one apparatus type input after determining the patient characteristic. In some implementations, determining the instructions for assisting the caregiver in treating the patient experiencing the medical emergency is based on the determined apparatus type.

In some implementations, the at least one processor and memory is configured to determine the instructions for assisting the caregiver in treating the patient by eliminating options that are not available to the caregiver based on the determined apparatus type of the portable medical treatment and guidance apparatus. In some implementations, the at least one processor and memory is configured to store, in a memory, information pertaining to the determined patient characteristic and/or the determined apparatus type of portable medical treatment and guidance apparatus, wherein the instructions are determined based on the stored information in memory.

In some implementations, determining the instructions for assisting the caregiver in treating the patient experiencing the medical emergency includes prioritizing an immediate life threat emergency corresponding to a condition that requires treatment within a first time limit over a breathing related emergency corresponding to a condition that requires treatment within a second time limit. In some examples, the first time limit is 3 minutes and the second time limit is 6 minutes. In some examples, the first time limit is 5 minutes or less, and the second time limit is larger than the first time limit.

In some implementations, determining the instructions for assisting the caregiver in treating the patient experiencing the medical emergency includes prioritizing the breathing related emergency corresponding to a condition that requires treatment within a second time limit over a minor emergency corresponding to a condition that is treatable beyond the second time limit. In some implementations, the patient is experiencing an immediate life threat emergency that is at least one of a major bleeding event, a penetrating chest wound, and unconscious identification.

In some implementations, the patient is experiencing a breathing related emergency that is at least one of an allergic reaction, chest pain, chest trauma, seizures, overdose, diabetic ketoacidosis, and altered mental status. In some implementations, the patient is experiencing a minor emergency that is at least one of minor chest pain, minor bleeding, fractures, burns, hypothermia, and general pain. In some implementations, the patient is a first patient and determining the instructions for assisting the caregiver in treating the first patient experiencing the medical emergency includes prioritizing a treatment of a first priority medical emergency of a second patient over a treatment of a second priority medical emergency of the first patient.

In some implementations, the at least one processor and memory is configured to present one or more warning screens on the user interface. In some implementations, the one or more warning screens include warning text about administering medication. In some implementations, the medication is a prescription medicine and the warning text includes instructions to administer prescription medication to the patient when a consent of the patient is received by the caregiver. In some implementations, the medication is a prescription medicine and the warning text includes instructions to administer prescription medication to the patient when a consent of a legal guardian of the patient is received by the caregiver.

In some implementations, the at least one processor and memory is configured to determine at least one injury of the patient based on the at least one input and determine subsequent instructions based on the at least one injury of the patient. In some implementations, the subsequent instructions includes instructions to reduce complication of the determined at least one injury. In some implementations, the patient characteristic at least one of an age classification, a type of injury, and a gender of the patient.

In another aspect, a computer-implemented method for assisting a caregiver in evaluating and treating a patient experiencing a medical emergency according to a time sensitive prioritization of the medical emergency is provided. The computer-implemented method can include: presenting, via an user interface, at least one inquiry as part of an interactive query flow; receiving, via the user interface, at least one user input in response to the at least one inquiry; determining a patient characteristic based on at least one characteristic type input; determining instructions for assisting the caregiver in treating the patient experiencing the medical emergency based on the determined patient characteristic, the instructions including instructions for using at least one medical supply of a plurality of medical supplies to treat the medical emergency of the patient; and presenting, via the user interface, the determined instructions to assist the caregiver in treating the medical emergency of the patient using the at least one medical supply.

In some implementations, the computer-implemented method includes determining an apparatus type of a portable medical treatment and guidance apparatus based on at least one apparatus type input after determining the patient characteristic. In some implementations, determining the instructions for assisting the caregiver in treating the patient experiencing the medical emergency includes determining the instructions based on the determined apparatus type.

In some implementations, the computer-implemented method includes determining the instructions for assisting the caregiver in treating the patient by eliminating options that are not available to the caregiver based on the determined apparatus type of the portable medical treatment and guidance apparatus. In some implementations, the computer-implemented method includes storing, in a memory, information pertaining to the determined patient characteristic and/or the determined apparatus type of portable medical treatment and guidance apparatus.

In some implementations, determining the instructions includes determining the instructions based on the stored information in memory. In some implementations, determining the instructions for assisting the caregiver in treating the patient experiencing the medical emergency includes prioritizing an immediate life threat emergency corresponding to a condition that requires treatment within a first time limit over a breathing related emergency corresponding to a condition that requires treatment within a second time limit. In some examples, the first time limit is 3 minutes and the second time limit is 6 minutes. In some examples, the first time limit is 5 minutes or less, and the second time limit is larger than the first time limit.

In some implementations, determining the instructions for assisting the caregiver in treating the patient experiencing the medical emergency includes prioritizing the breathing related emergency corresponding to a condition that requires treatment within a second time limit over a minor emergency corresponding to a condition that is treatable beyond the second time limit.

In some implementations, the patient is experiencing an immediate life threat emergency that is at least one of a major bleeding event, a penetrating chest wound, and unconscious identification. In some implementations, the patient is experiencing a breathing related emergency that is at least one of an allergic reaction, chest pain, chest trauma, seizures, overdose, diabetic ketoacidosis, and altered mental status. In some implementations, the patient is experiencing a minor emergency that is at least one of minor chest pain, minor bleeding, fractures, burns, hypothermia, and general pain.

In some implementations, the patient is a first patient and determining the instructions for assisting the caregiver in treating the first patient experiencing the medical emergency includes prioritizing a treatment of a first priority medical emergency of a second patient over a treatment of a second priority medical emergency of the first patient.

In some implementations, the computer-implemented method includes presenting one or more warning screens on the user interface. In some implementations, presenting the one or more warning screens including presenting text about administering a medication. In some implementations, the medication is a prescription medicine and presenting the text includes presenting instructions to administer prescription medication to the patient when a consent of the patient is received by the caregiver. In some implementations, the medication is a prescription medicine and the presenting the text includes presenting instructions to administer prescription medication to the patient when a consent of a legal guardian of the patient is received by the caregiver.

In some implementations, the computer-implemented method includes determining at least one injury of the patient based on the at least one input and determining subsequent instructions based on the at least one injury of the patient. In some implementations, determining the subsequent instructions include instructions to reduce a complication of the determined at least one injury. In some implementations, the patient characteristic at least one of an age classification, a type of injury, and a gender of the patient.

In another aspect, a portable medical treatment and guidance apparatus for assisting a caregiver in evaluating and treating a patient experiencing a medical emergency according to a time sensitive prioritization of the medical emergency is provided. The apparatus can include: a housing having at least one compartment; a plurality of medical supplies housed within the at least one compartment; a user interface configured to provide an interactive query flow for assisting the caregiver in providing medical treatment; and at least one processor and memory communicatively coupled to the user interface, the at least one processor and memory configured to: present, via the user interface, at least one inquiry according to a first priority medical emergency as part of the interactive query flow; receive, via the user interface, at least one user input in response to the at least one inquiry according to the first priority medical emergency; present, via the user interface, at least one inquiry according to a second priority medical emergency after receiving the at least one user input in response to the at least one inquiry according to the first priority medical emergency; receive, via the user interface, at least one user input in response to the at least one inquiry according to the second priority medical emergency; present, via the user interface, at least one inquiry regarding an apparatus type of the portable medical treatment and guidance apparatus after receiving the at least one user input in response to the at least one inquiry according to the first priority medical emergency and after receiving the at least one user input in response to the at least one inquiry according to the second priority medical emergency; receive, via the user interface, at least one user input in response to the at least one inquiry regarding the apparatus type; determine the apparatus type based on at least one response from the user interface regarding the apparatus type; determine instructions for assisting the caregiver in treating the patient based on at least one of: i) the at least one user input according to the first priority medical emergency, ii) the at least one user input according to the second priority medical emergency, or iii) the determined apparatus type, the instructions including instructions for using at least one medical supply for treating the medical emergency of the patient; and present, via the user interface, the determined instructions to assist the caregiver in treating the medical emergency.

In some implementations, the first priority medical emergency includes an immediate life threat emergency that requires treatment within a first time limit. In some examples, the first time limit is 3 minutes. In some examples, the second priority medical emergency includes a breathing related emergency that requires treatment within a second time limit. In some examples, the second time limit is greater than the first time limit. In some examples, the second time limit is 6 minutes.

In some implementations, the user interface is part of a mobile device. In some implementations, the apparatus type is determined to be one of at least two apparatus types. In some implementations, at least one apparatus type has a splint to treat a broken bone and determining the instructions for assisting the caregiver in treating the patient is based on whether or not the portable medical treatment and guidance apparatus has the splint based on the determined apparatus type.

In another aspect, a computer-implemented method for assisting a caregiver in evaluating and treating a patient experiencing a medical emergency according to a time sensitive prioritization of the medical emergency is provided. The computer-implemented method can include: presenting, via a user interface, at least one inquiry according to a first priority medical emergency as part of an interactive query flow; receiving, via the user interface, at least one user input in response to the at least one inquiry according to the first priority medical emergency; presenting, via the user interface, at least one inquiry according to a second priority medical emergency after receiving the at least one user input in response to the at least one inquiry according to the first priority medical emergency; receiving, via the user interface, at least one user input in response to the at least one inquiry according to the second priority medical emergency; presenting, via the user interface, at least one inquiry regarding an apparatus type of an portable medical treatment and guidance apparatus after receiving the at least one user input in response to the at least one inquiry according to the first priority medical emergency and after receiving the at least one user input in response to the at least one inquiry according to the second priority medical emergency; receiving, via the user interface, at least one user input in response to the at least one inquiry regarding the apparatus type; determining the apparatus type based on at least one response from the user interface regarding the apparatus type; determining instructions for assisting the caregiver in treating the patient based on at least one of: i) the at least one user input according to the first priority medical emergency, ii) the at least one user input according to the second priority medical emergency, or iii) the determined apparatus type, the instructions including instructions for using at least one medical supply for treating the medical emergency of the patient; and presenting, via the user interface, the determined instructions to assist the caregiver in treating the medical emergency.

In some implementations, the first priority medical emergency includes an immediate life threat emergency that requires treatment within a first time limit. In some examples, the first time limit is 3 minutes. In some examples, the second priority medical emergency includes a breathing related emergency that requires treatment within a second time limit. In some examples, the second time limit is greater than the first time limit. In some examples, the second time limit is 6 minutes.

In some implementations, the user interface is part of a mobile device. In some implementations, determining the apparatus type includes determining the apparatus type of at least two apparatus types. In some implementations, at least one apparatus type has a splint to treat a broken bone and determining the instructions for assisting the caregiver in treating the patient is based on whether or not the portable medical treatment and guidance apparatus has the splint based on the determined apparatus type.

In another aspect, a portable medical treatment and guidance apparatus for evaluating and assisting a caregiver in treating a patient experiencing a medical emergency according to available medical supplies is provided. The apparatus can include: a housing having at least one compartment; a plurality of medical supplies housed within the at least one compartment; a user interface configured to provide an interactive query flow for assisting the caregiver in providing medical treatment; and at least one processor and memory communicatively coupled to the user interface. The at least one processor and memory can be configured to: present, via the user interface, at least one inquiry as part of the interactive query flow, receive, via the user interface, at least one user input in response to the at least one inquiry, determine whether a first choice medical supply of the plurality of medical supplies is available based on at least one user input; responsive to determining that the first choice medical supply is available, determine instructions for assisting the caregiver in treating the patient using the first choice medical supply; responsive to determining that the first choice medical supply is unavailable: determine whether a second choice medical supply of the plurality of medical supplies is available based on at least one additional user input; and responsive to determining that the second choice medical supply is available, determine instructions for assisting the caregiver in treating the patient using the second choice medical supply; and present, via the user interface, the determined instructions for administering medical treatment.

In some implementations, the at least one processor and the user interface is provided on a mobile device located within the housing of the portable medical treatment and guidance apparatus. In some implementations, the mobile device is removable from the portable medical treatment and guidance apparatus and the at least one processor and memory of the mobile device is configured to perform any and/or all of the steps of the at least one processor described herein when the mobile device is removed from the portable medical treatment and guidance apparatus.

In some implementations, the plurality of medical supplies include at least one tourniquet, at least one chest seal, and at least one pair of gloves. In some implementations, the first choice medical supply is a tourniquet and the second choice medical supply is a quick clot gauze.

In some implementations, the at least one processor and memory is configured to, responsive to determining that the second choice medical supply is unavailable, determine whether a third choice medical supply of the plurality of medical supplies is available based on at least one additional user input, wherein the determined instructions for administering medical treatment include instructions for using the third choice medical supply.

In some implementations, the first choice medical supply is a tourniquet, the second choice medical supply is a quick clot gauze, and the third choice medical supply is a pressure dressing.

In another aspect, a computer-implemented method for evaluating and assisting a caregiver in treating a patient experiencing a medical emergency according to available medical supplies is provided. The computer-implemented method can include: presenting, via a user interface, at least one inquiry as part of an interactive query flow, receiving, via the user interface, at least one user input in response to the at least one inquiry, determining whether a first choice medical supply of a plurality of medical supplies is available based on at least one user input; responsive to determining that the first choice medical supply is available, determining instructions for assisting the caregiver in treating the patient using the first choice medical supply; responsive to determining that the first choice medical supply is unavailable: determining whether a second choice medical supply of the plurality of medical supplies is available based on at least one additional user input; and responsive to determining that the second choice medical supply is available, determining instructions for assisting the caregiver in treating the patient using the second choice medical supply; and presenting, via the user interface, the determined instructions for administering medical treatment.

In some implementations, the computer-implemented method is performed by at least one processor provided on a mobile device located within a housing of a portable medical treatment and guidance apparatus. In some implementations, the mobile device is removable from the portable medical treatment and guidance apparatus and the mobile device performs any and/or all of the computer-implemented methods described herein when the mobile device is removed from the portable medical treatment and guidance apparatus.

In some implementations, the plurality of medical supplies include at least one tourniquet, at least one chest seal, and at least one pair of gloves. In some implementations, the first choice medical supply is a tourniquet and the second choice medical supply is a quick clot gauze.

In some implementations, the computer-implemented method includes responsive to determining that the second choice medical supply is unavailable, determining whether a third choice medical supply of the plurality of medical supplies is available based on at least one additional user input, wherein the determined instructions for administering medical treatment include instructions for using the third choice medical supply.

In some implementations, the first choice medical supply is a tourniquet, the second choice medical supply is a quick clot gauze, and the third choice medical supply is a pressure dressing.

In another aspect, a non-transitory computer readable medium storing instructions for assisting a caregiver in evaluating and treating a patient experiencing a medical emergency according to a time sensitive prioritization of the medical emergency is provided. The instructions, when executed, can cause a processor to perform any and/or all of the operations described herein.

BRIEF DESCRIPTIONS OF THE DRAWINGS

Many advantages of the present disclosure will be apparent to those skilled in the art with a reading of this specification in conjunction with the attached drawings, wherein like reference numerals are applied to like elements and wherein.

Figure 5A:
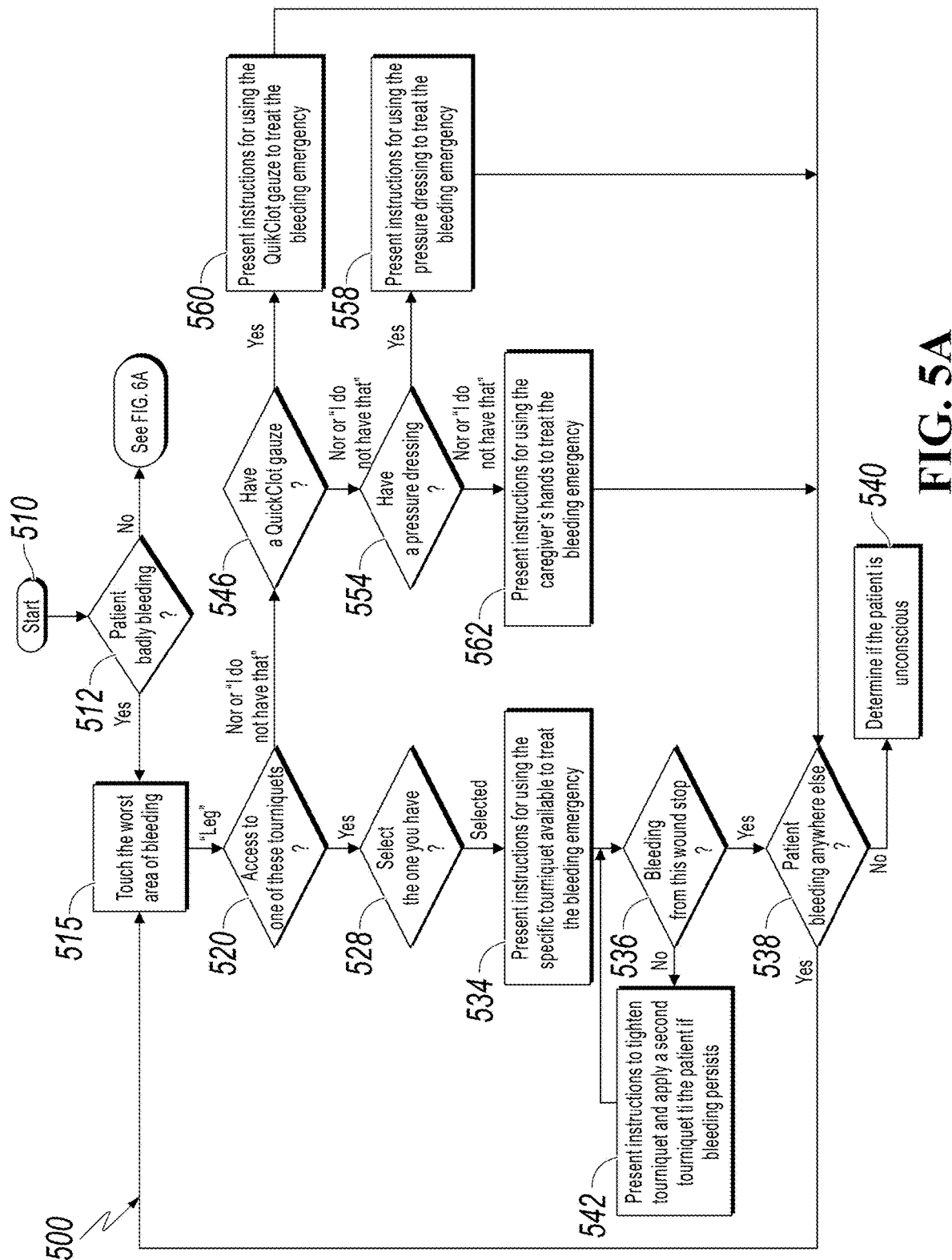
FIG. 5A shows a process of the operations performed by the medical treatment and guidance system accounting for substitute medical supplies in accordance with some embodiments.
Figure 6A:
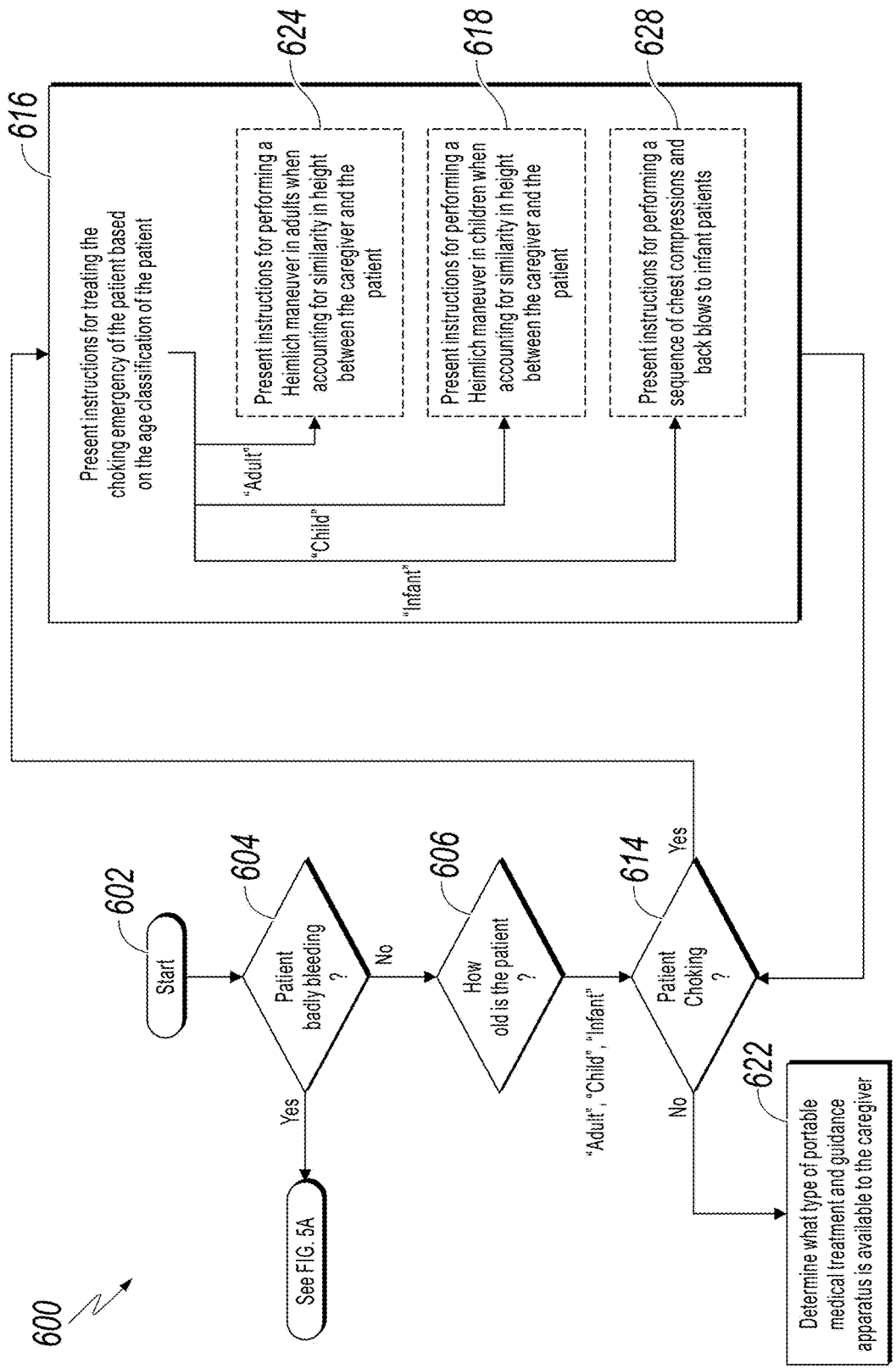
Figure 6C:
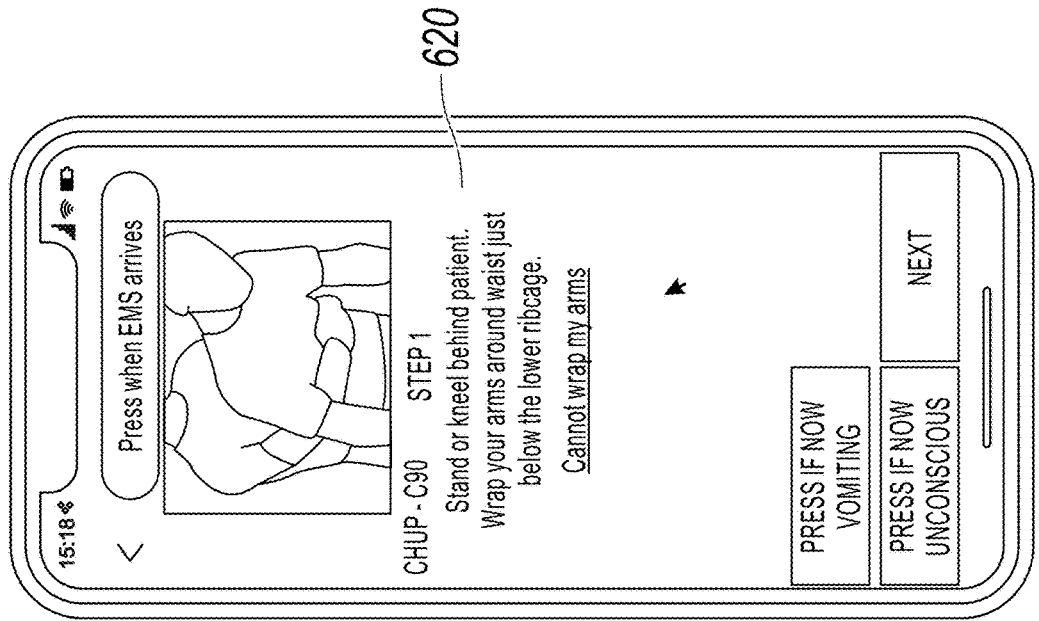
Figure 7A:
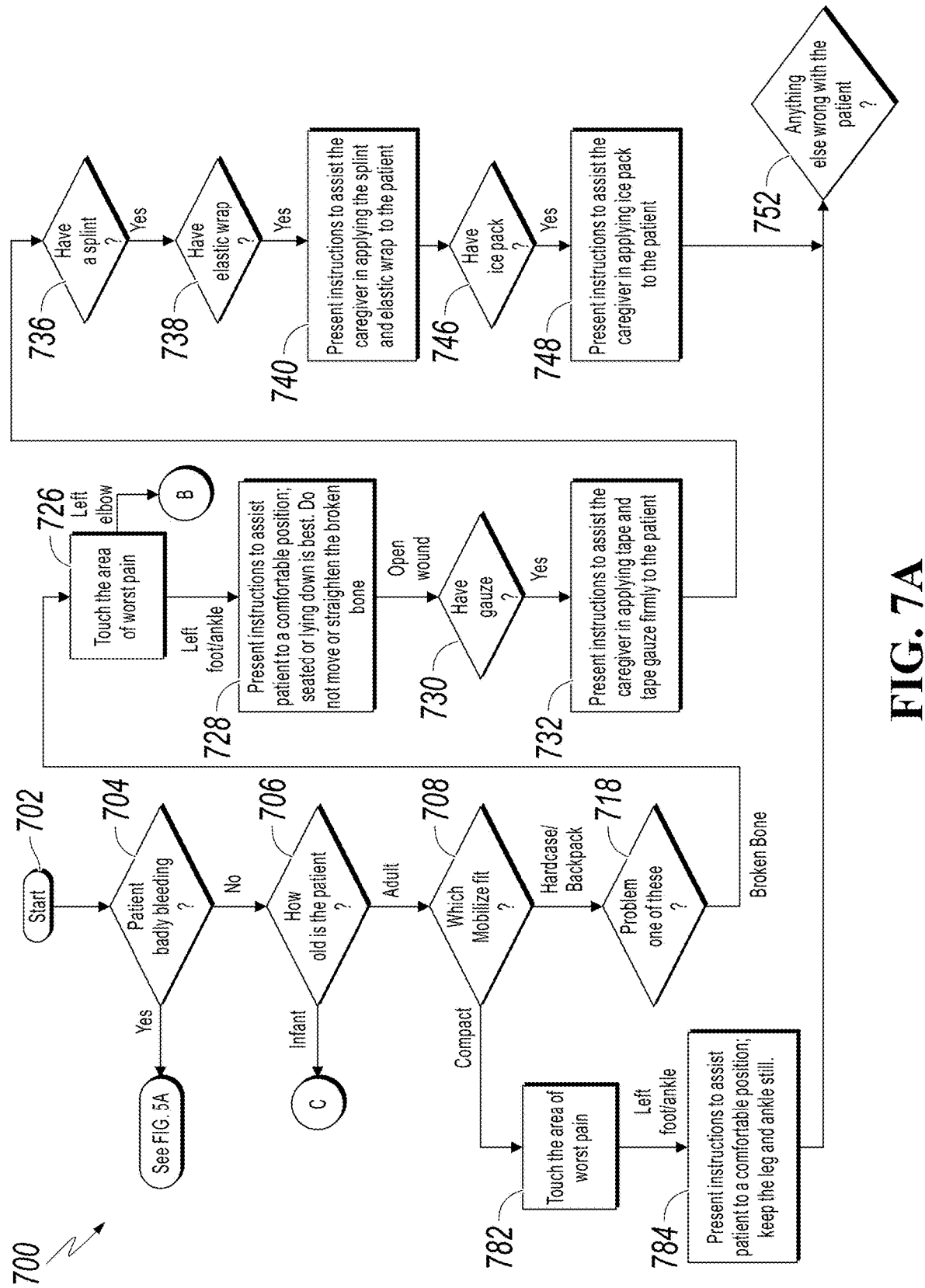
Figure 7B:
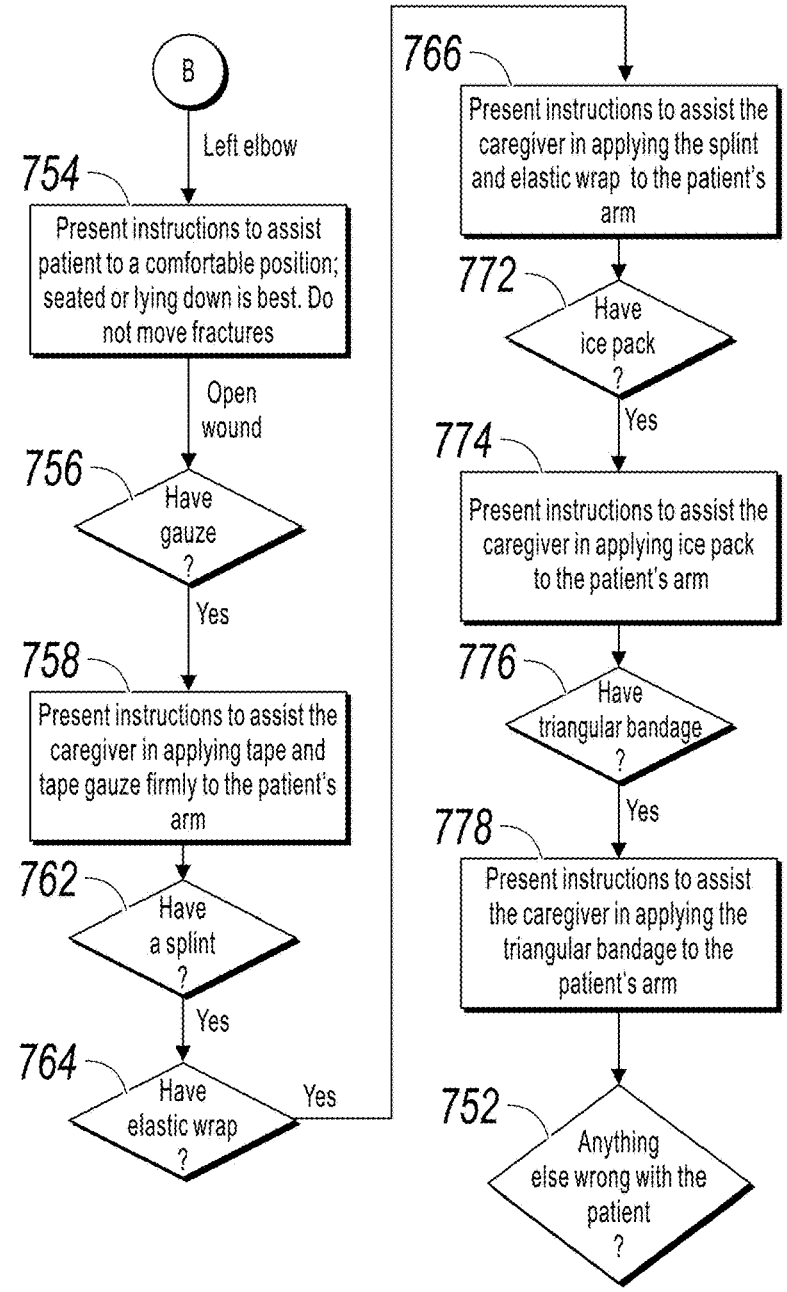
Figure 7C:
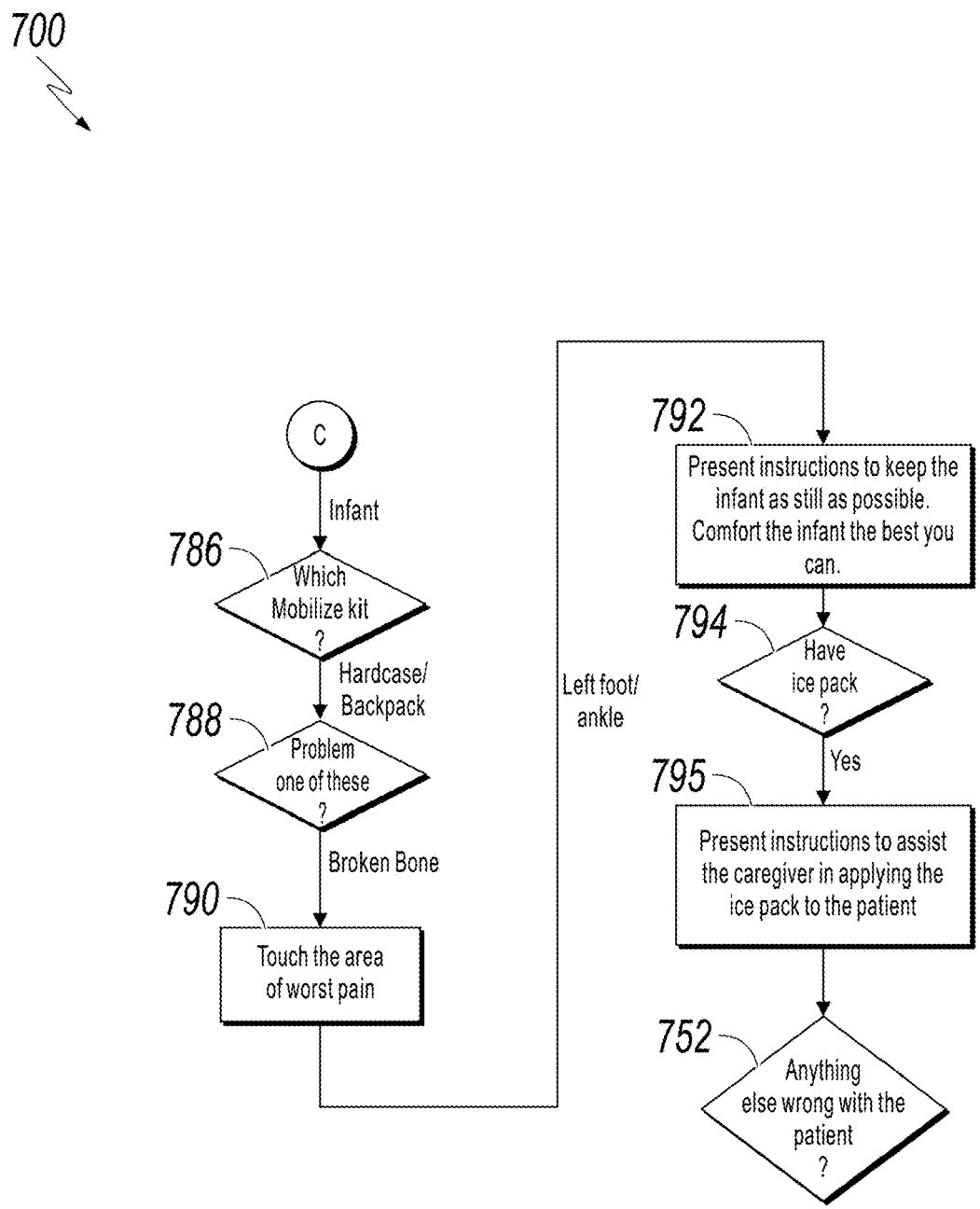
Figure 8A:
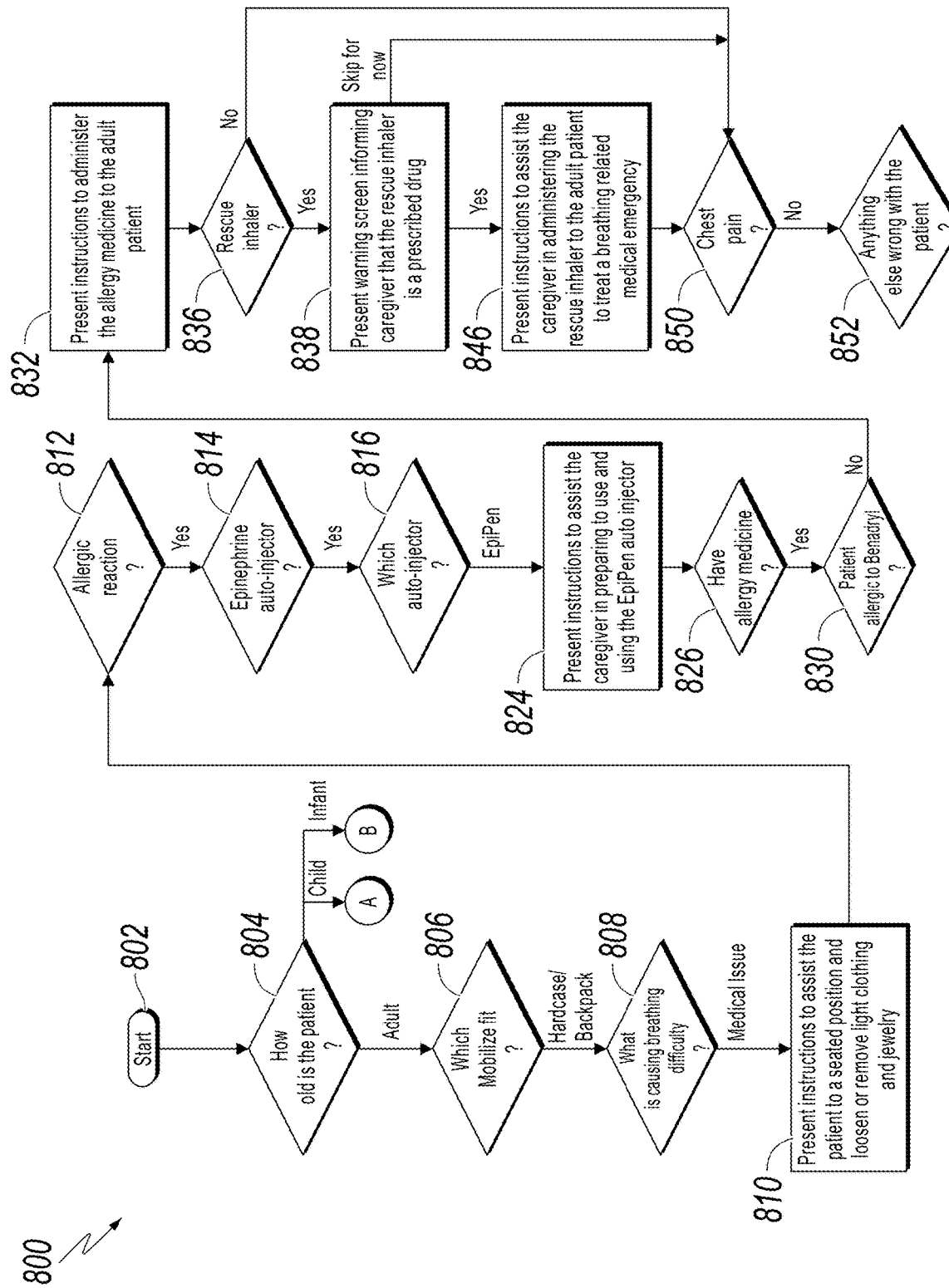
Figure 8B:
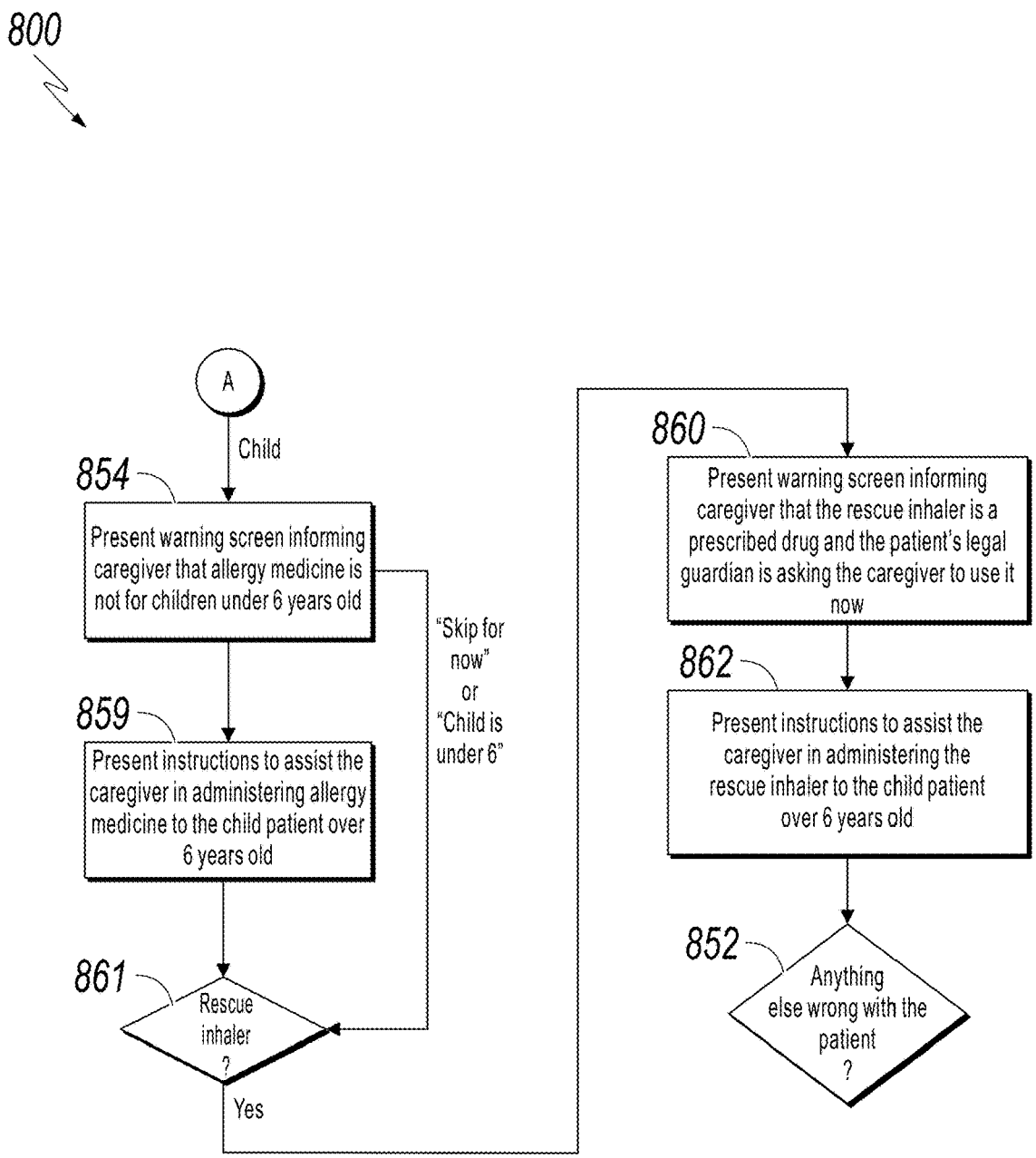
Figure 8C:
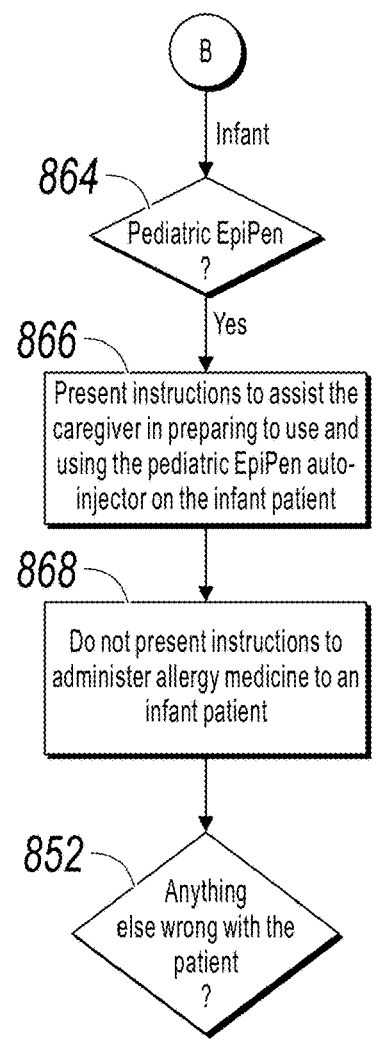
Figure 8E:
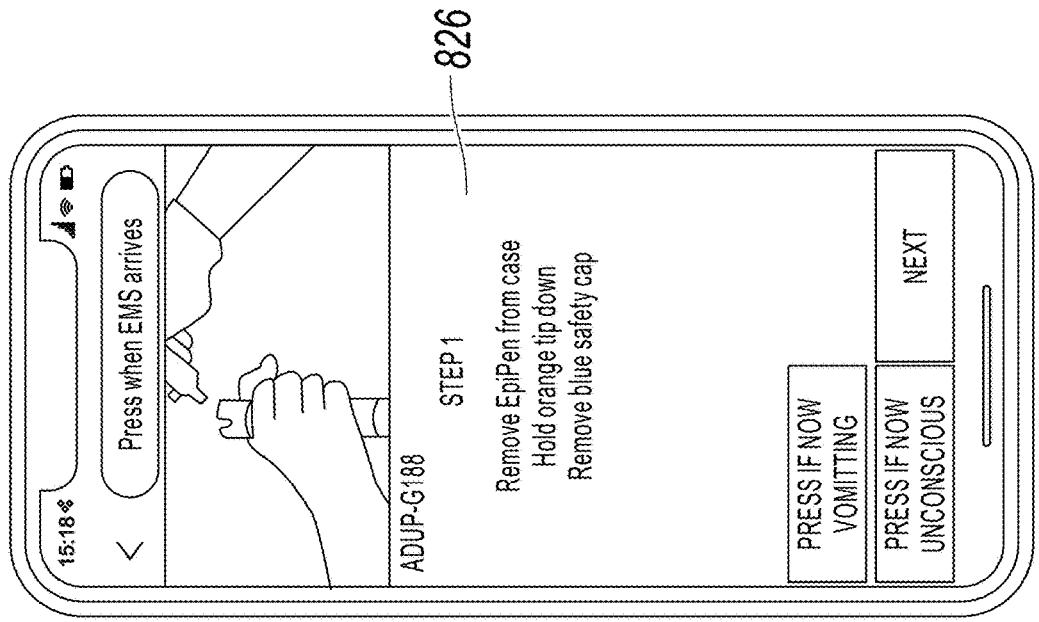
Figure 8D:
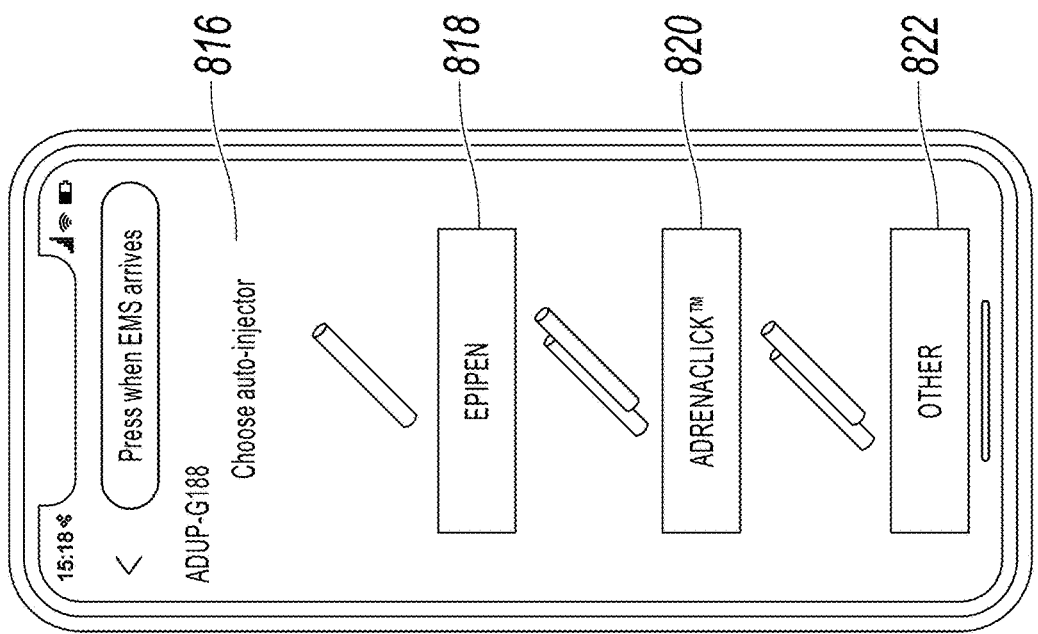
Figures 9A, 9B:
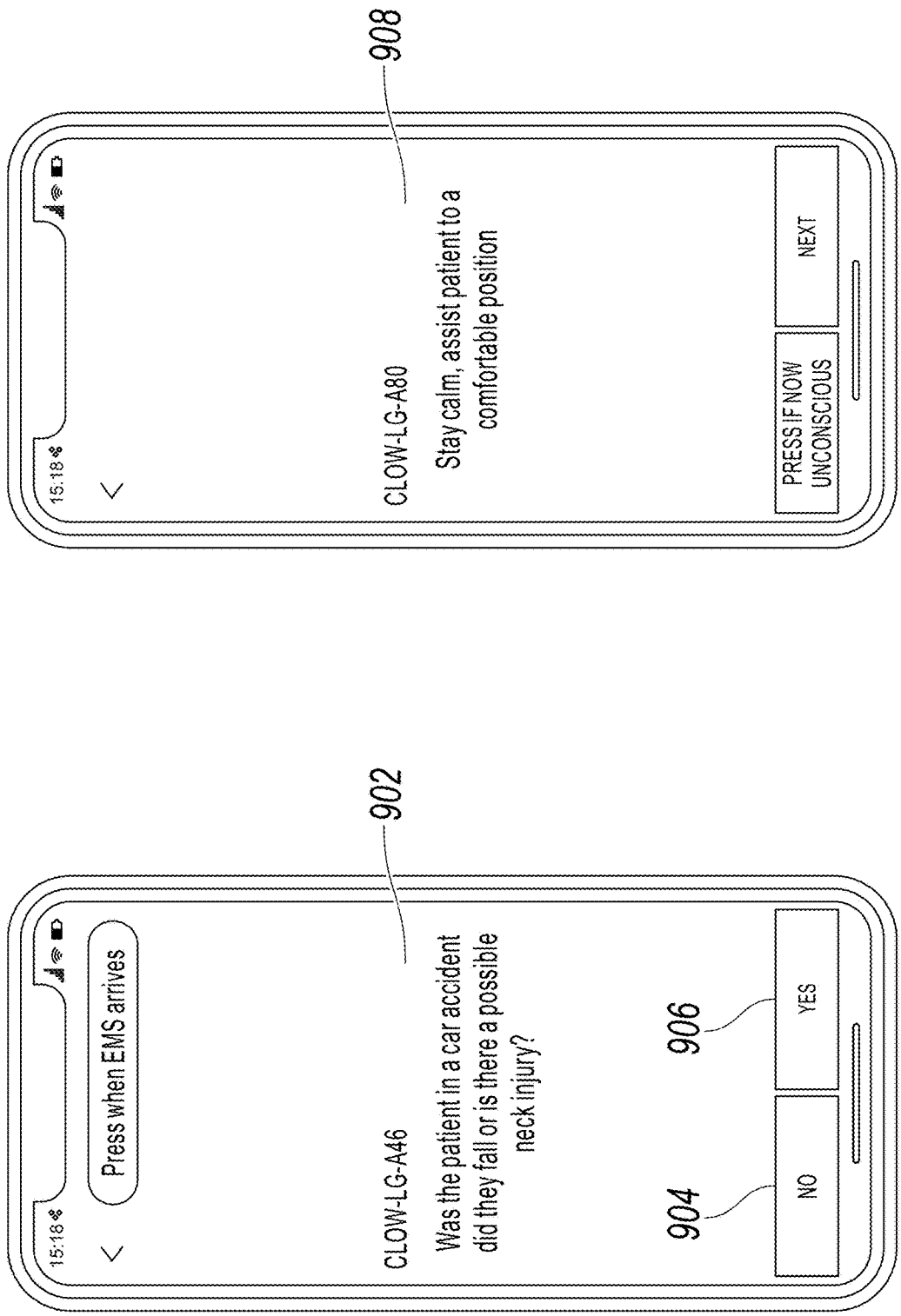
Figure 9C:
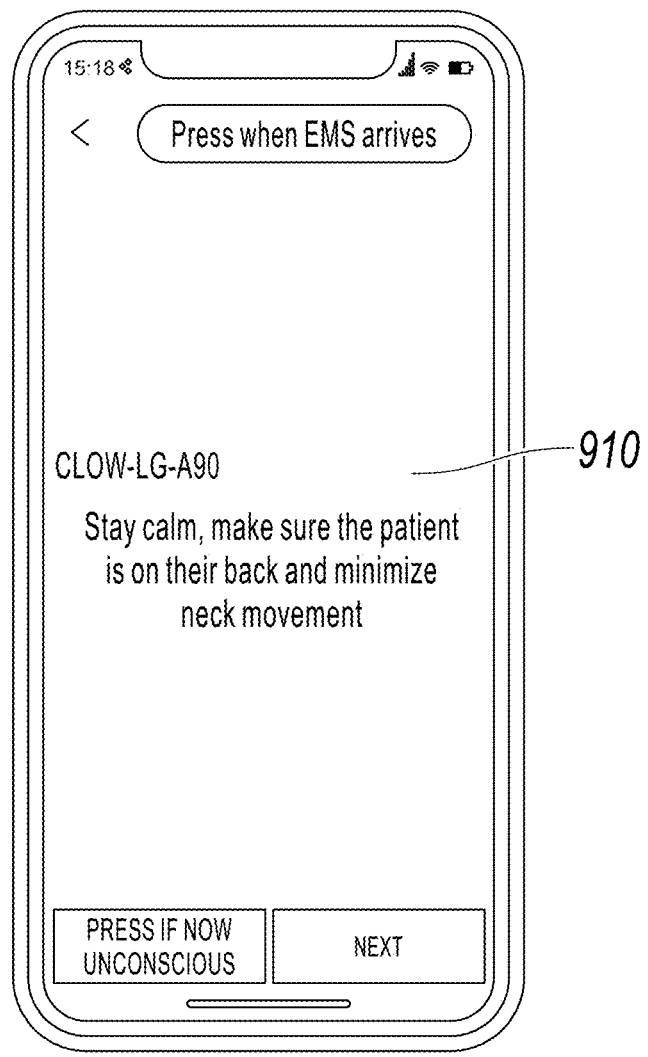
Figure 10A:
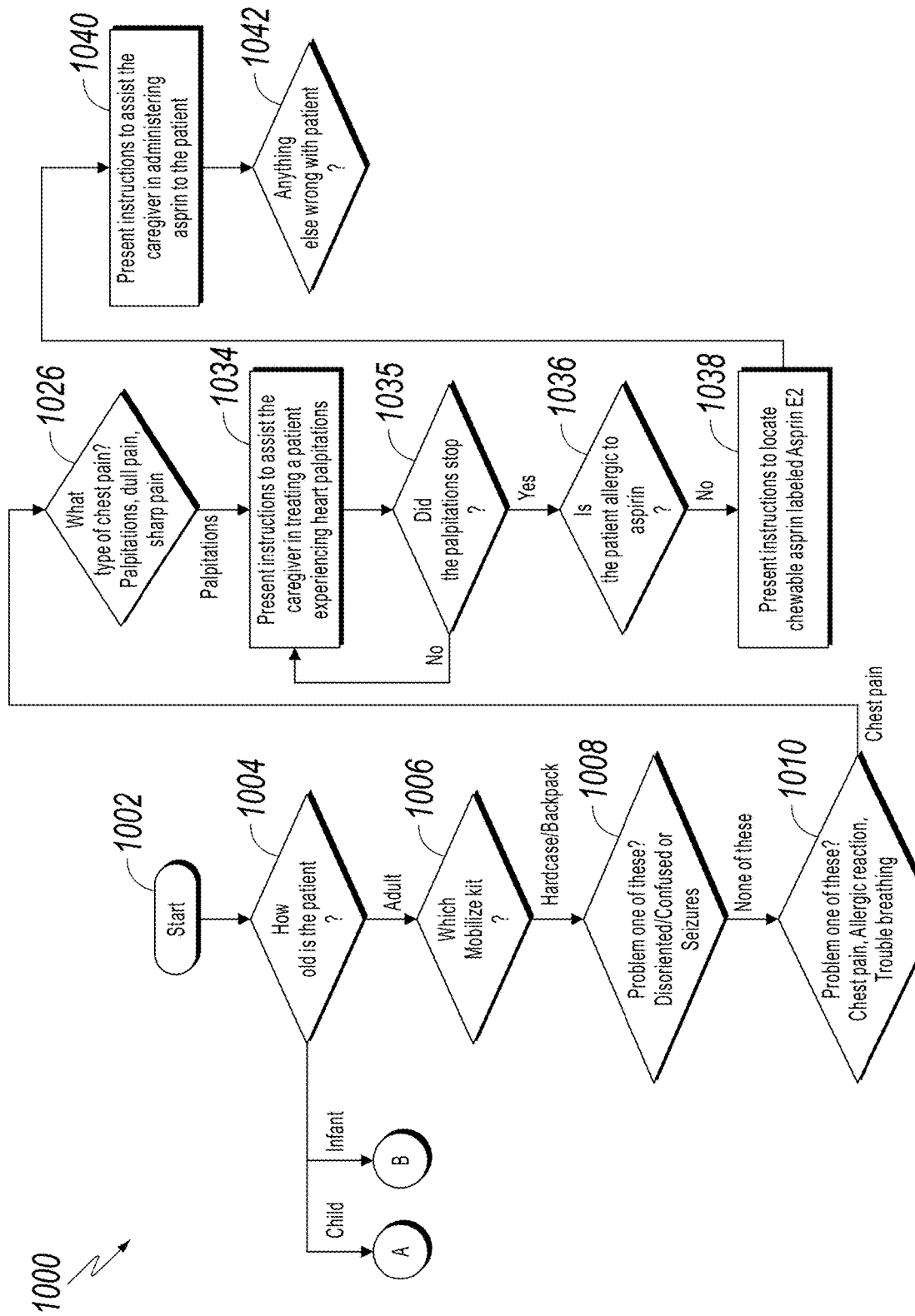
Figure 10B:
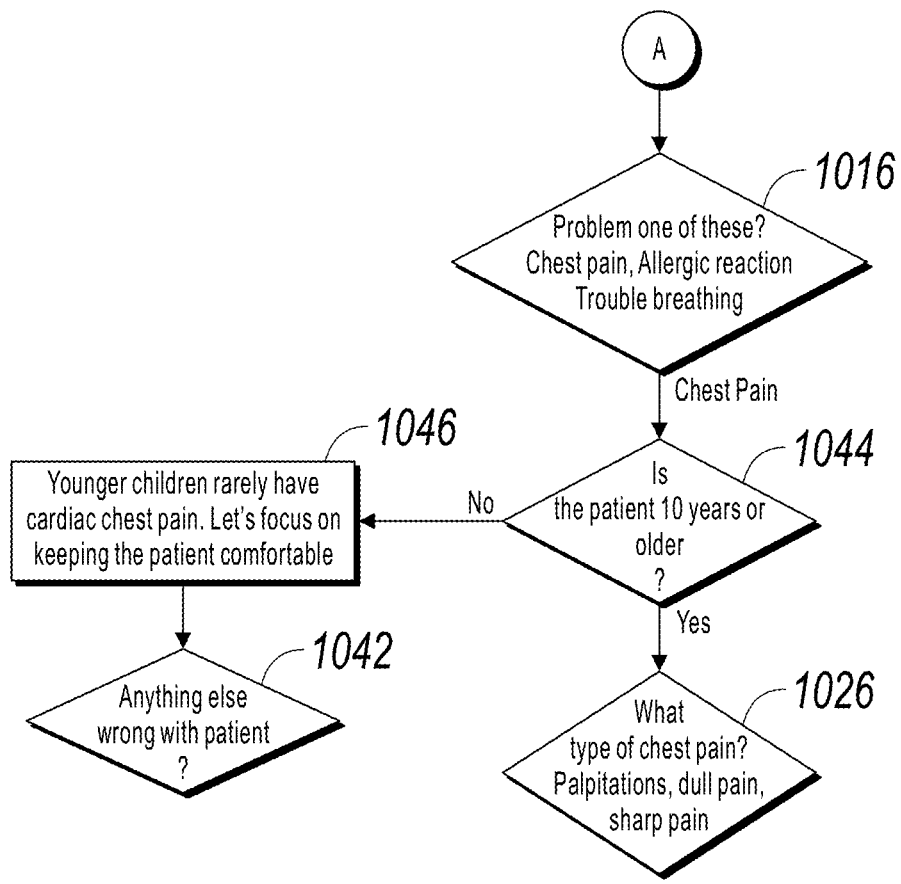
Figure 10C:
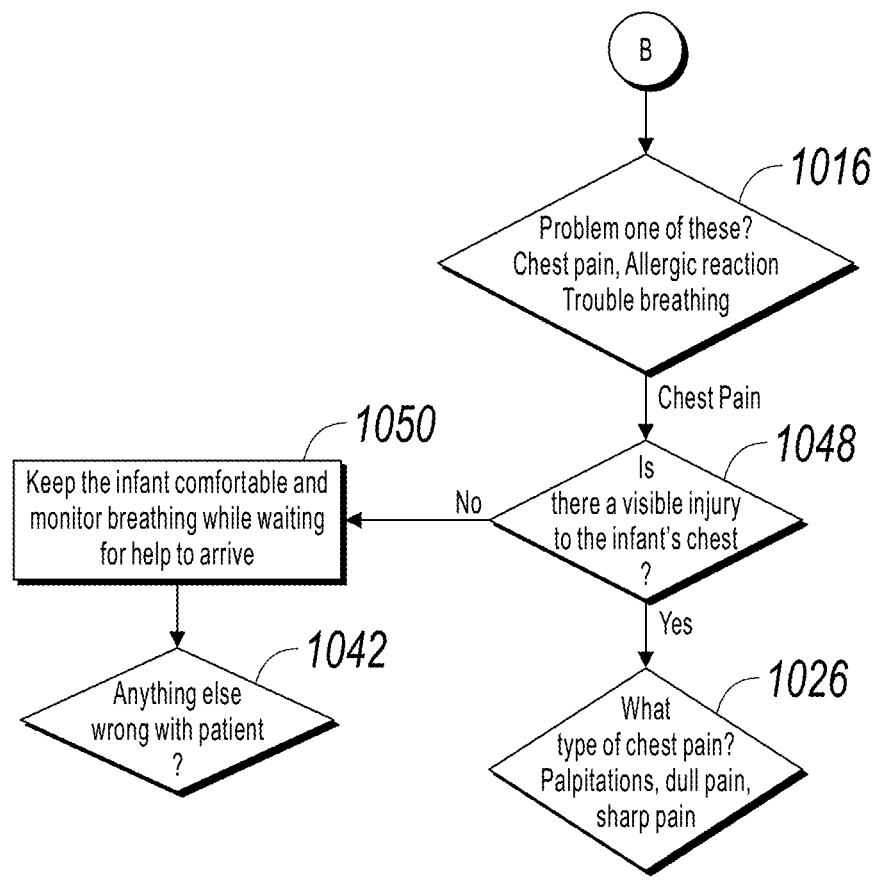
Figures 10D, 10E:
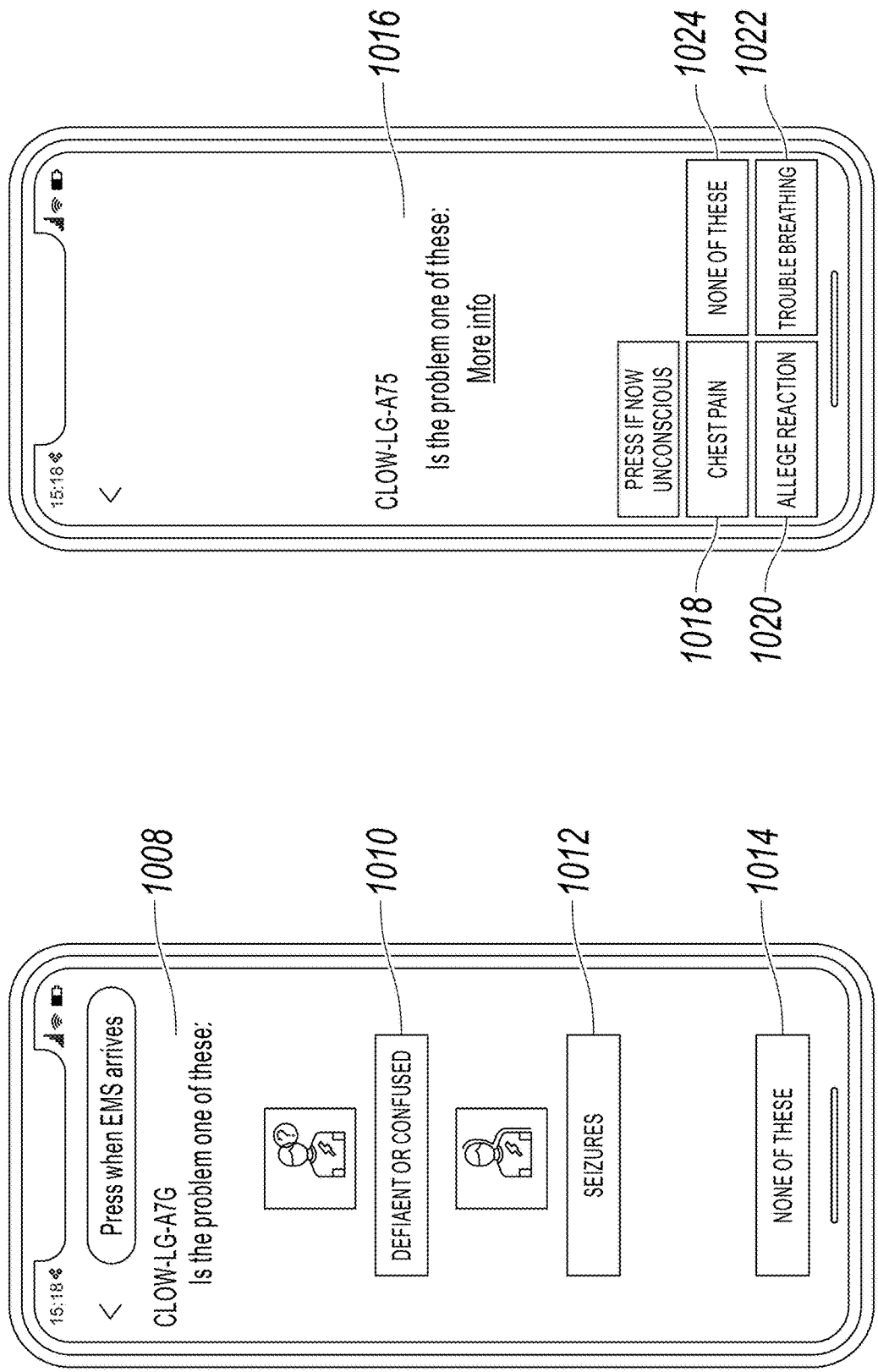
Figure 10F:
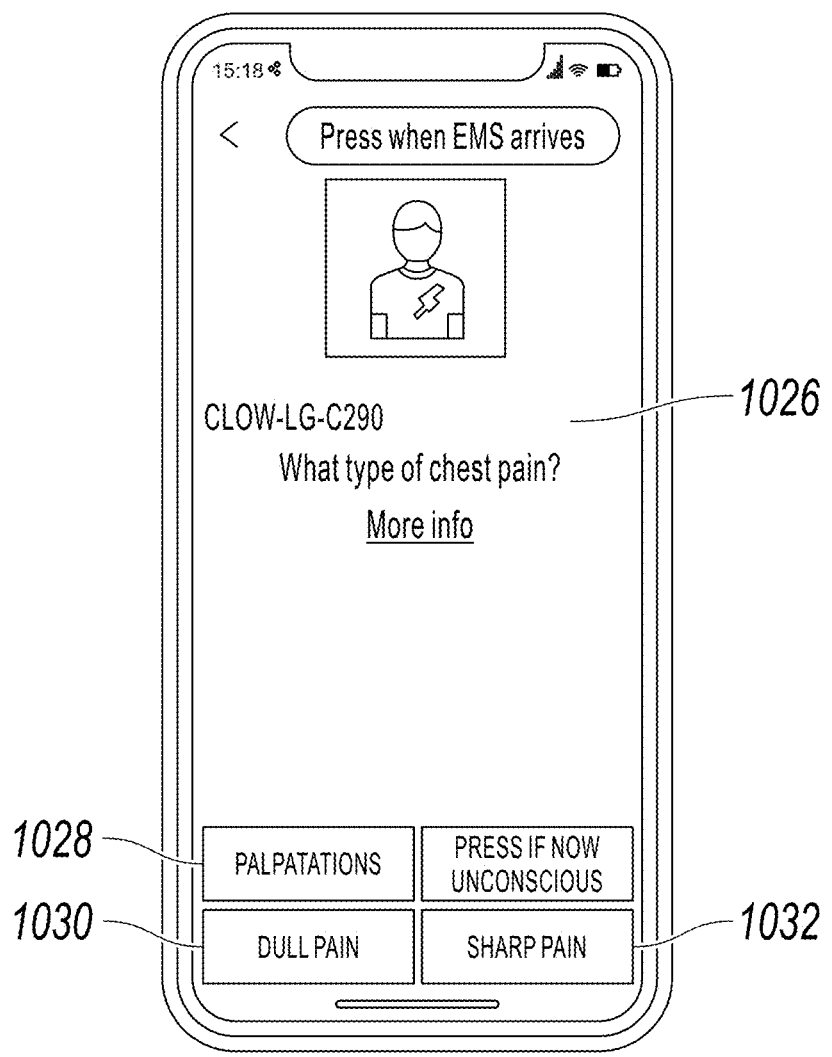
Figure 11A:
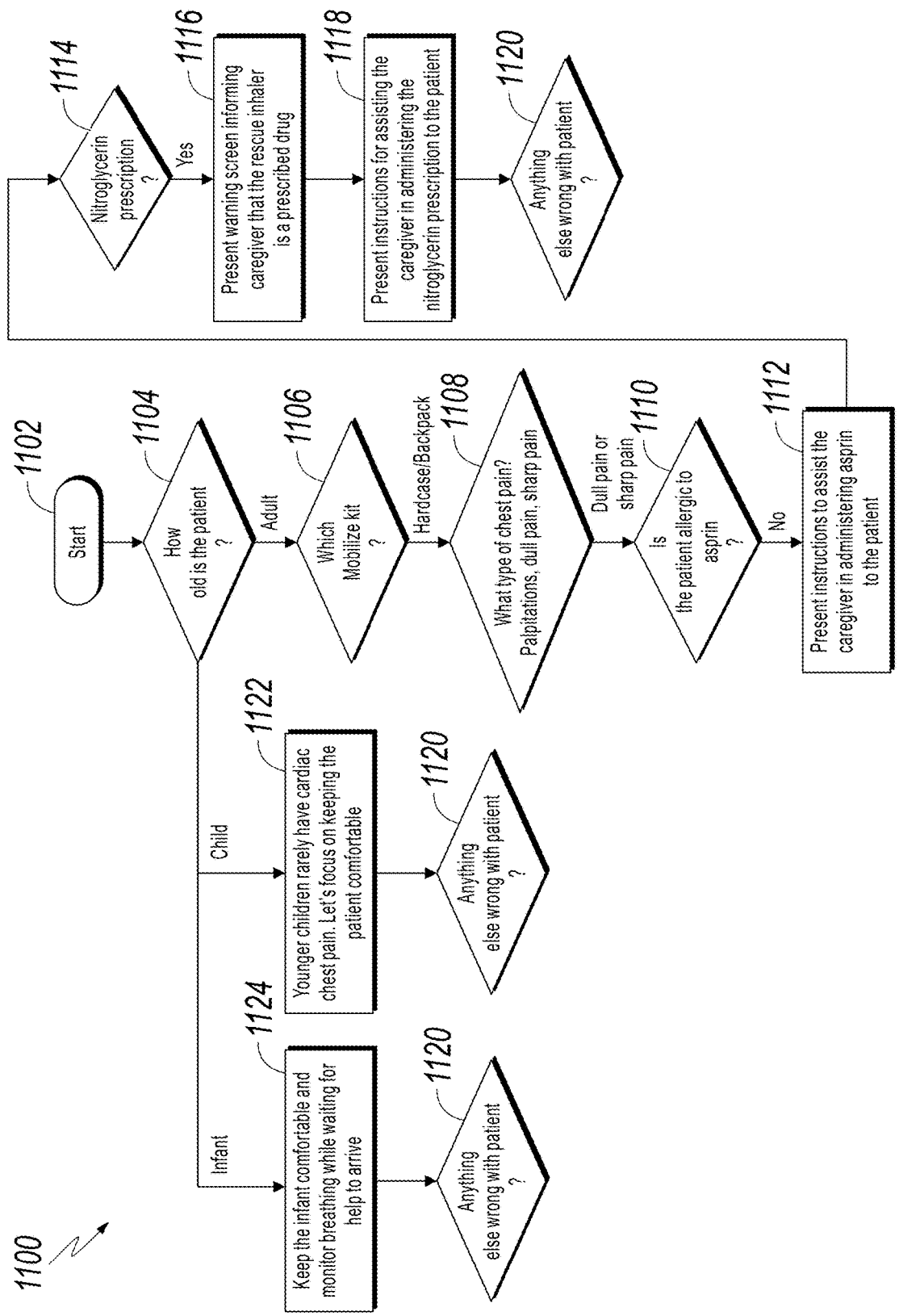
Figure 11C:
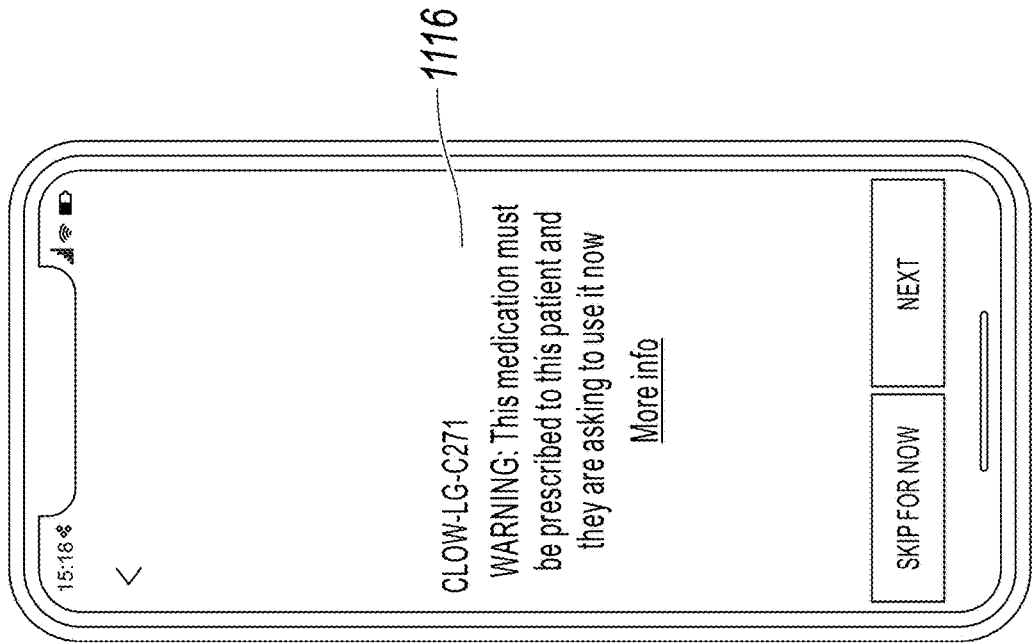
Figure 11B:
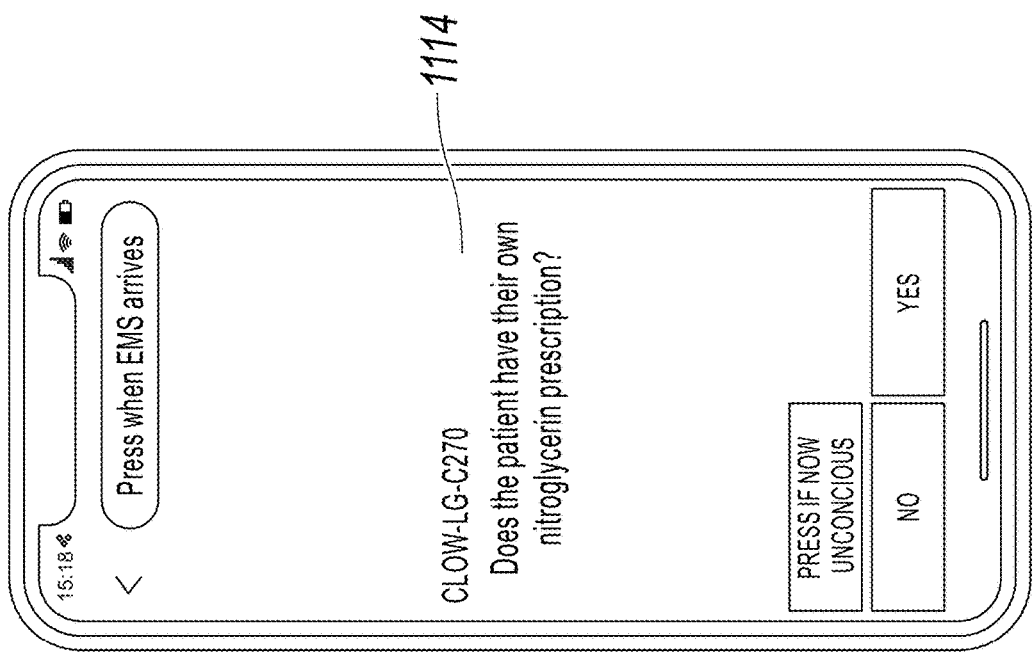
Figure 11D:
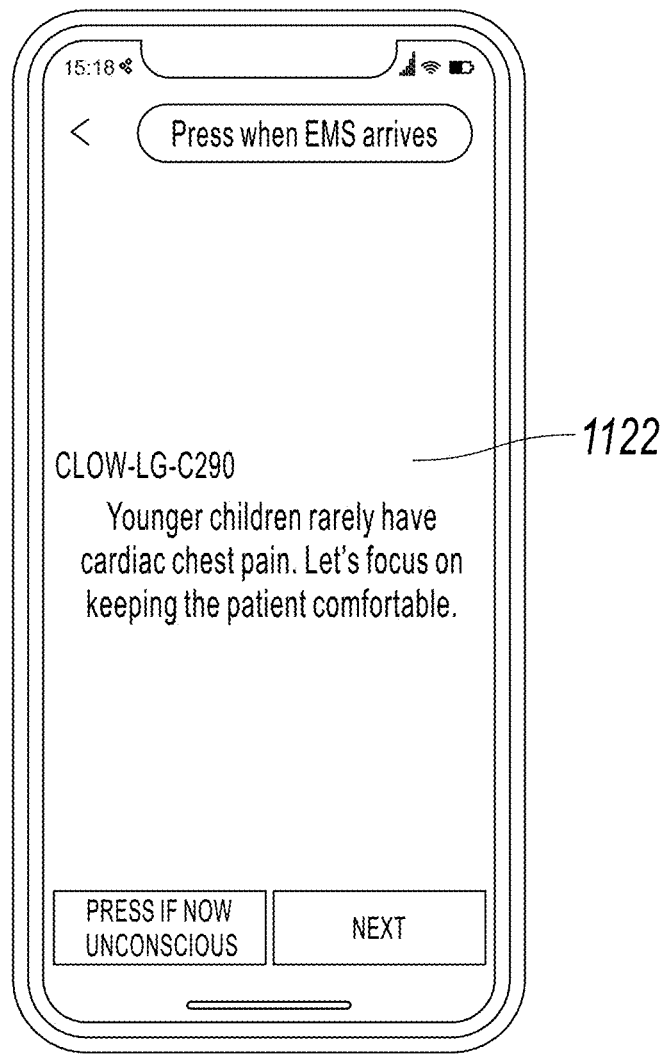
Figure 12A:
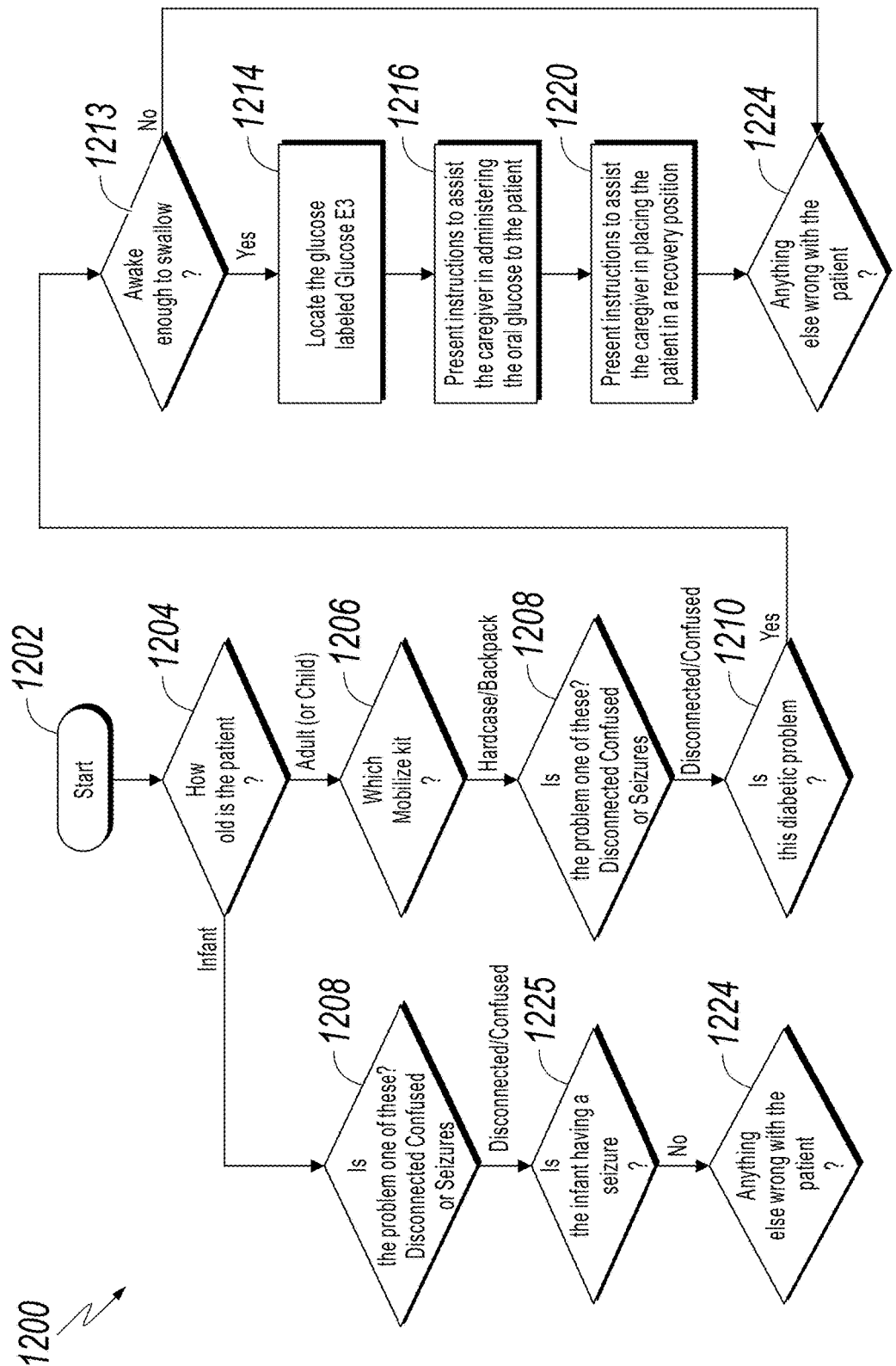
Figure 12C:
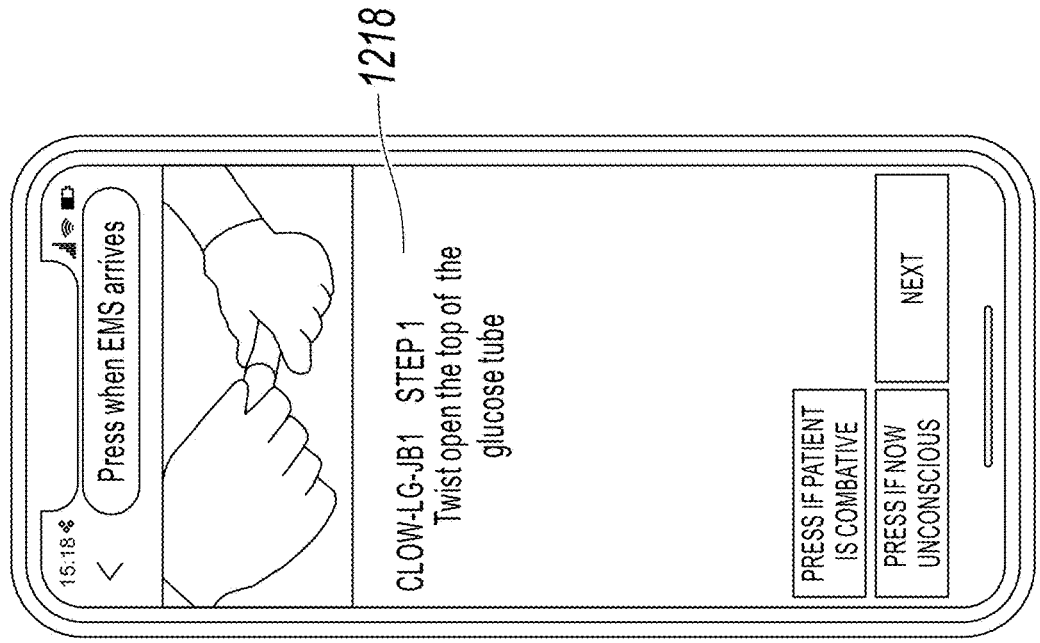
Figure 12B:
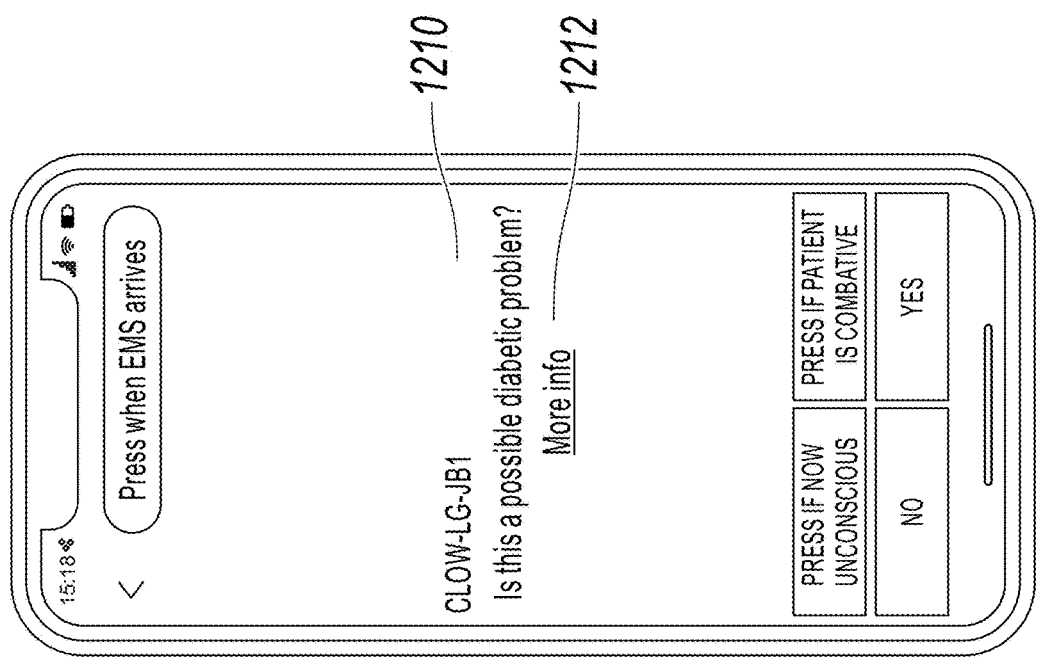
Figure 12D:
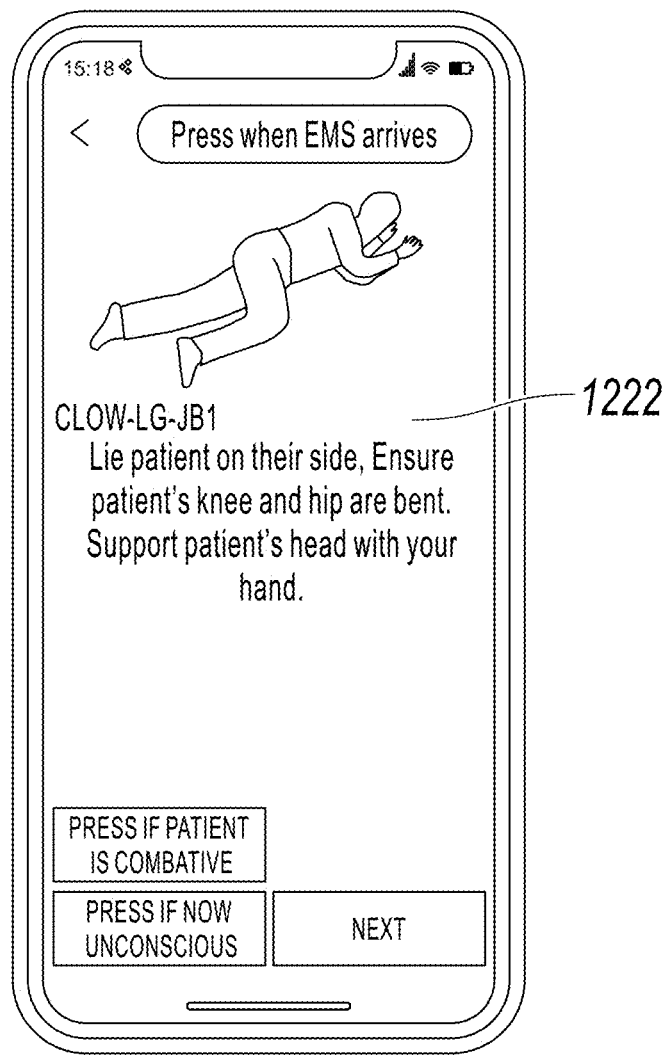
Figure 13A:
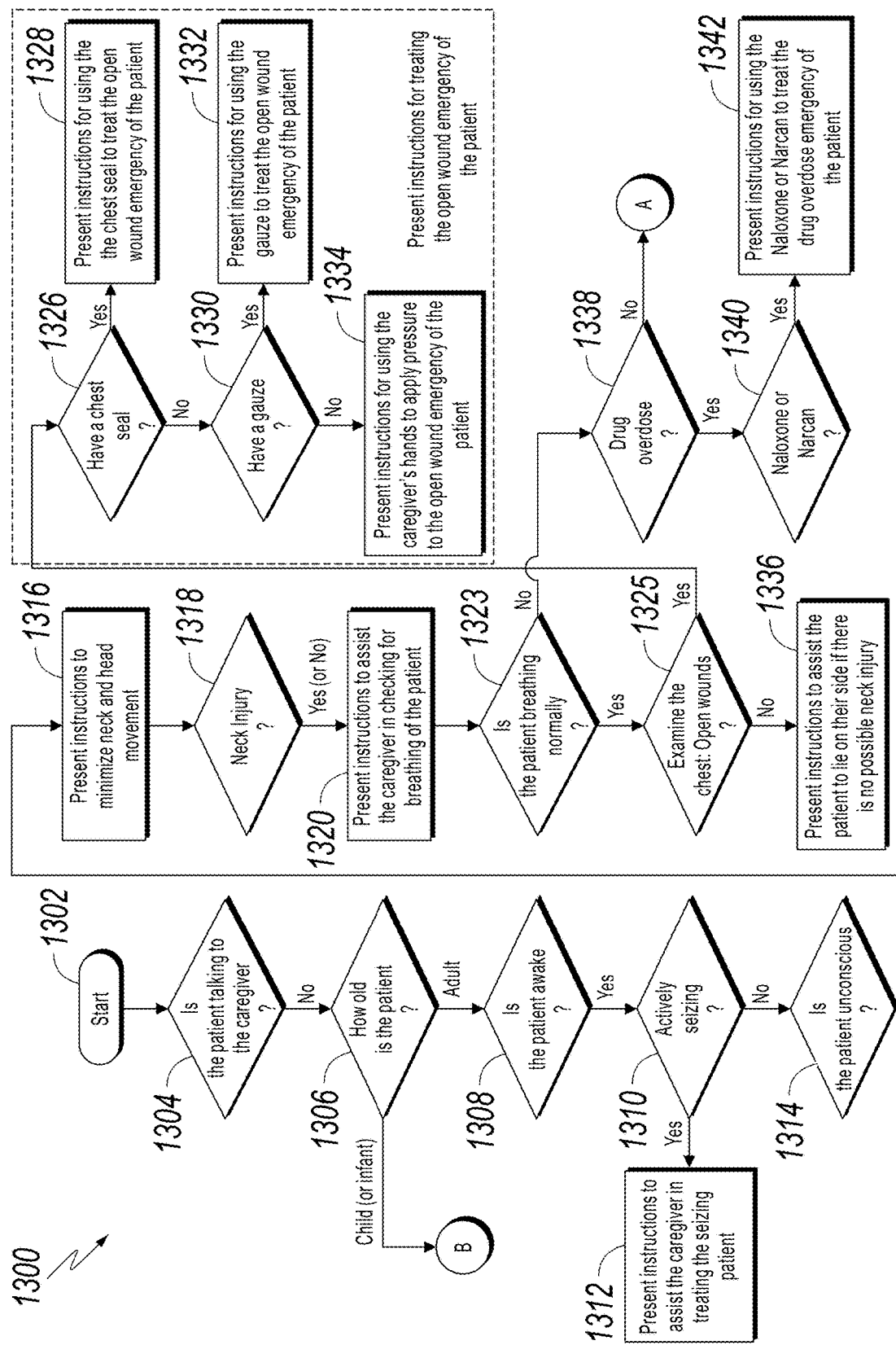
Figure 13B:
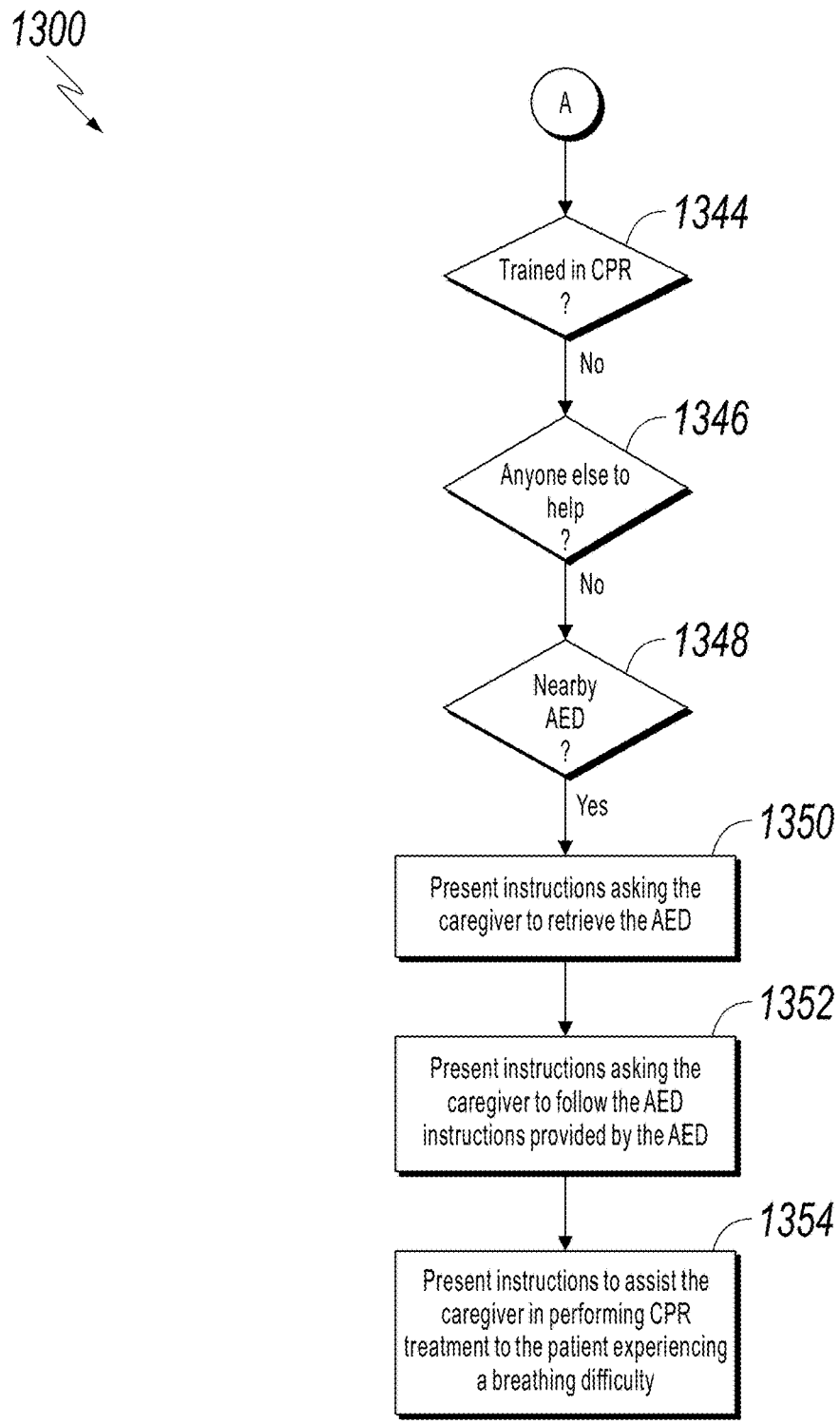
Figure 13C:
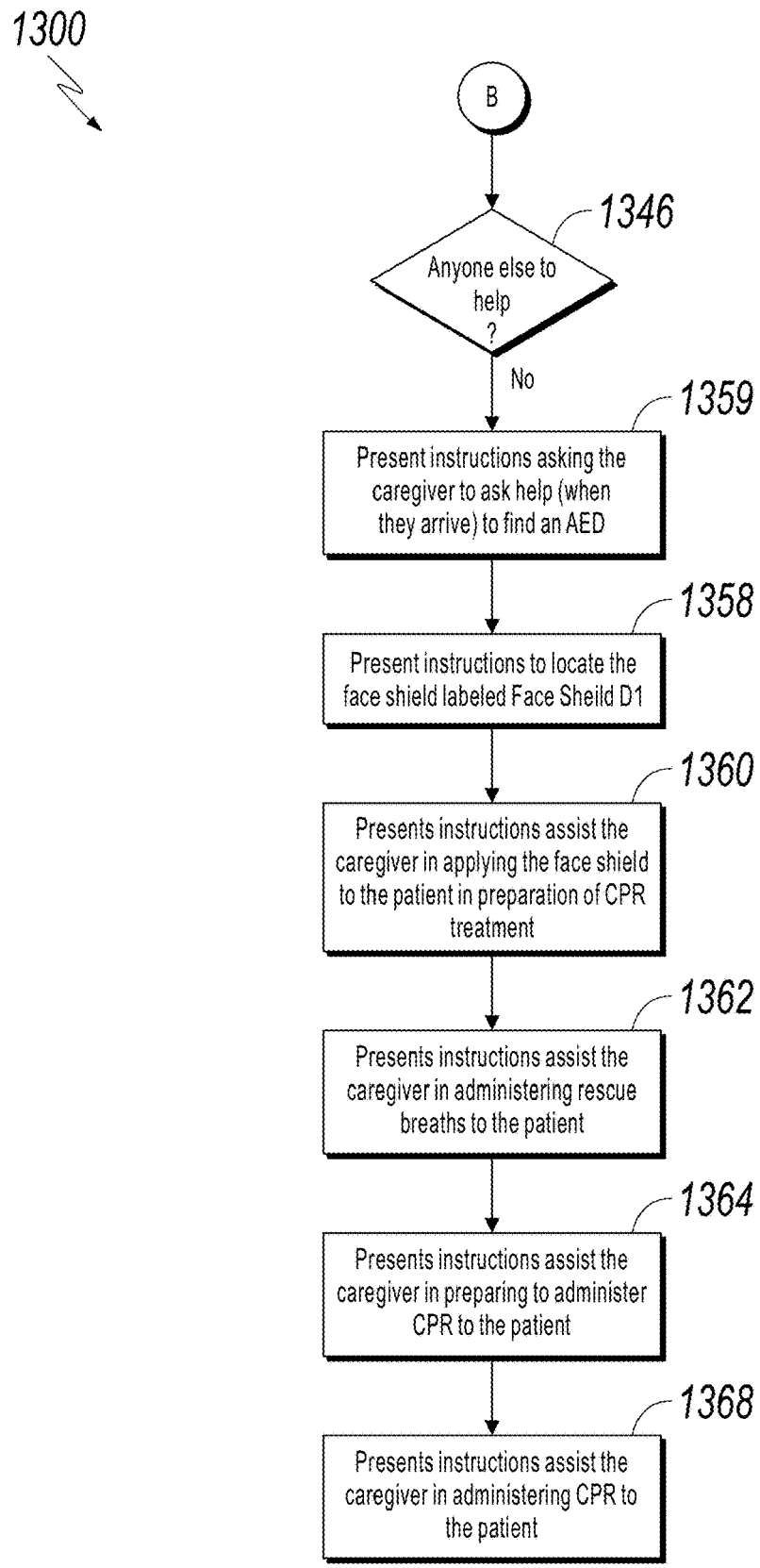
Figure 13E:
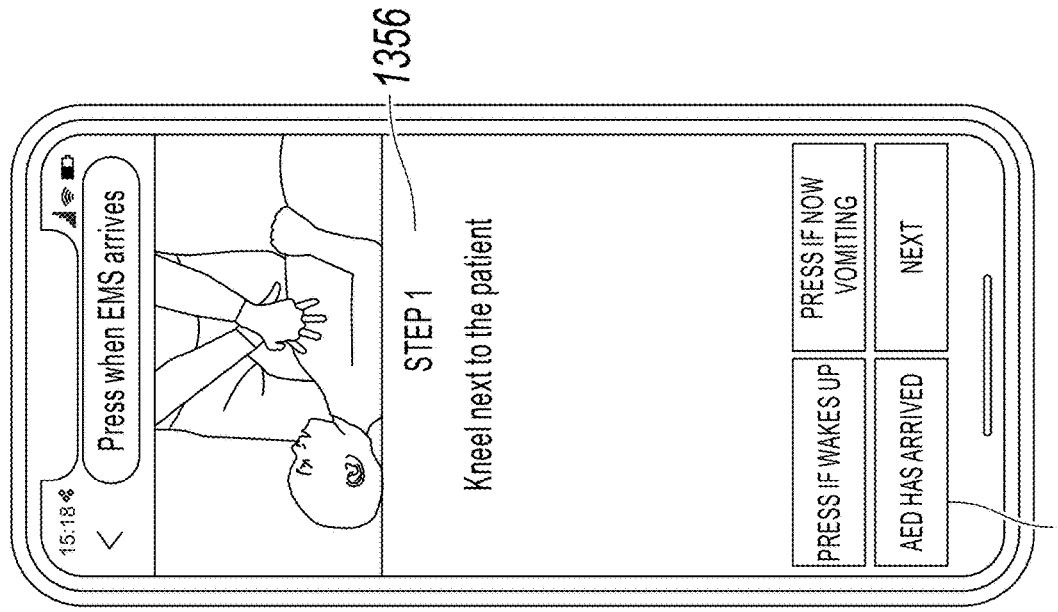
Figure 13D:
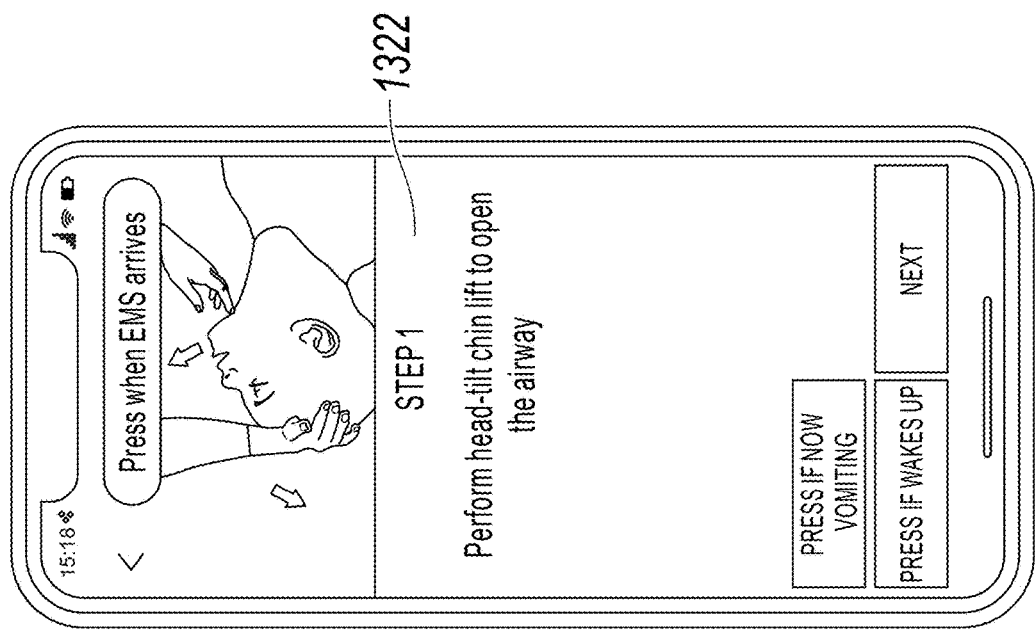
Figure 14A:
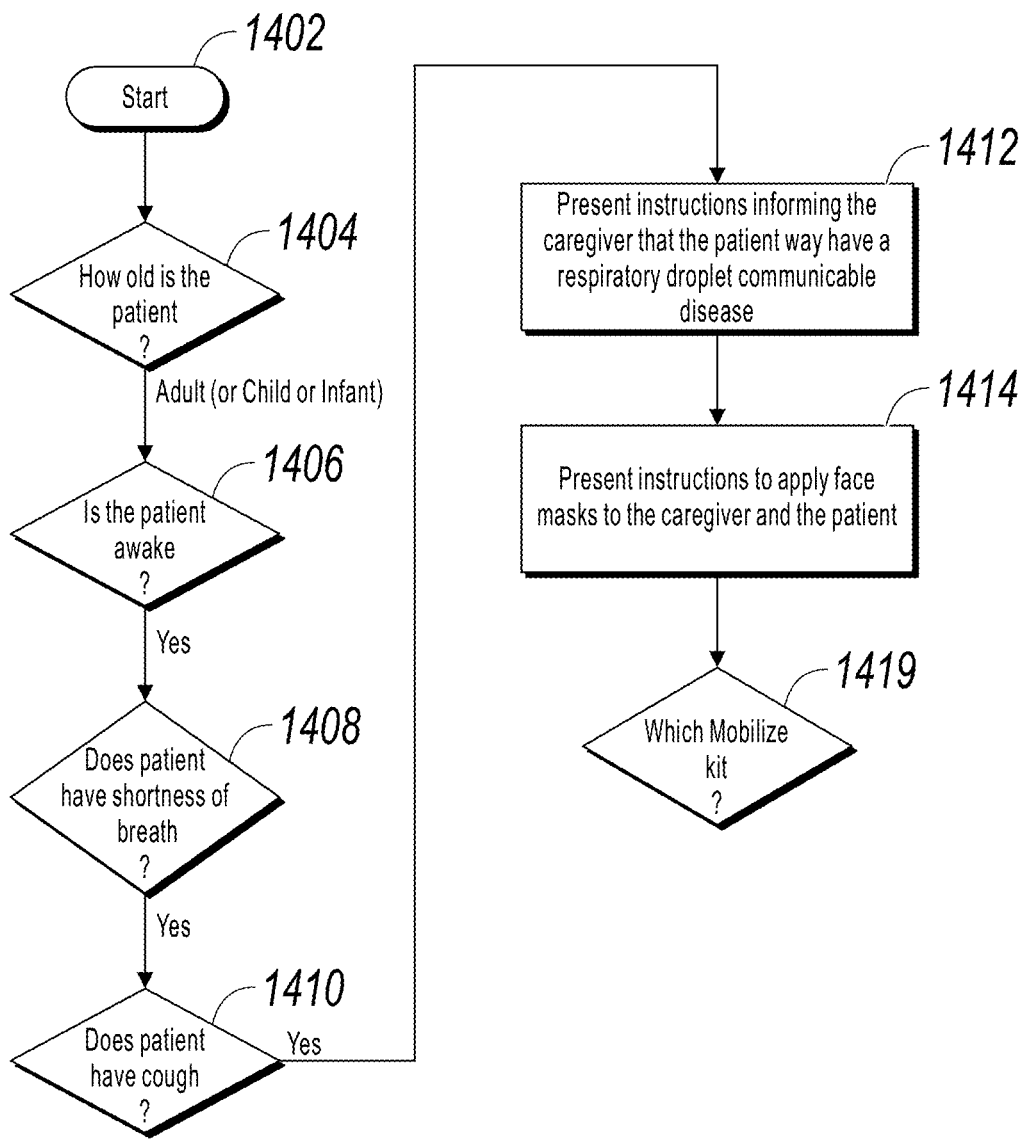
Figure 14C:
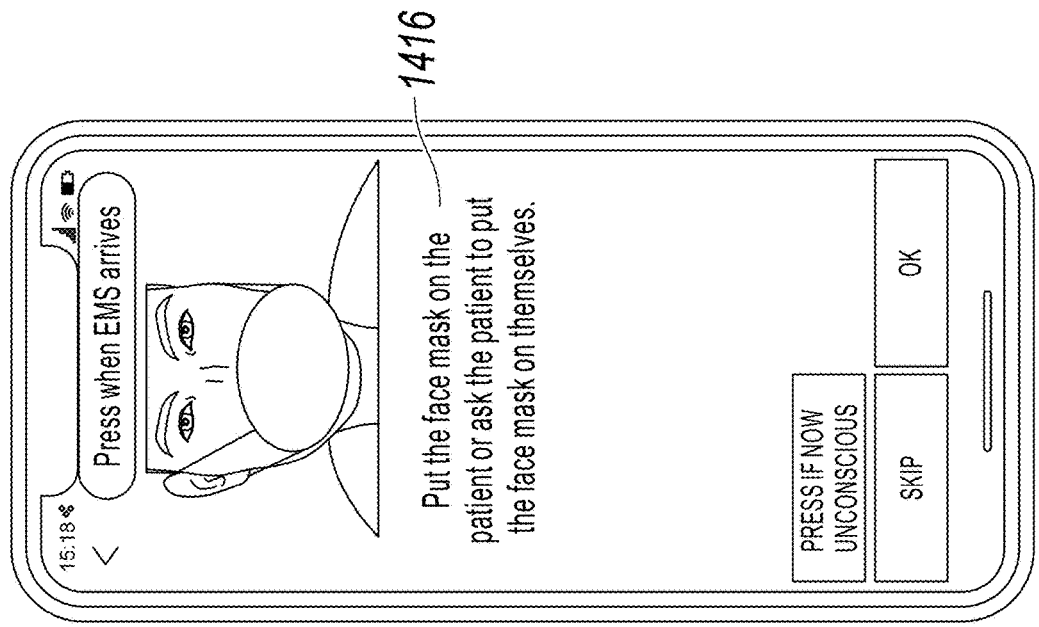
Figure 14B:
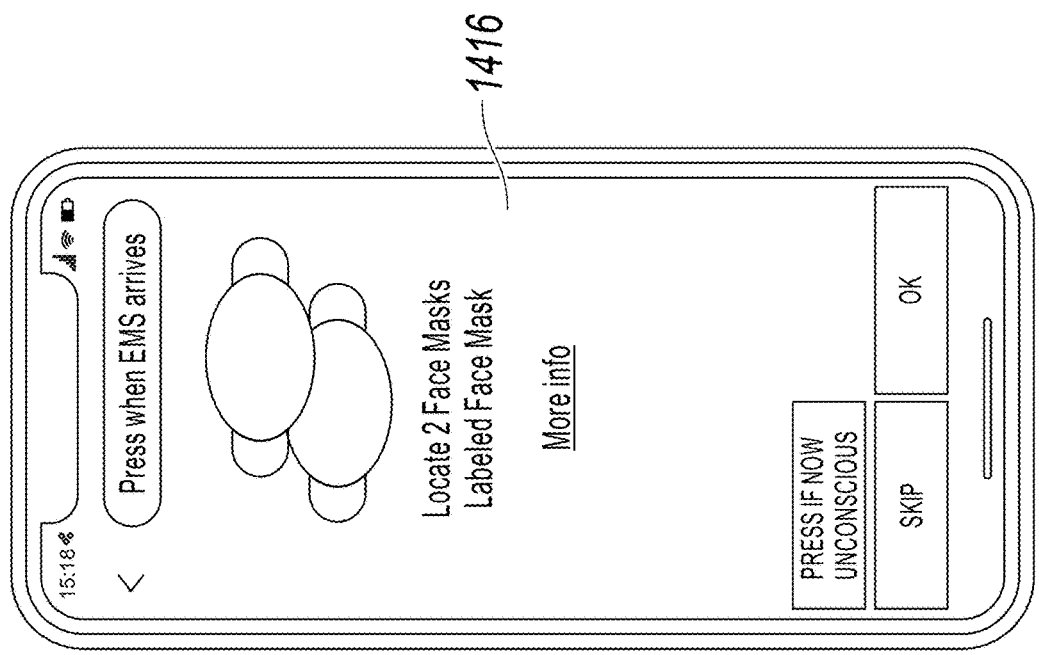
Figure 15A:
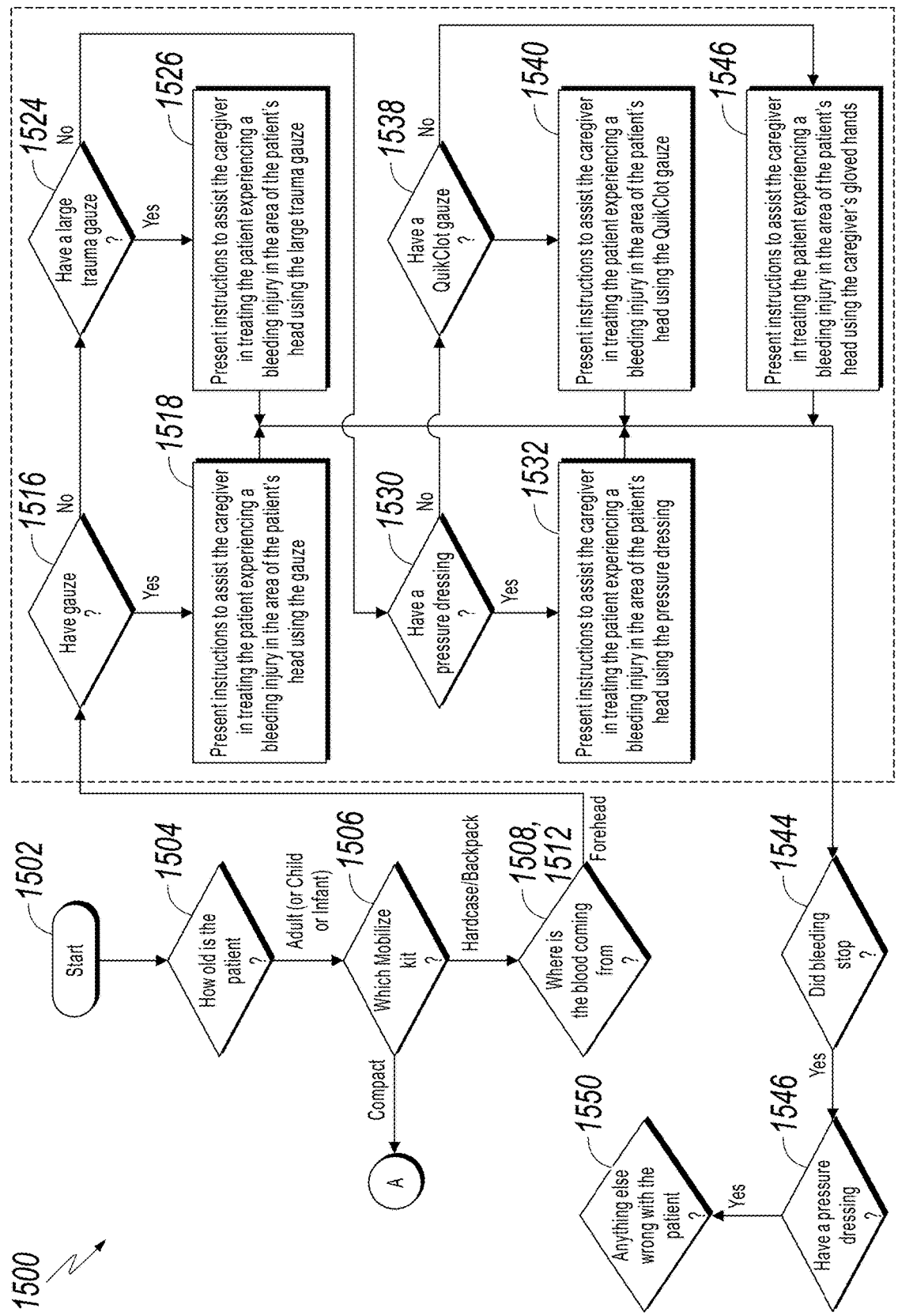
Figure 15B:
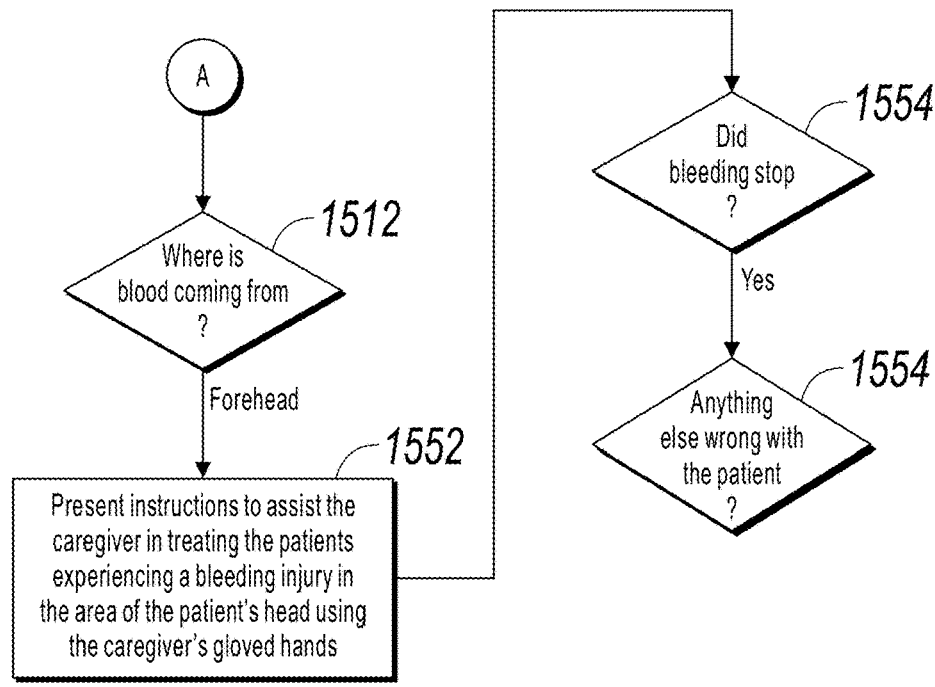
Figure 15D:
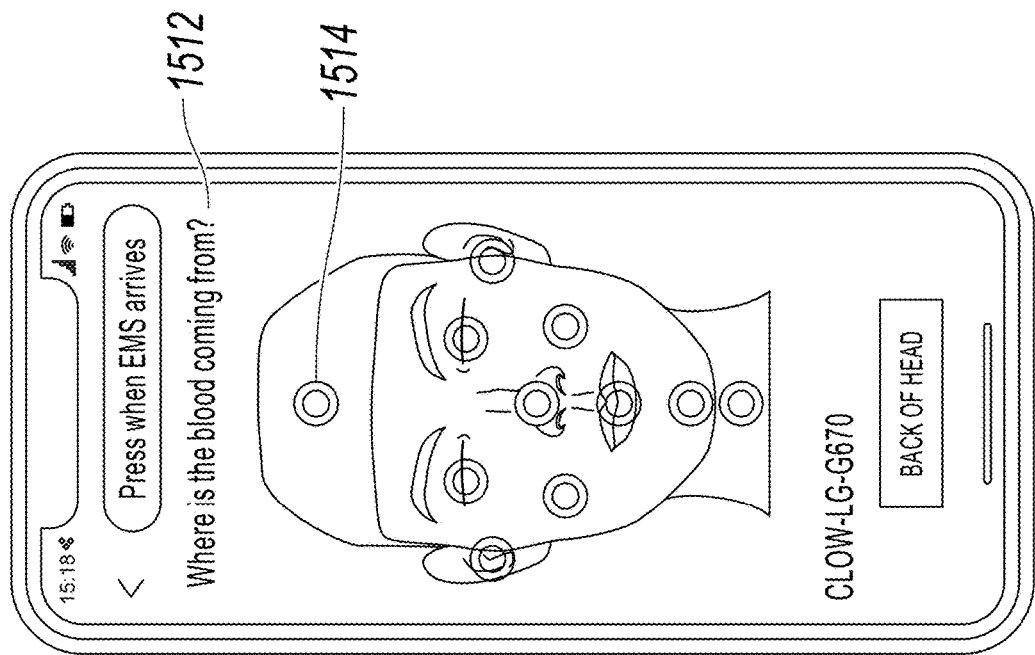
Figure 15C:
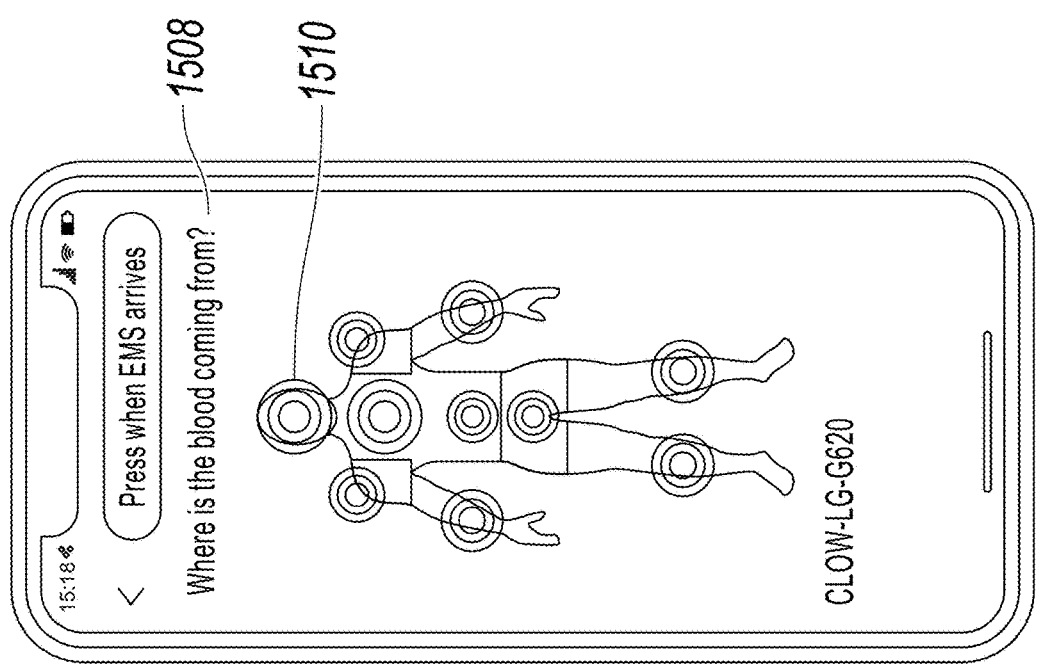
Figure 15F:
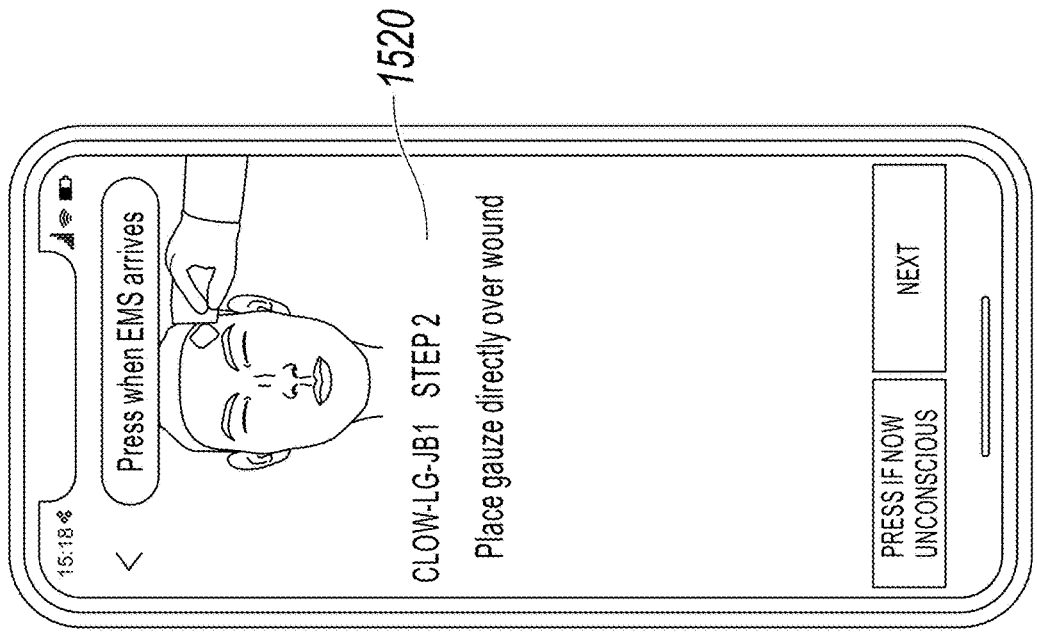
Figure 15E:
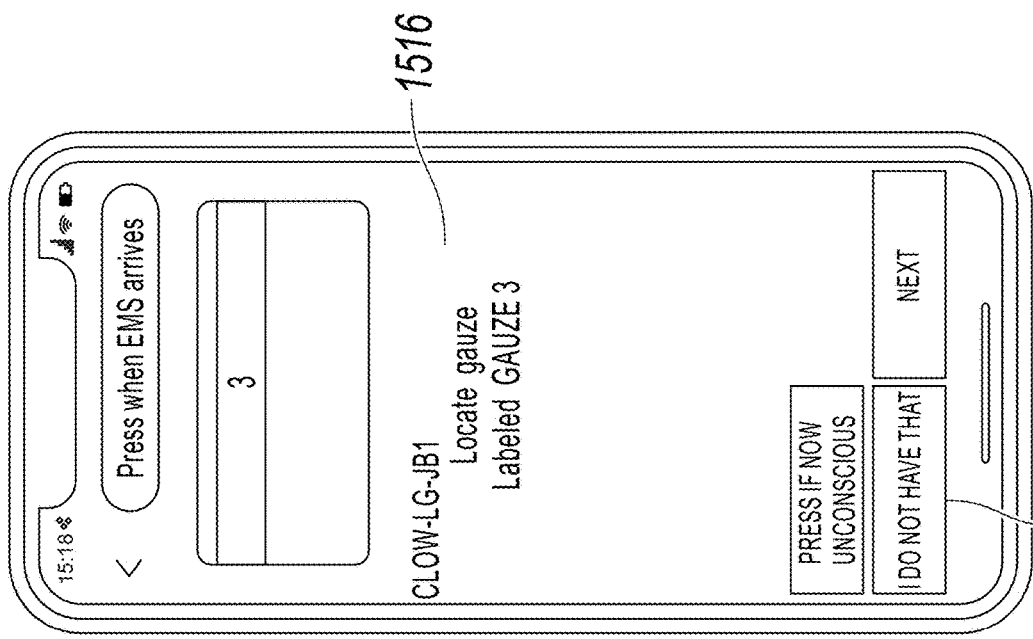
Figure 15H:
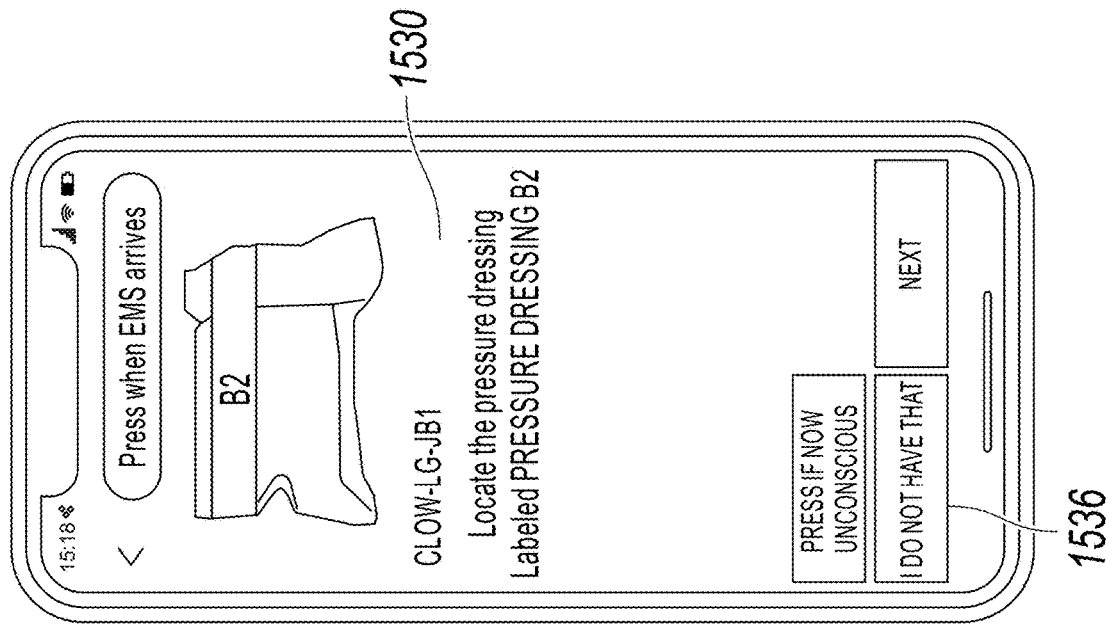
Figure 15G:
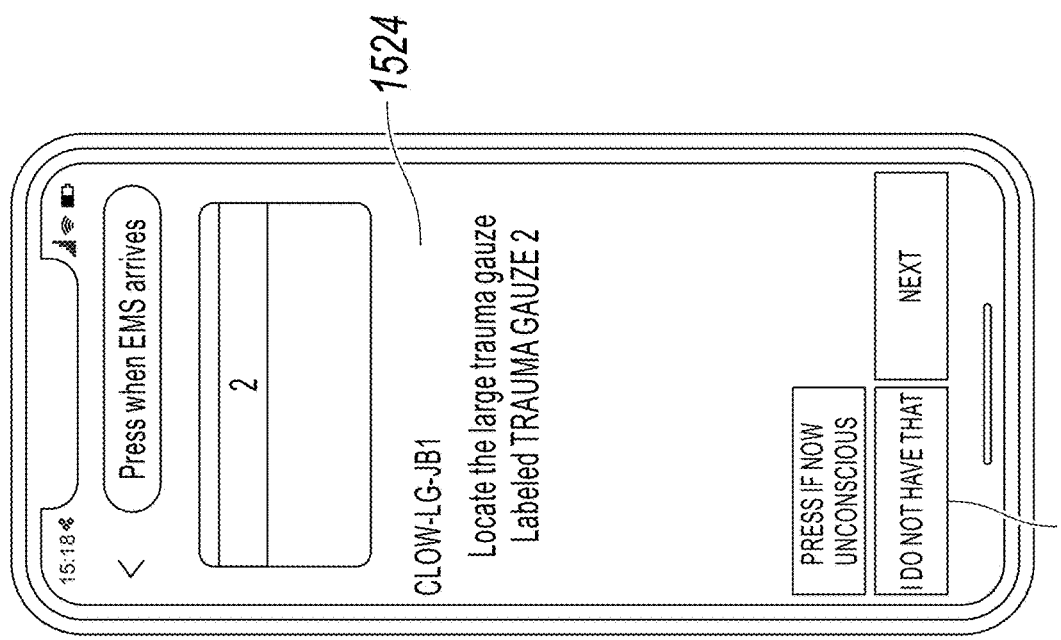
Figure 15J:
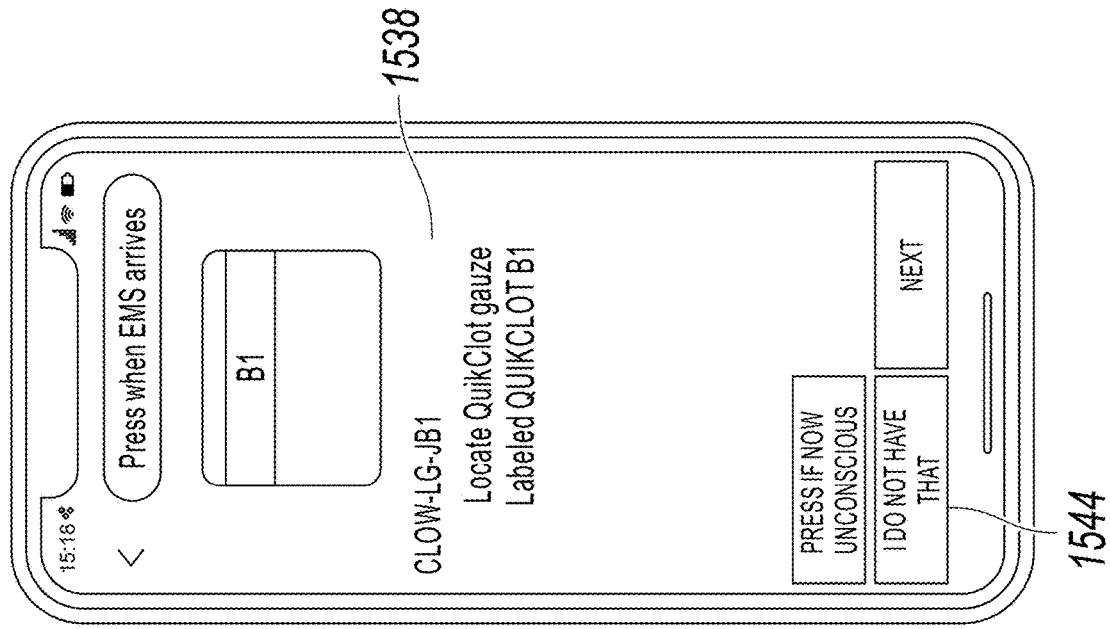
Figure 15I:
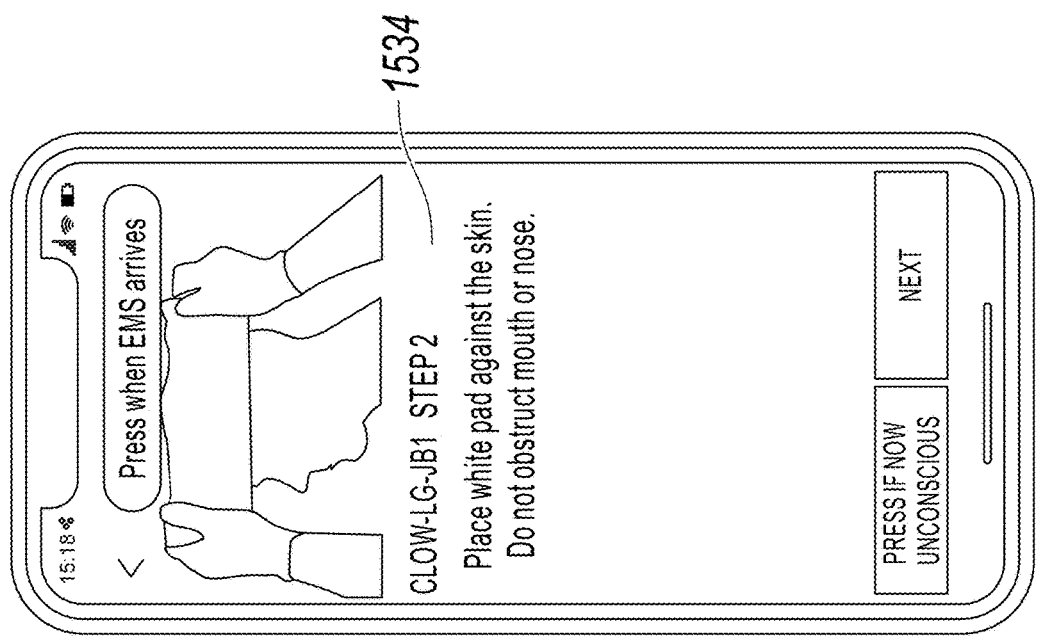
Figure 15L:
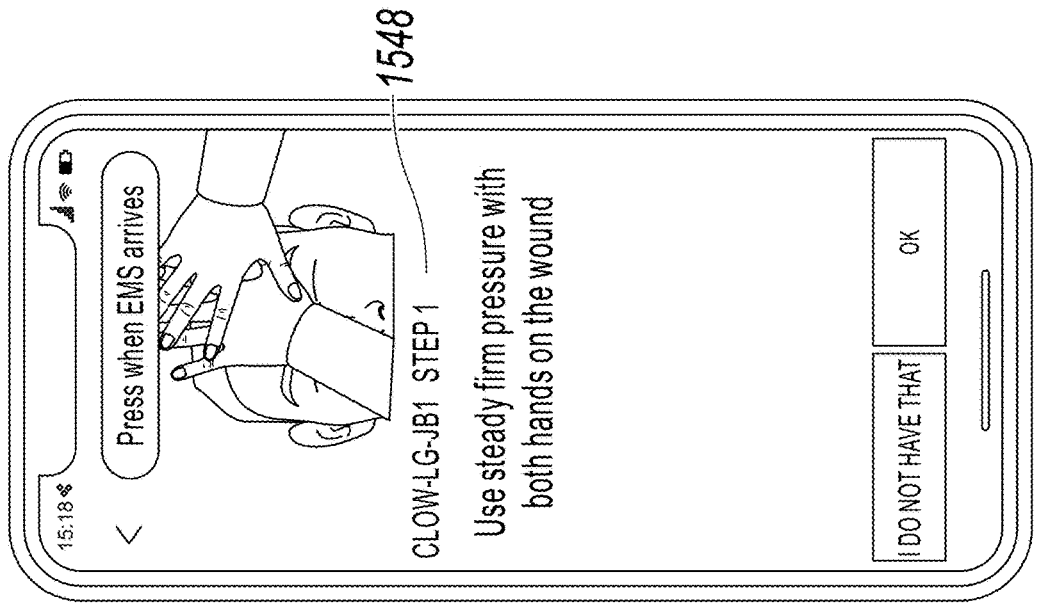
Figure 15K:
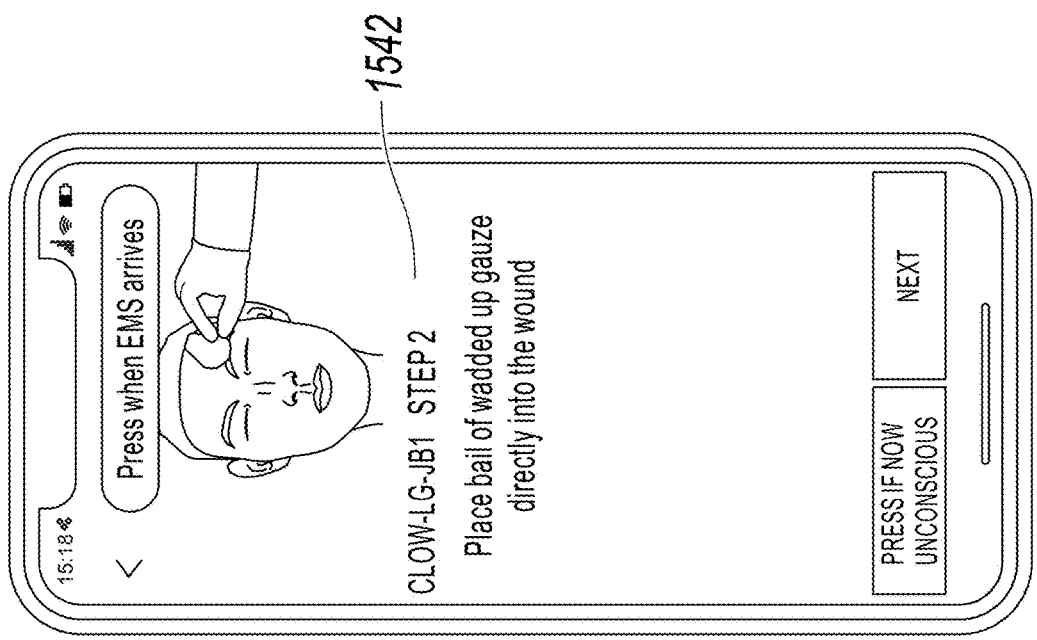
Figure 15M:
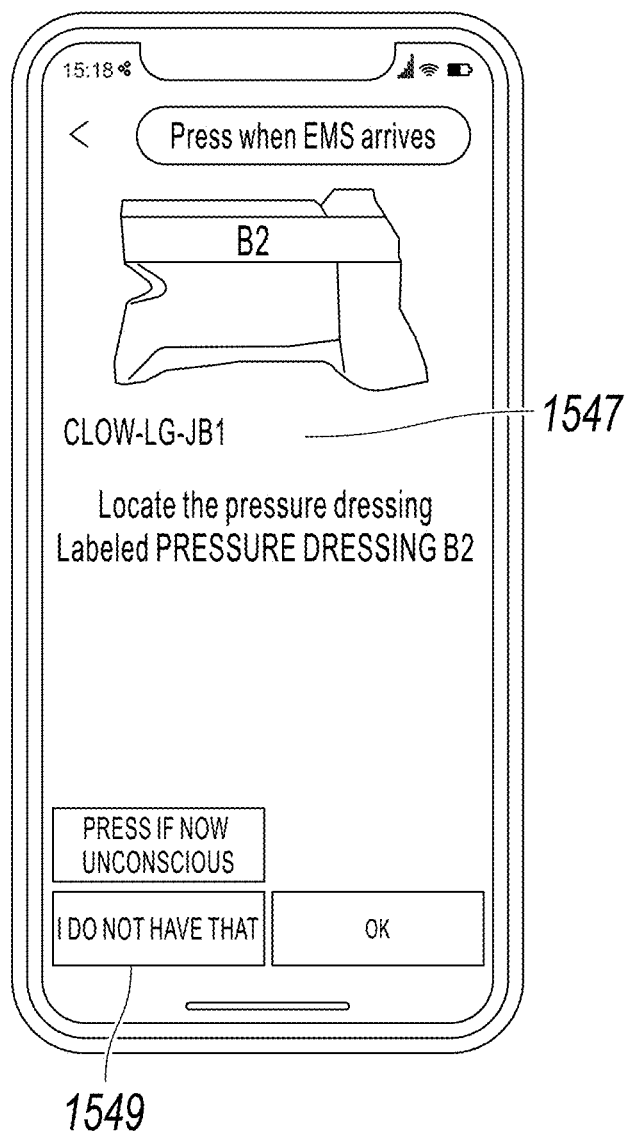
Figure 16:
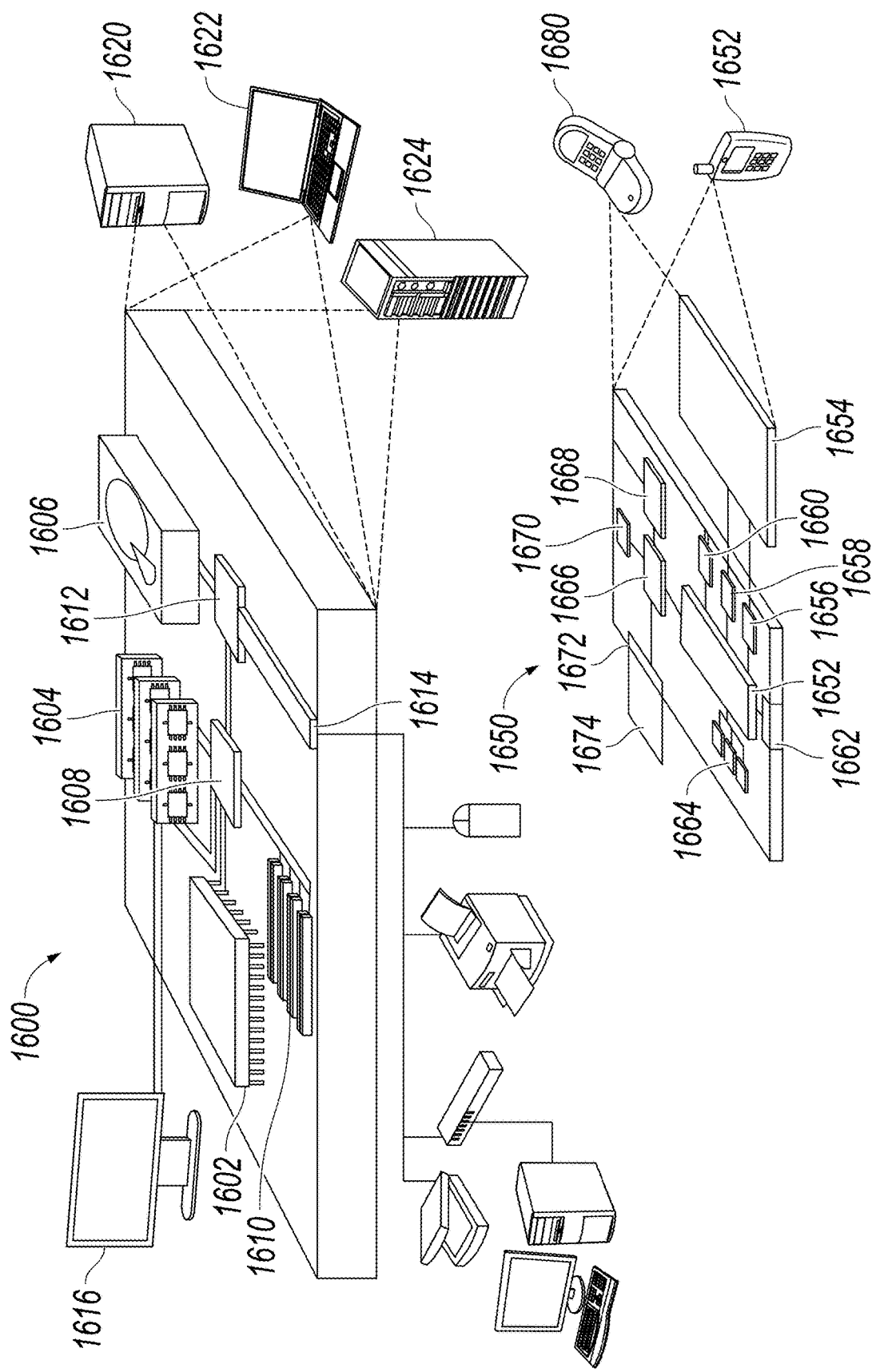

FIGS. 5B, 5C, 5D, 5E, 5F, and 5G illustrate the medical treatment and guidance application presenting medical instructions on a user interface of the electronic device associated with the operations of the process of FIG. 5A;

FIG. 6A shows a process of the operations performed by the medical treatment and guidance system accounting for a patient classification in accordance with some embodiments;

FIGS. 6B, 6C, 6D, and 6E illustrate the medical treatment and guidance application presenting medical instructions on a user interface of the electronic device associated with the operations of the process of FIG. 6A;

FIGS. 7A, 7B, and 7C show a process of the operations performed by the medical treatment and guidance system based on a particular medical treatment and guidance apparatus available to the caregiver in accordance with some embodiments;

FIGS. 7D, 7E, 7F, 7G, 7H, 7I, 7J, 7K, 7L, 7M, and 7N illustrate the medical treatment and guidance application presenting medical instructions on a user interface of the electronic device associated with the operations of the process of FIGS. 7A-7C;

FIGS. 8A, 8B, and 8C show a process of the operations performed by the medical treatment and guidance system presenting warning screens that depend on a patient characteristic (e.g., age) in addition to providing instructions for treating allergic reactions in accordance with some embodiments;

FIGS. 8D, 8E, 8F, 8G, 8H, 8I, and 8J illustrate the medical treatment and guidance application presenting medical instructions on a user interface of the electronic device associated with the operations of the process of FIGS. 8A-8C;

FIGS. 9A, 9B, and 9C illustrate the medical treatment and guidance application presenting medical instructions on the user interface where the medical instructions are based on a memory of previous inquiries in accordance with some embodiments;

FIGS. 10A, 10B, and 10C show a process of the operations performed by the medical treatment and guidance system for presenting instructions to treat a patient experiencing chest palpitations in accordance with some embodiments;

FIGS. 10D, 10E, and 10F illustrate the medical treatment and guidance application presenting medical instructions on a user interface of the electronic device associated with the operations of the process of FIGS. 10A-10C;

FIG. 11A shows a process of the operations performed by the medical treatment and guidance system for presenting medical instructions to assist a patient experiencing a dull/sharp chest pain in accordance with some embodiments;

FIGS. 11B, 11C, and 11D illustrate the medical treatment and guidance application presenting medical instructions on a user interface of the electronic device associated with the operations of the process of FIG. 11A;

FIG. 12A shows a process of the operations performed by the medical treatment and guidance system for presenting medical instructions to assist a patient experiencing a diabetic problem in accordance with some embodiments;

FIGS. 12B, 12C, and 12D illustrate the medical treatment and guidance application presenting medical instructions on a user interface of the electronic device associated with the operations of the process of FIG. 12A;

FIGS. 13A, 13B, and 13C shows a process of the operations performed by the medical treatment and guidance system for presenting medical instructions to assist a patient in identifying and treating an unconscious patient in accordance with some embodiments;

FIGS. 13D, 13E, 13F, 13G, 13H, and 13I illustrate the medical treatment and guidance application presenting medical instructions on a user interface of the electronic device associated with the operations of the process of FIGS. 13A-13C;

FIG. 14A shows a process of the operations performed by the medical treatment and guidance system for presenting medical instructions to assist a patient that has an upper respiratory/droplet communicable disease in accordance with some embodiments;

FIGS. 14B and 14C illustrate the medical treatment and guidance application presenting medical instructions on a user interface of the electronic device associated with the operations of the process of FIG. 14A;

FIGS. 15A and 15B show a process of the operations performed by the medical treatment and guidance system for presenting medical instructions to assist a patient that is experiencing bleeding and the instructions include instructions for using medical supplies that depend on the apparatus type in accordance with some embodiments;

FIGS. 15C, 15D, 15E, 15F, 15G, 15H, 15I, 15J, 15K, 15L, and 15M illustrate the medical treatment and guidance application presenting medical instructions on a user interface of the electronic device associated with the operations of the process of FIGS. 15A and 15B; and FIG. 16 is a block diagram of computer systems forming part of a medical treatment and guidance system in according to some embodiments.

DETAILED DESCRIPTION

A medical treatment and guidance system is used for determining and providing instructions to a caregiver (e.g., a lay rescuer with little to no medical experience) for administering medical treatment to a patient experiencing a medical emergency. The instructions are provided on an electronic device (e.g., a mobile phone, mobile tablet, tablet built into a medical treatment and guidance apparatus, a medical treatment and guidance apparatus itself, smart watch, etc.) with a user interface (e.g., a touch-screen user interface) and are interactively controllable by the caregiver by responding to inquiries on the user interface. The medical treatment and guidance system provides medical instructions whose informational content can be found in complex emergency medicine protocols (e.g., Tactical Combat Casualty Care [TCCC], Trauma Emergency Causality Care [TECC] protocols, etc.), but where the features and functions of the medical treatment and guidance system enable caregivers with little to no medical experience to implement complex protocols involving life-threatening medical conditions with little to no training while at the same time delivering the life-saving treatments accurately and rapidly, thus saving lives and limbs.

Emergency medicine is a reactive practice where it is generally difficult to predict an occurrence of a medical event before it happens. For example, in a pre-hospital setting (e.g., schools, offices, airports, among others), it cannot be assumed that a medical doctor (or other medically trained responder) is immediately available to provide medical attention, and it cannot be assumed that caregivers in the vicinity of the patient will know how to treat any medical emergency that occurs, let alone which medical supplies are required and/or how to actually perform the treatment. In this setting, the focus is on helping the caregivers determine in a timely manner which medical supplies are needed for a particular medical emergency and guiding the caregivers on how to properly use the medical supplies to treat the medical emergency. Thus, it is preferable to maintain a fully-stocked portable medical treatment and guidance apparatus in various locations in these pre-hospital settings (e.g., classrooms of schools, hallways of offices, etc.) so that medical supplies are available to treat medical emergencies if they occur. For example, a caregiver can use the emergency medical treatment and guidance system for guidance on how to treat medical emergencies that occur. For example, the caregiver can use a mobile device such as a smartphone, tablet, or smart watch, for guidance on how to treat the medical emergency using the medical supplies of portable medical treatment and guidance apparatuses regardless of level of training of the caregiver.

By providing the guidance on a mobile device that the caregiver is comfortable with, e.g., their smart phone, the caregivers are more likely to have the guidance with them and the caregivers are more likely to use the guidance. The increased comfort helps avoid scenarios where bystanders standby without doing anything to help the patient because they are afraid of doing the wrong thing and harming the patient, and being exposed to liabilities for their mistakes. An important concept of the interactive inquiries described herein is that the interactive inquiries may assist caregivers in treating medical emergencies in the same way that a trained emergency responder would. For example, in certain instances, response times for emergency responders average about 9 minutes in urban areas, and these response times can increase to about 13 or 14 minutes in a rural area. These response times may be too long for life-threatening medical emergencies which often require treatment within 3 minutes and breathing related medical emergencies which often require treatment within 5 to 6 minutes. It is important for the caregiver to attend to at least these medical emergencies before emergency responders arrive.

In some embodiments, the emergency medical treatment and guidance system may incorporate diagnostic, therapeutic and other clinical protocol information in accordance with TCCC and TECC protocols sequenced and presented for people who have little to no experience to be able to provide timely and appropriate treatment for those suffering from a medical emergency. For example, in various embodiments of the present disclosure, the military concept of treating battle injuries of military patients according to TCCC is expanded to include medical instructions for civilian patients in non-combat zones. In this way, the emergency medical treatment and guidance system can be used in both civilian and military environments (e.g., for civilian medicine and military medicine). In some examples, expanding the protocols involves expanding the TCCC flows to include instructions for infants (e.g., pediatrics), the elderly (e.g., geriatrics), and providing the most relevant medical instructions as soon as possible (e.g., as soon as possible to minute zero when the medical emergency occurs). For example, initial responders in military combat zones have some formal training on how to identify certain medical emergencies but there is little training on how to assess the type of medical emergency and provide treatment for the medical emergencies in a timely fashion. In these scenarios, a military initial responder can use the emergency medical treatment and guidance system for guidance on how to treat these medical emergencies in the same way as a civilian caregiver.

In some embodiments, the medical treatment and guidance system is pre-configured to provide medical instructions to address medical emergencies in order of medical priority (e.g., how likely are they to cause non-recoverable harm to the patient). In some embodiments, the medical emergencies are ranked by immediate life-threatening medical emergencies that require treatment within 3 minutes first, followed by breathing-related medical emergencies that require treatment within 5 to 6 minutes, followed by other medical emergencies that require treatment by 5 to 6 minutes followed by minor non-life-threatening medical emergencies. This medical priority ranking allows the caregiver to focus on the medical emergencies that require medical attention first before attending to medical emergencies that can wait at least a few more minutes, so as to address issues that more immediately threaten the patient's life.

In some embodiments, the medical treatment and guidance system also accounts for characteristics of the patient (e.g., age, injury, gender, etc.) when determining the medical instructions. For example, a patient characteristic can include one of more of a patient age classification (e.g., whether the patient is an adult, a child, or an infant), a patient gender (e.g., whether the patient is a biological male or female), and a patient injury and/or injury type (e.g., what type of acute injury may have occurred, whether the patient has a medical history such as previous broken bones or a history of seizures). In some examples, the age classification of the patient strongly affects the medical instructions (e.g., CPR or other medical procedures administered to an infant is different than CPR or other medical procedures administered to an adult, appropriate drug dosages will differ between infants, children, adults, etc.). In another example, the medical treatment and guidance system will avoid presenting certain inquires based on patient age classification. For instance, the medical treatment and guidance system may avoid presenting inquiries about how the infant is feeling, etc., since an infant cannot communicate how they are feeling to a caregiver. In another example, the medical treatment and guidance system will avoid providing instruction to administer aspirin to children since, e.g., aspirin use in children has been linked to a rare but potentially fatal illness known as Reye's syndrome. As a result, determining the medical instructions based on age improves the medical instructions and avoids unnecessary inquires which saves time. Further details regarding patient characteristics are described with reference to FIGS. 6A-6E below.

In some embodiments, the medical treatment and guidance system also determines medical instructions that involve using medical supplies of an emergency medical treatment and guidance apparatus. Examples of such emergency medical treatment and guidance apparatuses are the ZOLL Mobilize Public Access Utility Kit and the ZOLL Mobilize Compact Rescue System, e.g., as described in Intl. Patent Application No. PCT/US2021/062591, entitled "Inventory Management Of Portable Medical Treatment And Guidance Apparatuses," filed Dec. 9, 2021, which claims priority to U.S. Application No. 63/123,997, filed Dec. 10, 2020, the disclosures of which are hereby incorporated by reference in their entireties. Each portable medical treatment and guidance apparatus includes medical supplies for administering medical treatment for treating the medical emergency of the patient. Another benefit of providing instructions that specifically relate to the medical supplies of the medical treatment and guidance apparatus is that the likelihood that the caregiver will use knockoff replacement medical supplies is reduced. Further details regarding medical treatment and guidance apparatuses are described with reference to FIGS. 3A-3F below.

In some embodiments, the medical treatment and guidance system provides instructions that assist the caregiver in using medical supplies of the medical treatment and guidance apparatuses based on the apparatus type of the medical treatment and guidance apparatus available to the caregiver. In some examples, the apparatus type includes a comprehensive medical treatment and guidance apparatus with a built-in user interface (e.g., as described with reference to FIGS. 3A and 3B), a comprehensive medical treatment and guidance apparatus with a removable user interface (e.g., as described with reference to FIGS. 3C and 3D), and/or a compact medical treatment and guidance apparatus (e.g., as described with reference to FIGS. 3E and 3F). Determining the instructions based on the apparatus type helps avoid scenarios where the caregiver is instructed to use a medical supply that is not available which results in the caregiver becoming confused and/or wasting time looking for the medical supply elsewhere. Further details regarding apparatus types are described with reference to FIGS. 7A-7N below.

In some embodiments, the medical treatment and guidance system maintains a predetermined list of substitute medical supplies that can be used to treat the medical emergency if a particular medical supply is unavailable to a caregiver (e.g., if the medical supply is missing from the portable medical treatment and guidance apparatus or is otherwise unavailable). For example, if the medical emergency is a major bleeding event, the medical instructions may include instructions to use a tourniquet. If the caregiver responds to an inquiry indicating that the tourniquet is not available, the system will update the medical instructions to use the next best medical supply (e.g., a QuikClot® gauze). This process repeats (e.g., by further changing the instructions to include instructions for a pressure dressing) until a medical supply is available or no medical supply is needed (e.g., the caregiver is instructed to use their hands to control the bleeding by applying pressure to the wound). Determining the instructions based on substitute medical supplies also helps avoid scenarios where the caregiver is instructed to use a medical supply that is not available which results in the caregiver becoming confused and/or wasting time looking for the medical supply elsewhere. Further details regarding apparatus types are described with reference to FIGS. 5A-5G below.

In some embodiments, the medical treatment and guidance system maintains information about state when making subsequent inquiries so that the subsequent instructions and inquiries depend from the previous input from the caregiver. State information is information determined about one or more current (e.g., contemporaneous) characteristics of the patient, the apparatus, or anything else that is the subject of an inquiry by the medical treatment and guidance system. In some examples, a current condition of a patient is an example of patient state information. For example, if the caregiver indicates that the patient may be experiencing a neck injury, subsequent medical instructions of the medical treatment and guidance system will not include instructions to lay the patient on their side in a rescue position because such action is contraindicated by the patient state. In this scenario, there is a potential for a cervical neck injury of the patient, and the medical treatment and guidance system will instead provide instructions that reduce the risk of further injury. In general, the instructions aim to minimize movement of the patient, as cervical motion restriction reduces risk of further injury. The caregiver may thus be reassured by the medical treatment and guidance system that the caregiver is providing effective assistance to the patient by keeping the patient as still, safe, and comfortable as possible while awaiting for medical assistance to arrive. For example, instead of instructing the patient to lay on their side, the medical instructions will instead instruct the patient to lay flat on their back instead. Further details regarding maintaining state information are described with reference to FIGS. 9A-9C below.

In addition to reducing the risk of further injury, retention of state information (such as patient state information) enables the medical treatment and guidance system to avoid asking duplicate questions for the same patient (e.g., questions that are redundant because they have already been answered by the caregiver). In this way, the medical treatment and guidance system recalls information about a previous input and uses that previous information to skip one or more inquiries. Skipping questions (e.g., questions made unnecessary according to the state information) avoids unnecessary delays and enables the medical treatment and guidance system to provide medical instructions to the caregiver faster than an interactive flow that involves one or more inquiries that would otherwise be unnecessary (e.g., inquiries that are duplicative of earlier inquiries, inquiries that are irrelevant due to the patient state, etc.).

In some embodiments, the medical treatment and guidance system provides warning screens to warn the caregiver before administering prescription medication and controlled substances. For example, the warning screens can include warnings that the patient is requesting the caregiver to administer the prescription medication. Such warning screens may depend on the inputs provided in response to previous inquiries. For example, the warning screen may indicate to a caregiver that the caregiver is about to administer prescription medication to a child based on a patient age classification and that a legal guardian of the child is requesting the caregiver to administer the prescription medication (e.g., as opposed to the medical instructions prescribing the medication). In other examples, the warning screen may indicate to a caregiver that the caregiver is about to administer prescription medication to an adult based on a patient age classification and that the patient must consent to the use of the prescription medication. Further details regarding warning screens are described with reference to FIGS. 8A-8J below.

In some embodiments, the medical treatment and guidance system accounts for upper respiratory/droplet communicable diseases (e.g., COVID-19, influenza, etc.). In some examples, the medical treatment and guidance system recognizes upper respiratory/droplet communicable diseases based on responses to inquiries. For example, the medical treatment and guidance system can determine shortness of breath as a symptom for a communicable disease and provides instructions to the caregiver to apply facial covering to the patient. This can be advantageous because the medical treatment and guidance system can alert the caregiver to potential risks and instruct the caregiver to step back, cover their face, and offer the patient a facial covering before continuing to provide medical assistance to the patient. Further details regarding respiratory/droplet communicable diseases are described with reference to FIGS. 15A-15M below.

As noted above, prioritization of medical emergencies is an important concept. Immediate life-threatening medical emergencies require medical attention as fast as possible, preferably within 3 minutes from when the emergency occurred to reduce the risk of loss of life (e.g., bleed to death from a large vessel injury). Examples of immediate life-threatening emergencies include a major bleeding event (e.g., within any of the extremities, chest, back, abdomen, head, face, etc.), a penetrating chest wound (e.g., a lung injury that could progress from a pneumothorax to a tension pneumothorax causing the patient's heart to stop), and unconscious identification. Unconscious identification is included in this list, at least in part, because it is important to at least identify whether the patient is unconscious quickly because subsequent steps depend on the consciousness of the patient. In some examples, inquires related to an unconscious identification are performed immediately after inquiries related to a major bleeding event. Further, a victim of cardiac arrest, which is another life-threatening medical emergency, may be unconscious. For example, medical instructions to use to tourniquet to stop bad bleeding of an extremity is within the scope of immediate life-threatening emergencies medical emergencies. In general, "bad" bleeding means there is blood uncontrollably coming out of the wound of the patient.

Breathing-related medical emergencies require medical attention within 5 to 6 minutes from when the emergency occurred to reduce the risk of brain injury (e.g., anoxic brain injury) leading to permanent brain damage. Examples of breathing-related medical emergencies include repository issues and choking. For example, medical instructions to administer a Heimlich maneuver is within the scope of breathing-related medical emergencies.

Other medical emergencies that require medical attention within 5 to 6 minutes when the emergency occurred include an allergic reaction, chest pain, chest trauma, seizures, overdose, diabetic ketoacidosis, and altered mental status. These are typically addressed after the breathing-related medical emergencies because those are more urgent. For example, instructions to administer CPR and defibrillation (e.g., via an automated external defibrillator (AED)) are within the scope of these other medical emergencies that require medical attention within 5 to 6 minutes.

Minor non-life-threatening medical emergencies are generally treatable after 6 minutes has passed from when the emergency occurred (e.g., even after 10 minutes is acceptable). Examples of minor non-life-threatening medical emergencies include minor chest pain, minor bleeding, fractures, burns, hypothermia, and general pain (e.g., headaches, aches, soreness, etc.).

Figure 1:
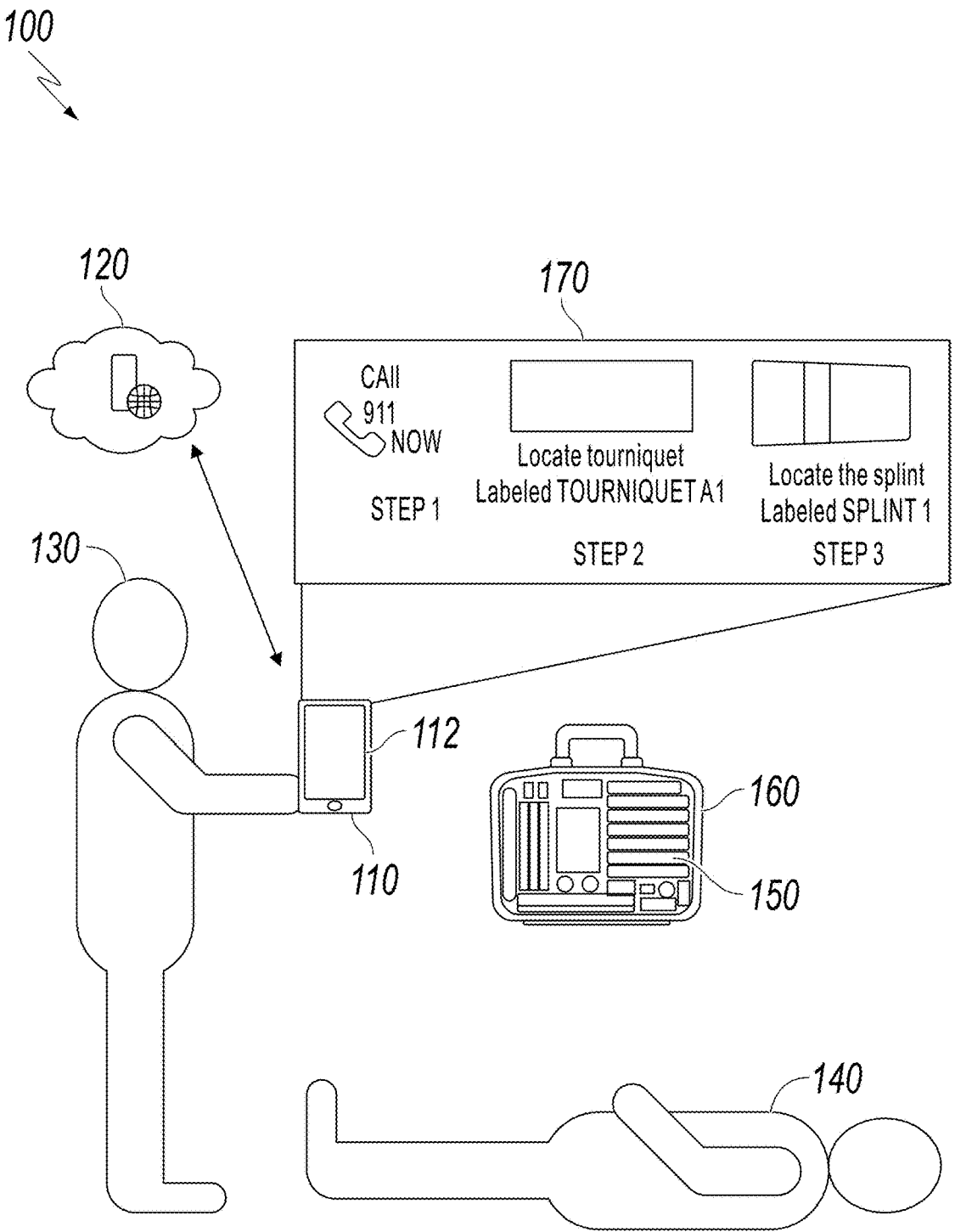
FIG. 1 shows a scenario where a caregiver is providing medical treatment to a patient according to instructions provided by an emergency medical treatment and guidance application running on a user interface of a mobile device in accordance with some embodiments.

FIG. 1 shows a medical treatment and guidance system 100 that includes an electronic device 110 in network communication (e.g., cellular, Wi-Fi, etc.) with a remote server 120 via the Internet. The electronic device 110 has processor(s) and memory to execute a software application (e.g., a medical treatment and guidance application such as the ZOLL Mobilize Rescue App) downloaded via the Internet. The electronic device 110 also includes a user interface 112 for presenting interactive inquiries, presenting instructions, and receiving input from a caregiver 130. The medical treatment and guidance system 100, via the medical treatment and guidance application, provides real-time instructions (e.g., during the medical treatment) to help caregivers assess, manage, and treat patients experiencing medical emergencies. Such an application is compatible with any of the emergency medical treatment and guidance apparatus described herein. Additional examples of interactive queries are described in Intl. Patent Publication No. WO 2021/202292, entitled "Portable Medical Treatment Apparatus With Interactive Guidance And Cardiopulmonary Resuscitative Functionality", published Oct. 7, 2021, which claims priority to U.S. Application No. 63/002,962, filed Mar. 31, 2020, the disclosures of which are hereby incorporated by reference in their entireties.

In this example, the software application provides medical instructions 170 to assist the caregiver 130 (who is generally a lay person without formal medical training) in treating one or more medical emergencies of a patient 140. In particular, the medical treatment and guidance application provides medical instructions to use one or more medical supplies 150 of a portable medical treatment and guidance apparatus 160 to treat the medical emergency of the patient 140. For example, as shown in FIG. 1, the medical instructions 170 can include one or more steps such as calling emergency medical services (EMS) (e.g., "911"), locating and using a tourniquet, and locating and using a splint. The medical treatment and guidance system 100 also includes the one or more portable medical treatment and guidance apparatuses 160.

In this example, the medical treatment and guidance system 100 will prioritize medical treatment for a patient 140 with an immediate life-threatening medical emergency such as bad bleeding such as hemorrhage over medical treatment for another patient with a minor non-life-threatening medical emergency such as fracture. In this way, the medical treatment and guidance system 100 prioritizes first priority medical emergencies over second priority medical emergencies and so on.

Figure 2A:
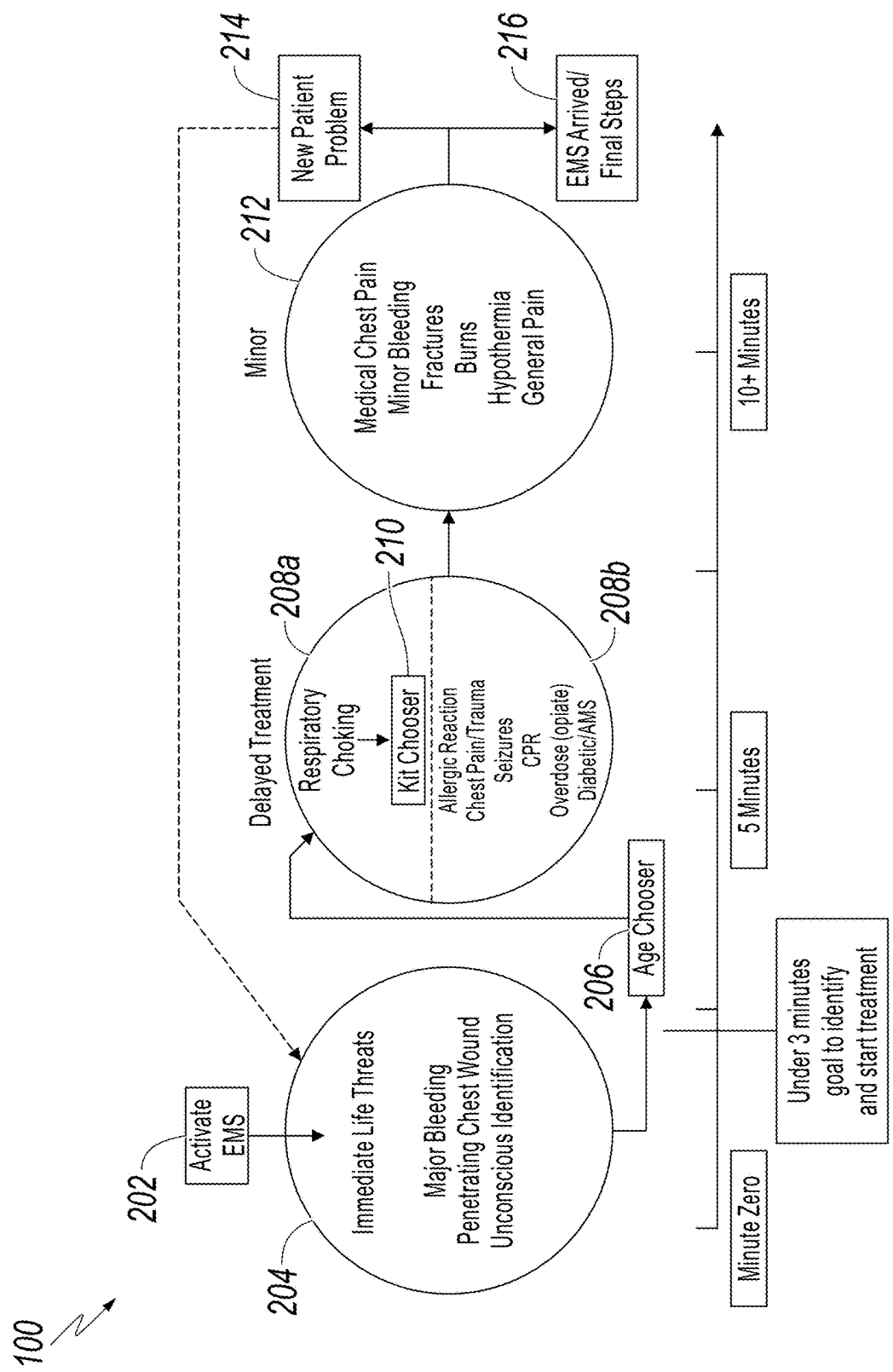
FIG. 2A shows a flowchart of medical emergencies addressable with a medical treatment and guidance application reflecting a prioritization of medical treatment guidance in accordance with some embodiments.
Figure 2B:
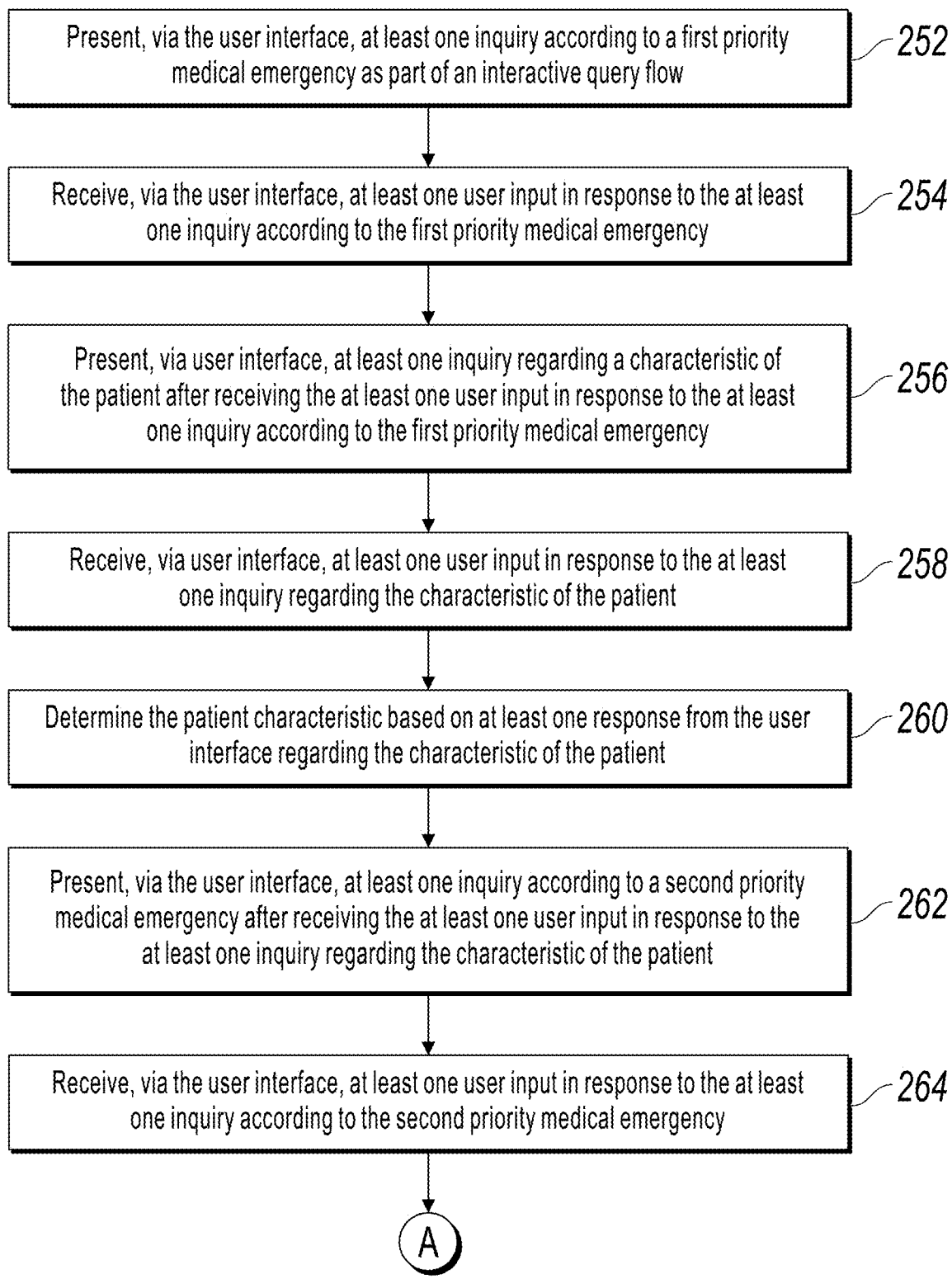
FIGS. 2B and 2C show a flowchart of the operations performed by the emergency medical treatment and guidance system accounting for medical emergency priority in accordance with some embodiments.
Figure 2C:
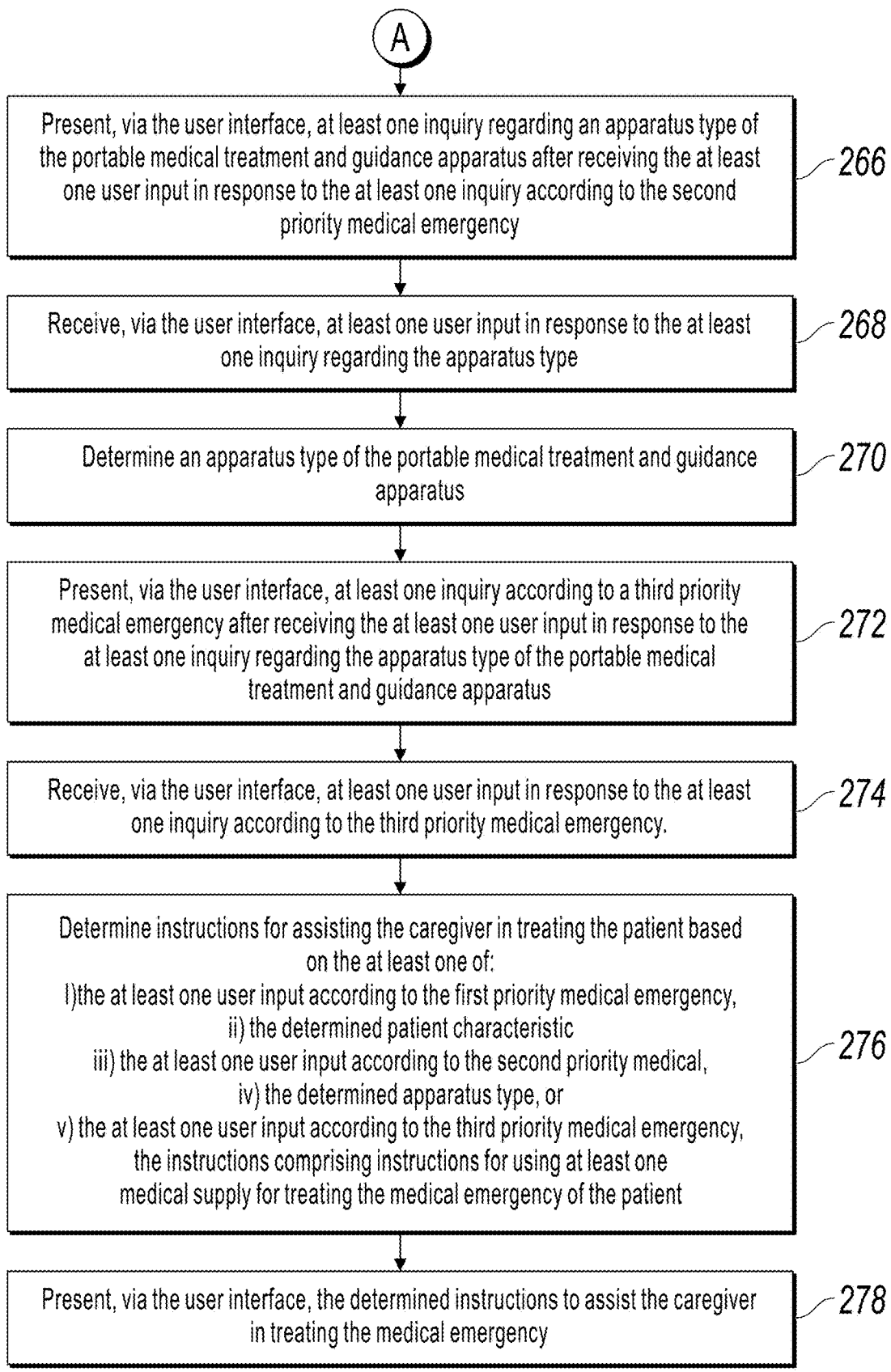

FIG. 2A shows a flowchart of the prioritization of the medical emergencies of the medical treatment and guidance system 100. FIGS. 2B and 2C show a flowchart of the operations performed by the emergency medical treatment and guidance system 100 accounting for medical emergency priority. Referring to FIG. 2A, once EMS is activated (step 202), first priority (e.g., immediate life-threatening medical emergencies) are addressed (step 204). The first priority medical emergencies require treatment within a time limit (e.g., within 1 minute, within 2 minutes, within 3 minutes, within 5 minutes, etc.). In other words, the first priority medical emergency can be an immediate life threat emergency that requires treatment without delay, such as within a time limit of 2 minutes. In order to address these types of urgent medical emergencies, the medical treatment and guidance system 100 performs step 252 of FIG. 2B to present, via the user interface (e.g., user interface 112 of the electronic device 110), at least one inquiry according to a first priority medical emergency as part of an interactive query flow. For example, the medical treatment and guidance system 100 can present an inquiry asking the caregiver 130 "Is the patient badly bleeding?"

In response, the caregiver 130 provides input and the medical treatment and guidance system 100 performs step 254 of FIG. 2B to receive, via the user interface, at least one user input in response to the at least one inquiry according to the first priority medical emergency. This process (e.g., presenting inquiries and receiving input) is part of a "flow" that repeats as necessary until the medical treatment and guidance system 100 determines which medical instructions to present to the caregiver 130 to assist the caregiver 130 in treating the medical emergency of the patient 140. Examples of particular flows are described in further details with references to FIGS. 5A-5G, FIGS. 6A-6E, FIGS. 7A-7N, FIGS. 8A-8J, FIGS. 9A-9C, FIGS. 10A-10F, FIGS. 11A-11D, FIGS. 13A-13I, FIGS. 14A-14C, and FIGS. 15A-15M below.

Once the medical treatment and guidance system 100 determines, based on the received input, that the patient 140 is not experiencing a first priority medical emergency, the medical treatment and guidance system 100 may present one or more inquires about other patients. In this way, the medical treatment and guidance system 100 determines the instructions for assisting the caregiver in treating the patient experiencing the medical emergency by prioritizing a treatment of a first priority medical emergency of a second patient over a treatment of a second priority medical emergency of the first patient.

Once the medical treatment and guidance system 100 determines that the patient 140 and other patients are not experiencing a first priority medical emergency, the medical treatment and guidance system 100 proceeds to step 256 of FIG. 2B to present, via the user interface, at least one inquiry regarding a characteristic of the patient after receiving the at least one user input in response to the at least one inquiry according to the first priority medical emergency. In response, the caregiver 130 provides input and the medical treatment and guidance system 100 performs step 258 to receive, via the user interface, at least one user input in response to the at least one inquiry regarding the characteristic of the patient. The medical treatment and guidance system 100 performs step 260 to determine the patient characteristic based on at least one response from the user interface regarding the characteristic of the patient. Steps 256, 258, and 260 are examples of step 206 of FIG. 2A (e.g., an "age chooser" step). Detailed examples of inquiries regarding patient characteristics are described in detail with reference to FIGS. 6A-6E below.

The temporal location of the inquiry about the patient characteristic in the flow is after the first priority medical emergencies so that the medical treatment and guidance system 100 provides medical instructions to first priority medical emergencies as fast as possible. Asking the caregiver 130 the age of the patient 140 before providing medical instructions to first priority medical emergencies would unnecessarily slow down the process of providing medical instructions to these medical emergencies. At the same time, it is important to ask the caregiver 130 the age of the patient 140 as early as possible in the interactive flow so that the medical treatment and guidance system 100 can determine the most appropriate medical instructions for the situation based on the age of the patient. Information such as the patient age is stored as state information of the patient, e.g., as described below with respect to FIGS. 9A-9C.

Once the medical treatment and guidance system 100 determines a patient characteristic based on the received input, the medical treatment and guidance system 100 proceeds to inquire about second priority medical emergencies (e.g., breathing-related medical emergencies) that require medical attention within a time limit (e.g., within 5 minutes, within 6 minutes, etc.) (step 208a). Put another way, the second priority medical emergency can be a breathing-related medical emergency that requires treatment within a time limit of 6 minutes. In some examples, the breathing related medical emergency is a cardiac arrest with breathing emergency or cardiopulmonary-related medical emergencies. In some examples, the time limit for addressing second priority medical emergencies is greater than the time limit for addressing first priority medical emergencies. In some examples, the time limit for addressing first priority medical emergencies is 5 minutes or less, and the time limit for addressing second priority medical emergencies is larger than the time limit for addressing first priority medical emergencies.

The medical treatment and guidance system 100 performs step 262 to present, via the user interface, at least one inquiry according to a second priority medical emergency after receiving the at least one user input in response to the at least one inquiry regarding the characteristic of the patient. In response, the caregiver provides input and the medical treatment and guidance system 100 performs step 264 to receive, via the user interface, at least one user input in response to the at least one inquiry according to the second priority medical emergency.

Once the medical treatment and guidance system 100 determines, based on the received input, that the patient (as well as other patients) are not experiencing second priority breathing-related medical emergencies, the medical treatment and guidance system 100 proceeds to present an inquiry about which apparatus type is available to the caregiver (step 210) (e.g., a "kit chooser" step).

For example, the medical treatment and guidance system 100 performs step 266, as shown in FIG. 2C, to present, via the user interface, at least one inquiry regarding an apparatus type of the portable medical treatment and guidance apparatus after receiving the at least one user input in response to the at least one inquiry according to the second priority medical emergency. In turn, the medical treatment and guidance system 100 performs step 268 to receive, via the user interface, at least one user input in response to the at least one inquiry regarding the apparatus type. Then the medical treatment and guidance system 100 performs step 270 to determine an apparatus type of the portable medical treatment and guidance apparatus. For example, the medical treatment and guidance system 100 determines the apparatus type to be one of at least two apparatus types (e.g., a compact medical treatment and guidance apparatus and a comprehensive medical treatment and guidance apparatus—both described with reference to FIGS. 3A-3F below).

The medical treatment and guidance system 100 performs step 272 to present, via the user interface, at least one inquiry according to a third priority medical emergency after receiving the at least one user input in response to the at least one inquiry regarding the apparatus type of the portable medical treatment and guidance apparatus. In response, the caregiver provides input and the medical treatment and guidance system 100 performs step 274 to receive, via the user interface, at least one user input in response to the at least one inquiry according to the third priority medical emergency.

The medical treatment and guidance system 100 performs step 276 to determine instructions for assisting the caregiver in treating the patient based on at least one of: i) the at least one user input according to the first priority medical emergency, ii) the determined patient characteristic, iii) the at least one user input according to the second priority medical emergency, iv) the determined apparatus type, or v) the at least one user input according to the third priority medical emergency.

The instructions include instructions for using at least one medical supply for treating the medical emergency of the patient. For example, determining the instructions can be performed within the application by querying the predetermined spreadsheet of instructions based on the at least one user input according to the first priority medical emergency, the determined patient characteristic, and/or the at least one user input according to the second priority medical emergency. Once the medical instructions are determined, the medical treatment and guidance system 100 performs step 278 to, present, via the user interface, the determined instructions to assist the caregiver in treating the medical emergency.

Detailed examples of inquiries regarding apparatus type are described in detail with reference to FIGS. 7A-7N below. The temporal location of the inquiry about apparatus type in the interactive flow is after the first priority medical emergencies and after the second priority breathing-related medical emergencies so that the system provides medical instructions to these medical emergencies as fast as possible. Asking the caregiver 130 which portable emergency treatment and guidance apparatus they have before providing medical instructions to life-threatening medical emergencies and/or breathing-related medical emergencies would unnecessarily slow down the process of providing medical instructions to these medical emergencies. At the same time, it is important for the system to receive information about which portable emergency treatment and guidance apparatus the caregiver 130 has access to as early as possible in the interactive flow so that the medical treatment and guidance system 100 can determine the medical instructions based on which medical supplies are available to the caregiver 130.

Once the medical treatment and guidance system 100 receives an input about an apparatus type, the medical treatment and guidance system 100 proceeds to inquire about other second priority medical emergencies that require attention within 5 to 6 minutes (step 208b). Once the medical treatment and guidance system 100, based on received input, determines that the patient (as well as other patients) are not experiencing medical emergencies that require attention within 5 to 6 minutes, the medical treatment and guidance system 100 proceeds to inquire about third priority medical emergencies (e.g., minor non-life-threatening medical emergencies) (step 212). In this way, the medical treatment and guidance system 100 prioritizes breathing related emergencies corresponding over a minor emergency that corresponds to a condition that is treatable beyond the time limit for treating the breathing related emergencies.

In some examples, the medical treatment and guidance system 100 performs a step to present, via the user interface, at least one inquiry according to a third priority medical emergency after receiving the at least one user input in response to the at least one inquiry regarding the apparatus type of the portable medical treatment and guidance apparatus. In turn, the medical treatment and guidance system 100 performs a step to receive, via the user interface, at least one user input in response to the at least one inquiry according to the third priority medical emergency. Then the medical treatment and guidance system 100 performs a step to determine the instructions for assisting the caregiver in treating the patient are based on the at least one user input according to the third priority medical emergency.

Once the medical treatment and guidance system 100 determines that the patient (as well as other patients) are not experiencing any minor medical emergencies, the medical treatment and guidance system 100 proceeds to inquire about other patients and/or medical problems (step 214). If other patients and/or problems are identified, the flow restarts and proceeds back to step 204. During any part of the flow, the caregiver can invoke an escape button on the user interface to cause the medical treatment and guidance system 100 to proceed to step 216. Invoking this escape button indicates to the medical treatment and guidance system 100 that EMS has arrived and, in turn, the medical treatment and guidance system 100 compiles and provides a treatment summary to the caregiver to conclude the medical treatment administered by the caregiver for this patient.

Figure 3A:
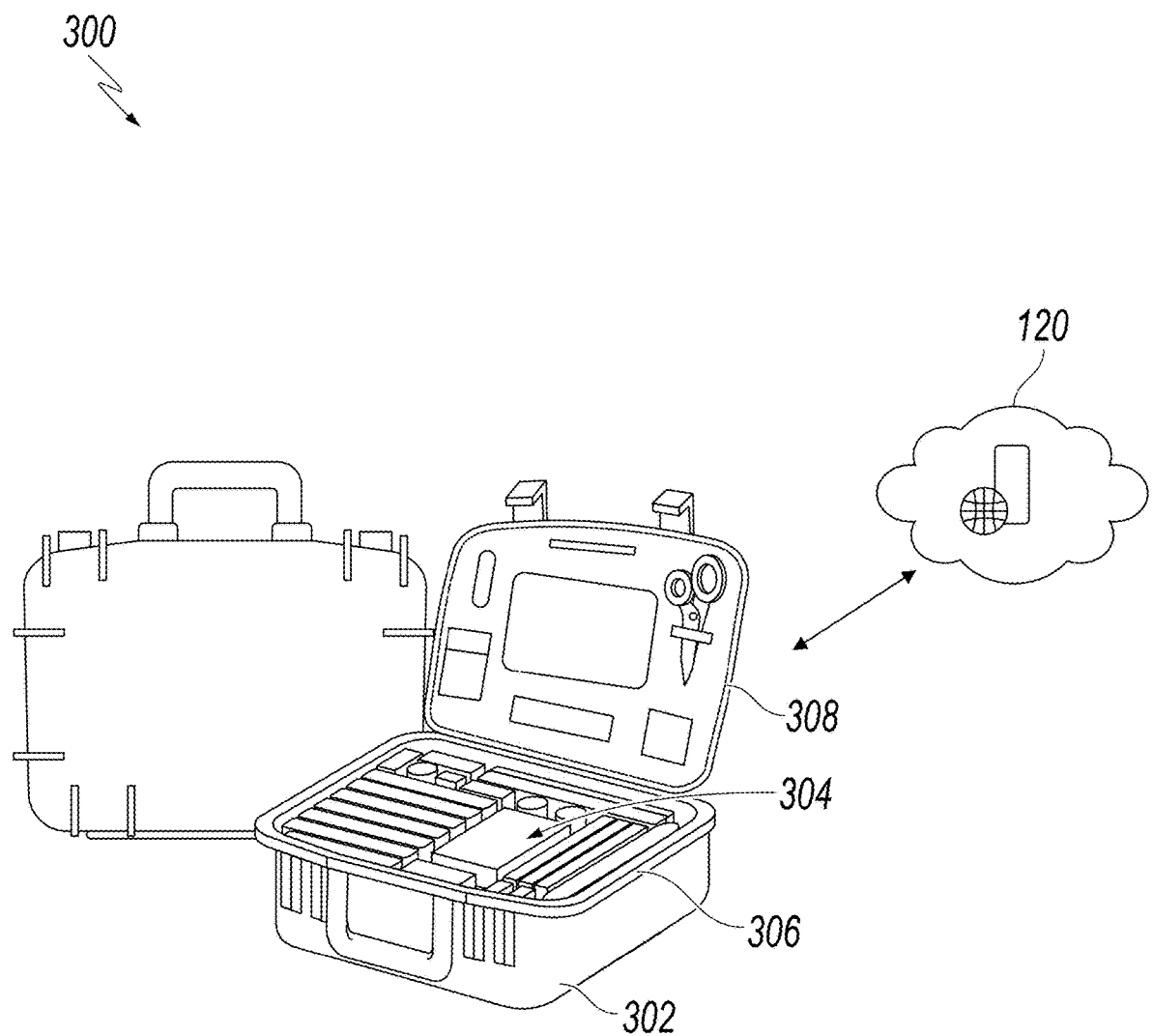
FIGS. 3A and 3B show perspective and top open views, respectively, of a comprehensive emergency medical treatment and guidance apparatus with a built-in user interface in a hard case in accordance with some embodiments.
Figure 3B:
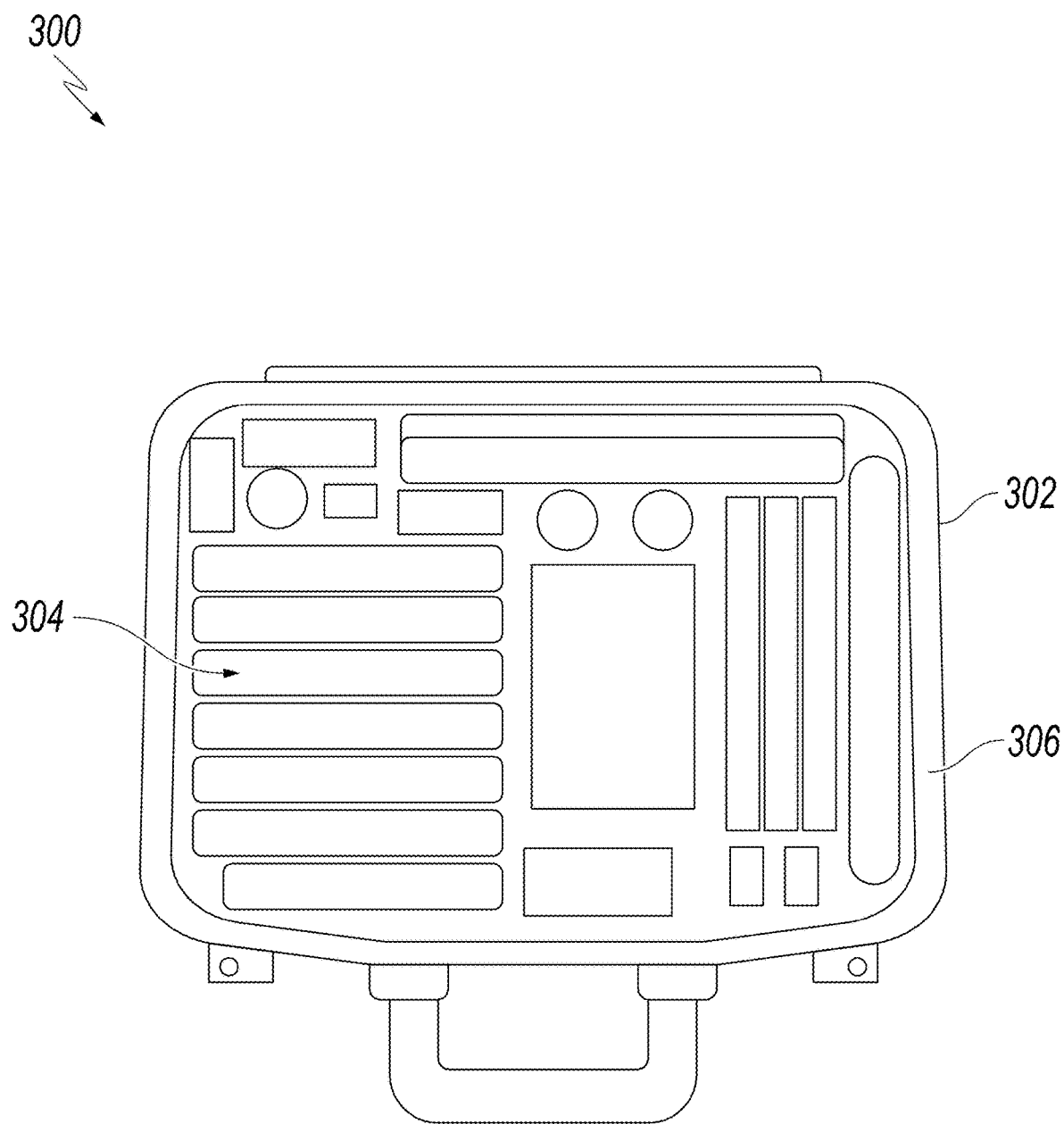

FIGS. 3A and 3B show a comprehensive emergency medical treatment and guidance apparatus 300 with a built-in user interface in accordance with some embodiments. FIG. 3A is a perspective view and FIG. 3B is a top view of the comprehensive emergency medical treatment and guidance apparatus 300 as part of the medical treatment and guidance system 100 described with reference to FIGS. 1 and 2A-2C. Examples of comprehensive emergency medical treatment and guidance apparatuses 300 are the Mobilize Comprehensive Rescue System by ZOLL Medical Corporation of Chelmsford, Massachusetts.

Each emergency medical treatment and guidance apparatus 300 includes a case 302 (e.g., a housing) with a plurality of medical supplies 304 (or medical items) for administering medical treatment (e.g., including, but not limited to, 4×SOF-T Wide tourniquet, 2× QuikClot bleeding control dressing, 2×6" flat emergency trauma dressing, 2× Hyfin chest seal, 2× Water-Jel universal burn dressing, 2× triangular bandage, 2×4.5" sterile conforming stretch gauze, 4×5"×9" sterile combine ABD pads, 2×10"×30" sterile multi-trauma dressing, a 36" SAM emergency splint, 2×4" elastic wrap bandage, a 4"×5" cold compress, an adhesive tape 2.5 yd, a CPR face shield with bite block, a 81 mg chewable aspirin (bottle), a 9 mg dissolvable allergy tablets (box), a 15 mg Insta-Glucose, 2× emergency space Mylar blanket, a portable charger and charging cord, a USB charging cube, an inspection card, 9× proof seals, 2× bag with biohazard markings, a pair of trauma shears, 10× nitrile gloves, a user manual and inventory card, 2 eye pads, 16× adhesive bandages (assorted sizes), 10× burn cream packets, 10× triple antibiotic ointment packets, 10× antiseptic wipes, a pair of tweezers, 10× hand sanitizer packets, an eye wash, a first aid guide, and 10× face masks). The medical supplies 304 are located within an inside compartment 306 of the emergency medical treatment and guidance apparatus 300. In this way, the medical treatment and guidance apparatus 300 includes at least one tourniquet, at least one chest seal, and at least one pair of gloves.

As shown in FIG. 3A, the emergency medical treatment and guidance apparatus 300 includes a built-in user interface 308 housed within the case 302 of the emergency medical treatment and guidance apparatus 300 (e.g., the user interface 308 is a touch-screen user interface that is electrically attached to an electronic device (e.g., a processor with memory) within the case 302). The electronic device is configured to run the previously mentioned emergency medical treatment and guidance application (e.g., the ZOLL Mobilize Rescue App) to provide real-time instructions to help caregivers assess, manage, and treat patients experiencing medical emergencies. The electronic device includes a transceiver operable to communicate with the remote server 120 via the Internet. Further aspects of the medical treatment and guidance application are described below with respect to FIGS. 3A-3F.

Figure 3C:
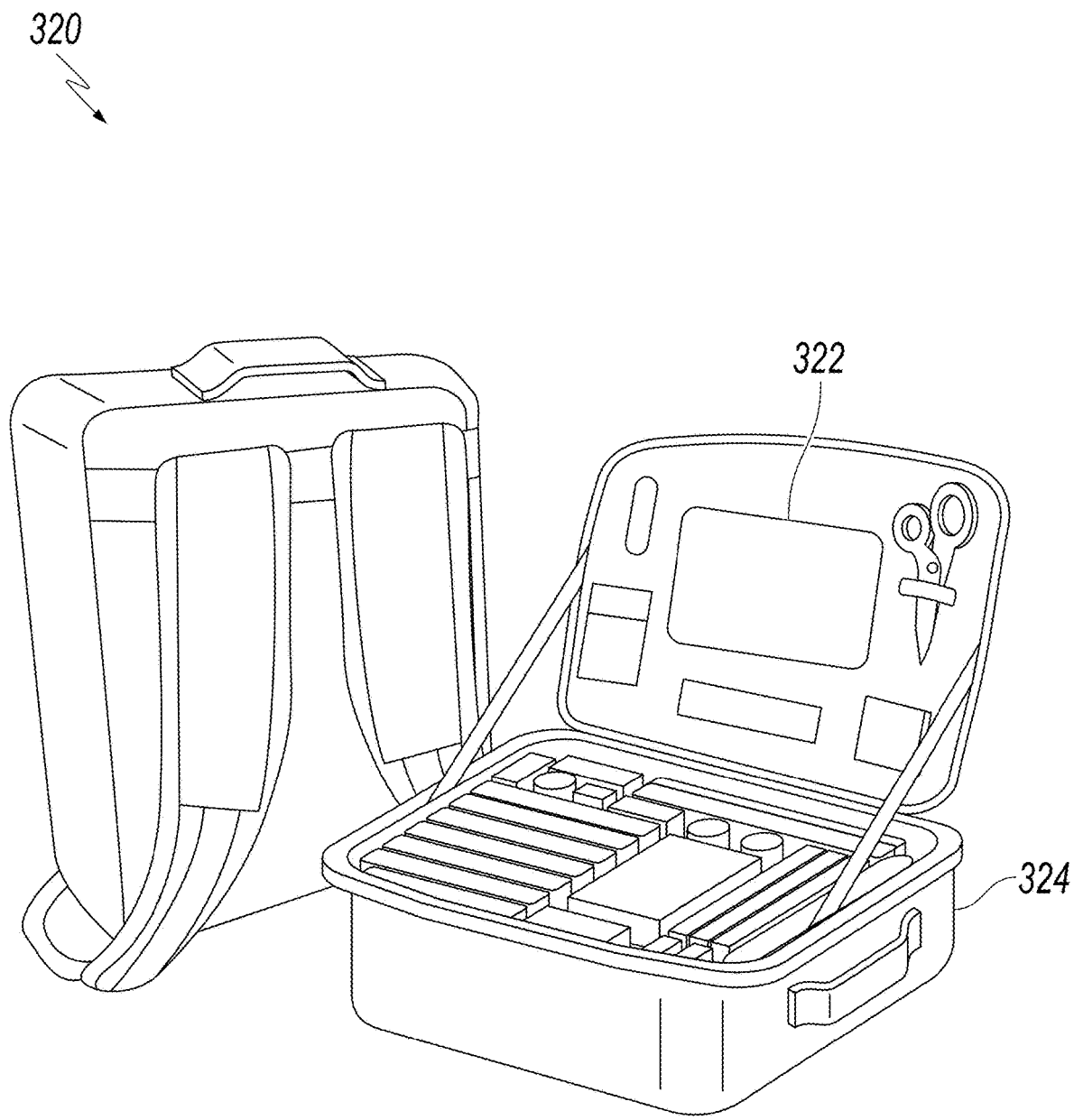
FIGS. 3C and 3D show perspective and front views, respectively, of a comprehensive emergency medical treatment and guidance apparatus with a removable user interface in a back pack case in accordance with some embodiments.
Figure 3D:
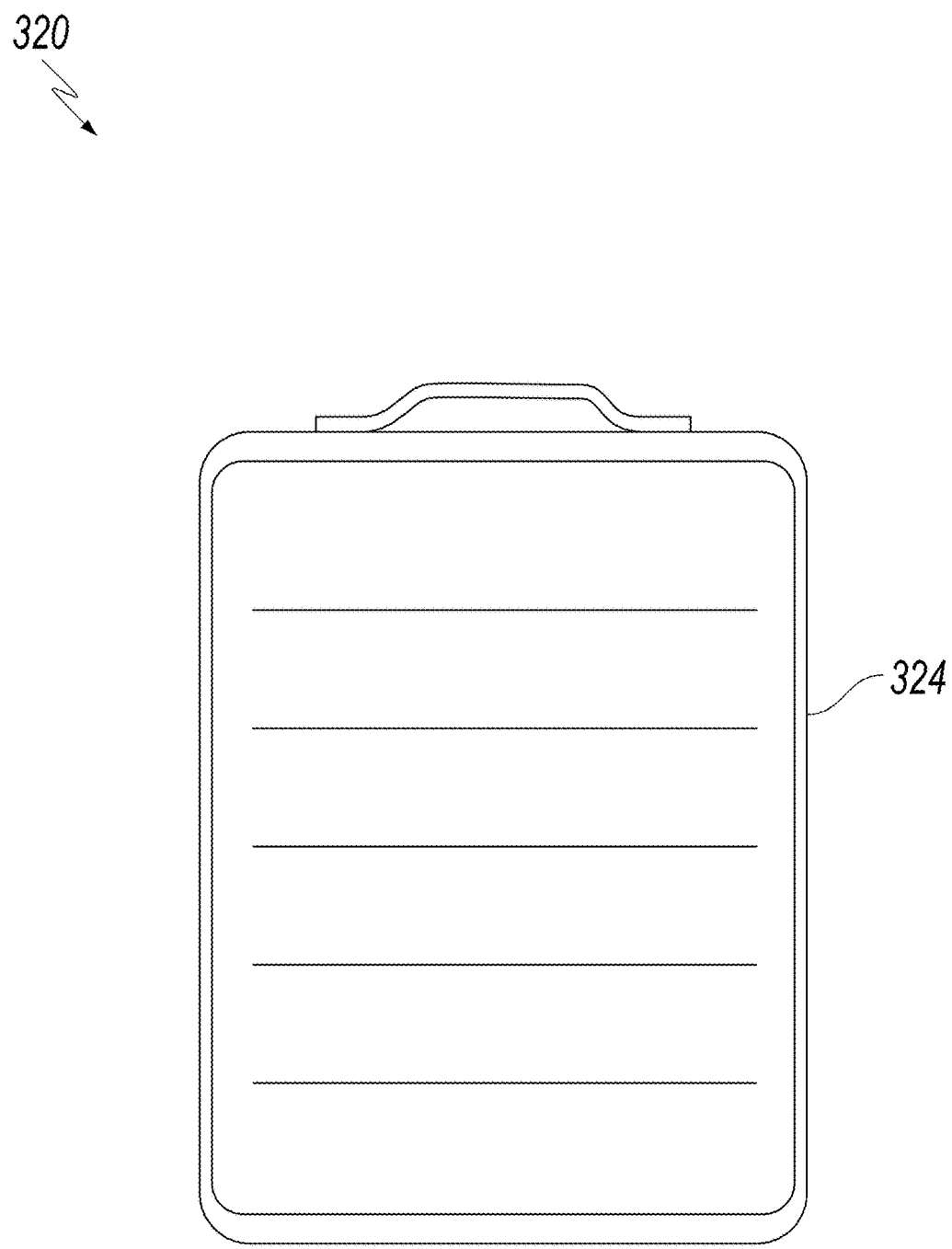

FIGS. 3C and 3D show a comprehensive portable emergency medical treatment and guidance apparatus 320 with removable a user interface 322 in accordance with some embodiments. The emergency medical treatment and guidance apparatus 320 is substantially similar to the emergency medical treatment and guidance apparatus 300 described with reference to FIGS. 3A and 3B but uses a removable user interface 322 instead of a built-in user interface. The user interface 322 is part of a removable mobile electronic device (e.g., a removable tablet) that includes a touch-screen user interface for providing an interactive query to a caregiver or patient and can be located within a housing 324 of the portable medical treatment and guidance apparatus 320. In this way, the user interface can be provided on a mobile device located within a housing of a portable medical treatment and guidance apparatus. Since the removable user interface 322 is provided on a mobile device and is removable, the removable user interface 322 is configured to perform the steps of the emergency medical treatment and guidance application both when the mobile device is located within the medical treatment and guidance apparatus and also when the mobile device removed from the portable medical treatment and guidance apparatus.

The medical treatment and guidance apparatus 320 also includes at least one tourniquet, at least one chest seal, and at least one pair of gloves. The emergency medical treatment and guidance apparatus 320 also includes a soft housing 324 (e.g., a soft backpack style housing as shown) opposed to a hard (or substantially rigid) housing 302 of the emergency medical treatment and guidance apparatus 300.

Figure 3E:
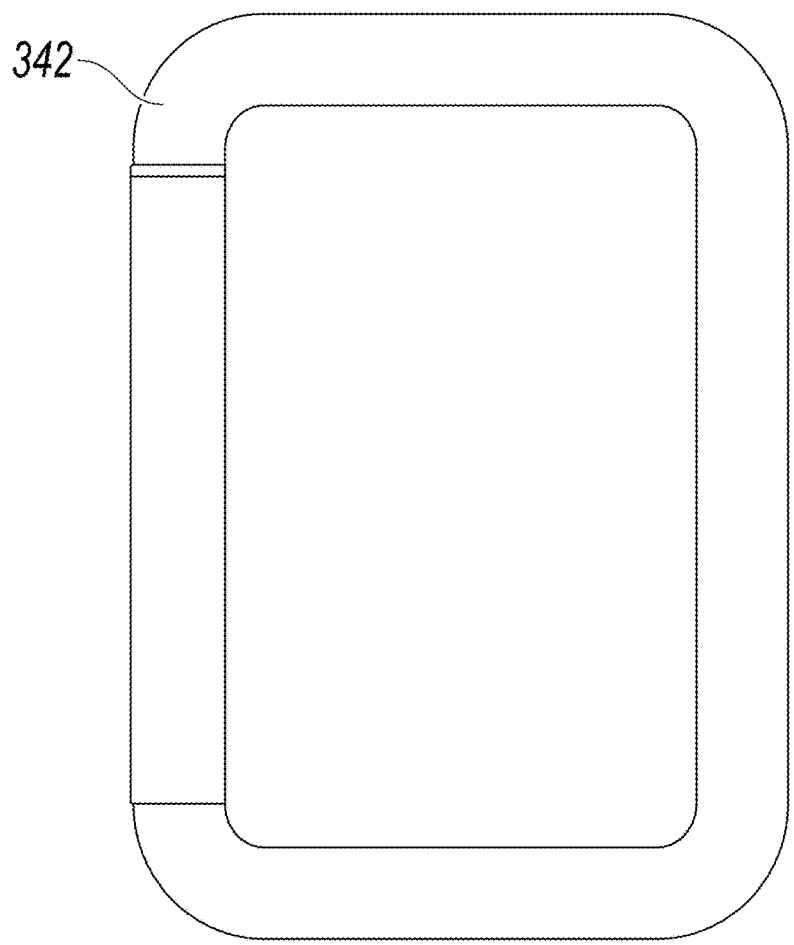
FIGS. 3E and 3F show closed and open views, respectively, of a compact emergency medical treatment and guidance apparatus in accordance with some embodiments.
Figure 3F:
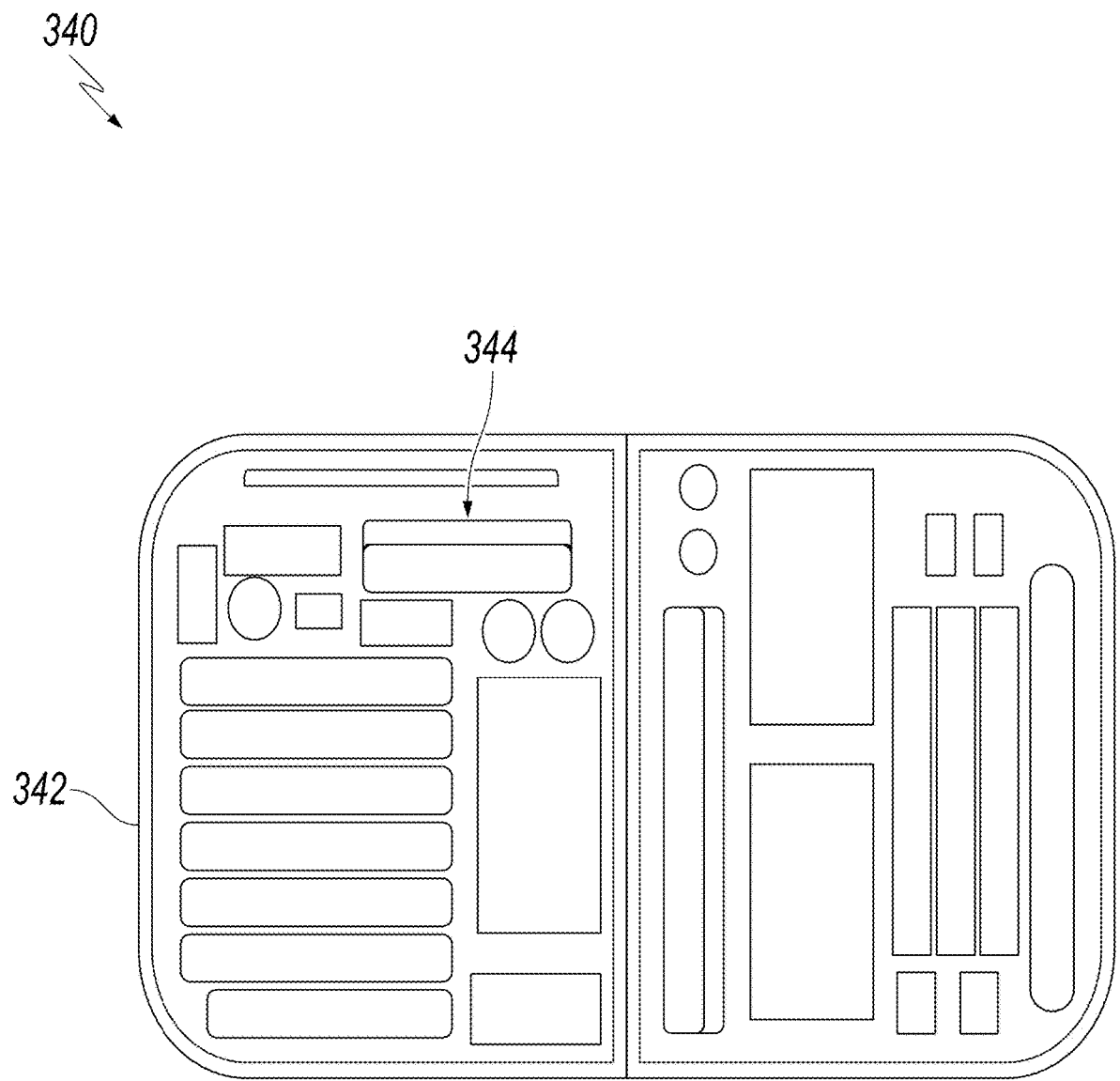

FIGS. 3E and 3F show a portable emergency medical treatment and guidance apparatus 340 in accordance with some embodiments. In some examples, the emergency medical treatment and guidance apparatus 340 is part of a multi-pack system that includes four emergency medical treatment and guidance apparatuses 340 for treating medical emergencies (the four-pack system is not shown). Examples of such multi-pack systems are the Mobilize Public Access Rescue System of ZOLL Medical Corporation of Chelmsford, Massachusetts.

In certain embodiments, each emergency medical treatment and guidance apparatus 340 includes a case 342 (i.e., a housing) with a plurality of medical supplies 344 (as shown in FIG. 3F) for administering medical treatment (e.g., but not limited to, a SOF-T Wide tourniquet, a 4" emergency trauma dressing, a QuikClot bleeding control dressing, a Hyfin chest seal, a CPR face shield with bite block, an emergency space Mylar blanket, a trauma shears, 10× nitrile gloves, and 10× face masks). In this way, the medical treatment and guidance apparatus 340 includes at least one tourniquet, at least one chest seal, and at least one pair of gloves. Examples of such emergency medical treatment and guidance apparatuses 340 are the ZOLL Mobilize Compact Rescue System. The housing 342 is a soft fabric material and includes a zipper to seal the contents of the housing 342.

In some embodiments, the portable medical treatment and guidance apparatuses described herein are stored in deployment stations for access by caregivers and patients. Examples of such deployment stations are described in Intl. Application No. PCT/US2022/013700, entitled "Deployment Stations For Emergency Medical Treatment And Guidance Apparatuses," filed Jan. 25, 2022, which claims priority to U.S. Application No. 63/141,645, filed Jan. 26, 2021, the disclosures of which are hereby incorporated by reference in their entireties.

As noted above, the portable medical treatment and guidance system includes a medical treatment and guidance application to provide real-time instructions to help caregivers assess, manage, and treat patients experiencing medical emergencies. In some embodiments, the medical treatment and guidance application queries a spreadsheet table stored in memory to determine the next step in the interactive flow based on one of more inputs from the caregiver. The spreadsheet table includes conditional formatting that links information between cells in the spreadsheet table to account for maintaining patient state information. The conditional formatting also reduces the number of predetermined medical emergency permutations via the linking of information between the cells of the spreadsheet.

In some embodiments, the medical treatment and guidance application queries a spreadsheet table that includes three distinct listings for page links (e.g., page links to a particular flow), text (e.g., text of medical instructions, inquiries, and buttons), and images (e.g., images of medical instructions, inquiries, and buttons). By having the text in a distinct listing from the page links and images, the medical treatment and guidance application can translate the text into other languages for presenting on the user interface. In other words, if the text were included in an image then it would be harder for the application to translate the text because it would first need to separate the text from the image (e.g., via image processing). Similarly, the distinct listings enable the application to use substitute medical supplies without having to fork into a new flow path.

In some embodiments, the medical treatment and guidance application is compiled so it can be presented on user interfaces with various resolutions and aspect ratios. For example, the medical treatment and guidance application can execute on both smart phones and tablet devices without having to compile the application separately. In other words, the application can execute on either an electronic device of a caregiver (e.g., electronic device 110 shown in FIG. 1 such as their smart phone, their tablet, their smart watch, etc.) as well as a built-in user interface of a medical treatment and guidance apparatus (e.g., the user interface 308 of medical treatment and guidance apparatus 320 shown in FIG. 3A and/or the user interface 322 of medical treatment and guidance apparatus 340 shown in FIG. 3C). In addition, the medical treatment and guidance application can execute on any of these user interfaces and electronic devices at the same time. In these examples, the medical treatment and guidance application has the same interactive flow functionality regardless of the electronic device executing the application. In this way, a medical treatment and guidance application executing on the caregiver's smart phone includes instructions for using all of the medical supplies of the compact medical treatment and guidance apparatus 300 and all of the medical supplies of the comprehensive medical treatment and guidance apparatuses 320, 340, depending on which is available to the caregiver which is described in detail below with reference to FIGS. 7A-7N.

Figure 4:
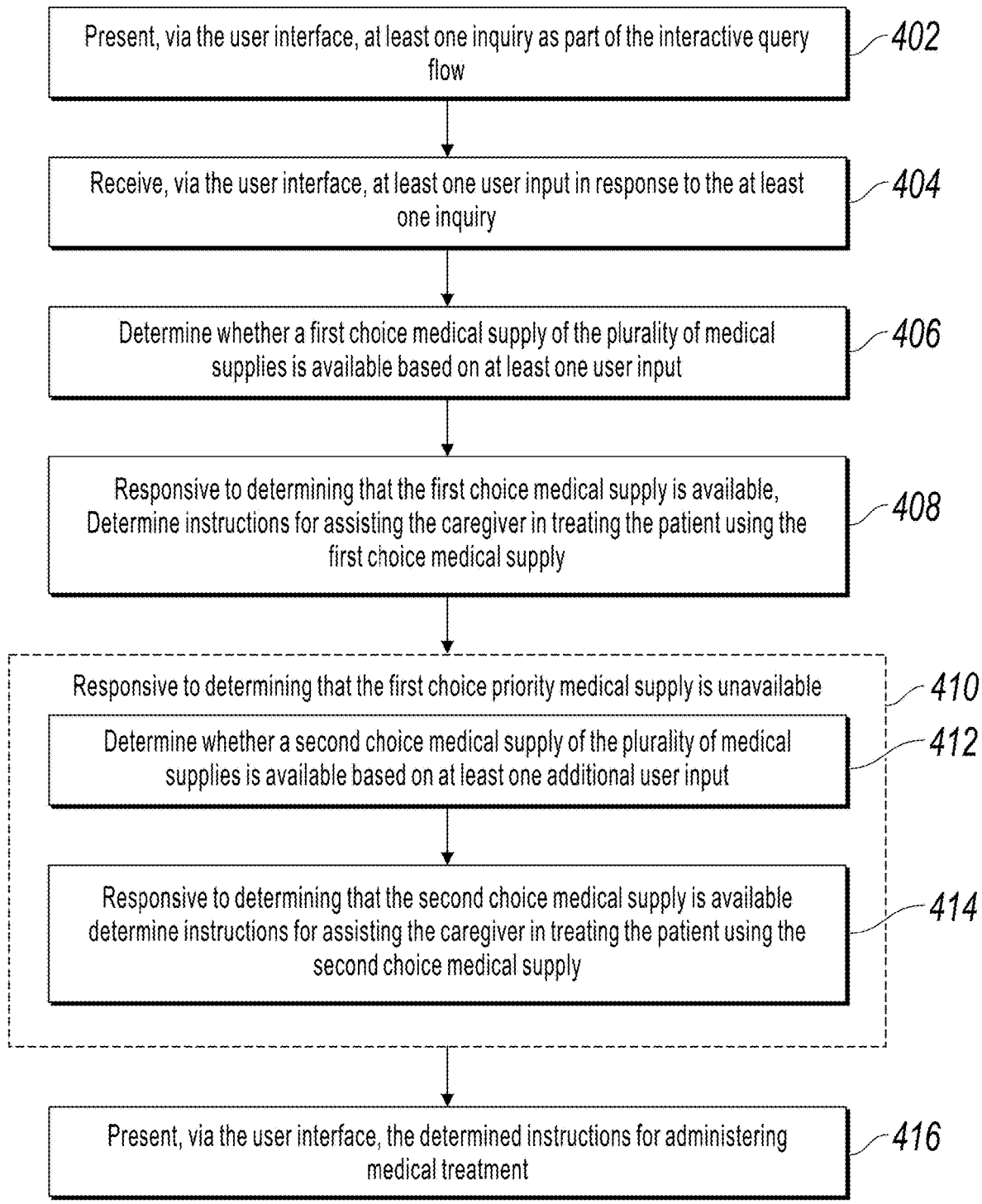
FIG. 4 shows a flowchart of the operations performed by the medical treatment and guidance system accounting for substitute medical supplies in accordance with some embodiments.

FIG. 4 shows a flowchart of the operations performed by the medical treatment and guidance system 100 accounting for substitute medical supplies in accordance with some embodiments. The features of FIG. 4 are described along with the example shown in FIGS. 5A-5G. FIG. 5A shows a process 500 of the operations performed by the medical treatment and guidance system 100 accounting for substitute medical supplies in accordance with some embodiments. FIGS. 5B-5G illustrate the medical treatment and guidance application presenting medical instructions on a user interface of the electronic device associated with the operations of the process 500.

FIGS. 5A-5G illustrate an example where the medical treatment and guidance system 100 instructs a caregiver to use substitute medical supplies when a particular medical supply is unavailable to the caregiver. By way of example, a medical treatment and guidance application, such as the ZOLL Mobilize Rescue App, runs on an electronic device and provides an inquiry on a user interface 502 as part of the medical treatment and guidance system 100. In this example, the electronic device is a smart phone 504, but in other examples it is, e.g., a tablet or smart watch. The medical treatment and guidance application renders action buttons, escape buttons, images, and medical instructions on the user interface. The buttons provide input so the application can receive input from a user. In particular, action buttons are used to receive input as part of the interactive flow (e.g., from step to step). Escape buttons are used to indicate a change in environment or a change in the patient's condition (e.g., to exit the interactive flow).

In some interactive flows, the system presents an instruction to "Take a deep breath. Mobilize will help you." This instruction, which in this example is provided via an application identified as "Mobilize," indicates that the medical treatment and guidance system 100 will assist the caregiver in performing medical treatment when the patient experiences a medical emergency. When the caregiver invokes a button to start the flow, the medical treatment and guidance system 100 presents an instruction to "Make sure 911 has been called." This step is to make sure the caregiver called professional assistance before beginning the treatment of the patient since it is important that the professional assistance arrive as soon as possible. The medical treatment and guidance system 100 also presents an inquiry for the caregiver to acknowledge that is it ok for the medical treatment and guidance system 100 to continue. The caregiver can respond to the inquiry by invoking an action button to indicate to the medical treatment and guidance system 100 that it is ok to continue.

In response, the medical treatment and guidance system 100 proceeds to step 510 to begin presenting instructions to the caregiver. The medical treatment and guidance system 100 presents an inquiry 512 asking "Is the patient badly bleeding?" In some examples, the caregiver can invoke a hyperlink labeled "What is bad bleeding?" to cause the medical treatment and guidance system 100 to present an explanation of bad bleeding. For example, the explanation can be: "Bad bleeding is when blood is uncontrollably coming out of the wound." In some examples, the caregiver can invoke an escape button labeled "Press when EMS arrives" at any point in the process shown in FIG. 5A to indicate to the medical treatment and guidance system 100 that EMS has arrived and that it is ok to conclude treatment for this patient.

If the caregiver invokes a button labeled "No" in response to the inquiry 512 asking if the patient is badly bleeding, the medical treatment and guidance system 100 proceeds along a flow path described with reference to FIG. 6A below.

If the caregiver invokes a button labeled "Yes" in response to the inquiry 512 asking if the patient is badly bleeding, the medical treatment and guidance system 100 presents an image of the human body 514 (shown in FIG. 5B) so the caregiver can indicate to the medical treatment and guidance system 100 where the patient is bleeding. The medical treatment and guidance system 100 also presents an instruction 516 asking to "Touch the worst area of bleeding." In this example, the image of the human body 514 includes 10 radio buttons 518 where each radio button indicates a different part of the body (e.g., head, chest, torso, groin, left and right shoulders, left and right arms, and left and right legs)

For example, if the caregiver invokes the radio button 518 in an area of the patient's left leg, the medical treatment and guidance system 100 determines a first choice medical supply that can be used to treat the patient experiencing a badly bleeding left leg. In this example, the first choice medical supply is a tourniquet. The tourniquet is a first choice medical supply in this scenario because the medical treatment and guidance system 100 determined that the tourniquet is the preferred medical supply to use in treating a badly bleeding leg. The medical treatment and guidance system 100 also determines the tourniquet as the first choice medical supply because a tourniquet is included in all of the treatment and guidance apparatuses (e.g., the compact medical treatment and guidance apparatus 300 and the comprehensive medical treatment and guidance apparatuses 320, 340 include a tourniquet). In this way, the medical treatment and guidance system 100 determines the medical supply based on whether the medical supply is available in all the portable emergency treatment and guidance apparatuses 300, 320, 340.

In some embodiments, the medical treatment and guidance system 100 provides different instructions depending on the medical supply to which the caregiver has access. For example, when the caregiver invokes the radio button 518, the medical treatment and guidance system 100 presents an inquiry 520 (shown in FIG. 5C) asking the caregiver "Do you have access to one of these tourniquets?" In this example, two tourniquets 522, 524 are displayed on the user interface. Tourniquet 522 is a SOF-Tourniquet (SOF-T) and tourniquet 524 is a Combat Application Tourniquet (CAT).

Figure 5C:
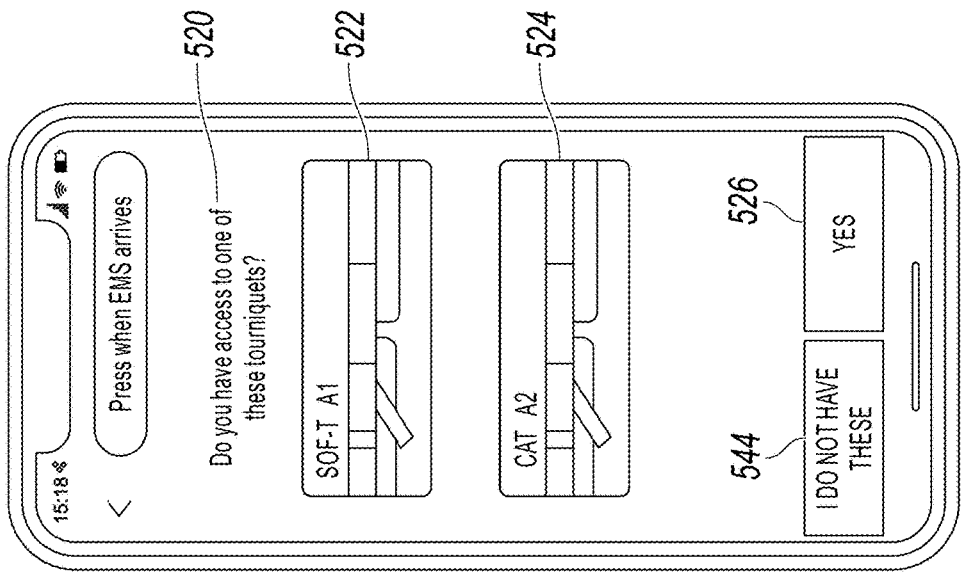
Figure 5B:
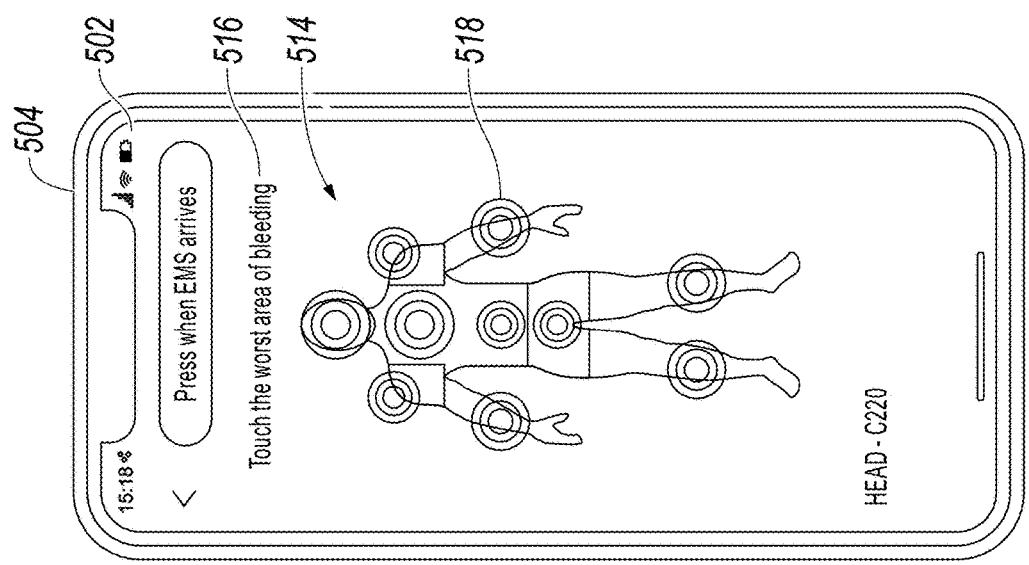

If the caregiver invokes a button 526 labeled "yes" indicating that the caregiver has access to at least one of these two tourniquets, the medical treatment and guidance system 100 presents an inquiry 528 (shown in FIGS. 5A and 5D) asking the caregiver to "Select the one you have." The medical treatment and guidance system 100 presents two buttons 530 and 532 representing the SOF-T and the CAT, respectively. In some embodiments, the inquiries shown in FIGS. 5C and 5D are combined into a single step in the flow to allow the caregiver to progress through the interactive flow quicker than in the example shown.

Referring back to FIG. 5A, the medical treatment and guidance system 100 then presents instructions 534 for using the specific tourniquet available to treat the bleeding emergency. For example, if the caregiver invokes the button 530 to select the SOF-T, the medical treatment and guidance system 100 presents instructions for using a SOF-T to treat the bleeding emergency. As part of presenting instructions, the medical treatment and guidance system 100 can present an inquiry asking the caregiver to "Locate tourniquet labeled Tourniquet A1." The medical treatment and guidance system 100 can also present an image of the tourniquet to aid the caregiver in recognizing the tourniquet from the other medical supplies in the portable emergency treatment and guidance apparatus. Once the caregiver has located the tourniquet and indicated that the tourniquet has been located, e.g., by invoking a button on the user interface labeled "OK" in response to the inquiry asking to locate the tourniquet, the system 100 can present instructions for assisting the caregiver in using the particular tourniquet selected.

While a SOF-T and CAT are explicitly depicted here, other types and/or brands of tourniquets can also be used with the medical treatment and guidance system 100. For example, the medical treatment and guidance system 100 can provide instructions to use a particular medical supply based on the type and/or brand of the medical supply predetermined to be expected within a particular medical treatment and guidance apparatus based on the apparatus type.

As a result, once the medical treatment and guidance system 100 determines that a particular medical supply is needed for the medical instruction (in this example, a tourniquet) via the interactive flow, the medical treatment and guidance system 100 can present an inquiry about a particular type of medical supply available to the caregiver (in this example, a CAT vs. a SOF-T) and present medical instructions for that particular medical supply.

In this example, the instructions 534 include specific instructions for treating a bleeding medical emergency of the patient's leg using a SOF-T. In some examples, the instructions 534 include one or more of the following instructions. The medical treatment and guidance system 100 can present instructions stating "STEP 1: Open loop of tourniquet. Slide loop above the wound and as high as possible on limb." The medical treatment and guidance system 100 can also present an image of an open loop of a tourniquet to aid the caregiver in recognizing what an open looped tourniquet looks like.

The medical treatment and guidance system 100 can also present an inquiry implicitly asking if the caregiver is having trouble following these directions. For example, if the caregiver invokes a button indicating that the caregiver is having difficulty applying the tourniquet, then the medical treatment and guidance system 100 is informed that the caregiver needs assistance and the medical treatment and guidance system 100 will provide this additional assistance in the form of additional inquiries and instructions. In this scenario, the medical treatment and guidance system 100 can proceed to determine why the tourniquet cannot be applied to the patient. In particular, the medical treatment and guidance system 100 presents an inquiry asking "Why can't you apply the tourniquet?" In response, the caregiver can respond by indicting that they can't get the tourniquet above the wound or the caregiver can respond by indicating that they can't get the loop on the leg of the patient. In this way, the medical treatment and guidance system 100 can provide assistance to help the caregiver use the medical supplies of the medical treatment and guidance system 100.

Referring back to the instructions 534, the medical treatment and guidance system 100 can present an instruction of "STEP 2: Place as high on limb as possible." The medical treatment and guidance system 100 can then present an instruction of "STEP 3: Pull tight to remove slack." The medical treatment and guidance system 100 can then present an instruction of "STEP 4: Twist rod until bleeding stops. Patient may feel pain from this." The medical treatment and guidance system 100 can then present an instruction of "STEP 5: Tuck black rod into black triangle clip. Do not remove tourniquet." As noted above, any or all of these instructions can be included in the instructions 534. The medical treatment and guidance system 100 can then present an inquiry 536 asking the caregiver "Did the bleeding from this wound stop?"

If the caregiver invokes a button indicating that bleeding from this wound has stopped in response to the inquiry 536, the medical treatment and guidance system 100 presents an inquiry 538 asking "Does the patient appear to be bleeding anywhere else?" If the caregiver invokes a button indicating that the patient appears to be bleeding elsewhere, the medical treatment and guidance system 100 can then present the image of body for the caregiver to select bleeding areas of the body. In some examples, this image is the same as the image shown in FIG. 5B. In this scenario, the medical treatment and guidance system 100 loops back to the inquiry 516 asking the caregiver to touch the worst area of bleeding. If on the other hand, the caregiver responds that the patient does not appear to be bleeding anywhere else, e.g., by invoking a button, the medical treatment and guidance system 100 proceeds to step 540 to determine if the patient is unconscious.

If the caregiver indicates that the patient is still bleeding from the wound that the tourniquet was applied to, e.g., by invoking a button, then the medical treatment and guidance system 100 presents instructions 542 to tighten the tourniquet and apply a second tourniquet to the patient if bleeding persists. In some examples, instructions 542 include one or more of the following instructions. For example, the medical treatment and guidance system 100 can present an instruction to "Prepare to tighten tourniquet." The medical treatment and guidance system 100 can then present an instruction of "STEP 1: Unlock metal rod from triangle." The medical treatment and guidance system 100 can then present an instruction of "STEP 2: Pull tight to remove slack." The medical treatment and guidance system 100 can then present an instruction of "STEP 3: Twist rod until bleeding stops. Patient will feel pain from this." The medical treatment and guidance system 100 can then present an instruction to "Tuck black rod into black triangle clip. Do not remove tourniquet." The medical treatment and guidance system 100 can then loop back and again present the inquiry 536 asking "Did the bleeding from this wound stop?" In this way, the interactive flow continues where inquiry 536 left off.

If the caregiver indicates that the patient is still bleeding, e.g., by invoking a button, then the medical treatment and guidance system 100 returns to present instructions 542 on using a second tourniquet on the patient to control the bleeding. In this way, the medical instructions in general can include instructions for using multiple medical supplies to address the same medical emergency.

Returning back to the inquiry 520 of FIG. 5A and shown in FIG. 5C, if the caregiver invokes a button 544 labeled "I do not have these," the medical treatment and guidance system 100 is informed that the caregiver does not have any of the required tourniquets (e.g., tourniquets 522 and 524) and the medical treatment and guidance system 100 updates the instructions to use a different medical supply of the medical supplies within the portable emergency treatment and guidance apparatuses.

Referring back to FIG. 4, the medical treatment and guidance system 100 performs step 402 to present, via the user interface, at least one inquiry as part of the interactive query flow. In turn, the medical treatment and guidance system 100 performs step 404 to receive, via the user interface, at least one user input in response to the at least one inquiry. In this example, the input is when the caregiver invokes the button 544 labeled "I do not have these" or when the caregiver invokes the button 526 labeled "YES" in response to the inquiry 520 asking if the caregiver has access to one of the tourniquets. In turn, then the medical treatment and guidance system 100 performs step 406 to determine whether a first choice medical supply (e.g., either of the tourniquets) of the plurality of medical supplies is available based on at least one user input (e.g., the medical treatment and guidance system 100 determines that the both the tourniquets are unavailable when the caregiver invokes the button 544 labeled "I do not have these" and the medical treatment and guidance system 100 determines that at least one of the tourniquets is available when the caregiver invokes the button 526 labeled "Yes"). The medical treatment and guidance system 100 performs step 408 to determine instructions for assisting the caregiver in treating the patient using the first choice medical supply when the first choice medical supply is available (e.g., the instructions 542 for using one of the tourniquets in this example).

This process of updating the instructions based on absent or otherwise unavailable medical supplies is repeated until either the caregiver has the required medical supply necessary for treating the medical emergency and/or a medical supply is not required to perform a particular action (e.g., when the caregiver is directed to use their hands instead of a medical supply e.g., as a last resort). In other words, the medical treatment and guidance system 100 first asks the caregiver to use a first choice medical supply and, if the first choice medical supply is unavailable, the medical treatment and guidance system 100 asks the caregiver to use a second choice medical supply, then a third choice medical supply, and so on.

Referring back to the inquiry 520 of FIG. 5A and shown in FIG. 5C, once the caregiver invokes the button 544 labeled "I do not have these," the medical treatment and guidance system 100 proceeds to block 410 of FIG. 4 and performs step 412 to determine whether a second choice medical supply of the plurality of medical supplies is available based on at least one additional user input when the first choice priority medical supply is unavailable. In this example, the medical treatment and guidance system 100 predetermined that a QuikClot® gauze is a second choice medical supply for treating a badly bleeding leg of a patient. In turn, the medical treatment and guidance system 100 presents an inquiry 546 (shown in FIG. 5E) asking the caregiver to "Locate QuikClot gauze labeled QuikClot B1."

Tying in with FIG. 4, if the caregiver invokes a button 548 labeled "OK" in response to the inquiry 546 asking to locate the QuikClot® gauze, the medical treatment and guidance system 100 proceeds to step 414 to determine instructions for assisting the caregiver in treating the patient using the second choice medical supply. In this way, the medical treatment and guidance system 100 proceeds to step 416 to present, via the user interface, the determined instructions for administering medical treatment. In this way, the medical treatment and guidance system 100 presents instructions 550 (see FIG. 5A) for using the QuikClot® gauze to treat the bleeding emergency.

In some examples, the instructions 550 include one or more of the following instructions. For example, the medical treatment and guidance system 100 can present an instruction to "Prepare to apply direct pressure with QuickClot®." In some examples, the medical treatment and guidance system 100 presents the instruction using inverted colors (e.g., the text is white and the background is black) to emphasize the instruction for this particular step.

The medical treatment and guidance system 100 can then present an instruction of "STEP 1: Open QuickClot® package. Unravel rolled gauze and wad gauze into a ball." The medical treatment and guidance system 100 can then present an instruction of "STEP 2: Place ball of wadded up gauze directly into the wound." The medical treatment and guidance system 100 can then present an instruction of "STEP 3: Use steady firm pressure with both hands on gauze." The medical treatment and guidance system 100 can then present an instruction of "STEP 4: Hold firm pressure for 3 minutes. Time remaining 02:59." In this way, the time remaining is shown in a MM:SS format and counts down so the caregiver knows how long to apply pressure to the wound.

The medical treatment and guidance system 100 then presents an inquiry (e.g., substantially the same as the inquiry 536) asking "Did the bleeding from this wound stop?" If the response is "No," the medical treatment and guidance system 100 presents instructions to apply a second QuikClot® gauze to the wound. For example, the medical treatment and guidance system 100 can present an instruction to "Locate another QuickClot® gauze labeled QuickClot® B1." The medical treatment and guidance system 100 can then repeat the instructions 550 to apply the second QuikClot® gauze to the wound. If the response is "Yes," in response to the inquiry asking "Did the bleeding from this wound stop?" then the interactive flow proceeds to inquiry 538 asking the caregiver if the patient is bleeding anywhere else (as described above).

Figure 5E:
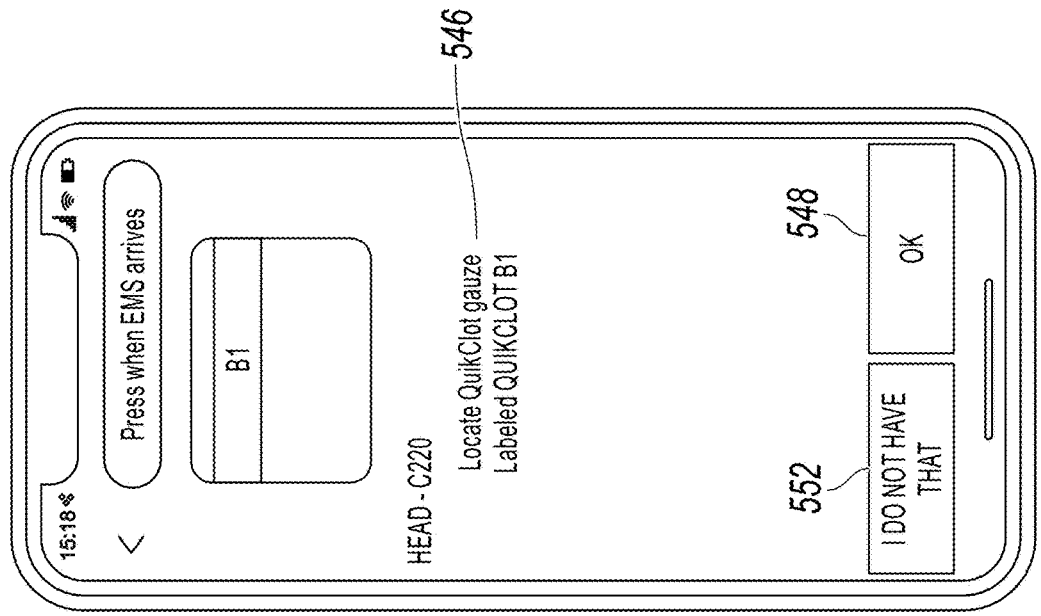
Figure 5D:
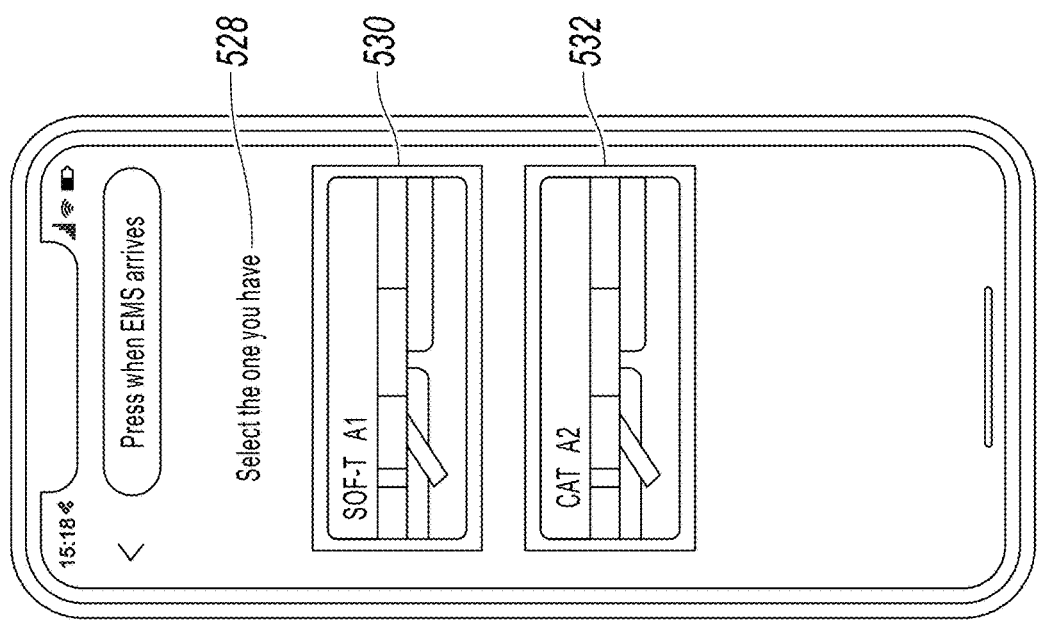
Figure 5G:
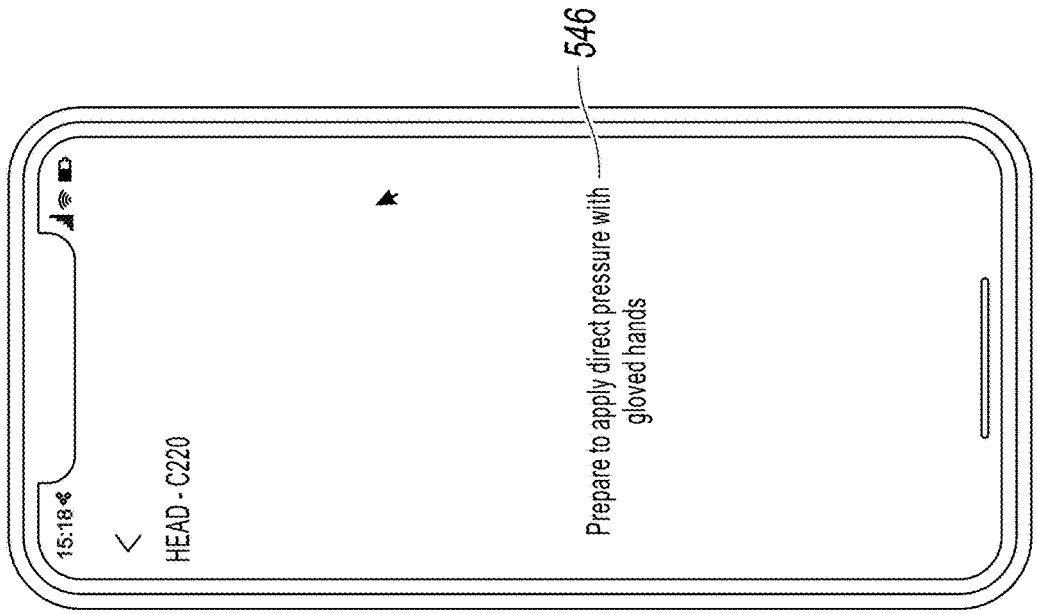
Figure 5F:
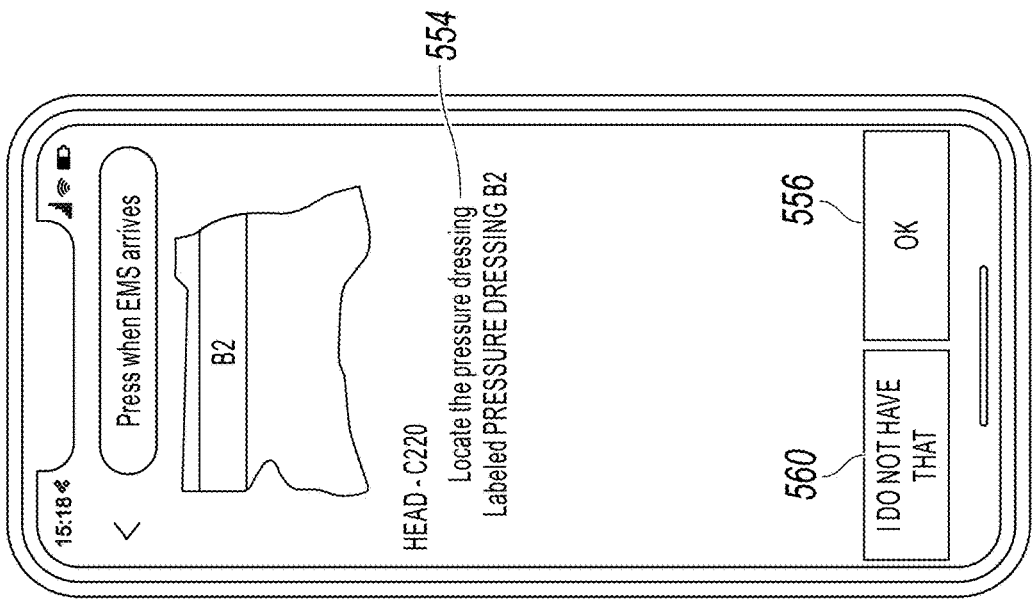

Referring to FIG. 5E, if the caregiver invokes a button 552 labeled "I do not have that," in response to the inquiry 546 to locate the QuikClot® gauze, the medical treatment and guidance system 100 is informed that the caregiver does not have the QuikClot® gauze and the medical treatment and guidance system 100 determines a third choice medical supply for treating the medical emergency. In this example, the third choice medical supply is a pressure dressing and is predetermined.

The medical treatment and guidance system 100 proceeds to determine whether the third choice medical supply of the plurality of medical supplies is available based on at least one additional user input when the second choice medical supply is unavailable. In this example, the medical treatment and guidance system 100 presents an inquiry 554 (shown in FIG. 5F) asking the caregiver to "Locate the pressure dressing labeled Pressure Dressing B2." A pressure dressing is included in all of the portable emergency treatment and guidance apparatuses. If the caregiver invokes a button 556 labeled "OK" in response to the inquiry 554 asking to locate the pressure dressing, the medical treatment and guidance system 100 presents instructions 558 (see FIG. 5A) for assisting the caregiver in using the pressure dressing to treat the patient experiencing the bleeding. In this way, the determined instructions for administering medical treatment include instructions for using the third choice medical supply.

In some examples, the instructions 558 include one or more of the following instructions. For example, the medical treatment and guidance system 100 can present an instruction of "STEP 1: Open the package and expose white pad. Do not touch white pad." The medical treatment and guidance system 100 can then present an instruction of "STEP 2: Place the white pad against the wound." The medical treatment and guidance system 100 can then present an instruction of "STEP 3: Hold pad in place with one hand and wrap bandage snugly around limb." The medical treatment and guidance system 100 can then present an instruction of "STEP 4: Secure bandage to itself. Dressing should be tight to keep pressure on wound."

The medical treatment and guidance system 100 can then present an inquiry (e.g., substantially similar to inquiry 536) asking "Did the bleeding from this wound stop?" If the response is "No," the medical treatment and guidance system 100 presents instructions to apply a second pressure dressing to the wound. For example, the medical treatment and guidance system 100 can present an instruction to "Locate another pressure dressing labeled Pressure Dressing B2." The medical treatment and guidance system 100 can then repeat the instructions 558 to apply the second pressure dressing to the wound. If the response is "Yes," in response to the inquiry asking "Did the bleeding from this wound stop?" then the interactive flow resumes where the instructions for the tourniquet left off and presents an inquiry 538 asking the caregiver if the patient is bleeding anywhere else (as described above).

Referring back to FIG. 5F, if the caregiver invokes a button 560 labeled "I do not have that," in response to the inquiry 554 to locate the pressure dressing, the medical treatment and guidance system 100 is informed that the caregiver does not have the pressure dressing and the medical treatment and guidance system 100 updates the instructions again. In this example, the medical treatment and guidance system 100 presents an instruction 562 (shown in FIG. 5G) to "Prepare to apply direct pressure with gloved hands." In this example, the caregiver's hands are used in lieu of a medical supply, e.g., as a last resort. The medical treatment and guidance system 100 presents the instruction using inverted colors (e.g., the text is white and the background is black) to emphasize the instruction for this particular step.

In some examples, the instructions 562 include one or more of the following instructions. For example, the medical treatment and guidance system 100 can present an instruction stating "Step 1: Use steady firm pressure with both hands on the wound." The medical treatment and guidance system 100 can also present an image of a person applying pressure to a wound on the leg of a patient to assist the caregiver in understanding the instructions. In some examples, the medical treatment and guidance system 100 accounts for dexterity by presenting an image of the right leg of a patient when the patient is experiencing an injury to their right leg and by presenting an image of the left leg of a patient when the patient is experiencing an injury to their left leg. The medical treatment and guidance system 100 can then present an instruction stating "Step 2: Hold pressure for 3 minutes." The medical treatment and guidance system 100 can also present a 3 minute countdown with time remaining in a MM:SS format so the caregiver knows how long to hold pressure for. When the caregiver invokes a button to continue, the medical treatment and guidance system 100 can present an instruction stating "Continue to hold direct pressure on the wound until the bleeding stops."

When the caregiver invokes a button to continue, the medical treatment and guidance system 100 presents an inquiry asking "Does the patient appear to be bleeding anywhere else?" as described above. If the caregiver invokes a button labeled "Yes," the process 500 loops back to the inquiry 520 (shown in FIGS. 5A and 5B) so the caregiver can identify where else the patient is bleeding. In this way, the medical treatment and guidance system 100 repeats the process to address all bleeding wounds until all bleeding is stopped.

While the above example referred to the first choice medical supply being a tourniquet, the second choice medical supply being a QuikClot® gauze, the third choice medical supply being a pressure dressing, and using hands as a last resort, other medical supplies are used in other scenarios. These examples are presented below in Table 1.

TABLE 1

| Medical supply substitutions. | | | | |
|---|---|---|---|---|
| Medical Emergency | First choice | Second choice | Third choice | Fourth choice |
| Bad Bleeding extremity | Tourniquet | QuikClot® gauze | Pressure dressing | Caregiver's Hands |
| Chest wound | Chest seal | Gauze | Cover with gloved hand | |
| Bad Bleeding junctional | QuikClot® gauze | Regular Gauze | Rolled Gauze | Gloved hand |
| Burns | Burn Dressing | Trauma Gauze | | |
| Broken Bone | Splint | Sling | Ace Bandage | Caregiver's hands |
| Not normal breathing/Drug Overdose | Naloxone Nasal Spray | CPR/AED | | |

After all bleeding is addressed (e.g., the caregiver responds that the patient is not bleeding anywhere else), the medical treatment and guidance system 100 seeks to determine if the patient is conscious. This step is reflected by step 540 in FIG. 5A. In some examples, the medical treatment and guidance system 100 seeks to determine if the patient has an open airway by presenting an inquiry asking "Is the patient talking to you?" This inquiry is important to handle scenarios, for example, where a caregiver thought the patient was only experiencing major bleeding, but instead the patient was not only experiencing major bleeding but was also in cardiac arrest. The patient talking is also an important inquiry because it can indicate whether the patient's airway is blocked, as the patient talking indicates that the airway is not blocked and thus that the patient is breathing. If the caregiver invokes a button indicating that the patient is not talking to them, the medical treatment and guidance system 100 presents instructions to the caregiver to handle situations where the patient is unconscious. Example situations of identifying and treating an unconscious patient are described with reference to FIGS. 13A-13I below.

If the caregiver indicates that the patient is talking to them (e.g., by invoking a button), the medical treatment and guidance system 100 determines that all life-threatening medical emergencies of the patient are being attended to and seeks to determine if there are other patients that have life threatening medical emergencies. In some examples, the medical treatment and guidance system 100 presents an inquiry asking "Is anyone else nearby bleeding badly or unconscious?" If the caregiver indicates that others are bleeding badly or unconscious (e.g., by invoking a button labeled "Yes" in response to the inquiry asking if anyone else is bleeding badly or unconscious), the medical treatment and guidance system 100 can provide an instruction to the caregiver to change their gloves and the medical treatment and guidance system 100 loops back to the beginning of the flow, e.g. the inquiry 512 shown in FIG. 5A asking if the patient is badly bleeding followed by presenting inquiries related to the consciousness of the patient in accordance with the process 500. Switching to others who are bleeding or unconscious is important in scenarios where someone is undergoing a cardiac arrest, in which case it may be needed to treat that person as soon as possible. In this way, the medical treatment and guidance system 100 attends to the bleeding and lack of consciousness emergencies of the other patients before moving on to treat delayed medical emergencies of the patients.

If the caregiver indicates that no one is badly bleeding or unconscious (e.g., by invoking a button labeled "No," in response to the inquiry asking if anyone else nearby is badly bleeding or unconscious, the medical treatment and guidance system 100 proceeds to provide instructions for treating delayed medical emergencies of the patient (e.g., emergencies that need to be treated within 5-6 minutes). At this point, the medical treatment and guidance system 100 seeks to determine a patient characteristic of the patient (e.g., an age classification, a gender, and/or medical injuries of the patient) so that the medical treatment and guidance system 100 can provide medical instructions based on the patient characteristic. These details are further described with reference to FIGS. 6A-6E below.

FIG. 6A shows a process 600 of operations performed by the medical treatment and guidance system 100 accounting for a patient characteristic in accordance with some embodiments. FIG. 6B-6E illustrate the medical treatment and guidance application presenting medical instructions on a user interface of the electronic device associated with the operations of the process 600.

Specifically referring back to the patient characteristic, FIGS. 6A-6E show an example of a patient characteristic that includes an age classification and how the patient characteristic affects the presented medical instructions. In this example, the medical treatment and guidance system 100 presents instructions to assist a caregiver in performing a Heimlich maneuver to treat a choking adult or child while presenting instructions to assist a caregiver in performing a sequence of chest compressions and back blows to treat a choking infant. In some examples, the medical treatment and guidance system 100 begins by presenting the same instructions described with reference to FIG. 5A above. Then the process 600 begins at step 602. The medical treatment and guidance system 100 then presents an inquiry 604 asking the caregiver to "Is the patient badly bleeding?" In this example, the inquiry 604 is the same as the inquiry 512. In this way, if the caregiver indicates that the patient is badly bleeding (e.g., by invoking a button), the medical treatment and guidance system 100 proceeds down the flow path described with reference to FIG. 5A.

On the other hand, if the caregiver indicates that the patient is not badly bleeding, the medical treatment and guidance system 100 then presents an inquiry 606 (shown in FIG. 6B) asking "How old is the patient?" In this way, the medical treatment and guidance system 100 inquires about the age of the patient after the medical treatment and guidance system 100 inquires about bad bleeding of the patient.

Figure 6B:
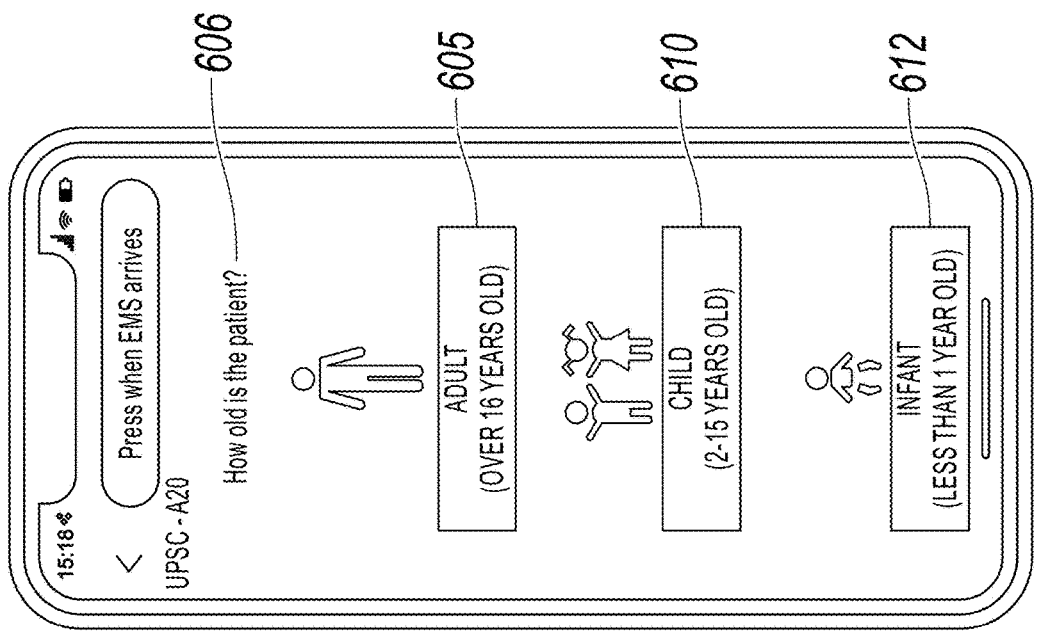
Figure 6E:
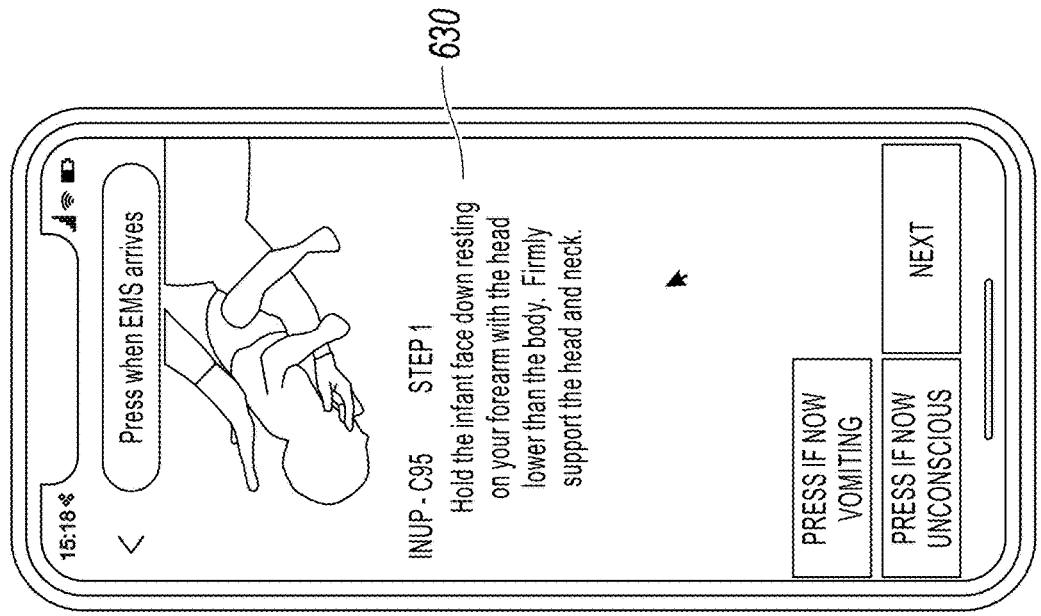
Figure 6D:
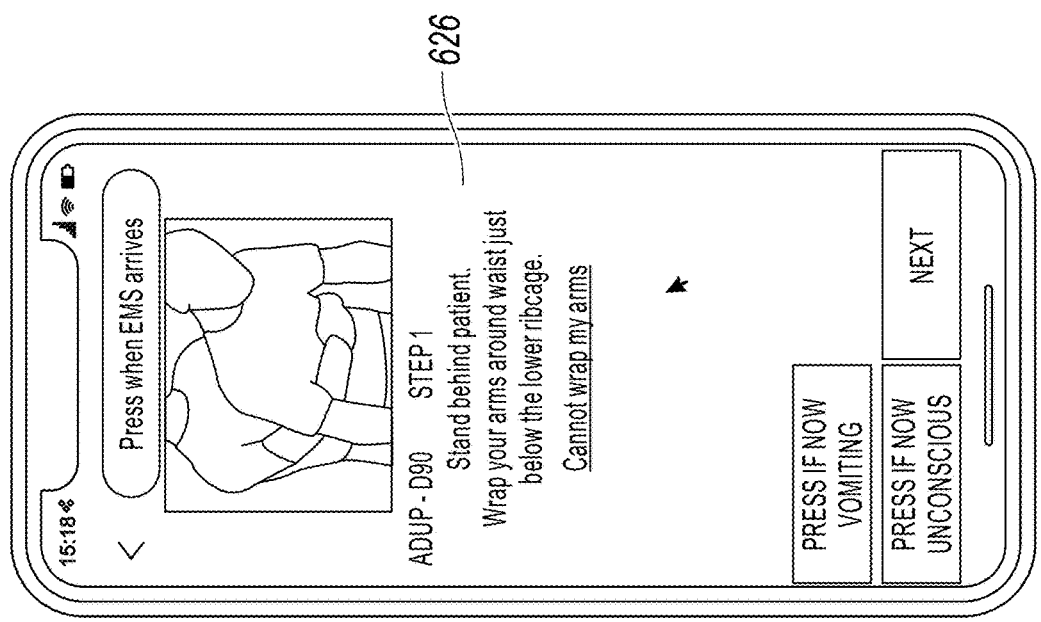

As shown in FIG. 6B, the medical treatment and guidance system 100 presents different buttons for each age classification. In this example, the medical treatment and guidance system 100 presents a button 608 for an adult (e.g., someone older than 15 years old), a button 610 for a child (e.g., someone between the ages of 1 to 15 years old), and a button 612 for an infant (e.g., someone younger than 1 year old). The medical treatment and guidance system 100 also presents an image representing an adult, a child, and an infant adjacent to each respective button 608, 610, and 612 to assist the user in recognizing the age classification of the patient.

For the most part, the medical treatment and guidance system 100 asks the same questions for each age classification but there are some differences. For example, if the caregiver invokes the button 610 indicating that the patient is a child, the medical treatment and guidance system 100 presents an inquiry asking "Is the patient awake?" For example, this inquiry can be part of a consciousness determination where the medical treatment and guidance system 100 is requesting input on whether the patient is awake to rule out the patient being unconscious. In this way, the medical treatment and guidance system 100 inquires about the consciousness of the patient after the medical treatment and guidance system 100 inquires about age of the patient.

If the caregiver indicates that the patient is not awake (e.g., by invoking a button labeled "No" in response to the inquiry asking if the patient is awake), the medical treatment and guidance system 100 seeks to determine if the patient is having a seizure and if CPR is needed. For example, these inquires can be part of identifying and treating an unconscious patient which is described in further detail with reference to FIGS. 13A-13I below. (The example of FIGS. 6A-6E is intended to focus on a choking patient scenario.) If the caregiver indicates that the patient is awake (e.g., by invoking a button labeled "Yes" in response to the inquiry asking if the patient is awake), the medical treatment and guidance system 100 presents an inquiry asking "Was the patient in a car accident, did they fall or is there a possible neck injury?"

The medical treatment and guidance system 100 stores this response of this inquiry as patient state information in memory. This information is stored in memory so that the medical treatment and guidance system 100 can recall this information later and determine medical instructions based on the possibility that the patient may be experiencing a neck injury. Additional details about these techniques are described with reference to FIGS. 9A-9C below.

If the caregiver indicates that the caregiver was in a car accident, fell or has a possible neck injury (e.g., by invoking a button labeled "Yes" in response to the inquiry asking if the patient was in a car accident, fell or has a possible neck injury), the medical treatment and guidance system 100 presents an inquiry asking "Is the patient having trouble breathing?"

In this example, the medical treatment and guidance system 100 includes additional responses to the inquiry asking if the patient is having trouble breathing. In some examples, the medical treatment and guidance system 100 includes a button labeled "Press if now unconscious" to indicate that the patient has become unconscious. This is important in scenarios where the patient becomes nonresponsive while the system 100 is guiding the caregiver via the application. For example, if the caregiver invokes button to indicate that the patient has become unconscious, the medical treatment and guidance system 100 proceeds to provide medical instructions to treat the unconscious patient as described below with reference to FIGS. 13A-13I.

In some examples, the medical treatment and guidance system 100 includes a button to indicate that the patient is vomiting. This is important in scenarios where the patient is vomiting so the medical treatment and guidance system 100 can instruct the caregiver to turn the patient over to avoid choking on vomit. For example, if the caregiver invokes the button to indicate that the patient is vomiting, the medical treatment and guidance system 100 presents instructions to move the patient into a recovery position, allow vomit to drain from the patient's mouth, and roll the patient back, before continuing with the flow. For example, the medical treatment and guidance system 100 can present instructions to "Prepare to place patient in the recovery position," followed by "Allow vomit to drain from the mouth. Roll patient back." Then the medical treatment and guidance system 100 can present the inquiry again asking if the patient is having trouble bleeding. In this way, the medical treatment and guidance system 100 continues where it left off before the caregiver indicated that the patient was vomiting.

If the caregiver indicates that the caregiver is not having trouble breathing (e.g., by invoking a button labeled "No," in response to the inquiry asking if the patient is having trouble breathing), the medical treatment and guidance system 100 proceeds to provide instructions for treating minor medical emergencies of the patient (e.g., emergencies that can be treated after 6 minutes). At this point, the medical treatment and guidance system 100 seeks to determine what type of portable medical treatment and guidance apparatus is available to the caregiver so that the medical treatment and guidance system 100 can provide medical instructions based on the particular medical supplies available to the caregiver. For example, if the caregiver invokes a button to indicate that the patient is not choking, the medical treatment and guidance system 100 proceeds to determine what type of portable medical treatment and guidance apparatus is available to the caregiver. This functionality is further described with reference to FIGS. 7A-7N below.

Returning back to FIG. 6A, if the caregiver indicates that the patient is having trouble breathing (e.g., by invoking a button labeled "Yes," in response to the inquiry asking if the patient is having trouble bleeding), the medical treatment and guidance system 100 presents an inquiry 614 asking "Is the patient choking?"

If the caregiver indicates that the patient is choking (e.g., by invoking a button), the medical treatment and guidance system 100 presents medical instructions 616 instructing the caregiver to treat the choking emergency of the patient based on the age classification of the patient. In examples where the age classification represents a child patient, the medical treatment and guidance system 100 presents instructions 618 for performing a Heimlich maneuver in children while accounting for a difference in height between the caregiver and the patient. In some examples, instructions 618 include one or more of the following instructions. For example, the medical treatment and guidance system 100 presents instructions 620 shown in FIG. 6C that include "STEP 1: Stand or kneel behind patient. Wrap your arms around waist just below the lower ribcage." In this scenario, the medical treatment and guidance system 100 provides instructions to "Stand or kneel behind patient" because the patient is identified as a child and the caregiver may need to kneel to be at the correct height to perform the Heimlich maneuver. In this way, the instructions account for a difference in height between the caregiver and the patient. Accounting for this difference in height is important because it allows for the upward compressions to force an obstruction up and out instead of just lifting up the patient. If the patient were identified as an adult, the instructions would be changed to "Stand behind patient" as explained with reference to FIG. 6D below.

Progressing the instructions through the various steps can be achieved by invoking a button on the user interface and/or by swiping left/right with the caregiver's finger. The instructions 618 can also include one or more of the following instructions. For example, for step 2, the medical treatment and guidance system 100 presents instructions that include "STEP 2: Make a first with one hand and grasp first with the other hand." For step 3, the medical treatment and guidance system 100 presents instructions that include "STEP 3: Thrust in and up with quick, hard thrusts." For step 4, the medical treatment and guidance system 100 presents instructions that include "STEP 4: Repeat until item comes out."

If, on the other hand, the caregiver invokes the button 608 for an adult shown in FIG. 6B, the medical treatment and guidance system 100 presents the same inquires as the child patient, except now the instructions for administering a Heimlich maneuver do not ask the caregiver to kneel behind the patient. For example, the medical treatment and guidance system 100 presents instructions 624 (see FIG. 6A) for performing a Heimlich maneuver in adults while accounting for a similarity in height between the caregiver and the patient. In some examples, the instructions 624 include one or more of the following instructions. For example, the medical treatment and guidance system 100 presents instructions 626 (shown in FIG. 6D) of "STEP 1: Stand behind patient. Wrap your arms around waist just below the lower ribcage." In this example, the medical treatment and guidance system 100 presents different instructions based on the patient's age classification.

If, on the other hand, the caregiver invokes the button 612 for an infant shown in FIG. 6B, the medical treatment and guidance system 100 presents the same inquires shown as the adult and child patients, except now the instructions include administering a sequence of chest compressions and back blows to the infant patient instead of a Heimlich maneuver. This is because a Heimlich maneuver describes a sub-diaphragmatic thrust for adults and children while the sequence of chest compressions and back blow is for infants. In this example, the medical treatment and guidance system 100 presents an instruction 628 (see FIG. 6A) for performing a sequence of chest compressions and back blows to infant patients. In some examples, the instructions 628 include one or more of the following instructions. For example, the medical treatment and guidance system 100 presents an instruction to "Prepare to give 5 back blows then 5 chest compressions." The medical treatment and guidance system 100 presents the instruction using inverted colors (e.g., the text is white and the background is black) to emphasize the instruction for this particular step.

The medical treatment and guidance system 100 then presents instructions 630 (shown in FIG. 6E) including "STEP 1: Hold the infant face down resting on your forearm with the head lower than the body. Firmly support the head and neck." Progressing the instructions through the various steps can be achieved by invoking a button on the user interface and/or by swiping left/right with the caregiver's finger. For example, for step 2, the medical treatment and guidance system 100 presents instructions that include "STEP 2: Give 5 hard blows high on the back between the shoulder blades." For step 3, the medical treatment and guidance system 100 presents instructions that include "STEP 3: Place the infant on a hard surface or forearm." For step 4, the medical treatment and guidance system 100 presents instructions that include "STEP 4: Place ads of two fingers in the center of the chest. Push down about 1.5 inches. Perform 5 compressions." The medical treatment and guidance system 100 then presents instructions to "Hold the infant in a comfortable position with their head slightly elevated." In this example, the medical treatment and guidance system 100 presents different instructions based on the patient's age classification.

Once all of the instructions 616 have been presented, the medical treatment and guidance system 100 presents an inquiry 614 asking if the patient is still choking, and if so, the medical treatment and guidance system 100 continues to provide instructions 616 to treat the choking emergency based on the age classification of the patient. If the patient is not choking (e.g., if the caregiver invokes a button labeled "No" to indicate that the patient is not choking) or the patient is no longer choking, the medical treatment and guidance system 100 proceeds to step 622 to determine what type of portable medical treatment and guidance apparatus is available to the caregiver. This example is described in further detail with reference to FIGS. 7A-7N below.

This example illustrates a scenario where the patient characteristic is an age classification and determining the instructions for assisting the caregiver in treating the patient are determined based on the age classification. In particular, the instructions include instructions for treating a choking medical emergency and the instructions are different depending on whether the patient is an infant, a child, or an adult based on the age classification. The instructions for treating the choking medical emergency account for the height of the patient's waist based on whether the patient is a child or an adult based on the age classification. The instructions for treating the choking medical emergency follow a Heimlich maneuver for adults and children and follow a sequence of chest compressions and back blows for infants based on the age classification. In this way, the medical treatment and guidance system 100 presents instructions for treating the choking medical emergency that include instructions for a administering a Heimlich maneuver to adult patients and children patients based on the age classification and instructions for administering a sequence of chest compressions and back blows for infant patients based on the age classification.

In some embodiments, the medical treatment and guidance system 100 presents instructions that depend on the gender of the patient. For example, the medical treatment and guidance system 100 can present modified instructions for male patients vs. female patients. In some examples, the medical treatment and guidance system 100 can present modified instructions for pregnant female patients.

While the example shown in FIGS. 6A-6E highlighted the dependency of age on a Heimlich maneuver (or sequence of chest compressions and back blows), other aspects of the medical treatment and guidance system 100 are based on an age classification as well. For example, all of the medical emergencies shown in Table 2 below include a dependency on patient age.

TABLE 2

Medical instructions depend on patient age.

| Unconscious | Trouble Breathing | Allergic Reaction | Allergy Medicine |
|---|---|---|---|
| Prescription medicine (regulatory) | CPR | Choking | Chest injury |
| Fracture care | Diabetic problems | Seizures | Chest pain |
| Airway management | Palpitations | Medication assistance | Pain |

For example, the medical treatment and guidance system 100 includes medical instructions that depend on age for a patient experiencing a choking medical emergency according to Table 3 below (e.g., this example corresponds to the example described with reference to FIGS. 6A-6E above). Note: in the following tables "medical treatment and guidance system 100" is abbreviated as "system."

TABLE 3

Medical instructions for treating a choking patient based on patient age.

| | |
|---|---|
| Adult | The system provides instructions to stand behind the patient and perform a Heimlich maneuver in compliance with American Heart Association standards for adults. The system provides instructions to administer chest compressions if the patient becomes unconscious. The system provides modified instructions for large or pregnant patients. For example, Step 1 has a link labeled "cannot wrap my arms" (see FIGS. 6C and 6D) and the pop up shows a modification in technique. For example, the modification in technique can be for the caregiver to move their arms up on the patient's torso. |
| Child | The system provides instructions to stand or kneel behind the patient and perform a modified Heimlich maneuver in compliance with American Heart Association standards for children. For example, the modification relates to getting into the right position behind a child who is shorter. This allows for the upward compressions to force an obstruction up and out instead of just lifting up the patient. The system provides instructions to administer chest compressions if the patient becomes unconscious. |
| Infant | The system provides instructions to hold the infant face down and perform a sequence of chest compressions and back blows in compliance with American Heart Association standards for infants. For example, the Heimlich maneuver is describing a sub-diaphragmatic thrust for adults and children while the sequence of chest compressions and back is for infants. |

As another example, the medical treatment and guidance system 100 includes medical instructions that depend on age for a patient experiencing diabetic problems and/or seizures according to Table 4 below.

TABLE 4

Medical instructions for treating diabetic problems and/or seizures based on patient age.

| | |
|---|---|
| Adult | The system provides instructions to administer oral glucose with altered mental status and perceived hypoglycemia. The system provides instructions for the swallowing the glucose. |
| Child | The system provides instructions to administer oral glucose with altered mental status and perceived hypoglycemia. The system provides instructions for the swallowing the glucose. |
| Infant | The system does not recommend administering oral glucose with altered mental status to infants. |

As another example, the medical treatment and guidance system 100 includes medical instructions that depend on age for a patient experiencing a chest pain medical emergency according to Table 5 below. An example flow relating to treating chest palpitations is described in detail with reference to FIGS. 10A-10F below and an example flow relating to treating dull and/or sharp chest pain is described in detail with reference to FIGS. 11A-11D below.

TABLE 5

Medical instructions for treating chest pain based on patient age.

| | |
|---|---|
| Adult | The system provides instructions to administer aspirin for dull/ache chest pain. The system provides instructions to administer nitroglycerin for patients that currently have a prescription for nitroglycerin. |
| Child | The system presents an inquiry asking if the child is older than 10 years old. If so, the system provides instructions for administering aspirin. If not, the system does not recommend administering aspirin. For example, the system does not provide instructions to administer aspirin to children aged 10 years old or younger due to a potential condition called Reye's Syndrome. The system does not inquire about nitroglycerin. |
| Infant | The system skips instructions for infants as infants cannot provide verbal answers to the inquiries. |

As another example, the medical treatment and guidance system 100 includes medical instructions that depend on age for a patient experiencing an allergic reaction medical emergency according to Table 6 below. An example flow relating to treating allergic reactions based on patient age is described in detail with reference to FIGS. 8A-8J below.

TABLE 6

Medical instructions for treating an allergic reaction based on patient age.

| | |
|---|---|
| Adult | The system provides instructions to administer medication including an adult dosage of diphenhydramine. The system provides instructions to assist with a prescribed inhaler. |
| Child | The system provides instructions to administer medication including a dose of diphenhydramine based on the weight and/or size of the patient. The system provides instructions to assist with a prescribed inhaler. |
| Infant | The system does not recommend administering allergy medicine to infants. The system provides instructions to care for stings. The system provides instructions to assist with a prescribed inhaler. |

As another example, the medical treatment and guidance system 100 includes medical instructions that depend on age for a patient requiring CPR according to Table 7 below. An example flow relating to administering CPR to an unconscious patient based on patient age is described in detail with reference to FIGS. 13A-13I below.

TABLE 7

Medical instructions for administering CPR based on patient age.

| | |
|---|---|
| Adult | The system provides instructions to retrieve an AED first, then the system provides instructions to administer hands-only CPR to adults after an AED has been found. The system provides additional instructions to a second caregiver when a second caregiver is available to assist. |
| Child | The system provides instructions to start CPR first then the system provides instructions to retrieve an AED after CPR has begun. The system provides instructions to administer breathing steps of the CPR process to children. The system provides instructions that alternate between rescue breathing and compressions for children. The system provides additional instructions to a second caregiver when a second caregiver is available to assist. |

TABLE 7-continued

Medical instructions for administering CPR based on patient age.

| | |
|---|---|
| Infant | The system provides instructions to start CPR first then the system provides instructions to retrieve an AED after CPR has begun. The system provides instructions that focus on the airway and repositioning of the airway (e.g., arrest of an infant's respiratory airway can lead to infant cardiac arrest). The system provides instructions that alternate between rescue breathing and compressions for infants. The system provides additional instructions to a second caregiver when a second caregiver is available to assist. |

As another example, the medical treatment and guidance system 100 includes medical instructions that depend on age for a patient experiencing a broken bone fracture according to Table 8 below. In some examples, the medical treatment and guidance system 100 skips instructions to treat fractures when the caregiver does not have access to a portable medical treatment and guidance apparatus with medical supplies to treat fractures (e.g., if the portable medical treatment and guidance apparatus does not have a splint, the medical treatment and guidance system 100 may not provide instructions to treat the fracture). Additional details regarding fractures and apparatus type are described with reference to FIGS. 7A-7N below.

TABLE 8

Medical instructions for treating fractures based on patient age.

| | |
|---|---|
| Adult/Child | The system provides instructions based on which body part is fractured. The system provides instructions to avoid manipulation of fractures above the elbow or knee. The system provides positioning instructions for the patient based on memory (e.g., whether or not the patient is experiences a neck injury.) |
| Infant | The system provides instructions to treat the fracture with ice packs. The system provides instructions for the caregiver to maintain the comfort of the infant. |

For example, all of the portable medical treatment and guidance apparatuses have the capability to treat life threatening medical emergencies such as major bleeding and chest wounds because each portable medical treatment and guidance apparatus includes a tourniquet and a chest seal. However, not all have a splint or other medical supplies to treat minor medical emergencies. As a result, the medical treatment and guidance system 100 determines which medical instructions to present based on the apparatus available to the caregiver based on the apparatus type.

FIGS. 7A-7C show a process 700 of the operations performed by the medical treatment and guidance system 100 based on a particular medical treatment and guidance apparatus available to the caregiver in accordance with some embodiments. FIG. 7D-7N illustrate the medical treatment and guidance application presenting medical instructions on a user interface of the electronic device associated with the operations of the process 700.

In this example, the medical treatment and guidance system 100 determines an apparatus type (e.g., pouch, backpack, hard case) of the portable medical treatment and guidance apparatus based on at least one apparatus type input after determining the patient characteristic. In turn, the medical treatment and guidance system 100 provides medical instructions based on the particular medical supplies available to the caregiver based on the apparatus type. For example, the medical treatment and guidance system 100 presents instructions for assisting the caregiver in treating the patient experiencing the medical emergency based on the determined apparatus type.

In this example, the medical treatment and guidance system 100 presents inquiries and instructions to assist a caregiver in treating a fracture. The medical treatment and guidance system 100 begins similarly to the processes 500, 600 described above with respect to FIGS. 5A and 6A. In particular, the medical treatment and guidance system 100 can begin at step 702 and then present an inquiry 704 asking the caregiver "Is the patient badly bleeding?" In response to the inquiry 704, if the caregiver indicates that the patient is badly bleeding (e.g., by invoking a button), the medical treatment and guidance system 100 proceeds down the flow path described with reference to FIG. 5A. In response to the inquiry 704, if the caregiver indicates that the patient is not badly bleeding (e.g., by invoking a button), the medical treatment and guidance system 100 presents an age classification inquiry 706 (shown in FIG. 7D) asking the caregiver to indicate whether the patient is an adult, a child, or an infant. So far this flow example is the same as the process 600 of FIG. 6A described above.

In response, if the caregiver indicates "Adult," the medical treatment and guidance system 100 presents an inquiry asking "Is the patient awake?" In response, if the caregiver indicates "Yes," the medical treatment and guidance system 100 presents an inquiry asking the caregiver "Was the patient in a car accident, did they fall or is there a possible neck injury?" In response, if the caregiver indicates "No," the medical treatment and guidance system 100 presents an inquiry asking the caregiver "Is the patient having trouble breathing?" In response, if the caregiver indicates "No," the medical treatment and guidance system 100 presents an inquiry 708 (shown in FIG. 7E) asking the caregiver to select which apparatus type is available to the caregiver. In this example, the medical treatment and guidance system 100 presents inquiry 708 asking the caregiver to "Press the button for the Mobilize kit you are using." In this example, a portable medical treatment and guidance apparatus is identified as a "Mobilize kit." In this example, the medical treatment and guidance system 100 presents two portable medical treatment and guidance apparatuses for the caregiver to choose from. The medical treatment and guidance system 100 presents an image 710 of the compact (or "pouch type") portable medical treatment and guidance apparatus 340 and a button 712 for the caregiver to choose the compact type portable medical treatment and guidance apparatus 340. The medical treatment and guidance system 100 also presents an image 714 of the comprehensive (or "hardcase/backpack type") portable medical treatment and guidance apparatus 300, 320, and a button 716 for the caregiver to choose the comprehensive portable medical treatment and guidance apparatus. In other examples, the medical treatment and guidance system 100 presents more than two portable medical treatment and guidance apparatuses to choose from (e.g., 3, 4, etc.).

If the caregiver invokes the button 716 to select the comprehensive portable medical treatment and guidance apparatuses, the medical treatment and guidance system 100 presents an inquiry asking the caregiver "Are there any other patients with bad bleeding, unconscious or having trouble breathing?" In this way, the medical treatment and guidance system 100 presents instructions to assist patients experiencing bad bleeding, unconscious or having trouble breathing before treating patients with non-life-threatening medical emergencies. In response, if the caregiver indicates that no other patients are experiencing bad bleeding, unconscious or having trouble breathing, the medical treatment and guidance system 100 presents an inquiry asking the caregiver "What is wrong with the patient?"

In some examples, the medical treatment and guidance system 100 presents a response button to indicate a medical issue, a response button to indicate an injury, and a response button to indicate that the caregiver is not sure what is wrong with the patient. In response, if the caregiver indicates "I am not sure," the medical treatment and guidance system 100 presents an inquiry asking the caregiver "Is there bleeding from an injury?" In response, if the caregiver indicates "No," the medical treatment and guidance system 100 presents an inquiry 718 (shown in FIG. 7F) asking the caregiver "Is the problem one of these:" and presents a response button 720 to indicate that the patient has burns, a response button 722 to indicate that the patient has a possible broken bone, and a response button 724 to indicate that the patient does not have any of these problems. In response, if the caregiver indicates "Possible broken bone," the medical treatment and guidance system 100 presents an inquiry 726 (see FIG. 7A) asking the caregiver to "Touch the area of worst pain" to identify where the patient has a possible broken bone injury. In some examples, inquiry 726 is the same as inquiry 516 shown in FIG. 5B.

If the caregiver invokes a radio button associated with a left foot/ankle of the patient, the medical treatment and guidance system 100 presents an instruction 728 asking the caregiver to "Assist patient to a comfortable position; seated or lying down is best. Do not move or straighten the broken bone." The medical treatment and guidance system 100 then presents an inquiry asking the caregiver "Is there a visible open wound?" If the caregiver indicates "Yes," as in this example, the medical treatment and guidance system 100 presents an instruction 730 asking if the caregiver has gauze, e.g., by asking the caregiver to "Locate gauze labeled Gauze 3" from the comprehensive kit that was selected in inquiry 708. In some examples, the medical treatment and guidance system 100 presents a button for indicating that the gauze is unavailable.

The medical treatment and guidance system 100 then presents instructions 732 to assist the caregiver in applying tape and tape gauze firmly to the patient. For example, medical treatment and guidance system 100 can present the instruction 734 (shown in FIG. 7G) asking the caregiver to "Locate tape and tape gauze firmly" on the patient.

The medical treatment and guidance system 100 then presents an instruction 736 asking if the caregiver has a splint, e.g., by asking the caregiver to "Locate the splint labeled Splint 1." In this way, the medical treatment and guidance system 100 asks the caregiver to use a medical supply that is expected to be present in the comprehensive kit selected per inquiry 708. In some examples, the medical treatment and guidance system 100 presents a button for indicating that the splint is unavailable. In these cases, the medical treatment and guidance system 100 will proceed to determine alternative medical supplies and/or skip instructions associated with the unavailable medical supplies.

Similarly, the medical treatment and guidance system 100 presents an instruction 738 asking if the caregiver has elastic wrap, e.g., by asking the caregiver to "Locate elastic wrap labeled Elastic Wrap 9." In some examples, the medical treatment and guidance system 100 presents a button for indicating that the elastic wrap is unavailable.

If the caregiver indicates that both the splint and elastic wrap are available and located (e.g., by invoking one or more buttons), as in this example, the medical treatment and guidance system 100 presents instructions 740 to assist the caregiver in applying the splint and elastic wrap to the patient. In some examples, the instructions 740 include one or more of the following instructions. For example, the medical treatment and guidance system 100 can present an instruction asking the caregiver to "Prepare to apply the splint to ankle/foot." The medical treatment and guidance system 100 can present an instruction 742 (shown in FIG. 7H) of "STEP 1: Bend the splint into a u-shape." The medical treatment and guidance system 100 then presents an instruction of "STEP 2: Form the splint around the patient's foot and ankle." The medical treatment and guidance system 100 then presents an instruction of "STEP 3: Ensure entire injured area is supported by the splint." The medical treatment and guidance system 100 then presents an instruction of "STEP 4: Ask patient to help hold the splint." In some examples, the instructions 740 also include one or more of the following instructions. After the splinting of the foot/ankle, the medical treatment and guidance system 100 presents an instruction asking the caregiver to "Prepare to apply the elastic wrap." The medical treatment and guidance system 100 then presents an instruction 744 (shown in FIG. 7I) of "STEP 1: Start at the highest point on the splint." The medical treatment and guidance system 100 then presents an instruction of "STEP 2: Wrap around leg and splint working towards the toes." The medical treatment and guidance system 100 then presents an instruction of "STEP 3: Wrap should be snug, but no so tight it cuts off circulation." The medical treatment and guidance system 100 then presents an instruction of "STEP 4: Secure wrap with clips."

The medical treatment and guidance system 100 then presents an instruction 746 (see FIG. 7A) asking if the caregiver has an ice pack, e.g., by asking the caregiver to "Locate the ice pack labeled Ice Pack 8." In some examples, the medical treatment and guidance system 100 presents a button for indicating that the ice pack is unavailable and, in response, skips the instructions associated with the ice pack. If the caregiver indicates that the ice pack is available and located (e.g., by invoking a button), as in this example, the medical treatment and guidance system 100 presents instructions 748 to assist the caregiver in applying the ice pack to the patient.

In some examples, the instructions 748 include one or more of the following instructions. For example, the medical treatment and guidance system 100 can present an instruction asking the caregiver to "Prepare to apply the ice pack to the injured area." The medical treatment and guidance system 100 can present an instruction 750 (shown in FIG. 7J) of "STEP 1: Activate cold pack by firmly squeezing pouch. Place on injured area." The medical treatment and guidance system 100 then presents an instruction of "STEP 2: Ask patient to hold cold pack in place." Then the medical treatment and guidance system 100 presents an inquiry 752 (shown in asking the caregiver "Is there anything else wrong with the current patient?"

In the above example, the caregiver selected the comprehensive medical treatment and guidance apparatus in response to inquiry 708 and the caregiver indicated that the patient may have a broken foot or ankle in response to the inquiry 718. In turn, the medical treatment and guidance system 100 provided instructions to use a splint, an elastic wrap, and an ice pack to treat the broken foot or ankle. In this particular example, is the wound was indicated to be an open wound, the medical treatment and guidance system 100 also provides instructions to use gauze.

In the following example, the same adult patient and comprehensive medical treatment and guidance apparatus is identified, but the broken bone injury is changed from an ankle or foot fracture to an elbow fracture. As a result, the medical treatment and guidance system 100 provides instructions that depend on where the broken bone fracture is located on the patient's body.

To illustrate this scenario, the caregiver indicates that the broken bone fracture is an elbow fracture. The medical treatment and guidance system 100 provides the same inquiries and instructions as the above example, except the caregiver presses a different radio button in response to inquiry 726 (see FIG. 7A). For example, if the caregiver invokes a radio button indicating a possible fracture near the elbow area of the patient, a left elbow in this example, the medical treatment and guidance system 100 proceeds down the flow path shown in FIG. 7B. (The connection between FIGS. 7A and 7B is represented by connection marker B.)

Referring to FIG. 7B, the medical treatment and guidance system 100 presents instructions 754 asking the caregiver to "Assist patient to a comfortable position; seated or lying down is best. Do not move fractures." The medical treatment and guidance system 100 then presents an inquiry asking the caregiver "Is there a visible open wound?" In response, if the caregiver indicates that the patient has a visible open wound, as in this example, the medical treatment and guidance system 100 presents an instruction 756 asking if the caregiver has gauze, e.g., by asking the caregiver to "Locate gauze labeled Gauze 3." So far in this example flow, the instructions and inquiries are the same as the above example with the fractured ankle.

The medical treatment and guidance system 100 then presents instructions 758 to assist the caregiver in applying tape and tape gauze firmly to the patient's arm. In some examples, the instructions 758 include one or more of the following instructions. For example, the medical treatment and guidance system 100 can present instructions 760 (shown in FIG. 7K) asking the caregiver to "Locate tape and tape gauze firmly." In this example, the medical treatment and guidance system 100 presents an image of an elbow instead of an image of an ankle or foot to assist the caregiver in visualizing how to administer the treatment to the patient. In other words, the medical instructions can depend on the particular area of the body that is injured.

The medical treatment and guidance system 100 then presents an instruction 762 asking if the caregiver has a splint, e.g., by asking the caregiver to "Locate the splint labeled Splint 1." Similarly, the medical treatment and guidance system 100 presents an instruction 764 asking if the caregiver has elastic wrap, e.g., by asking the caregiver to "Locate elastic wrap labeled Elastic Wrap 9." In some examples, the medical treatment and guidance system 100 presents a button for indicating that the splint and/or elastic wrap is unavailable. In these cases, the medical treatment and guidance system 100 will proceed to determine alternative medical supplies and/or skip instructions associated with the unavailable medical supplies.

If the caregiver indicates that the caregiver has a splint and elastic wrap, as in this example, the medical treatment and guidance system 100 then presents instructions 766 to assist the caregiver in applying the splint and elastic wrap to the patient's arm. In some examples, the instructions 766 include one or more of the following instructions. For example, the medical treatment and guidance system 100 can present instruction asking the caregiver to "Prepare to apply splint to arm." The medical treatment and guidance system 100 can then present an instruction 768 (shown in FIG. 7L) of "STEP 1: Open splint and bend, roll one end into a handle." The medical treatment and guidance system 100 then presents an instruction of "STEP 2: Shape lengths of the splint into a cup shape for stability." The medical treatment and guidance system 100 then presents an instruction of "STEP 3: Place the splint against the arm." The medical treatment and guidance system 100 then presents an instruction of "STEP 4: Ask patient to help hold the splint."

Similarly, the instructions 766 can include one or more of the following instructions. The medical treatment and guidance system 100 presents an instruction asking the caregiver to "Prepare to apply elastic wrap." The medical treatment and guidance system 100 then presents an instruction 770 (shown in FIG. 7M) of "STEP 1: Start at the highest point on the arm." The medical treatment and guidance system 100 then presents an instruction of "STEP 2: Wrap around arm and splint working towards the fingers." The medical treatment and guidance system 100 then presents an instruction of "STEP 3: Wrap should be snug, but not so tight it cuts off circulation." The medical treatment and guidance system 100 then presents an instruction of "STEP 4: Secure wrap with clips."

The medical treatment and guidance system 100 then presents an instruction 772 asking if the caregiver has an ice pack, e.g., by asking the caregiver to "Locate the ice pack labeled ice pack 8." In response, if the caregiver indicates that the caregiver has an ice pack, as in this example, the medical treatment and guidance system 100 then presents instructions 774 to assist the caregiver in applying the ice pack to the patient's arm. For example, the medical treatment and guidance system 100 presents an instruction asking the caregiver to "Prepare to apply the ice pack to the injured area." The medical treatment and guidance system 100 then presents an instruction of "STEP 1: Activate cold pack by firmly squeezing pouch. Place on injured area." The medical treatment and guidance system 100 then presents an instruction of "STEP 2: Ask patient to hold cold pack in place."

The medical treatment and guidance system 100 then presents an instruction 776 asking if the caregiver has a triangular bandage, e.g., by asking the caregiver to "Locate the triangular bandage labeled triangular bandage 11." In response, if the caregiver indicates that the caregiver has a triangular bandage, as in this example, the medical treatment and guidance system 100 then presents instructions 778 to assist the caregiver in applying the triangular bandage to the patient's arm. In some examples, the instructions 778 include one or more of the following instructions. For example, the medical treatment and guidance system 100 presents an instruction 780 (shown in FIG. 7N) of "Wrap triangular bandage around the arm to splint the arm." In some examples, the medical treatment and guidance system 100 presents a button for indicating that the triangular bandage is unavailable.

The medical treatment and guidance system 100 then presents the inquiry 752 (described above) asking the caregiver "Is there anything else wrong with the current patient."

In the above example, the medical treatment and guidance system 100 provided instructions that depend on where the injury is located on the patient's body. In particular, the instructions included different images and different text depending on whether the injury was an injured ankle/foot or an injured elbow. The instructions also included different medical supplies depending on where the injury is located on the patient's body. In particular, the instructions included instructions for using a triangular bandage in the case where the injury was an injured elbow, but the instructions did not include instructions for using a triangular bandage in the case where the injury was an injured ankle or foot. The medical treatment and guidance system 100 provided instructions for using gauze, a splint, elastic wrap, and ice to treat the patient experiencing a possible broken ankle or foot injury and provided instructions for using gauze, a splint, elastic wrap, ice, and a triangular bandage to treat the patient experiencing a possible broken elbow injury.

The above example also related to the use of a comprehensive medical treatment and guidance apparatus as the apparatus type. The medical treatment and guidance system 100 had access to predetermined information of what medical supplies were present within the particular medical treatment and guidance apparatus available to the caregiver and provided instructions that used at least some of those available medical supplies. In this example, the medical supplies known to the system 100 as being present within a comprehensive medical treatment and guidance apparatus include gauze, a splint, elastic wrap, an ice pack, and a triangular bandage and are thus the medical supplies asked about in various inquiries in FIGS. 7A-7C. However, in some instances, one or more of these medical supplies may not be available to the caregiver, in which case the caregiver would indicate "No" as to whether the caregiver has that particular medical supply and the system 100 would not provide any instruction on that particular medical supply's use and can in some examples present an inquiry as to whether a second choice medical supply is available, as discussed herein. One or more of medical supplies may not be available to the caregiver despite the medical supplies being predetermined as available in a comprehensive medical treatment and guidance apparatus for any of a variety of reasons. For example, the medical supply may have been used in a previous emergency situation and inadvertently not restocked in the comprehensive medical treatment and guidance apparatus. For another example, the medical supply may actually be present but not quickly found by the caregiver in the chaos and stress of an emergency situation. For yet another example, multiple injuries and/or multiple patients may be being treated with the same comprehensive medical treatment and guidance apparatus and there are not an adequate number of a particular medical supply stocked in the comprehensive medical treatment and guidance apparatus for each injury or patient.

In the following example, a compact medical treatment and guidance apparatus is identified as the apparatus type instead of the comprehensive medical treatment and guidance apparatus. As a result, the medical treatment and guidance system 100 changes the inquiries and instructions based on the predetermined medical supplies within the compact medical treatment and guidance apparatus. The following example also assumes the scenario with an injured ankle.

Figure 7E:
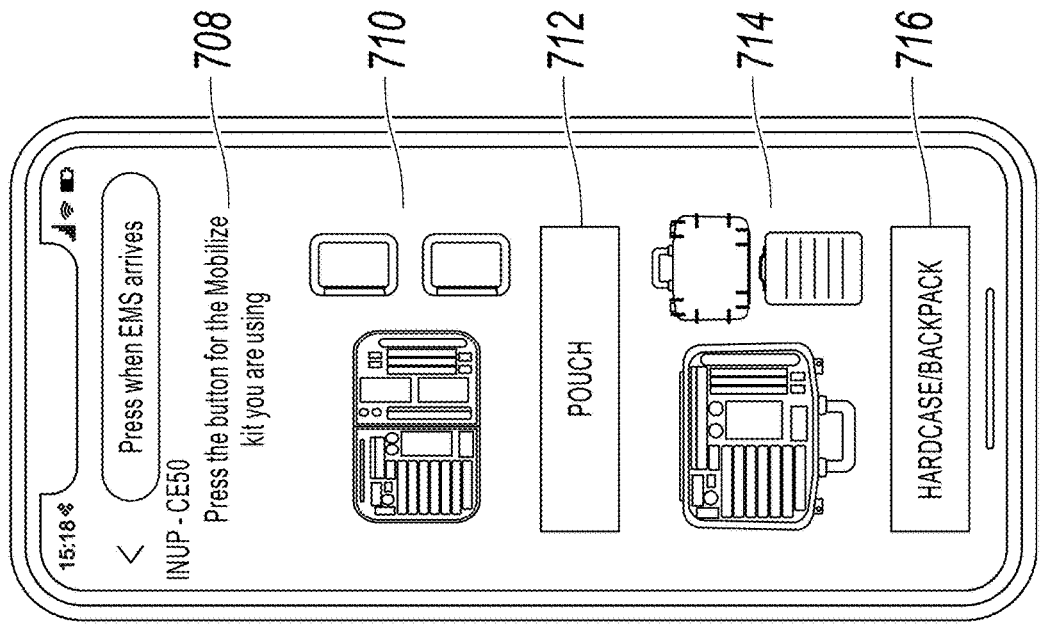
Figure 7D:
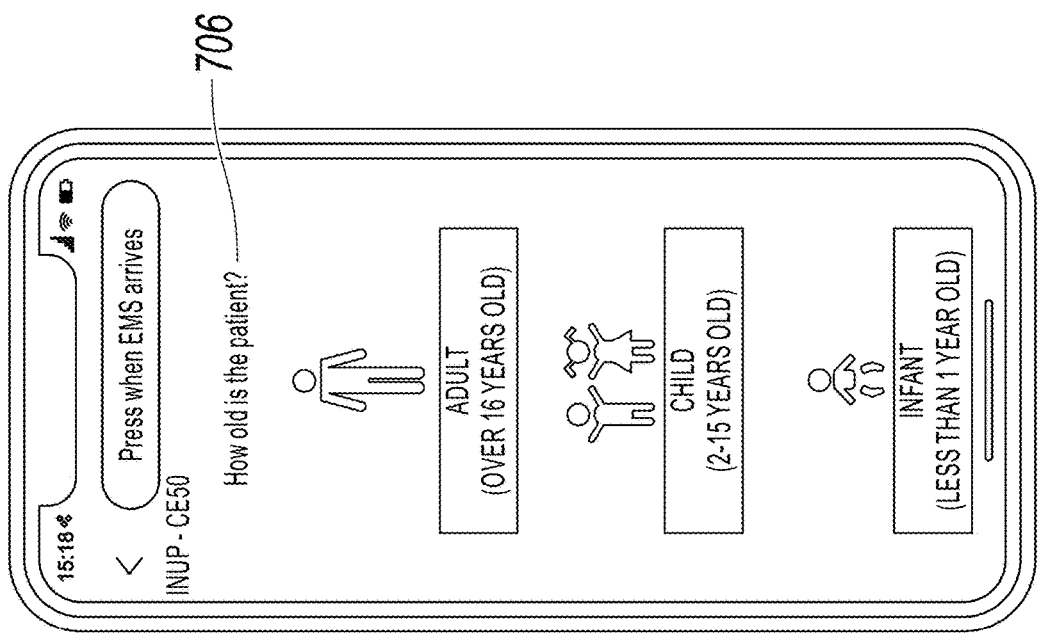
Figure 7G:
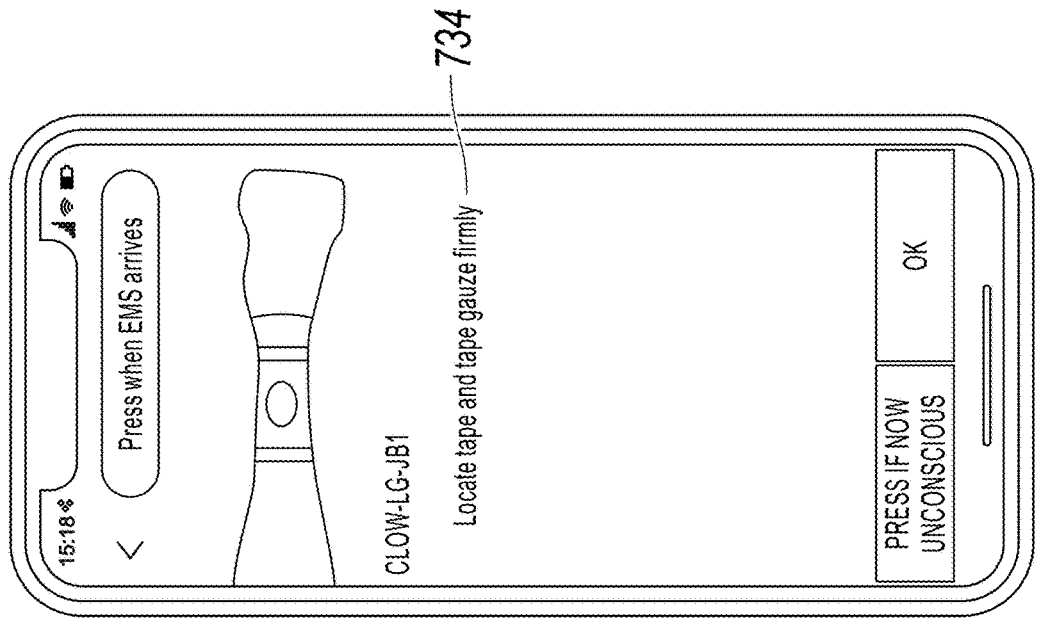
Figure 7F:
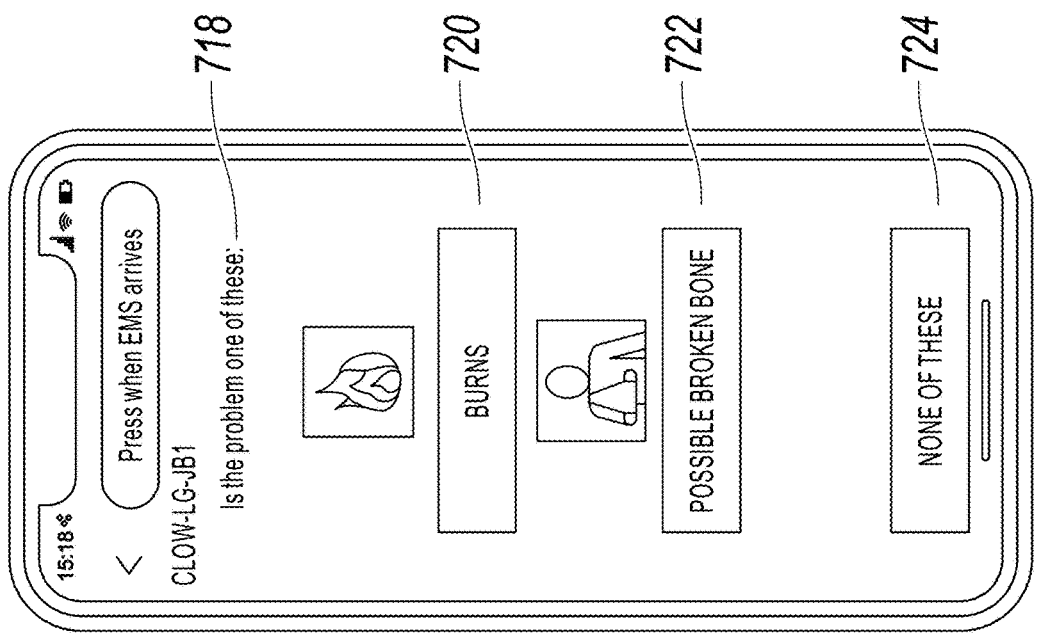
Figure 7I:
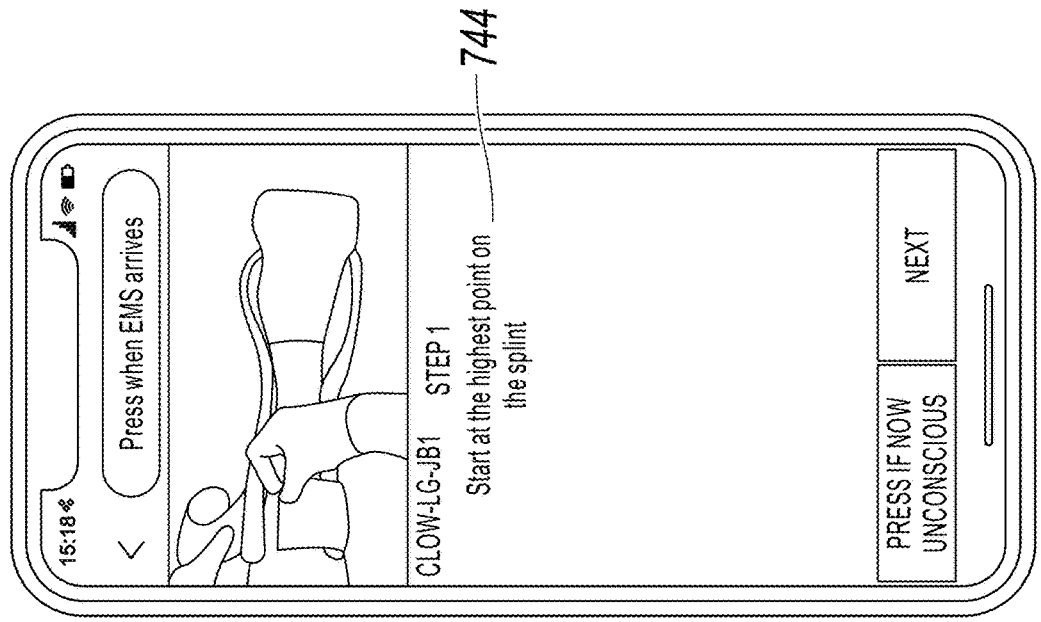
Figure 7H:
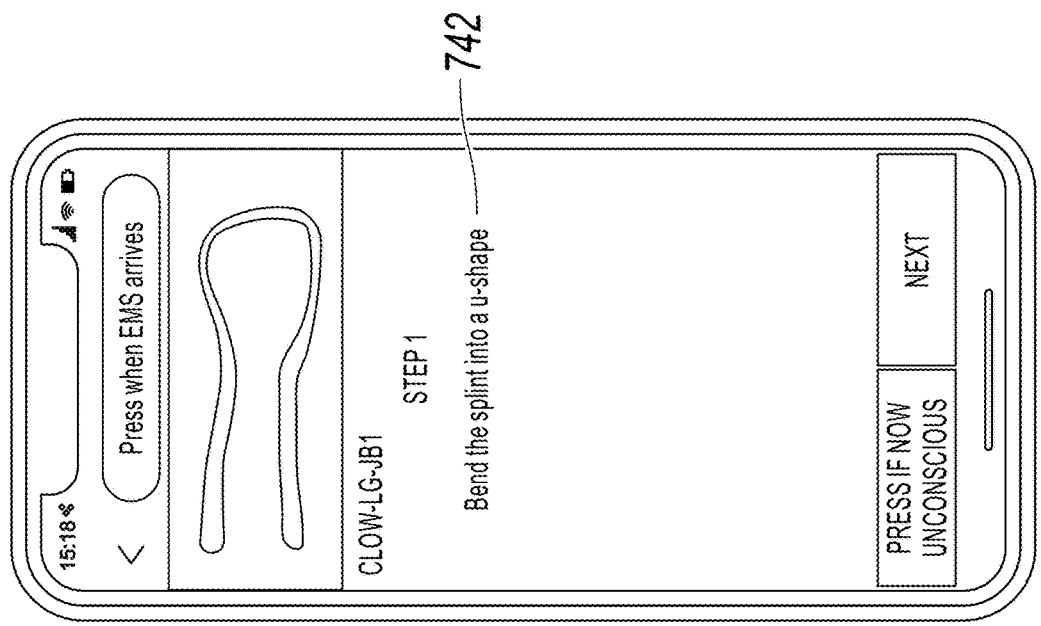
Figure 7K:
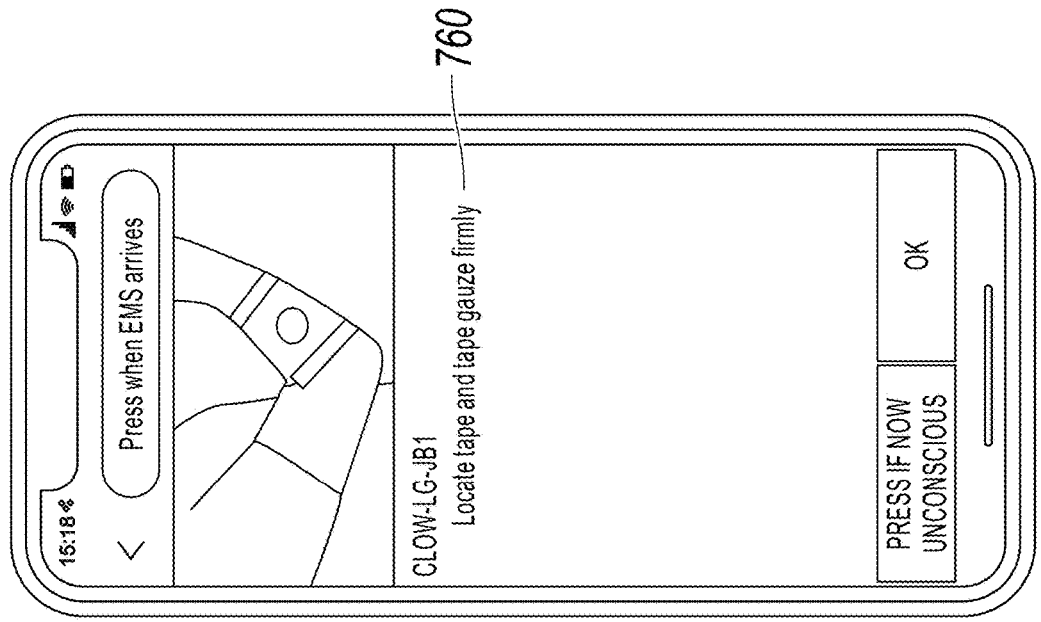
Figure 7J:
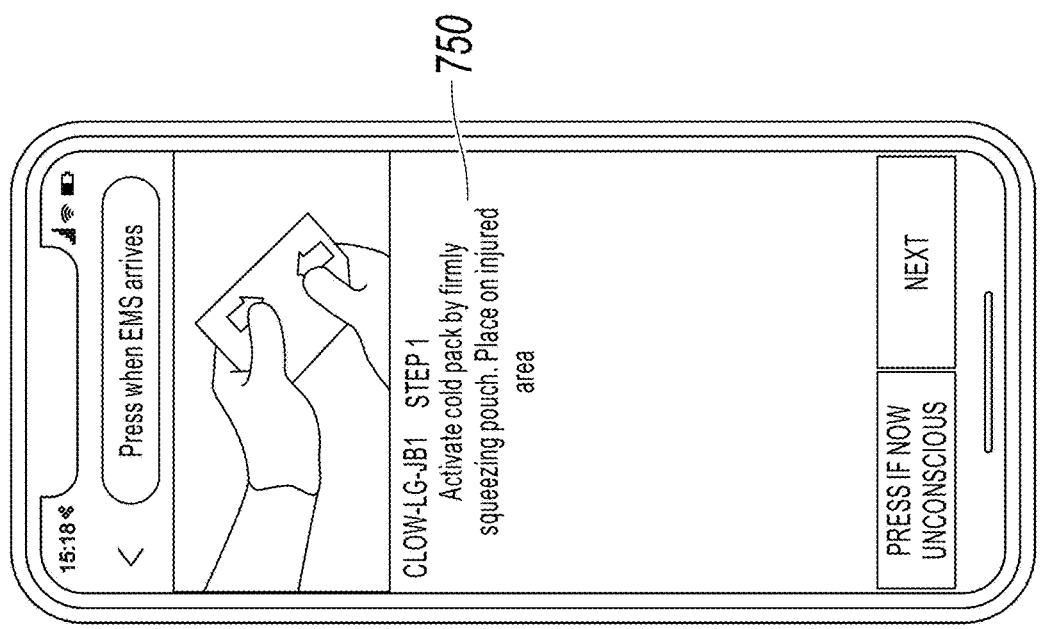
Figure 7M:
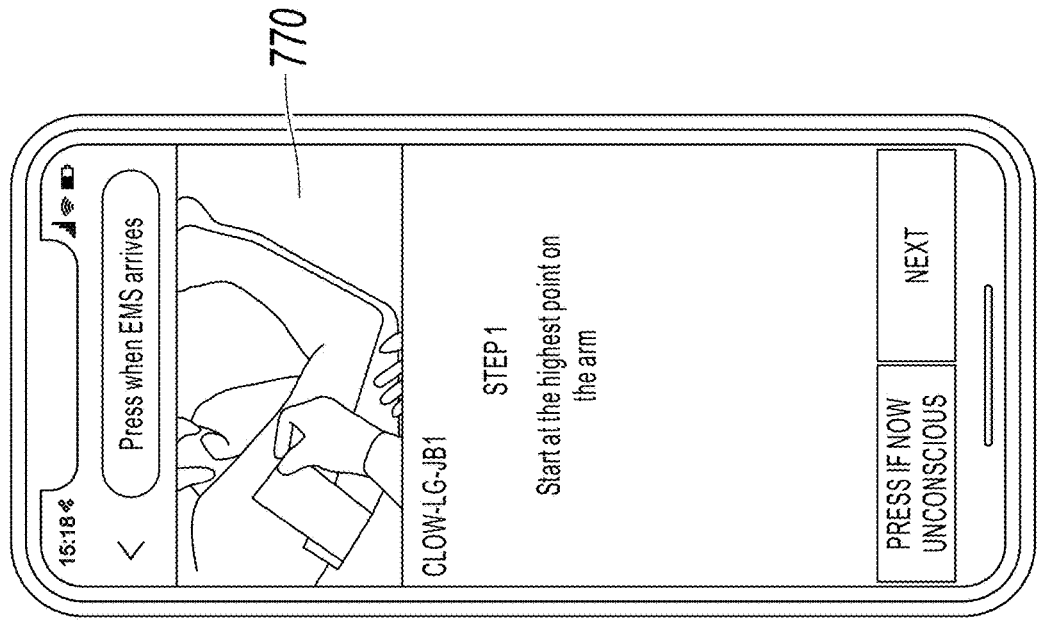
Figure 7L:
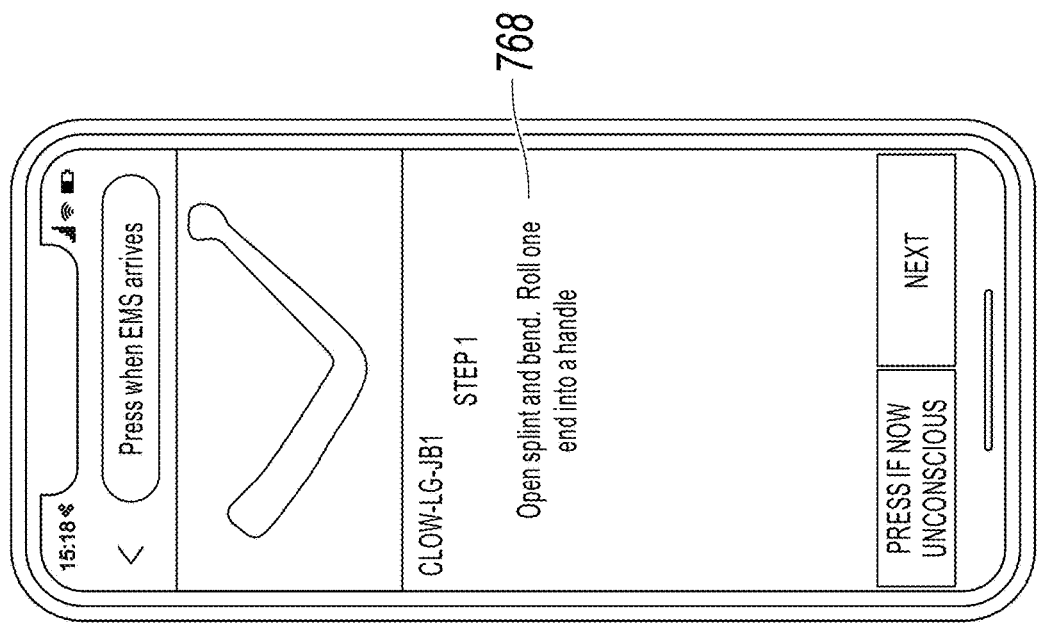

Referring to FIG. 7A, after the caregiver identifies the compact medical treatment and guidance apparatus as the apparatus type from inquiry 708 (e.g., by invoking button 712 as shown in FIG. 7E), the medical treatment and guidance system 100 presents an inquiry 782 (see FIG. 7A) asking the caregiver to "Touch the area of worst pain." The medical treatment and guidance system 100 presents the same image as presented in inquiry 726. If the caregiver invokes a radio button representing the patient's ankle or foot, which is the left ankle or foot in this example, the medical treatment and guidance system 100 presents instructions 784 to assist the patient to a comfortable position and to keep the affected leg and ankle of the patient still. The medical treatment and guidance system 100 then presents the inquiry 752 (described above) asking the caregiver "Is there anything else wrong with the current patient?"

In other words, because the compact medical treatment and guidance apparatus is used in this scenario, the medical treatment and guidance system 100 skips over or otherwise withholds the instructions 732, 740, 748 relating to the gauze, the splint, the elastic wrap, and the ice pack because these medical supplies are not predetermined to exist in the compact medical treatment and guidance apparatus. In this way, the medical treatment and guidance system 100 determines the instructions for assisting the caregiver in treating the patient by skipping inquires and instructions that are not applicable to the caregiver based on the apparatus type of the portable medical treatment and guidance apparatus.

In some examples, the medical treatment and guidance system 100 determines the medical instructions based on both the apparatus type and the patient characteristic. For example, referring to the above example where the apparatus type is a comprehensive medical treatment and guidance apparatus and the patient injury is a possible broken ankle or foot, if the patient is changed from an adult and instead identified as an infant patient, the medical treatment and guidance system 100 proceeds as follows.

Referring to FIG. 7A, if the caregiver indicates that the patient is an infant (e.g., by invoking a button in response to inquiry 706), the medical treatment and guidance system 100 proceeds down the flow path shown in FIG. 7C. (The connection between FIGS. 7A and 7C is represented by connection marker C.)

Referring to FIG. 7C, the medical treatment and guidance system 100 presents an inquiry 786 asking the caregiver to select which apparatus type is available to the caregiver. In this example, the inquiry 786 is the same as the inquiry 708 of FIG. 7A. In this example, the caregiver selects the comprehensive portable medical treatment and guidance apparatus. The medical treatment and guidance system 100 then presents an inquiry asking the caregiver "Are there any other patients with bad bleeding, unconscious or having trouble breathing?" In response, if the caregiver indicates that no other patients are experiencing bad bleeding, unconscious or having trouble breathing, the medical treatment and guidance system 100 presents an inquiry asking the caregiver "What is wrong with the patient?" If the caregiver selects the compact portable medical treatment and guidance apparatus, the system 100 can provide instructions similar to that discussed above regarding FIG. 7A.

In some examples, the medical treatment and guidance system 100 presents a response button to indicate a medical issue, a response button to indicate an injury, and a response button to indicate that the caregiver is not sure what is wrong with the patient. In response, if the caregiver indicates "I am not sure," the medical treatment and guidance system 100 presents an inquiry asking the caregiver "Is there bleeding from an injury?" In response, if the caregiver indicates "No," the medical treatment and guidance system 100 presents an inquiry 788 asking the caregiver "Is the problem one of these:" and presents a response button to indicate that the patient has burns, a response button to indicate that the patient has a possible broken bone, and a response button to indicate that the patient does not have any of these problems. In this example, the inquiry 788 is the same as the inquiry 718 of FIG. 7A. In response, if the caregiver indicates "Possible broken bone," as in this example, the medical treatment and guidance system 100 presents an inquiry 790 asking the caregiver to "Touch the area of worst pain" to identify where the patient has a possible broken bone injury. In this example, the inquiry 790 is the same as the inquiry 726 of FIG. 7A.

If the caregiver indicates pain associated with the patient's foot or ankle (e.g., by invoking a radio button representing the patient's ankle), as in this example in which the left foot or ankle is the area of worst pain, the medical treatment and guidance system 100 provides instructions 792 to "Keep the infant as still as possible. Comfort the infant the best you can." The medical treatment and guidance system 100 then presents an inquiry 794 asking if the caregiver has an ice pack, e.g., by asking the caregiver to "Locate the ice pack labeled Ice Pack 8." In response, if the caregiver indicates that the caregiver has an ice pack as in this example, the medical treatment and guidance system 100 then presents instructions 796 to assist the caregiver in applying the ice pack to the infant patient. In some examples, the instructions 796 include one or more of the following instructions. For example, the medical treatment and guidance system 100 can present an instruction of "STEP 1: Activate cold pack by firmly squeezing pouch. Place on injured area." The medical treatment and guidance system 100 can then present instructions of "STEP 2: Hold cold pack in place." The medical treatment and guidance system 100 then proceeds to the inquiry 752 asking the caregiver if anything else is wrong with patient.

In the above examples, the medical treatment and guidance system 100 provides instructions for treating a fracture emergency of adults and children based on which body part is fractured. The medical treatment and guidance system 100 provides instructions to avoid manipulation of fractures above the elbow or knee for adults and children. The medical treatment and guidance system 100 provides positioning instructions for the patient based on state information (e.g., whether or not the patient is experiencing a neck injury) for adults and children. The medical treatment and guidance system 100 provides instructions to treat the fracture emergency of infants with ice packs and provides instructions for the caregiver to maintain the comfort of the infant patient.

In the above examples, the instructions to treat the injured ankle or foot depend on whether the patient characteristic represents an infant or an adult, whether the apparatus type is a compact medical treatment and guidance apparatus or a comprehensive medical treatment and guidance apparatus, and where on the patient the injury is located.

In the above examples, the first choice medical supply is a splint to treat a broken ankle or foot bone and the medical treatment and guidance system 100 determines the instructions for assisting the caregiver in treating the patient based on whether or not the apparatus has the splint based on the determined apparatus type. In other words, the medical treatment and guidance system 100 can determine the first, second, third medical supply choices based on what apparatus type is available. An example illustrating how the medical treatment and guidance system 100 determines the first, second, and third medical supply that depends on whether the apparatus type is a compact medical treatment and guidance apparatus or a comprehensive medical treatment and guidance apparatus is described with reference to FIGS. 15A-15M below.

Figure 7N:
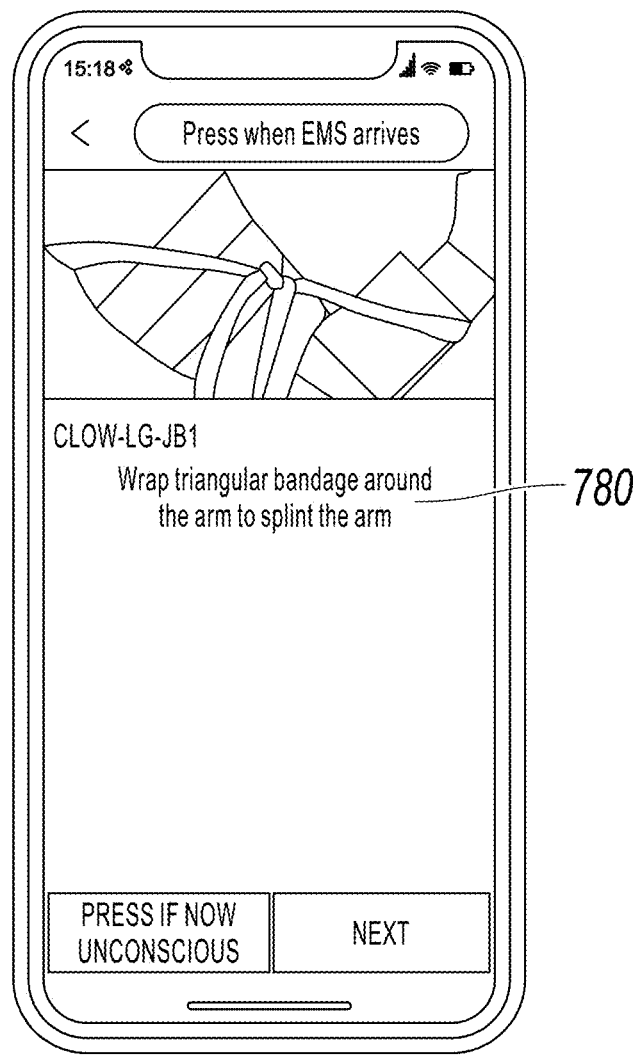

The examples in FIGS. 7A-7N illustrate that the medical treatment and guidance system 100 can account for both patient characteristics and apparatus type simultaneously. Furthermore, while the examples of FIGS. 7A-7N relate to fractures, the medical treatment and guidance system 100 also determines medical instructions based on apparatus type for other medical emergencies. For example, Table 9 indicates whether the medical treatment and guidance system 100 provides medical instructions emergencies for a particular medical emergency when a particular apparatus type is used. For example, the medical treatment and guidance system 100 provides different medical instructions based on apparatus type for allergic reactions, burns, chest pain, abdominal issues, and fractures. In this way, determining the available medical supplies can depend on a particular apparatus type.

TABLE 9

Medical instructions depend on apparatus type.

| Medical Emergency | Compact Treatment and Guidance Apparatus | Comprehensive Treatment and Guidance Apparatus |
| --- | --- | --- |
| Bad Bleeding (Extremity or Torso) | Yes | Yes |
| Chest wound | Yes | Yes |
| CPR | Yes | Yes |
| Allergy medicine | No | Yes |
| Burns dressing | No | Yes |
| Chest pain | No | Yes |
| Abdominal dressing | No | Yes |
| Splinting and fractures | No | Yes |
| Hypothermia | Yes | Yes |

FIGS. 8A-8C show a process 800 of operations performed by the medical treatment and guidance system 100 presenting warning screens that depend on a patient characteristic (e.g., age) in addition to providing instructions for treating allergic reactions in accordance with some embodiments. FIGS. 8D-8J illustrate the medical treatment and guidance application presenting medical instructions on a user interface of the electronic device associated with the operations of the process 800.

In this example, the medical treatment and guidance system 100 begins 802 the same way as the processes 500, 600, 700 of FIGS. 5A, 6A, and 7A-7C described above. Then, after the caregiver responds indicating that the patient is not badly bleeding, the medical treatment and guidance system 100 presents an age classification inquiry 804 asking the caregiver to indicate whether the patient is an adult, a child, or an infant.

In response, if the caregiver indicates "Adult," the medical treatment and guidance system 100 presents an inquiry asking "Is the patient awake?" In response, if the caregiver indicates "Yes," the medical treatment and guidance system 100 presents an inquiry asking the caregiver "Was the patient in a car accident, did they fall or is there a possible neck injury?" In response, if the caregiver indicates "No," the medical treatment and guidance system 100 presents an inquiry asking the caregiver "Is the patient having trouble breathing?" In response, if the caregiver indicates "Yes," the medical treatment and guidance system 100 presents an inquiry asking the caregiver "Is the patient choking?" In response, if the caregiver indicates "No," the medical treatment and guidance system 100 presents an inquiry 806 asking the caregiver to select which apparatus type is available to the caregiver. At this point, the example represented by the process 800 is the same as described the process 700 of FIGS. 7A-7C, for example.

In response, if the caregiver selects the compact portable medical treatment and guidance apparatus, the system 100 can provide instructions similar to that discussed above regarding FIG. 7A. If the caregiver indicates "Hardcase/ Backpack" to select the comprehensive medical treatment and guidance apparatus, the medical treatment and guidance system 100 presents an inquiry 808 asking the caregiver "What is causing the breathing difficulty?" In response, if the caregiver indicates "Medical issue," the medical treatment and guidance system 100 presents instructions 810 to assist the patient to a seated position and loosen or remove tight clothing and jewelry.

The medical treatment and guidance system 100 then presents an inquiry 812 asking the caregiver "Is the patient having a serious allergic reaction?" In response, if the caregiver indicates "Yes," the medical treatment and guidance system 100 presents an inquiry 814 asking the caregiver if an epinephrine auto-injector is available, e.g., by asking the caregiver "Does the patient have an epinephrine auto-injector?" In response, if the caregiver indicates "Yes," the medical treatment and guidance system 100 presents an inquiry 816 (shown in FIG. 8D) asking the caregiver to "Choose auto-injector" and presents a button 818 to indicate that the patient has an EpiPen™ auto-injector, a button 820 to indicate that the patient has an ADRENACLICK™ auto-injector, and a button 822 to indicate that the patient has a different auto-injector.

In response, if the caregiver indicates that an EpiPen™ auto-injector is available, the medical treatment and guidance system 100 presents instructions 824 to assist the caregiver in preparing to use and in using the EpiPen™ auto-injector. In some examples, the instructions 824 include one or more of the following instructions. For example, the medical treatment and guidance system 100 can present an instruction asking the caregiver to "Prepare to assist the patient with the EpiPen." The medical treatment and guidance system 100 can then present an instruction 826 (shown in FIG. 8E) of "STEP 1: Remove EpiPen from the case. Hold orange tip down. Remove blue safety cap." The medical treatment and guidance system 100 can then present an instruction of "STEP 2: Grasp EpiPen tightly. Place orange tip against patient's thigh." The medical treatment and guidance system 100 can then present an instruction of "STEP 3: Press firmly into the thigh. EpiPen will click. Hold in pace for 10 seconds." The medical treatment and guidance system 100 can then present an instruction of "STEP 4: Massage the injection site for 10 seconds."

The medical treatment and guidance system 100 then presents an inquiry asking the caregiver "Was the patient stung?" In response, if the caregiver indicates "No," the medical treatment and guidance system 100 presents an inquiry 828 asking the caregiver has allergy medicine, e.g., by asking the caregiver to "Locate the allergy medicine labeled Allergy E1." In some examples, the medical treatment and guidance system 100 presents a button that the caregiver can invoke to indicate that "Allergy E1" is unavailable. In such situations, the medical treatment and guidance system 100 will skip all instructions related to administering allergy medicine.

In response, if the caregiver indicates that the allergy medicine is available and located (e.g., by invoking a button), the medical treatment and guidance system 100 presents an inquiry 830 asking the caregiver if the patient is allergic to the allergy medicine, e.g., by asking "Is the patient allergic to Benadryl (diphenhydramine)?" In response, if the caregiver indicates "No," the medical treatment and guidance system 100 presents instructions 832 to administer the allergy medicine to the adult patient. In some example, the instructions 832 include one or more of the following instructions. For example, the medical treatment and guidance system 100 can present an instruction stating "Adult Patients: prepare to administer allergy medicine." The medical treatment and guidance system 100 can then present an instruction 834 (shown in FIG. 8F) of "STEP 1: Follow dosage direction on package of Allergy E1." The medical treatment and guidance system 100 can then present an instruction of "STEP 2: Allow to dissolve completely before swallowing." The medical treatment and guidance system 100 can then present an instruction of "STEP 3: Allergy medicine may make patient feel drowsy."

The medical treatment and guidance system 100 then presents an inquiry 836 asking the caregiver whether the patient has a recue inhaler with them, e.g., by asking "Does the patient have a rescue inhaler with them?" In response, if the caregiver indicates "Yes," the medical treatment and guidance system 100 presents a warning screen 838 (shown in FIG. 8G) informing the caregiver that the rescue inhaler is a prescribed drug. In this example, the warning screen 838 states "WARNING: This medication must be prescribed to the patient and they are asking to use it now."

If the caregiver invokes a hyperlink 840 on the warning screen 838 labeled "More Info," the medical treatment and guidance system 100 presents additional details, which can state, for example, "The patient must be conscious and asking to use their prescription medication. The patient exhibits signs/symptoms that indicate the use of this medication. Do not use any medication that is not labeled with the patient's name and instructions for use." In this way, the medical treatment and guidance system 100 presents one or more warning screens on the user interface. In some examples, the warning screen(s) each include one or more lines of text about administering medication. In some examples, the warning text is intended to warn the caregiver of an important step in the instructions.

Figure 8G:
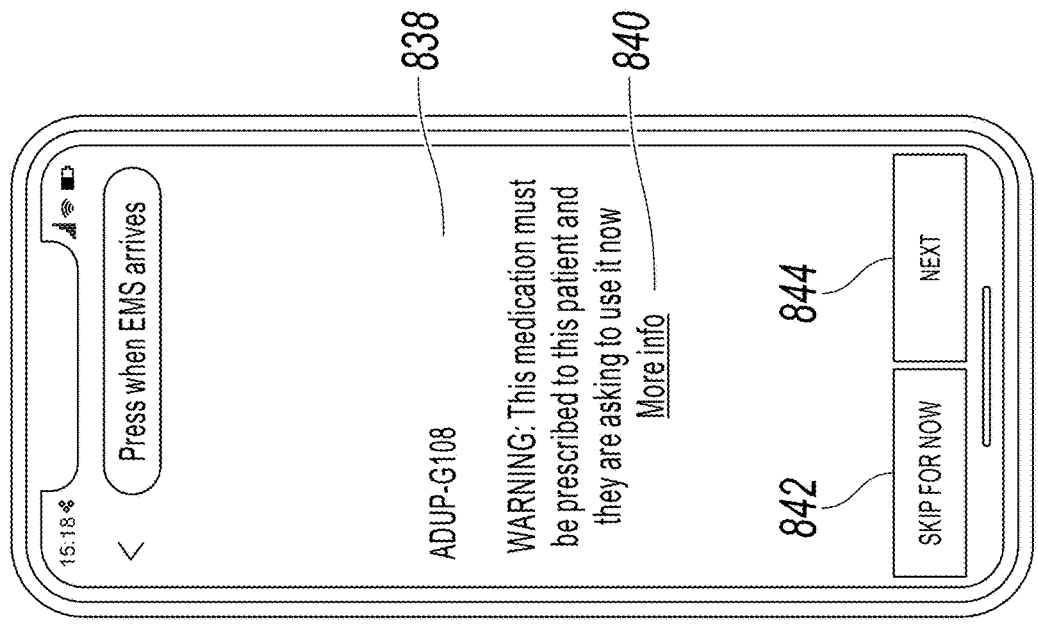
Figure 8F:
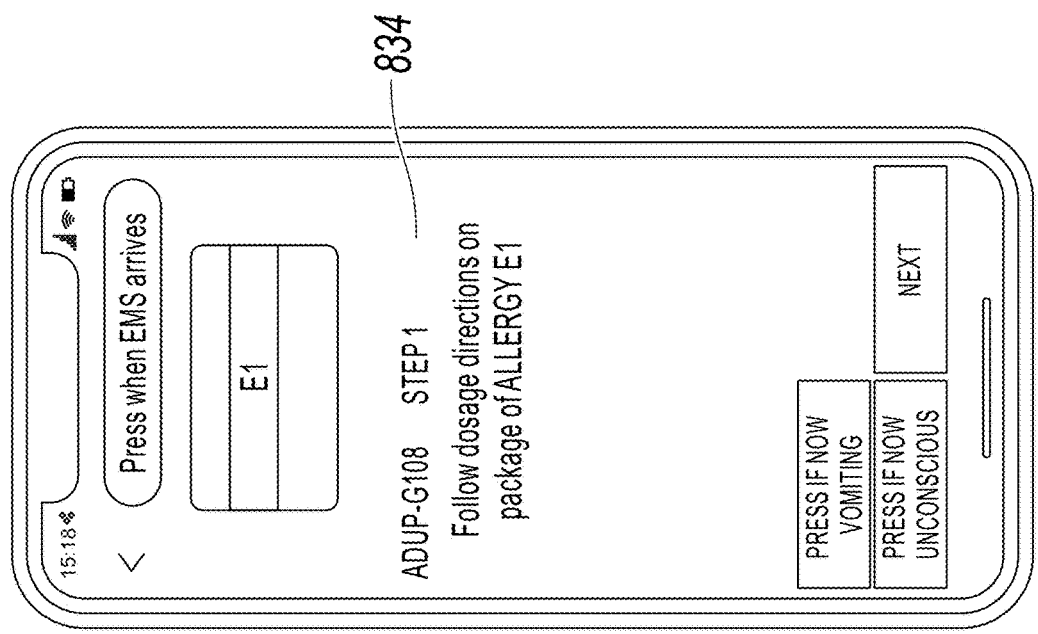

In this example, the warning screen shown in FIG. 8G provides a warning to the caregiver because use of an inhaler requires a prescription. The warning indicates that the caregiver must i) confirm that the patient is conscious, ii) obtain approval to administer this prescription medication from the adult patient, iii) confirm the patient is the recipient of the prescription, and iv) confirm that the prescription medication is labeled with instructions for use.

If the caregiver invokes a button 842 (shown in FIG. 8G) labeled "Skip for now," the medical treatment and guidance system 100 skips the instructions relating to administering the prescription medication. In this way, at least some warning screens can include an option to skip the step of administering medication.

If the caregiver invokes a button 844 (shown in FIG. 8G) labeled "Next," the medical treatment and guidance system 100 presents instructions 846 (see FIG. 8A) to assist the caregiver in administering the rescue inhaler to the adult patient. In some examples, the instructions 846 include one or more of the following instructions.

For example, the medical treatment and guidance system 100 can present an instruction asking the caregiver to "Prepare to assist the patient with their rescue inhaler." The medical treatment and guidance system 100 can present an instruction 848 (shown in FIG. 8H) of "STEP 1: Shake the inhaler vigorously." The medical treatment and guidance system 100 can then present an instruction of "STEP 2: Remove the cap from the mouthpiece and assist the patient to place the inhaler in their mouth." The medical treatment and guidance system 100 can then present an instruction of "STEP 3: Press the top of the inhaler as the patient inhales." The medical treatment and guidance system 100 can then present an instruction of "STEP 4: Patient should hold their breath for a few seconds before exhaling again." The medical treatment and guidance system 100 can then present an instruction of "STEP 5: Follow the prescription on the inhaler for how many puffs to deliver." The instructions for step 5 specifically indicate that the caregiver is to follow the dosage on the prescription.

The medical treatment and guidance system 100 then presents an inquiry 850 asking the caregiver "Is the patient having chest pain?" In response, if the caregiver indicates "No," the medical treatment and guidance system 100 presents an inquiry 852 asking the caregiver "Is there anything else wrong with the current patient?" In this example, the inquiry 852 is the same as the inquiry 752 of the process 700.

In the above example, the medical treatment and guidance system 100 presented instructions to the caregiver to assist the adult patient experiencing a breathing-related medical emergency. In particular, the medical treatment and guidance system 100 presented instructions to the caregiver to assist the adult patient experiencing an allergic reaction. The instructions included instructions for administering an epinephrine auto-injector (e.g., an EpiPen™), allergy medicine (e.g., Benadryl [diphenhydramine]), and a rescue inhaler to the patient. The medical treatment and guidance system 100 presented warning screen(s) to warn the caregiver that the rescue inhaler is a prescribed medication. The instructions for administering treatment using the rescue inhaler included an instruction to administer a prescribed number puffs per the patient's rescue inhaler prescription.

In the following example, the adult patient is replaced with a child patient (e.g., the patient characteristic changes) and the medical treatment and guidance system 100 presents different warning screen(s) based on the different patient characteristics. In this way, at least some warning screens can include warning text indicating that the instructions are about to ask the caregiver to administer medication. In some examples, the medication is a prescription medicine and the warning text includes instructions to administer prescription medication to the patient when the patient's consent is received by the caregiver.

Referring to FIG. 8A, the caregiver selects a child patient in response to the inquiry 804 in this scenario. This causes process 800 to move down a flow path shown in FIG. 8B. (The flow path connection between FIGS. 8A and 8B are represented by connection marker A.) The steps shown in FIG. 8A between the inquiry 806 and the inquiry 830 is the same regardless of whether the patient is an adult patient or a child patient and are thus not shown again in FIG. 8B.

However, after the medical treatment and guidance system 100 presents the inquiry 830, the medical treatment and guidance system 100 presents a warning screen 854 informing the caregiver that the allergy medicine is not for children under 6 years old. The warning screen 854 is shown graphically in FIG. 8I, where in this example it states "Warning: use as directed on packaging. Not for children under 6 years old." In this way, the medical treatment and guidance system 100 provides instructions to administer allergy medicine based on the weight and/or size of the patient according to instructions on the packaging of the allergy medicine for children over 6 years old.

Referring to FIG. 8I, if the caregiver invokes a button 856 labeled "Child is under 6," the medical treatment and guidance system 100 skips over providing instructions regarding the allergy medicine. If the caregiver invokes a button 858 labeled "Next," the medical treatment and guidance system 100 presents instructions 859 to assist the caregiver in administering allergy medicine to the child patient over 6 years old. In some examples, the instructions 859 include one or more of the following instructions. For example, the medical treatment and guidance system 100 presents an instruction stating "Child over 6 years old: Prepare to administer allergy medicine." In some examples, additional instructions are the same as the instructions 832 described with reference to FIG. 8A above.

Figure 8J:
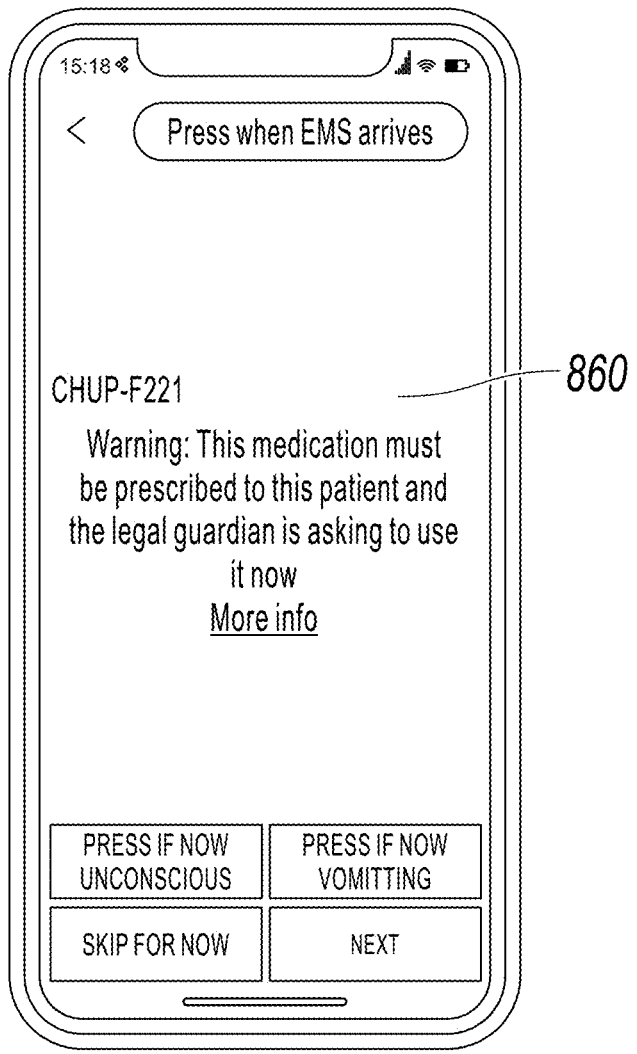

After the medical treatment and guidance system 100 provides instructions for administering the allergy medicine to the child patient, the medical treatment and guidance system 100 proceeds to inquire about whether the patient has a recue inhaler with them. For example, the medical treatment and guidance system 100 presents an inquiry 861 asking the caregiver "Does the patient have a rescue inhaler with them?" If the caregiver's response indicates that the child patient has an inhaler with them, then the medical treatment and guidance system 100 presents a warning screen 860 informing the caregiver that the rescue inhaler is a prescribed drug and the patient's legal guardian is asking the caregiver to use it now. An example warning screen 860 is shown in FIG. 8J and states "Warning: This medication must be prescribed to this patient and the legal guardian is asking to use it now."

The warning screen 860 of FIG. 8J differs from the warning screen 838 of FIG. 8G in that the instructions for the child explicitly state that the legal guardian is asking the caregiver to use the prescription medication because the child is a minor. Said another way, one or more warning screens include text indicating that a legal guardian is authorizing the caregiver to administer the prescribed rescue inhaler to a child patient. In this way, the warning screen(s) can include warning text indicating that the instructions are about to ask the caregiver to administer prescription medicine to the patient. In this example, the warning screen(s) are based on whether the patient is an adult or a child. In some examples, the warning text also includes instructions to administer prescription medication to the patient when the patient's legal guardian's consent is received by the caregiver. In this example, the medical treatment and guidance system 100 presents instructions 862 to assist the caregiver in administering the rescue inhaler to the child patient over 6 years old. In some examples, the instructions 862 include the same instructions as the instructions 846 for an adult patient.

After the instructions 862 are presented and completed, the medical treatment and guidance system 100 presents the inquiry 852 asking if anything else is wrong with the patient. In this way, the flow path for the child and the adult merge at inquiry 852.

The above example relates to a child patient. If the child patient were replaced with an infant patient in response to the inquiry 804, the process 800 would proceed down the flow path shown in FIG. 8C. (The connection between the portion of the process 800 shown in FIG. 8A and the portion of the process 800 shown in FIG. 8C is represented by the connection marker B.)

In this example, the medical treatment and guidance system 100 presents an inquiry 864 asking the caregiver "Does the patient have a pediatric EpiPen™ prescribed to them?" If the response is "Yes," the medical treatment and guidance system 100 presents instructions 866 to assist the caregiver in preparing to use and using the pediatric EpiPen™ auto-injector on the infant patient. The medical treatment and guidance system 100 presents an instruction asking the caregiver to "Watch the patient closely for signs of trouble breathing or swelling around face/lips."

In the above example relating to the infant, the medical treatment and guidance system 100 does not recommend administering allergy medicine to infants and thus does not present instructions to administer allergy medicine the infant patient (step 868). In some examples, the medical treatment and guidance system 100 provides instructions to care for stings and provides instructions to assist with a prescribed inhaler. Afterwards, the medical treatment and guidance system 100 presents the inquiry 852 asking if anything else is wrong with the patient. In this way, the flow path for the infant merges with the child and the adult merge at the inquiry 852.

In the above examples of the process 800, the instructions also depend on whether the patient is experiencing a neck injury. This concept is further described with reference to FIGS. 9A-9C below. However, in the above example, if the caregiver responded that the patient may not be experiencing a neck injury, the medical treatment and guidance system 100 can provide an instruction regarding positioning the patient, e.g., an instruction of "Ok, stay calm and continue. Assist the patient to a comfortable position; Seated or laying down are best." Alternatively, if the caregiver responded that the patient may be experiencing a neck injury, the medical treatment and guidance system 100 can present an instruction regarding positioning the patient, e.g., an instruction asking the caregiver to "Keep patient on their back. Limit neck movement." In this way, the instructions for assisting the patient with an allergic reaction can also depend on state information in memory indicating whether or not the patient is experiencing a possible neck injury. Further details and the use of state information is further described with reference to FIGS. 9A-9C below.

FIGS. 9A-9C illustrate an example where the medical treatment and guidance system 100 maintains state information during subsequent inquiries. In this example, the medical treatment and guidance system 100 recalls responses to previous inquiries, e.g., using state information stored in memory (e.g., flash memory, random access memory, etc.). The medical treatment and guidance system 100 stores responses in memory when subsequent inquiries are expected to depend from a particular response. For example, FIG. 9A shows the medical treatment and guidance system 100 presenting an inquiry 902 asking the caregiver "Was the patient in a car accident, did they fall or is there a possible neck injury?" The inquiry 902 is part of most, if not all, example flows, as described herein. Regardless of how the caregiver responds to this inquiry, the medical treatment and guidance system 100 stores this response in memory as patient state information. The patient state information regarding whether or not the patient was in a car accident, fell, or has a possible neck injury is relevant to an ending of a flow in which the caregiver is awaiting third party assistance, e.g., arrival of an ambulance. As discussed further below, how the system 100 instructs the caregiver to position the patient while awaiting assistance is based the patient state information regarding whether or not the patient was in a car accident, fell, or has a possible neck injury because, in general, the patient should be kept as comfortable as possible but without causing any further patient harm by positioning the patient in a potentially dangerous position.

If the caregiver invokes a button 904 labeled "No," the medical treatment and guidance system 100 determines that the patient is not experiencing a neck injury and stores information in memory that the patient is not experiencing have a neck injury. If the caregiver invokes a button 906 labeled "Yes," the medical treatment and guidance system 100 determines that the patient is experiencing a neck injury and stores information in memory that the patient is experiencing a neck injury. In this way, the medical treatment and guidance system 100 determines at least one injury of the patient based on at least one input from the user interface. In some examples, the medical treatment and guidance system 100 determines at least one injury of the patient based on at least one input from the user interface and subsequent inputs (e.g., in scenarios of multiple injury dependencies).

For example, subsequent instructions based on the response to the neck injury inquiry 902 are shown in FIGS. 9B and 9C. If the caregiver invoked the button 904 labeled "No," the medical treatment and guidance system 100 would proceed to through interactive flows and could reach the result shown in FIG. 9B. In this example, FIG. 9B shows the medical treatment and guidance system 100 presenting an instruction 908 asking the caregiver to "Stay calm, assist patient to a comfortable position." With these instructions, the caregiver may roll the patient onto their side without causing additional harm to the patient. If, on the other hand, the caregiver invoked the button 906 labeled "Yes," the medical treatment and guidance system 100 would proceed to through interactive flows and could reach the result shown in FIG. 9C. The example of FIG. 9C shows the medical treatment and guidance system 100 presenting an instruction 910 asking the caregiver to "Stay calm, make sure the patient is on their back and minimize neck movement."

With these instructions, the caregiver is instructed to leave the patient on their back to avoid causing additional harm to the patient. Whether the instruction 908 or the instruction 910 appears on the user interface is based on the response to the inquiry 902 asking about the possibility of neck injury to the patient. In this example, the subsequent instruction (e.g., the instruction 910) includes instructions to reduce complication of the determined injury. This is because moving a patient who is experiencing a neck injury onto their side could cause additional harm the patient and complicate the neck injury and risk a cervical spine injury by not limiting cervical spinal motion.

In some embodiments, the medical treatment and guidance system 100 stores information pertaining to the patient characteristic and/or the apparatus type of portable medical treatment and guidance apparatus into the memory. In some examples, the medical treatment and guidance system 100 determines instructions based on the stored information pertaining to the patient characteristic and/or the apparatus type in memory.

FIGS. 10A-10C show a process 1000 of operations performed by the medical treatment and guidance system 100 presenting medical instructions to assist a patient that is experiencing chest palpitations accordance with some embodiments. FIGS. 10D-10F illustrate the medical treatment and guidance application presenting medical instructions on a user interface of the electronic device associated with the operations of the process 1000.

In this example, the medical treatment and guidance system 100 begins 1002 the same way as various processes described above. Then, after the caregiver responds indicating that the patient is not badly bleeding, the medical treatment and guidance system 100 presents an age classification inquiry 1004 asking the caregiver to indicate whether the patient is an adult, a child, or an infant.

In response, if the caregiver indicates "Adult," the medical treatment and guidance system 100 presents an inquiry asking "Is the patient awake?" In response, if the caregiver indicates "Yes," the medical treatment and guidance system 100 presents an inquiry asking the caregiver "Was the patient in a car accident, did they fall or is there a possible neck injury?" In response, if the caregiver indicates "No," the medical treatment and guidance system 100 presents an inquiry asking the caregiver "Is the patient having trouble breathing?" In response, if the caregiver indicates "No," the medical treatment and guidance system 100 presents an inquiry 1006 asking the caregiver to select which apparatus type is available to the caregiver. In this example, a portable medical treatment and guidance apparatus is identified as a "Mobilize kit."

In response, if the caregiver indicates "Hardcase/Backpack," to select the comprehensive medical treatment and guidance apparatus, the medical treatment and guidance system 100 presents an inquiry asking the caregiver "Are there any other patients with bad bleeding, unconscious or having trouble breathing?" In response, if the caregiver indicates "No other patients," the medical treatment and guidance system 100 presents an inquiry asking the caregiver "What is wrong with the patient?" In response, if the caregiver indicates "I am not sure," the medical treatment and guidance system 100 presents an inquiry asking the caregiver "Is there bleeding from an injury?" In response, if the caregiver indicates "No," the medical treatment and guidance system 100 presents an inquiry asking the caregiver "Is the problem one of these:" and presents a response button to indicate that the patient has burns, a response button to indicate that the patient has a possible broken bone, and a response button to indicate that the patient does not have any of these problems. At this point, the process 1000 is substantially the same as the process 700.

In response, if the caregiver indicates "None of these," the medical treatment and guidance system 100 presents an inquiry 1008 (shown in FIGS. 10A and 10D) asking the caregiver "Is the problem one of these:" and presents a response button 1010 to indicate that the patient is disoriented or confused, a response button 1012 to indicate that the patient is experiencing seizures, and a response button 1014 to indicate that the patient does not have any of these problems.

In response, if the caregiver indicates "None of these," the medical treatment and guidance system 100 presents an inquiry 1016 (shown in FIGS. 10A and 10E) asking the caregiver "Is the problem one of these:" and presents a response button 1018 to indicate that the patient is experiencing chest pain, a response button 1020 to indicate that the patient is experiencing an allergic reaction, a response button 1022 to indicate that the patient is experiencing trouble breathing, and a response button 1024 to indicate that the patient does not have any of these problems.

In response, if the caregiver indicates "Chest pain," as shown in the example of FIG. 10A, the medical treatment and guidance system 100 presents an inquiry asking the caregiver to "Examine the chest: Are there any open wounds on the front, back or sides?" In response, if the caregiver indicates "No," the medical treatment and guidance system 100 presents an inquiry asking the caregiver "Did an object strike or hit the patient's chest?" In response, if the caregiver indicates "No," the medical treatment and guidance system 100 presents an inquiry asking the caregiver "Did they fall and strike their chest, back or side?" In response, if the caregiver indicates "No," the medical treatment and guidance system 100 presents an inquiry 1026 (shown in FIGS. 10A and 10F) asking the caregiver "What type of chest pain?" The medical treatment and guidance system 100 presents a response button 1028 to indicate that the patient is experiencing palpitations, a response button 1030 to indicate that the patient is experiencing dull pain, and a response button 1032 to indicate that the patient is experiencing sharp pain.

In response, if the caregiver indicates "Palpitations," as shown in the example of FIG. 8A, the medical treatment and guidance system 100 presents instructions 1034 to assist the caregiver in treating a patient experiencing heart palpitations. For example, the instructions 1034 can include an instruction asking the caregiver to "Ask the patient to turn their head away from you and forcefully cough." The medical treatment and guidance system 100 then presents an inquiry 1035 asking the caregiver "Did the palpitations stop?" In response, if the caregiver indicates that the palpitations have not stopped, the medical treatment and guidance system 100 repeats the instructions 1035. In this example, the medical treatment and guidance system 100 repeats the instruction asking the patient to turn their head away from the caregiver and forcefully cough.

If the caregiver indicates that the palpitations have stopped, the medical treatment and guidance system 100 presents an inquiry 1036 asking the caregiver "Is the patient allergic to aspirin?" In response, if the caregiver indicates "No," as in this example, the medical treatment and guidance system 100 presents an instruction 1038 asking if the caregiver has chewable aspirin, e.g., asking the caregiver to "Locate chewable aspirin labeled Aspirin E2." The medical treatment and guidance system 100 then presents instructions 1040 to assist the caregiver in administering the aspirin to the patient. For example, the instructions 1040 can include one or more of the following instructions. In some examples, the instructions 1040 include "STEP 1: Follow the dosage directions on the package of Aspirin E2." In some examples, the instructions 1040 include "STEP 2: Instruct patient to place tablets in their mouth." In some examples, the instructions 1040 include of "STEP 3: Chew and swallow tablets." The medical treatment and guidance system 100 then presents an inquiry 1042 asking the caregiver "Is there anything else wrong with the current patient?"

In this example, the medical instructions included an instruction asking about a patient aspirin allergy and instructions to locate and administer aspirin because the medical treatment and guidance system 100 predetermined that the aspirin was available to the caregiver based on the selection of the comprehensive medical treatment and guidance apparatus of the apparatus type. For example, if this example were repeated but the compact medical treatment and guidance apparatus were selected at inquiry 1006, the medical treatment and guidance system 100 would not provide instructions relating to aspirin allergy or to locating or administering aspirin because the medical treatment and guidance system 100 has predetermined that the compact medical treatment and guidance apparatus does not include aspirin. In this way, the medical treatment and guidance system 100 skips over medical instructions that relate to aspirin (e.g., the inquiries/instructions 1036, 1038, 1040 would have been skipped).

This example was also based on an adult patient. If the scenario changed and a child patient was selected at the inquiry 1004, the inquiries/instructions shown between the inquiries 1002 and 1016 would be the same and are thus not all shown in FIG. 10B. However, after the inquiry 1016, the medical treatment and guidance system 100 would proceed differently as shown in FIG. 10B.

Referring back to FIG. 10A, the caregiver selects a child patient in response to the inquiry 1004 in another scenario. This causes the process 1000 to move down a flow path shown in FIG. 10B. (The flow path connection between FIGS. 10A and 10B are represented by connection marker A.) The steps shown in FIG. 10A between the inquiry 1002 and the inquiry 1016 are the same regardless of whether the patient is an adult patient or a child patient.

Referring to FIG. 10B, the caregiver in this example has selected "chest pain" as the patient's problem, and the medical treatment and guidance system 100 presents an inquiry 1044 asking the caregiver "Is the patient 10 years or older?" In response, if the caregiver indicates "Yes," the medical treatment and guidance system 100 presents the same inquires/instructions as illustrated for the adult patient example (e.g., the steps 1026-1042). Only the inquiry 1026 is shown in FIG. 10B, but the process would continue as discussed above regarding FIG. 10A. If however, the caregiver indicates that the patient is under 10 years old in response to the inquiry 1044, the medical treatment and guidance system 100 presents an instruction 1046 of "Younger children rarely have cardiac chest pain. Let's focus on keeping the patient comfortable." The medical treatment and guidance system 100 then presents the inquiry 1042 asking the caregiver "Is there anything else wrong with the patient?"

In the above example relating to the child, the instructions further depend on whether the child is younger than age 10 or older than age 10. If the child is indicated to be younger than 10 years old, the medical treatment and guidance system 100 skips medical instructions relating to treating palpations and also skips instructions relating to administering aspirin to the patient.

If the scenario changed again and an infant patient was selected at inquiry 1004, the inquiries/instructions shown between the inquiry 1002 and the inquiry 1016 would be the same as discussed above regarding FIG. 10A. However, after the inquiry 1016, the medical treatment and guidance system 100 would proceed differently as shown in FIG. 10C.

Referring back to FIG. 10A, the caregiver selects an infant patient in response to the inquiry 1004 in this scenario. This causes the process 1000 to move down a flow path shown in FIG. 10C from the inquiry 1016. (The flow path connection between FIGS. 10A and 10C are represented by connection marker B.) The steps shown in FIG. 10A between the inquiry 1002 and the inquiry 1016 are the same regardless of whether the patient is an adult patient or an infant patient.

Referring to FIG. 10C, the caregiver in this example has selected "chest pain" as the patient's problem, and the medical treatment and guidance system 100 presents an inquiry 1048 asking the caregiver "Is there a visible injury to the infant's chest?" In response, if the caregiver indicates "No," the medical treatment and guidance system 100 would present an instruction 1050 asking the caregiver to "Keep the infant comfortable and monitor breathing while waiting for help to arrive." The medical treatment and guidance system 100 would then present the inquiry 1042 asking the caregiver "Is there anything else wrong with the current patient?" In response to the inquiry 1048, if the caregiver indicates "Yes," the medical treatment and guidance system 100 would present the instruction 1026 to the caregiver as discussed above with respect to FIG. 10A. The infant is presumed to not be able to provide a verbal indication of the type of chest pain being experienced, so the inquiry 1026 is to the caregiver to assess.

In the above example relating to the infant, the medical treatment and guidance system 100 skips medical instructions relating to treating palpations and also skips instructions relating to the administering aspirin to the patient.

In these examples, the portable medical treatment and guidance system 100 includes instructions for treating chest palpitations, and the instructions are different depending on whether the patient is an infant, a child, or an adult based on the age classification. In particular, the instructions for treating the chest palpitations include instructions for administering aspirin to adult patients and children over 10 years old based on the age classification (and based on whether the aspirin is available and whether the patient is allergic to aspirin). In this way, the portable medical treatment and guidance system 100 presents instructions for treating the chest palpitations that include instructions for administering aspirin to adult patients and children over 10 years old based on the age classification (and based on whether the aspirin is available and whether the patient is allergic to aspirin) and instructions for keeping children under 10 years old and infants comfortable based on the age classification.

FIG. 11A shows a process 1100 of operations performed by the medical treatment and guidance system 100 presenting medical instructions to assist a patient that is experiencing dull/sharp chest pain in accordance with some embodiments. FIGS. 11B-11D illustrate the medical treatment and guidance application presenting medical instructions on a user interface of the electronic device associated with the operations of the process 1100.

In this example, the medical treatment and guidance system 100 begins 1002 the same way as the process 1000 of FIG. 10A described above. However, in this example, instead of selecting palpitations in response to the inquiry 1026, the caregiver selects dull pain and sharp pain options. For example, the process 1100 begins at step 1102 and the medical treatment and guidance system 100 presents an inquiry 1104 asking the caregiver to select the age classification of the patient. In response, the caregiver identifies that the patient is an adult patient and then the medical treatment and guidance system 100 presents an inquiry 1106 asking the caregiver to select which medical treatment and guidance apparatus is available to the caregiver. In response, the caregiver identifies that a comprehensive medical treatment and guidance apparatus is available to the caregiver by selecting "Hardcase/Backpack." The medical treatment and guidance system 100 then presents an inquiry 1108 (e.g., the same as the inquiry 1026 shown in FIGS. 10A and 10F) asking the caregiver "What type of chest pain?" In response, the caregiver invokes the button 1030 indicating dull pain or the button 1032 indicating sharp pain (e.g., in some examples, as in this illustrated embodiment, the instructions are the same for either of these responses).

The medical treatment and guidance system 100 then presents an inquiry 1110 asking if the patient is allergic to aspirin. If the caregiver indicates that the patient is not allergic to aspirin, as in this example, then the medical treatment and guidance system 100 presents instructions 1112 for administering aspirin. In some examples, the instructions 1112 are the same as the instructions 1040 described with reference to FIG. 10A above.

After the medical treatment and guidance system 100 presents the instructions 1112 for administering aspirin, the medical treatment and guidance system 100 presents an inquiry 1114 (as shown in FIG. 11B) asking the caregiver "Does the patient have their own nitroglycerin prescription? In response, if the caregiver indicates "Yes," as in this example, the medical treatment and guidance system 100 presents a warning screen 1116 (as shown in FIG. 11C) with a warning to the caregiver about the nitroglycerin prescription. In some examples, the warning screen 1116 includes the following warning "WARNING: This medication must be prescribed to this patient and they are asking to use it now." In response, if the caregiver indicates "Next," the medical treatment and guidance system 100 presents instructions 1118 for assisting the caregiver in administering the nitroglycerin prescription to the patient. In some examples, the instructions 1118 include an instruction asking the caregiver to "Prepare to assist patient with their prescription nitroglycerin."

In some examples, the instructions 1118 include one or more of the following instructions. In some examples, the instructions 1118 include "STEP 1: Do not touch nitroglycerin with bare hands, use gloves." In some examples, the instructions 1118 include "STEP 2: Follow dosage and instructions on bottle. If indicated, place tablet under the tongue to dissolve." In some examples, the instructions 1118 include "STEP 2: Follow dosage and instructions on bottle. If indicated, place tablet under the tongue to dissolve." In some examples, the instructions 1118 include "STEP 3: Allow to dissolve. Patient should not crush, chew, or swallow the tablet." In some examples, the instructions 1118 include "STEP 4: Patient may develop a headache, this is normal." The medical treatment and guidance system 100 then presents an inquiry 1120 asking the caregiver "Is there anything else wrong with the current patient."

In the above example, the medical treatment and guidance system 100 provides instructions to assist the caregiver in administering the adult patient's prescribed nitroglycerin. If the scenario changed and a child patient was selected in reply to the inquiry 1104, instead of presenting instructions for administering aspirin and nitroglycerin, the medical treatment and guidance system 100 would present instructions 1122 (shown in FIG. 11D) of "Younger children rarely have cardiac chest pain. Let's focus on keeping the patient comfortable." The medical treatment and guidance system 100 then presents the inquiry 1120 asking the caregiver "Is there anything else wrong with the current patient." In this way, the medical treatment and guidance system 100 changes the instructions based on the patient's age. The medical treatment and guidance system 100 skips instructions to administer aspirin and nitroglycerin in scenarios where the patient is a child and the medical emergency is dull and/or sharp chest pain.

If the scenario changed again and an infant patient was selected in reply to the inquiry 1104, instead of presenting the inquiry 1108 about the type of chest pain, the medical treatment and guidance system 100 presents an instruction 1124 asking the caregiver to "Keep the infant comfortable and monitor breathing while waiting for help to arrive." In this way, the medical treatment and guidance system 100 skips instructions to administer aspirin and nitroglycerin in scenarios where the patient is an infant and the medical emergency is dull and/or sharp chest pain. In this way, the medical treatment and guidance system 100 presents instructions for treating the dull and/or sharp chest pain that include instructions for administering aspirin and prescribed nitroglycerin to adult patients based on the age classification and instructions for keeping child and infant patients comfortable based on the age classification.

FIG. 12A shows a process 1200 of operations performed by the medical treatment and guidance system 100 presenting medical instructions to assist a patient that is experiencing a diabetic issue in accordance with some embodiments. FIGS. 12B-12D illustrate the medical treatment and guidance application presenting medical instructions on a user interface of the electronic device associated with the operations of the process 1200.

This example follows the same example flow as the process 1000 shown in FIG. 10A. For example, the process 1200 begins at step 1202 and the medical treatment and guidance system 100 presents an inquiry 1204 about the age classification of the patient. In response, the caregiver selects an adult patient and the medical treatment and guidance system 100 presents an inquiry 1206 about the emergency medical treatment and guidance apparatus available to the caregiver. In response, the caregiver identifies in this example that a comprehensive emergency medical treatment and guidance system is available to the caregiver by selecting "Hardcase/Backpack." In this example, a portable medical treatment and guidance apparatus is identified as a "Mobilize kit."

The medical treatment and guidance system 100 presents an inquiry 1208 asking if the patient is disoriented/confused or is experiencing seizures. An example of the inquiry 1208 is described with reference in FIG. 10D above. In response, if the caregiver indicates that the patient is disoriented or confused (e.g., by invoking the disoriented or confused button 1010 of FIG. 10D), the medical treatment and guidance system 100 presents an instruction asking the caregiver to "Assist patient to a comfortable position; seated or lying down is best. Support their neck to limit movement." The medical treatment and guidance system 100 then presents an instruction asking the caregiver to "Remove constrictive clothing and jewelry."

The medical treatment and guidance system 100 then presents an inquiry 1210 (shown in FIG. 12B) asking the caregiver "Is this a possible diabetic problem?" If the caregiver invokes a hyperlink 1212 to view more info, the medical treatment and guidance system 100 presents an information screen with details about patients with diabetic problems. For example, the information screen can provides information of "A diabetic problem is: a problem regulating body sugar; patient may take insulin or have an insulin pump; may take pills to lower blood sugar; may have a medical alert bracelet."

In response to the inquiry 1210, if the caregiver indicates that the patient may be experiencing a diabetic problem, as in this example, the medical treatment and guidance system 100 presents an inquiry 1213 asking the caregiver "Is the patient awake enough to swallow?" In general, the medical treatment and guidance system 100 will not instruct the caregiver to administer oral glucose (or to administer any other oral medication or to place anything in the patient's mouth) if the patient is unable to swallow, as that may cause the patient to choke. If the caregiver invokes a hyperlink to view more info, the medical treatment and guidance system 100 presents an information screen with details about patients with being sufficiently awake to swallow. For example, the information screen can provide information of "To safely swallow the patient must be awake, able to hold up their head and not be drooling."

In response to the inquiry 1213, if the caregiver indicates that the patient is not awake enough to swallow, the medical treatment and guidance system 100 presents an inquiry 1224 asking the caregiver "Is there anything else wrong with this current patient?" as the caregiver awaits help. In response to the inquiry 1213, if the caregiver indicates that the patient is awake enough to swallow, the medical treatment and guidance system 100 presents an instruction 1214 asking if the caregiver has oral glucose, e.g., by asking the caregiver to "Locate the glucose labeled Glucose E3." The medical treatment and guidance system 100 then presents instructions 1216 for assisting the caregiver to administer the oral glucose to the adult patient. In some examples, the instructions 1216 include an instruction asking the caregiver to "Prepare to administer oral glucose."

In some examples, the instructions 1216 include one or more of the following instructions. In some examples, the instructions 1216 include an instruction 1218 (as shown in FIG. 12C) of "STEP 1: Twist open the top of the glucose tube." In some examples, the instructions 1216 include "STEP 2: Ask the patient to open their mouth as wide as possible." In some examples, the instructions 1216 include "STEP 3: Squeeze some glucose under the tongue." In some examples, the instructions 1216 include "STEP 4: After glucose has dissolved or swallowed, squeeze in more. Repeat until tube is empty." In some examples, the instructions 1216 include "It may take some time for glucose to have effect."

The medical treatment and guidance system 100 then presents instructions 1220 to assist the caregiver in placing the patient in a recovery position. In some examples, the instructions 1220 include an instruction asking the caregiver to "Prepare to place patient in the recovery position." In some examples, the instructions 1220 include an instruction 1222 (as shown in FIG. 12D) to "Lie patient on their side. Ensure patient's knee and hip are bent. Support patient's head with you hand." The medical treatment and guidance system 100 then presents an inquiry 1224 asking the caregiver "Is there anything else wrong with this current patient?"

In the above example, the medical treatment and guidance system 100 provides instructions to administer glucose to adult patients. These same instructions are provided in cases where a child patient is selected. However, the instructions are different in cases where an infant is selected. For example, if the caregiver indicates that the patient is an infant, and the caregiver indicates that the patient is disoriented or confused in response to the inquiry 1208, as in this example, the medical treatment and guidance system 100 presents an inquiry 1225 asking the caregiver "Is the infant having a seizure?" In response, if the caregiver indicates that the patient is not experiencing a seizure, as in this example, the medical treatment and guidance system 100 then presents an instruction asking the caregiver to "Keep the infant comfortable and monitor breathing while waiting for help to arrive." The medical treatment and guidance system 100 then presents the inquiry 1224 asking if anything else is wrong with the patient. The caregiver was previously given the option to indicate that the patient is having a seizure in the inquiry 1208, but the inquiry 1225 presents another opportunity for the caregiver to indicate that the patient is having a seizure for redundancy, which may maximize patient care and safety. Thus, in some instances, to provide redundancy the system 100 may ask the caregiver the same question more than once in the process 1200 (or in another process described herein) or be given more than one opportunity to provide the same information in the process 1200 (or in another process described herein). Depending on a caregiver's response to one or more prior inquiries in the process 1200 (or in another process described herein), redundancy may not occur, e.g., if the caregiver replied "Seizures" instead of "Dazed/Confused" to the inquiry 1208 the caregiver would not receive the inquiry 1225 asking if the patient is having a seizure.

In the example above, the medical treatment and guidance system 100 provides instructions to administer oral glucose with altered mental status and perceived hypoglycemia to child and adult patients. The medical treatment and guidance system 100 provides instructions for the swallowing the glucose. The system 100 does not recommend administering oral glucose with altered mental status to infants. In other words, the medical treatment and guidance system 100 skips instructions to administer glucose in scenarios where the patient is an infant. The medical treatment and guidance system 100 presents inquiries relating to seizures in response to the caregiver indicating that the patient is a dazed and/or confused infant patient. In other words, the portable medical treatment and guidance system 100 provides instructions for treating a diabetic problem and the instructions are different depending on whether the patient is an infant or is an adult or child based on the age classification. In some examples, the instructions for treating the diabetic problem include (i) instructions for administering oral glucose to child and/or adult patients based on the age classification, (ii) instructions for swallowing the oral glucose in child and/or adult patients, and (iii) instructions treating seizures in infant patients based on the age classification.

FIGS. 13A-13C shows a process 1300 of operations performed by the medical treatment and guidance system 100 presenting medical instructions to assist a patient that is unconscious in accordance with some embodiments. FIGS. 13C-13I illustrate the medical treatment and guidance application presenting medical instructions on a user interface of the electronic device associated with the operations of the process 1300.

The process 1300 begins the same way as various processes described herein. As shown in this example, the process 1300 begins at step 1302, and the medical treatment and guidance system 100 presents an inquiry 1304 asking if the patient is talking to the caregiver. If the caregiver indicates that the patient is not talking to the caregiver, as in this example, the medical treatment and guidance system 100 presents an inquiry 1306 asking about the patient's age (as previously described).

If the caregiver responds to the patient age inquiry 1306 by indicating that the patient is an adult, the medical treatment and guidance system 100 presents an inquiry 1308 asking "Is the patient awake?" If the caregiver responds by indicating "Yes", as in this example, the medical treatment and guidance system 100 proceeds to determine if the patient is having trouble breathing (e.g., because of choking as described above with reference to FIGS. 6A-6E and/or because of an allergic reaction as described above with reference to FIGS. 8A-8J). If the caregiver responds by indicating "Yes" in response to the inquiry 1308 asking if the patient is awake, as in this example, the medical treatment and guidance system 100 presents an inquiry 1310 asking "Is the patient actively seizing?"

If the caregiver indicates that the patient is actively seizing, the medical treatment and guidance system 100 presents instructions 1312 to assist the caregiver in treating the seizing patient. In some examples, the instructions include one or more of the following instructions. In some examples, the instructions 1312 include an instruction to "Approach the patient cautiously." In some examples, the instructions 1312 include "STEP 1: Do not touch or hold the patient." In some examples, the instructions 1312 include "STEP 2: Move objects away from the patient." In some examples, the instructions 1312 include "STEP 3: Do not put anything in the patient's mouth." In some examples, the instructions 1312 include "STEP 4: Press "Next" below when seizures stop."

After the medical treatment and guidance system 100 presents the instructions 1312, the medical treatment and guidance system 100 presents an inquiry 1314 asking "Is the patient unconscious?" If the caregiver responds "no" indicating that the patient is conscious, the medical treatment and guidance system 100 proceeds to determine if the patient is having trouble breathing (e.g., because of choking as described above with reference to FIGS. 6A-6E and/or because of an allergic reaction as described above with reference to FIGS. 8A-8J).

If the caregiver responds "yes" indicating that the patient is unconscious in response to the inquiry 1314 asking "Is the patient unconscious?" and/or if the caregiver responds "No" in response to the inquiry 1310 asking if the patient is actively seizing, the medical treatment and guidance system 100 presents instructions 1316 to minimize neck and head movement of the patient. In some examples, the instructions 1316 include an instruction to "Ensure the patient is on their back. Minimize head and neck movement as much as possible."

Then the medical treatment and guidance system 100 presents an inquiry 1318 asking "Was the patient in a car accident, did they fall or is there a possible neck injury?" The medical treatment and guidance system 100 stores the caregiver's response to the inquiry 1318 asking if the patient was in a car accident, fell or has a possible neck injury, in memory as described above with reference to FIGS. 9A-9C.

The medical treatment and guidance system 100 presents instructions 1320 to assist the caregiver in checking for breathing of the patient. In some examples, the instructions 1320 include one or more of the following instructions. In some examples, the instructions 1320 include an instruction to "Prepare to check for breathing." In some examples, the instructions 1320 include an instruction 1322 (shown in FIG. 13D) of "STEP 1: Perform head-tilt, chin lift to open the airway." In some examples, the instructions 1320 include "STEP 2: Lean close to the patient to listen for breathing." In some examples, the instructions 1320 include "STEP 3: Look for chest rise. Listen for breathing. Feel for air movement." In some examples, the instructions 1320 include "STEP 4: Look, listen and feel for no more than 10 seconds."

After the medical treatment and guidance system 100 presents the instructions 1320, the medical treatment and guidance system 100 presents an inquiry 1323 asking "Is the patient breathing normally?" If the caregiver responds by indicating "Yes," as in this example, the medical treatment and guidance system 100 presents an inquiry 1325 asking the caregiver to "Examine the chest: Are there any open wounds on the front, back or sides?"

If the caregiver responds indicating that the patient does have open wounds, the medical treatment and guidance system 100 presents an inquiry 1326 asking if a chest seal is available (e.g., as a first priority medical supply). If yes, the medical treatment and guidance system 100 presents instructions 1328 to use the chest seal to treat the open wound. If the caregiver indicates that a chest seal is unavailable, the medical treatment and guidance system presents an inquiry 1330 asking if a gauze is available (e.g., as a second priority medical supply). If yes, the medical treatment and guidance system 100 presents instructions 1332 for using the gauze to treat the open wound. If the caregiver indicates that a gauze is unavailable, the medical treatment and guidance system presents instructions 1334 for using the caregiver's hands to apply pressure to the open wound.

If the caregiver responds that there are no open wounds in response to the inquiry 1325, the medical treatment and guidance system 100 presents instructions 1336 for the caregiver to assist the patient to lie on their side if there is no possible neck injury. In some examples, the instructions 1336 include instructions to "Lie the patient on their side. Ensure patient's knees and hip are bent. Support patient's head with your hand." In this example, the instructions 1336 depend on the response of inquiry 1318 asking "Was the patient in a car accident, did they fall or is there a possible neck injury?" For example, if the caregiver responded "yes" that the patient may have a possible neck injury, the medical treatment and guidance system 100 would not present the instructions 1336 asking the patient to lie on their side.

Referring back to the inquiry 1323, if the caregiver indicates that the patient is not breathing normally, the medical treatment and guidance system 100 presents an inquiry 1338 asking "Is there a possible drug overdose?" If the caregiver responds by indicating "Yes," in response to the inquiry 1338 about a possible drug overdose, the medical treatment and guidance system 100 presents an inquiry 1340 asking if drug overdose medication is available, e.g., by asking "Is Naloxone or Narcan available?" If the caregiver indicates "Yes," in response to the inquiry about having drug overdose medication available, the medical treatment and guidance system 100 provides instructions 1342 for using the available drug overdose medication to provide medical treatment to the patient experiencing a drug overdose emergency.

Referring back to the inquiry 1338, if the caregiver indicates that the patient is not experiencing a possible drug overdose, the medical treatment and guidance system 100 presents an inquiry 1344 asking if the caregiver is trained in CPR, e.g., by asking "Are you trained in CPR?" The flow from the inquiry 1338 to the instructions 1344 is shown from FIG. 13A to FIG. 13B. (The connection between FIGS. 13A and 13B is represented by connection marker A.) If the caregiver indicates "No," in response to the inquiry 1344 about being trained in CPR, as in this example, the medical treatment and guidance system 100 presents an inquiry 1346 asking if someone else is present to help the caregiver, e.g., by asking "Is there someone else there to help you?" If the caregiver indicates "No," in response to the inquiry 1346 about there being someone else to help the caregiver, as in this example, the medical treatment and guidance system 100 presents an inquiry 1348 asking if the caregiver has access to a nearby AED, e.g., by asking "Is there an AED nearby you can get?"

If the caregiver indicates "Yes," in response to the inquiry 1348 about there being an AED nearby that the caregiver can get, as in this example, the medical treatment and guidance system 100 presents an instruction 1350 instructing the caregiver to retrieve the AED. In some examples, the instruction 1350 includes "Go and get the AED. Press 'Next' below when you have retrieved the AED." If the caregiver indicates "Next," as in this example, the medical treatment and guidance system 100 presents instructions 1352 asking the caregiver to follow the AED instructions provided by the AED. In some examples, the instructions 1352 include "Follow the AED instructions. Press Start CPR when prompted by AED."

If the caregiver invokes a button labeled "Start CPR" after following the AED instructions, the medical treatment and guidance system 100 presents instructions 1354 to assist the caregiver in performing CPR treatment on the patient experiencing a breathing difficulty. In some examples, the instructions 1354 include one or more of the following instructions. In some examples, the instructions 1354 include an instruction "Prepare to begin CPR." In some examples, the instructions 1354 include "If using Mobile on your phone, increase the volume." (The application is referred to in this example as "Mobilize.") This instruction is important because the medical instructions can include audible instructions. In these examples, the medical treatment and guidance system 100 broadcasts audible instructions using a speaker of the caregiver's mobile device or other electronic device being used by the caregiver while providing treatment to the patient.

In some examples, the instructions 1354 include an instruction 1356 (shown in FIG. 13E) of "STEP 1: Kneel next to the patient." In some examples, a button 1357 labeled "AED has arrived" is present on the user interface. This button 1357 generally only appears when the caregiver invokes a button labeled "No," in response to the inquiry 1348 about there being an AED nearby. In some examples, the instructions 1354 include "STEP 2: Place one hand on top of the other and lace fingers together." In some examples, the instructions 1354 include "STEP 3: Keep your arms straight. Lock your elbows. Position your shoulders and body over your hands." In some examples, the instructions 1354 include "STEP 4: Locate the center of the chest and place the heel of your bottom hand on it." In some examples, the instructions 1354 include "Start compression only CPR. Elapsed time 00:08." In this example, the medical treatment and guidance system 100 continues to present medical instructions for administering CPR to the adult patient. In this way, the medical instructions 1354 include instructions to administer CPR treatment to the patient.

The above example related to administering CPR to an adult patient. In this example, medical treatment and guidance system 100 presented instructions to retrieve an AED first, followed by instructions to administer hands-only CPR to the adult patient after the AED has been retrieved. In some examples, the medical treatment and guidance system 100 also presents instructions to a second caregiver when a second caregiver is available.

The following example illustrates some of the differences when the adult patient is changed to a child patient. For example, if the caregiver indicates that the patient is a child in response to the inquiry 1306, the medical treatment and guidance system 100 proceeds down the flow path shown in FIG. 13C and presents substantially similar inquiries and instructions to the inquires and instructions of the above scenario regarding an adult patient. (The connection between FIGS. 13A and 13C is represented by connection marker B.)

For example, the medical treatment and guidance system 100 presents the inquiry 1346 asking if someone else is present to help the caregiver, e.g., by asking "Is there someone else there to help you?" However, in this scenario, if the caregiver responds by indicating "No," as in this example, the medical treatment and guidance system 100 presents an instruction 1359 informing the caregiver that if help arrives ask them to find an AED. In some examples, the instruction 1359 includes "If help arrives, send them to find an AED." In other words, the medical treatment and guidance system 100 presents instructions to begin CPR before asking the caregiver to retrieve an AED when the patient is a child.

Figures 13F, 13G:
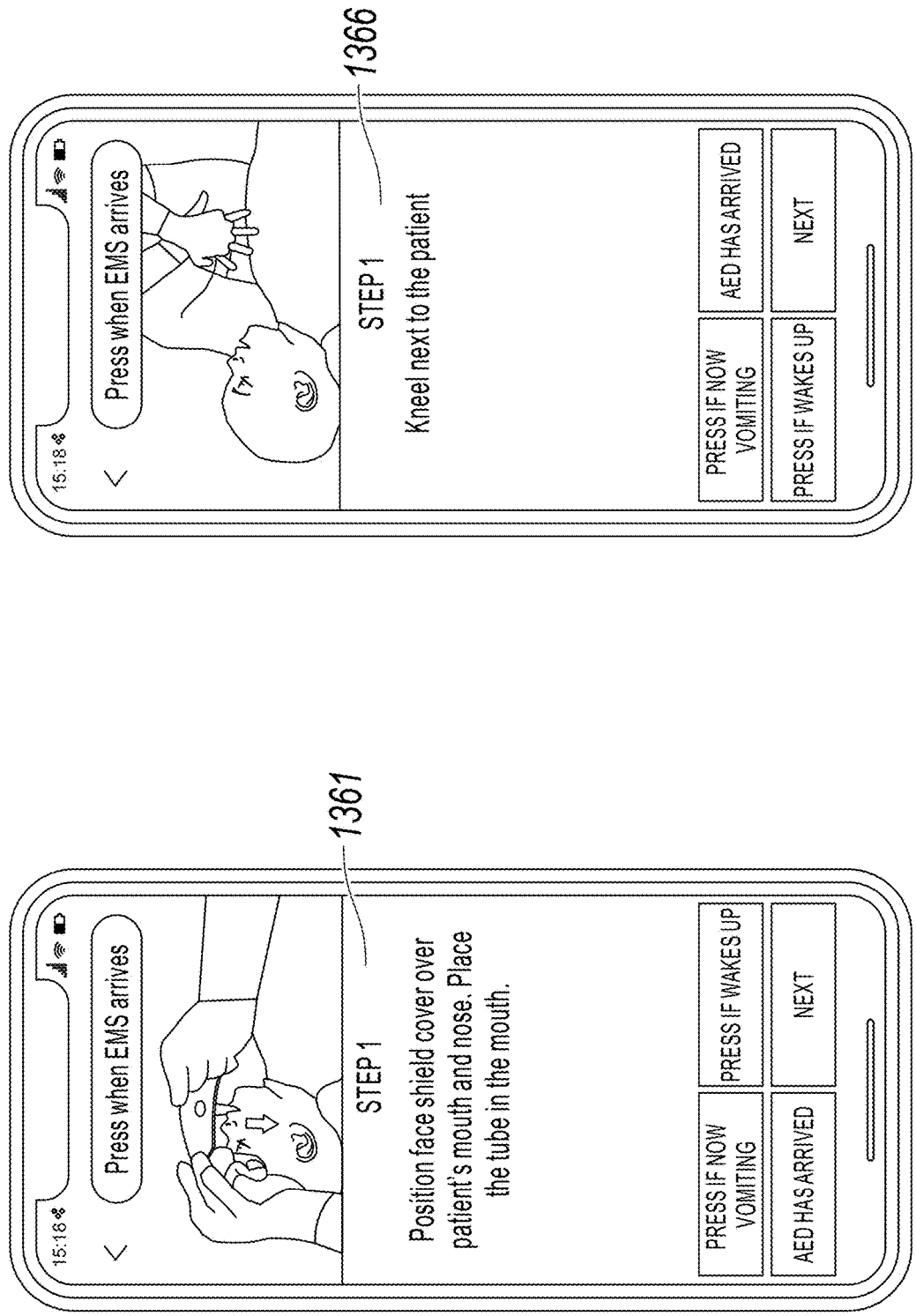
Figure 13I:
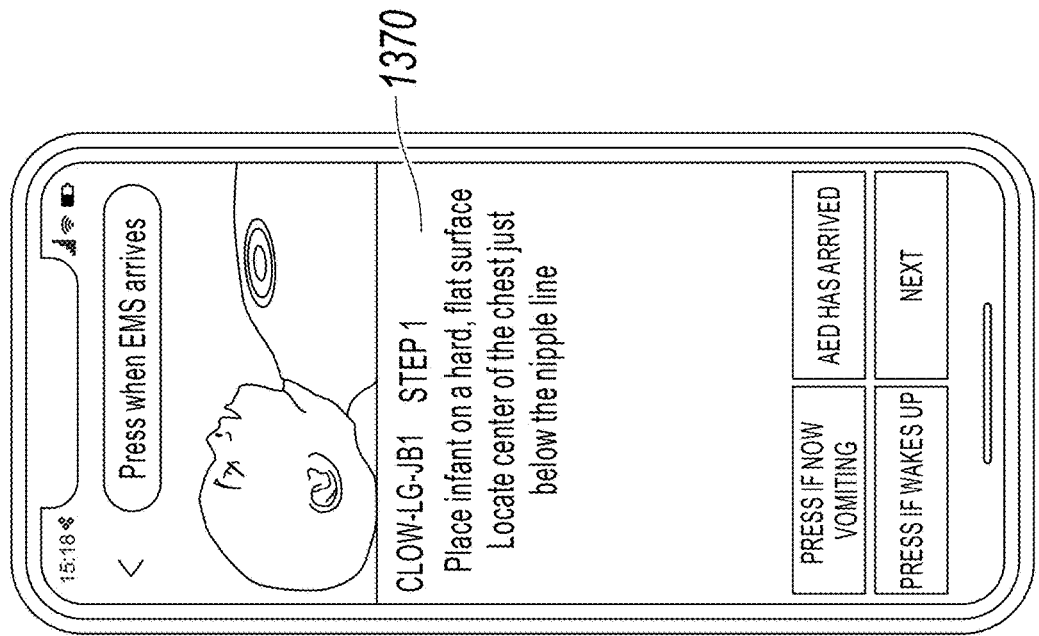
Figure 13H:
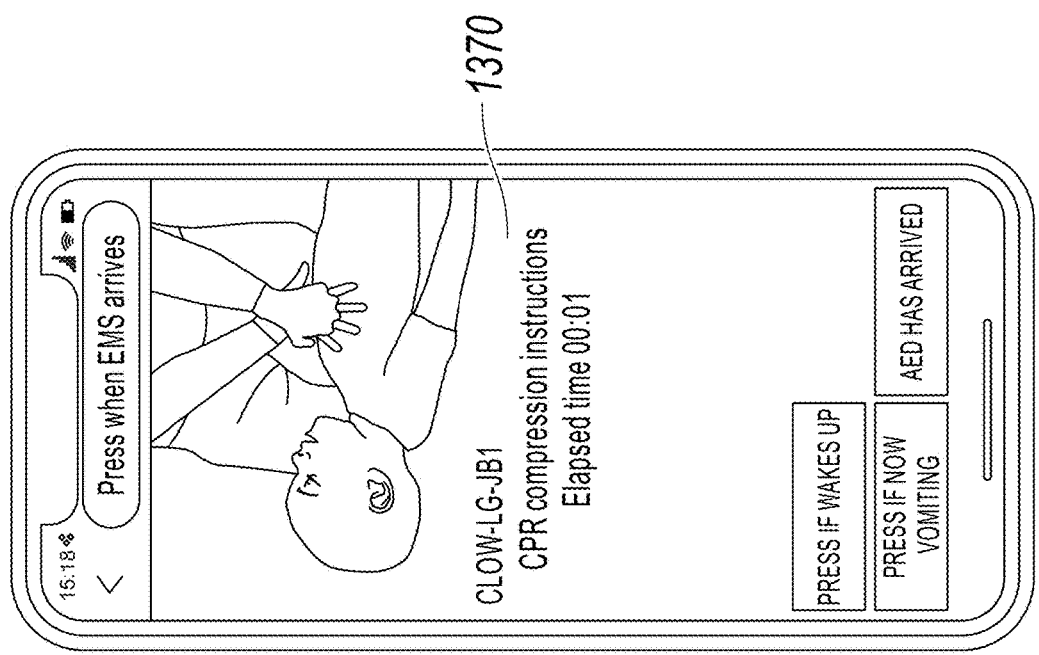

Then the medical treatment and guidance system 100 presents an instruction 1358 asking if the caregiver has a face shield, e.g., by asking to "Locate the face shield labelled Face Shield D1." Then the medical treatment and guidance system 100 presents instructions 1360 to assist the caregiver in using the face shield in preparation of a CPR treatment. In some examples, the instructions 1360 includes one or more of the following instructions. In some examples, the instructions 1360 include "Prepare to position the face shield." In some examples, the instructions 1360 include "Prepare to position the face shield." In some examples, the instructions 1360 include instructions 1361 (as shown in FIG. 13F) of "STEP 1: Position face shield cover over patient's mouth and nose. Place the tube in the mouth." In some examples, the instructions 1360 include "STEP 2: Perform head-tilt, chin lift to open the airway."

Then the medical treatment and guidance system 100 presents instructions 1362 to assist the caregiver in administering rescue breaths to the patient. In some examples, the instructions 1362 include an instruction asking the caregiver to "Prepare to give two rescue breaths." In some examples, the instructions 1362 include an instruction asking "Did breaths go in? Chest will rise and fall if the breaths went in." If a caregiver responds by indicating "Yes" that the breaths did go in, as in this example, the medical treatment and guidance system 100 presents an instruction asking the caregiver to "Prepare to begin CPR." Then the medical treatment and guidance system 100 presents instructions 1364 to prepare to begin administering CPR to the patient. In some examples, the instructions 1364 include one or more of the following instructions. In some examples, the instructions 1364 include "If using Mobilize on your phone, increase the volume." (The application is referred to in this example as "Mobilize.") In some examples, the instructions 1364 include an instruction 1366 (shown in FIG. 13G) of "STEP 1: Kneel next to the patient." In some examples, the instructions 1364 include "STEP 2: Place one hand on top of the other and lace fingers together." In some examples, the instructions 1364 include "STEP 3: Keep your arms straight. Lock your elbows. Position your shoulders and body over your hands." In some examples, the instructions 1364 include "STEP 4: Locate the center of chest and place the heel of your bottom hand on it. Use one hand for smaller children." In some examples, the instructions 1364 include "If you have help, alternate giving breaths and doing chest compressions."

If the caregiver invokes a button labeled "Start CPR," as in this example, the medical treatment and guidance system 100 presents instructions 1368 to assist the caregiver in administering CPR to the patient. In some examples, the instructions 1368 include one or more of the following instructions. In some examples, the instructions 1368 include an instruction 1370 (shown in FIG. 13H) of "CPR compression instructions. Elapsed time 00:01." In some examples, the instructions 1368 include "Prepare to give two rescue breaths." In some examples, the instructions 1368 include "Breathing instructions. Elapsed time 00:32." In some examples, the medical treatment and guidance system 100 continues to present medical instructions 1368 for administering CPR to the child patient.

In the above example, the medical treatment and guidance system 100 provides instructions to administer CPR treatment to the patient and the medical instructions depending on the age classification of the patient. In particular, the medical treatment and guidance system 100 presented instructions to begin CPR first, followed by instructions to locate an AED after the CPR has begun. The instructions to administer CPR to the child patient include alternating giving breaths and performing chest compressions to the child patient. In some examples, the medical treatment and guidance system 100 also presents instructions to a second caregiver when a second caregiver is available.

The above example relates to administering CPR to a child patient. The following example illustrates some of the differences when the patient is changed to an infant patient. For example, if the caregiver indicates that the patient is an infant in response to inquiry 1306, the medical treatment and guidance system 100 proceeds down the same flow path as the child example shown in FIG. 13C and presents substantially similar inquiries and instructions to the inquiries and instructions described above with reference to the child example.

In the infant example, the medical treatment and guidance system 100 presents instructions 1364 to assist the caregiver in preparing to administer CPR to the patient just like the child scenario. However, the instructions 1364 are different in the infant scenario than in the child scenario. For example, the instructions 1364 include one or more of the following instructions when the patient is an infant patient. In some examples, the instructions 1364 include instruction 1370 (shown in FIG. 13I) of "STEP 1: Place infant on a hard, flat surface. Locate center of the chest just below the nipple line." In some examples, the instructions 1364 include "STEP 2: Pick up the infant with both hands. Place thumbs on the center of chest." In some examples, the instructions 1364 include of "If you have help, alternate giving breaths and doing chest compressions." If a caregiver responds by invoking a button labeled "Start CPR," the medical treatment and guidance system 100 presents an instruction of "If you have help, alternate giving breaths and doing chest compressions." Then the medical treatment and guidance system 100 presents an instruction of "Prepare to give two rescue breaths." Then the medical treatment and guidance system 100 presents an instruction of "Breathing instructions. Elapsed time 00:31." The medical treatment and guidance system 100 continues to present medical instructions for administering CPR to the infant patient.

In this example, the medical treatment and guidance system 100 also presents instructions to begin CPR before asking the caregiver to retrieve an AED. The instructions to administer CPR to the infant patient include instructions that focus on the airway and repositioning of the airway of the infant (e.g., arrest of an infant's respiratory airway can lead to infant cardiac arrest). The instructions to administer CPR to the infant patient include instructions to alternate giving breaths and performing chest compressions to the infant patient. In some examples, the medical treatment and guidance system 100 also presents instructions to a second caregiver when a second caregiver is available. In this way, the medical instructions can depend on the age classification of the patient such that different medical instructions are presented on the user interface depending on the patient age.

FIG. 14A shows a process 1400 of operations performed by the medical treatment and guidance system 100 presenting medical instructions to assist a patient that has an upper respiratory/droplet communicable disease in accordance with some embodiments. FIGS. 14B-14C illustrate the medical treatment and guidance application presenting medical instructions on a user interface of the electronic device associated with the operations of the process 1400.

In this example, the medical treatment and guidance system 100 recognizes upper respiratory/droplet communicable diseases based on responses to inquiries. For example, the medical treatment and guidance system 100 determines that the patient has a communicable disease based on a shortness of breath and/or a cough of the patient as part of a second priority medical emergency inquiry. Then the medical treatment and guidance system 100 provides instructions for the caregiver to put on a face mask (e.g., a facial covering) and also put a face mask on the patient.

This example begins the same as the process 1000 shown in FIG. 10A. For example, the process 1400 begins at step 1402 and the medical treatment and guidance system 100 presents an inquiry 1404 about the age classification of the patient. In this example, the process 1400 does not depend on whether the patient is an adult, child, or infant, so the result of the reply to the inquiry 1404 is the same for adults, children, and infant patients, although the caregiver's reply can be stored in memory for later use in determining various instructions to provide to the caregiver, as discussed herein. In response, if the caregiver indicates "Adult" (or "child" or "infant"), the medical treatment and guidance system 100 presents an inquiry 1406 asking "Is the patient awake?" If the caregiver indicates that the patient is awake, as in this example, the medical treatment and guidance system 100 determines that the patient is conscious and proceeds to determine if the patient may have a communicable disease. For example, if the caregiver indicates that the patient is awake, e.g., by invoking a button in response to the inquiry 1406, the medical treatment and guidance system 100 presents an inquiry 1408 asking the caregiver "Does the patient have a shortness of breath?" If the caregiver responds by indicating yes, as in this example, the medical treatment and guidance system 100 presents an inquiry 1410 asking the caregiver "Does the patient have a cough?"

If the caregiver responds by indicating yes, as in this example, the medical treatment and guidance system 100 determines that the patient may have an upper respiratory/droplet communicable disease. When this occurs, the medical treatment and guidance system 100 presents an instruction 1412 informing the caregiver that the patient may have a respiratory/droplet communicable disease. In some examples, the instructions 1412 include "Patient may have an upper respiratory/droplet communicable disease. Step back from the patient. Prepare to apply face mask to yourself and to the patient." Then the medical treatment and guidance system 100 presents instructions 1414 to apply face masks to the caregiver and to the patient. In some examples, the instructions 1414 include one or more of the following instructions. In some examples, the instructions 1414 include instructions 1416 (shown in FIG. 14B) asking the caregiver to "Locate 2 face masks labeled face mask." In some examples, the instructions 1414 include instructions 1418 (shown in FIG. 14C) asking the caregiver to "Prepare to put the face mask on the patient or ask the patient to put the face mask on themselves." In some examples, the instructions 1414 include instructions asking the caregiver to "Put the face mask on the patient or ask the patient to put the face mask on themselves."

In this way, the medical treatment and guidance system 100 can determine instructions related to communicative diseases and can include instructions for applying at least one face mask. Also, the determined instructions can be based on at least one response to at least one inquiry related to shortness of breath and/or a patient cough. After presenting the instructions 1414, the medical treatment and guidance system 100 presents an inquiry 1419 asking the caregiver to select which apparatus type is available to the caregiver. In this example, a portable medical treatment and guidance apparatus is identified as a "Mobilize kit," as shown in FIG. 14A. In this way, the process 1400 resumes similarly to the other examples that include an inquiry similar to the inquiry 14919. In this example, the inquiry 1419 is asked of the caregiver after the system 100 presents instructions 1414 to apply the face masks because the medical treatment and guidance system 100 has predetermined that face masks are available in each medical treatment and guidance apparatus regardless of apparatus type.

FIGS. 15A and 15B show a process 1500 of operations performed by the medical treatment and guidance system 100 presenting medical instructions to assist a patient that is experiencing bleeding, and the instructions include instructions for using medical supplies that depend on the apparatus type in accordance with some embodiments. FIGS. 15C-15M illustrate the medical treatment and guidance application presenting medical instructions on a user interface of the electronic device associated with the operations of the process 1500.

The process 1500 begins the same way as various processes described herein. For example, the process 1500 begins at step 1502, and the medical treatment and guidance system 100 presents an inquiry 1504 asking about the patient's age (as previously described).

In response, if the caregiver indicates "Adult" (or "Child" or "Infant"), the medical treatment and guidance system 100 presents an inquiry asking "Is the patient awake?" In response, if the caregiver indicates "Yes," the medical treatment and guidance system 100 presents an inquiry asking the caregiver "Was the patient in a car accident, did they fall or is there a possible neck injury?" In response, if the caregiver indicates "No," the medical treatment and guidance system 100 presents an inquiry asking the caregiver "Is the patient having trouble breathing?" In response, if the caregiver indicates "No," as in this example, the medical treatment and guidance system 100 presents an apparatus type inquiry 1506 asking the caregiver to select which apparatus type is available to the caregiver. In this example, a portable medical treatment and guidance apparatus is identified as a "Mobilize kit," as shown in FIG. 15A.

In response, if the caregiver indicates "Hardcase/Backpack," to select the comprehensive medical treatment and guidance apparatus, as in this example, the medical treatment and guidance system 100 presents an inquiry asking the caregiver "Are there any other patients with bad bleeding, unconscious or having trouble breathing?" In response, if the caregiver indicates "No other patients," the medical treatment and guidance system 100 presents an inquiry asking the caregiver "What is wrong with the patient?"

In response, if the caregiver indicates "I am not sure," the medical treatment and guidance system 100 presents an inquiry asking the caregiver "Is there bleeding from an injury?" In response, if the caregiver indicates "Yes," the medical treatment and guidance system 100 presents an inquiry asking the caregiver "Is the bleeding caused by one of these?" and presents response buttons for a trapped limb, an impaled object, an amputation, and a button for "None of these." In response, if the caregiver indicates "None of these," as in this example, the medical treatment and guidance system 100 presents an inquiry 1508 (shown in FIG. 15C) asking the caregiver "Where is the blood coming from?" and presents an image of the human body with radio buttons 1510 that the caregiver can select.

In response, if the caregiver invokes the radio button 1510 located in an area of the patient's head to indicate that the blood is coming from the patient's head, the medical treatment and guidance system 100 presents an inquiry asking the caregiver to refine their selection of where the blood is coming from. In this example, the medical treatment and guidance system 100 presents an inquiry 1512 (shown in FIG. 15D) asking the caregiver "Where is the blood coming from?" and presents a set of radio buttons 1514 representing different areas of the patient's head. In response, if the caregiver invokes a radio button 1514 in an area of the patient's forehead to indicate that blood is coming from the patient's forehead (or otherwise the top of their head), as in this example, the medical treatment and guidance system 100 presents an instruction 1516 (shown in FIG. 15E) asking if the caregiver has small size gauze, e.g., by asking the caregiver to locate small size gauze. In some examples, the instruction 1516 includes an instruction to "Locate gauze labeled Gauze 3."

In response, if the caregiver indicates that the small size gauze has been located (e.g., by invoking a button labeled "Next"), as in this example, the medical treatment and guidance system 100 presents instructions 1518 to assist the caregiver in treating the patient experiencing a bleeding injury in the area of the patient's head using the small size gauze. In some examples, the instructions 1518 include one or more of the following instructions. In some examples, the instructions 1518 include "STEP 1: Open gauze package, then remove gauze." In some examples, the instructions 1518 include an instruction 1520 (shown in FIG. 15F) of "STEP 2: Place gauze directly over wound." In some examples, the instructions 1518 include "STEP 3: Use firm pressure with both hands on the gauze." In some examples, the instructions 1518 include "STEP 4: Hold firm pressure for 3 minutes. Time remaining 03:00."

If, however, the caregiver indicated that he/she does not have the small size gauze in response to the inquiry 1516, e.g., by invoking a button 1522 (shown in FIG. 15E) labeled "I don't have that," the medical treatment and guidance system 100 changes the instructions so that instead of using a first choice medical supply (the small size gauze in this example), the medical treatment and guidance system 100 provides instructions that use a second choice medical supply.

In particular, if the caregiver does not have the small size gauze, the medical treatment and guidance system 100 presents an instruction 1524 (shown in FIG. 15G) asking if the caregiver has large trauma gauze, e.g., asking to locate the large trauma gauze. In some examples, the instruction 1524 includes an instruction to "Locate the large trauma gauze labeled trauma gauze." In other words, the medical treatment and guidance system 100 presented instructions for using the first and second choice medical supplies because the medical treatment and guidance system 100 predetermined that these medical supplies are available within the apparatus type identified by the caregiver. In this example, the medical treatment and guidance system 100 changed the instructions from the small size gauze to the large trauma gauze.

In response, if the caregiver indicates that the "large trauma gauze" is available in response to the instruction 1524, the medical treatment and guidance system 100 presents instructions 1526 to assist the caregiver in treating the patient experiencing a bleeding injury in the area of the patient's head using the large trauma gauze. In some examples, the instructions for using the small size gauze vs. the large trauma gauze are identical.

If, however, the caregiver indicated that he/she does not have the large trauma gauze in response to the instruction 1524, e.g., by invoking a button 1528 (shown in FIG. 15G) labeled "I don't have that," the medical treatment and guidance system 100 changes the instructions so that instead of using a second choice medical supply (the large trauma gauze in this example), the medical treatment and guidance system 100 provides instructions that use a third choice medical supply. In particular, the medical treatment and guidance system 100 presents an instruction 1530 (shown in FIG. 15H) asking if the caregiver has a pressure dressing, e.g., by asking to "Locate the pressure dressing labeled Pressure Dressing B2." In this way, the medical treatment and guidance system 100 predetermined that a pressure dressing is also available within the apparatus type identified by the caregiver.

In response, if the caregiver indicates that the "pressure dressing" is available, the medical treatment and guidance system 100 presents instructions 1532 to assist the caregiver in treating the patient experiencing a bleeding injury in the area of the patient's head using the pressure dressing. In some examples, the instructions 1532 include one or more of the following instructions. In some examples, the instructions 1532 include "STEP 1: Expose white pad. Do not touch white pad." In some examples, the instructions 1532 include instructions 1534 (shown in FIG. 15I) of "STEP 2: Place white pad against the skin. Do not obstruct mouth or nose." In some examples, the instructions 1532 include "STEP 3: Hold pad in place with one hand and wrap bandage snugly around the head." In some examples, the instructions 1532 include "STEP 4: Dressing should be tight to keep pressure on wound. Clip in place. Do not cover the mouth."

If, however, the caregiver indicated that he/she does not have the pressure dressing in response to the instruction 1530, e.g., by invoking a button 1536 (shown in FIG. 15H) labeled "I don't have that," the medical treatment and guidance system 100 changes the instructions so that instead of using a third choice medical supply (the pressure dressing in this example), the medical treatment and guidance system 100 provides instructions that use a fourth choice medical supply. In particular, the medical treatment and guidance system 100 presents an instruction 1538 (shown in FIG. 15J) asking if the caregiver has quick clot gauze, e.g., by asking to locate a quick clot gauze. In some examples, instructions 1538 include an instruction of "Locate the QuikClot® gauze labeled QuickClot® B1." In this way, the medical treatment and guidance system 100 predetermined that a QuikClot® gauze is also available within the apparatus type identified by the caregiver.

In response, if the caregiver indicates that the "Quik-Clot®" is available, the medical treatment and guidance system 100 presents instructions 1540 to assist the caregiver in treating the patient experiencing a bleeding injury in the area of the patient's head using the quick clot gauze, e.g., QuikClot® gauze. In some examples, the instructions 1540 include one or more of the following instructions. In some examples, the instructions 1540 include "Prepare to apply direct pressure with QuikClot." In some examples, the instructions 1540 include of "STEP 1: Open QuikClot package. Unravel rolled gauze and wad gauze into a ball." In some examples, the instructions 1540 include an instruction 1542 (shown in FIG. 15K) of "STEP 2: Place ball of wadded up gauze directly on the wound." In some examples, the instructions 1540 include "STEP 3: Use steady firm pressure with both hands on gauze." In some examples, the instructions 1540 include "STEP 4: Hold firm pressure for 3 minutes. Time remaining 03:00."

If, however, the caregiver indicated that he/she did not have the quick clot gauze, e.g., by invoking a button 1544 (shown in FIG. 15J) labeled "I don't have that," the medical treatment and guidance system 100 changes the instructions so that instead of using a fourth choice medical supply (the QuikClot® gauze in this example), the medical treatment and guidance system 100 provides instructions that use a fifth choice medical supply and/or gloved hands. In particular, the medical treatment and guidance system 100 presents instructions 1546 to assist the caregiver in treating the patient experiencing a bleeding injury in the area of the patient's head using the caregiver's gloved hands. In some examples, the instructions 1546 include one or more of the following instructions. In some examples, the instructions 1546 include "Stay calm and continue." In some examples, the instructions 1546 include "Prepare to apply direct pressure with gloved hands." In some examples, the instructions 1546 include an instruction 1548 (shown in FIG. 15L) of "STEP 1: Use steady firm pressure with both hands on the wound." In some examples, the instructions 1546 include "STEP 2: Hold pressure for 3 minutes. Time Remaining 02:58." In this example, the medical treatment and guidance system 100 provides the instructions 1546 using the caregiver's gloved hands as a last resort (as a fifth priority).

Regardless of the medical supply used, the medical treatment and guidance system 100 presents an inquiry 1544 asking the caregiver "Did the bleeding from this wound stop?" In response, if the caregiver indicates that the bleeding has stopped, the medical treatment and guidance system 100 presents an instruction 1547 (shown in FIG. 15M) asking if the caregiver has pressure dressing, e.g., asking "Locate the pressure dressing labeled pressure dressing B2." In other words, the medical treatment and guidance system 100 presents instructions to apply a second pressure dressing to the wound if one is available. This response depends from the previous medical supply inquiries such that if the caregiver already responded that a pressure dressing is unavailable, then the medical treatment and guidance system 100 skips this step. The instruction 1547 occurs in the process 1500 after the instruction 1530 asking if the caregiver has a pressure dressing, to which the caregiver replied "Yes" in this example. The caregiver is asked about pressure dressing again in the instruction 1547 because, based on the caregiver's previous indication of a comprehensive medical treatment and guidance apparatus being available, the system 100 has predetermined that more than one pressure dressing should be available to the caregiver based on the predetermined medical supplies in the comprehensive medical treatment and guidance apparatus including multiple pressure dressings. Even if the caregiver previously indicated instead that a compact medical treatment and guidance apparatus was available, the system 100 can still present the instruction 1547 to the caregiver even though the system 100 has predetermined that only one pressure dressing is available in a compact medical treatment and guidance apparatus because, for example, the caregiver may have more than one compact medical treatment and guidance apparatus available and thus have more than one pressure dressing available. Patient treatment may thus be optimized by the system 100 asking the caregiver questions to yield best patient outcome, e.g., use of two pressure dressings instead of one, even if the caregiver's prior response to the type of medical treatment and guidance apparatus available would otherwise indicate that such patient treatment would not be possible because of the limited medical supplies predetermined to be present in the compact medical treatment and guidance apparatus.

In this example, if the caregiver indicates that the pressure dressing is unavailable, e.g., by invoking a button 1549 (shown in FIG. 15M) labeled "I do not have that," the medical treatment and guidance system 100 presents an instruction asking the caregiver to "Stay calm and continue." Then the medical treatment and guidance system 100 provides instructions to apply pressure using a gloved hand that is substantially similar to the example above with reference to the instructions 1546. In this way, the medical treatment and guidance system 100 determined that the pressure dressing is the first choice medical supply for this step and because the caregiver indicated that pressure dressing is unavailable, the medical treatment and guidance system 100 determined that providing instructions for the caregiver to assist the patient using a gloved hand is the next best option.

Then the medical treatment and guidance system 100 presents an inquiry asking the caregiver "Does the patient appear to be bleeding anywhere else?" In response, if the caregiver indicates that the patient is not bleeding anywhere else, as in this example, the medical treatment and guidance system 100 presents an inquiry 1550 asking the caregiver "Is there anything else wrong with the current patient?"

In the above example, the medical treatment and guidance system 100 provides instructions to treat an adult patient experiencing a bleeding head injury. The instructions include instructions for using medical supplies that were predetermined to exist within the available apparatus type of the comprehensive medical treatment and guidance apparatus. The instructions included providing instructions using a first choice medical supply, a second choice medical supply, a third choice medical supply, a fourth choice medical supply, and using gloved hands as a last resort. The medical treatment and guidance system 100 also saved which medical supplies were unavailable in memory so that subsequent questions would not repeatable ask the caregiver to use a medical supply that was already indicated to be unavailable.

In the following scenario, a compact medical treatment and guidance apparatus is indicated to be available to the caregiver in reply to the inquiry 1506 instead of the comprehensive medical treatment and guidance apparatus. The medical treatment and guidance system 100 determines different instructions based on the different apparatus type. For example, if the caregiver indicates that the compact medical treatment and guidance apparatus is available (e.g., by invoking a button in response to the inquiry 1506), the medical treatment and guidance system 100 presents proceeds with the process 1500 as shown in FIG. 15B. (The connection between FIG. 15A and FIG. 15B is represented by connection "A.") The flow of this example with a compact medical treatment and guidance apparatus is the same as the example above with reference to the comprehensive medical treatment and guidance apparatus. For example, the steps up to the inquiry 1512 are the same. In this example, the medical treatment and guidance system 100 presents the inquiry 1512 asking where the blood is coming from and the caregiver responds in the same way, e.g., by indicating that blood is coming from the top of the patient's head.

However, in this example, the medical treatment and guidance system 100 presents instructions 1552 to assist the caregiver in treating the patient experiencing a bleeding injury in the area of the patient's head using the caregiver's gloved hands. In some examples, the instructions 1552 include "Prepare to apply direct pressure with gloved hands." In some examples, the instructions 1552 include "STEP 1: Use steady firm pressure with both hands on the wound." In some examples, the instructions 1552 include "STEP 2: Hold pressure for 3 minutes. Time Remaining 03:00."

Then the medical treatment and guidance system 100 presents an inquiry 1554 asking the caregiver "Did the bleeding from this wound stop?" In response, if the caregiver indicates "Yes," as in this example, the medical treatment and guidance system 100 presents an inquiry asking the caregiver "Does the patient appear to be bleeding anywhere else?" In response, if the caregiver indicates "No," as in this example, the medical treatment and guidance system 100 presents an inquiry 1556 asking the caregiver "Is there anything else wrong with this patient?"

In the above example, the medical treatment and guidance system 100 skipped over instructions for medical supplies that the medical treatment and guidance system 100 predetermined to not exist within the available apparatus type of the compact medical treatment and guidance apparatus. In particular, the medical treatment and guidance system 100 presented instructions for the caregiver to apply pressure to the wound using a gloved hand in lieu of medical supplies because the medical treatment and guidance system 100 predetermined that gauze, a trauma gauze, a pressure dressing, and a QuikClot® gauze is not present within the compact medical treatment and guidance apparatus. In this way, the medical treatment and guidance system 100 can present instructions that depend on apparatus type. In particular, the instructions can include first choice and second choice medical supplies that depend on the apparatus type.

FIG. 16 is a block diagram of computer systems forming part of the portable emergency medical treatment and guidance apparatuses and/or defibrillators in according to some embodiments. For example, a computing device 1600 and example mobile computing device 1650 which can be used to implement the techniques previously described. Computing device 1600 is intended to represent various forms of digital computers, including, e.g., laptops, desktops, workstations, personal digital assistants, servers, blade servers, mainframes, and other appropriate computers. Computing device 1650 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 1600 includes processor 1602, memory 1604, storage device 1606, high-speed interface 1608 connecting to memory 1604 and high-speed expansion ports 1610, and low speed interface 1612 connecting to low speed bus 1614 and storage device 1606. Each of components 1602, 1604, 1606, 1608, 1610, and 1612, are interconnected using various busses, and can be mounted on a common motherboard or in other manners as appropriate. Processor 1602 can process instructions for execution within computing device 1600, including instructions stored in memory 1604 or on storage device 1606 to display graphical data for a GUI on an external input/output device, including, e.g., display 1616 coupled to high speed interface 1608. In other implementations, multiple processors and/or multiple busses can be used, as appropriate, along with multiple memories and types of memory. Also, multiple computing devices 1600 can be connected, with each device providing portions of the necessary operations (e.g., as a server bank, a group of blade servers, or a multi-processor system).

Memory 1604 stores data within computing device 1600. In one implementation, memory 1604 is a volatile memory unit or units. In another implementation, memory 1604 is a non-volatile memory unit or units. Memory 1604 also can be another form of computer-readable medium (e.g., a magnetic or optical disk. Memory 1604 may be non-transitory.)

Storage device 1606 is capable of providing mass storage for computing device 1600. In one implementation, storage device 1606 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 1604, storage device 1606, memory on processor 1602, and the like.)

High-speed controller 1608 manages bandwidth-intensive operations for computing device 1600, while low speed controller 1612 manages lower bandwidth-intensive operations. Such allocation of functions is an example only. In one implementation, high-speed controller 1608 is coupled to memory 1604, display 1616 (e.g., through a graphics processor or accelerator), and to high-speed expansion ports 1610, which can accept various expansion cards (not shown). In the implementation, low-speed controller 1612 is coupled to storage device 1606 and low-speed expansion port 1614. The low-speed expansion port 1614, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.)

Computing device 1600 can be implemented in a number of different forms, as shown in the FIG. 16. For example, it can be implemented as standard server 1620, or multiple times in a group of such servers. It also can be implemented as part of rack server system 1624. In addition or as an alternative, it can be implemented in a personal computer (e.g., laptop computer 1622.) In some examples, components from computing device 1600 can be combined with other components in a mobile device (not shown), e.g., device 1650. Each of such devices can contain one or more of computing device 1600, 1650, and an entire system can be made up of multiple computing devices 1600, 1650 communicating with each other.

Computing device 1650 includes processor 1652, memory 1664, an input/output device (e.g., display 1654, communication interface 1666, and transceiver 1668) among other components. Device 1650 also can be provided with a storage device, (e.g., a microdrive or other device) to provide additional storage. Each of components 1650, 1652, 1664, 1654, 1666, and 1668, are interconnected using various buses, and several of the components can be mounted on a common motherboard or in other manners as appropriate.

Processor 1652 can execute instructions within computing device 1650, including instructions stored in memory 1664. The processor can be implemented as a chipset of chips that include separate and multiple analog and digital processors. The processor can provide, for example, for coordination of the other components of device 1650, e.g., control of user interfaces, applications run by device 1650, and wireless communication by device 1650.

Processor 1652 can communicate with a user through control interface 1658 and display interface 1656 coupled to display 1654. Display 1654 can be, for example, a TFT LCD (Thin-Film-Transistor Liquid Crystal Display) or an OLED (Organic Light Emitting Diode) display, or other appropriate display technology. Display interface 1656 can comprise appropriate circuitry for driving display 1654 to present graphical and other data to a user. Control interface 1658 can receive commands from a user and convert them for submission to processor 1652. In addition, external interface 1662 can communicate with processor 1652, so as to enable near area communication of device 1650 with other devices. External interface 1662 can provide, for example, for wired communication in some implementations, or for wireless communication in other implementations, and multiple interfaces also can be used.

Memory 1664 stores data within computing device 1650. Memory 1664 can be implemented as one or more of a computer-readable medium or media, a volatile memory unit or units, or a non-volatile memory unit or units. Expansion memory 1674 also can be provided and connected to device 1650 through expansion interface 1672, which can include, for example, a SIMM (Single In Line Memory Module) card interface. Such expansion memory 1674 can provide extra storage space for device 1650, or also can store applications or other data for device 1650. Specifically, expansion memory 1674 can include instructions to carry out or supplement the processes described above, and can include secure data also. Thus, for example, expansion memory 1674 can be provided as a security module for device 1650, and can be programmed with instructions that permit secure use of device 1650. In addition, secure applications can be provided through the SIMM cards, along with additional data, (e.g., placing identifying data on the SIMM card in a non-hackable manner.)

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 1664, expansion memory 1674, and/or memory on processor 1652), which can be received, for example, over transceiver 1668 or external interface 1662.

Device 1650 can communicate wirelessly through communication interface 1666, which can include digital signal processing circuitry where necessary. Communication interface 1666 can provide for communications under various modes or protocols (e.g., GSM voice calls, SMS, EMS, or MMS messaging, CDMA, TDMA, PDC, WCDMA, CDMA1500, or GPRS, among others.) Such communication can occur, for example, through radio-frequency transceiver 1668. In addition, short-range communication can occur, e.g., using a Bluetooth®, WiFi, or other such transceiver (not shown). In addition, GPS (Global Positioning System) receiver module 1670 can provide additional navigation- and location-related wireless data to device 1650, which can be used as appropriate by applications running on device 1650. Sensors and modules such as cameras, microphones, compasses, accelerators (for orientation sensing), etc. may be included in the device.

Device 1650 also can communicate audibly using audio codec 1660, which can receive spoken data from a user and convert it to usable digital data. Audio codec 1660 can likewise generate audible sound for a user, (e.g., through a speaker in a handset of device 1650.) Such sound can include sound from voice telephone calls, can include recorded sound (e.g., voice messages, music files, and the like) and also can include sound generated by applications operating on device 1650.

Computing device 1650 can be implemented in a number of different forms, as shown in the FIG. 16. For example, it can be implemented as cellular telephone 1680. It also can be implemented as part of smartphone 1682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the present disclosure.

What is claimed is:

1. A portable medical treatment and guidance apparatus for assisting a caregiver in evaluating and treating a patient experiencing a medical emergency according to a time sensitive prioritization of the medical emergency, the apparatus comprising:
   a housing having at least one compartment;
   a plurality of medical supplies housed within the at least one compartment;
   a user interface configured to receive input and provide an interactive query flow for assisting the caregiver in providing medical treatment; and
   at least one processor and memory communicatively coupled to the user interface, the at least one processor and memory configured to:
      present, via the user interface, at least one inquiry according to a first priority medical emergency as part of the interactive query flow;
      receive, via the user interface, at least one user input in response to the at least one inquiry according to the first priority medical emergency;
      present, via the user interface, at least one inquiry regarding a characteristic of the patient after receiving the at least one user input in response to the at least one inquiry according to the first priority medical emergency;
      receive, via the user interface, at least one user input in response to the at least one inquiry regarding the characteristic of the patient;
      determine a patient characteristic based on at least one response from the user interface regarding the characteristic of the patient;
      present, via the user interface, at least one inquiry according to a second priority medical emergency after receiving the at least one user input in response to the at least one inquiry regarding the characteristic of the patient;
      receive, via the user interface, at least one user input in response to the at least one inquiry according to the second priority medical emergency;
      determine instructions for assisting the caregiver in treating the patient based on at least one of: i) the at least one user input according to the first priority medical emergency, ii) the determined patient characteristic, or iii) the at least one user input according to the second priority medical emergency, the instructions comprising instructions for using at least one medical supply for treating the medical emergency of the patient; and
      present, via the user interface, the determined instructions to assist the caregiver in treating the medical emergency.

2. The portable medical treatment and guidance apparatus of claim 1, wherein the at least one processor and memory is configured to:
   present, via the user interface, at least one inquiry regarding an apparatus type of the portable medical treatment and guidance apparatus after receiving the at least one user input in response to the at least one inquiry according to the second priority medical emergency;
   receive, via the user interface, at least one user input in response to the at least one inquiry regarding the apparatus type;
   determine an apparatus type of the portable medical treatment and guidance apparatus;
   present, via the user interface, at least one inquiry according to a third priority medical emergency after receiving the at least one user input in response to the at least one inquiry regarding the apparatus type of the portable medical treatment and guidance apparatus; and
   receive, via the user interface, at least one user input in response to the at least one inquiry according to the third priority medical emergency,
   wherein determining the instructions for assisting the caregiver in treating the patient are based on the at least one user input according to the third priority medical emergency.

3. The portable medical treatment and guidance apparatus of claim 2, wherein determining the instructions for assisting the caregiver in treating the patient are determined based on the determined patient characteristic and the determined apparatus type.

4. The portable medical treatment and guidance apparatus of claim 3, wherein the at least one processor and memory is configured to receive information that a first choice medical supply and a second choice medical supply are available within the portable medical treatment and guidance apparatus represented by the determined apparatus type.

5. The portable medical treatment and guidance apparatus of claim 1, wherein the first priority medical emergency comprises an immediate life threat emergency that requires treatment within a first time limit.

6. The portable medical treatment and guidance apparatus of claim 5, wherein the second priority medical emergency comprises a breathing related emergency that requires treatment within a second time limit.

7. The portable medical treatment and guidance apparatus of claim 1, wherein the patient characteristic at least one of an age classification, a type of injury, and a gender of the patient.

8. The portable medical treatment and guidance apparatus of claim 1, wherein the patient characteristic is an age classification and determining the instructions for assisting the caregiver in treating the patient are determined based on the age classification.

9. The portable medical treatment and guidance apparatus of claim 8, wherein the instructions comprise instructions for treating a choking medical emergency and the instructions are different depending on whether the patient is an infant, a child, or an adult based on the age classification.

10. The portable medical treatment and guidance apparatus of claim 9, wherein the instructions for treating the choking medical emergency account for a height of the waist of the patient based on whether the patient is a child or an adult based on the age classification; and
the instructions for treating the choking medical emergency comprise (i) instructions for a administering a Heimlich maneuver to adult patients and children patients based on the age classification and (ii) instructions for administering a sequence of chest compressions and back blows for infant patients based on the age classification.

11. The portable medical treatment and guidance apparatus of claim 8, wherein the instructions comprise instructions for treating chest palpitations and the instructions are different depending on whether the patient is an infant, a child, or an adult based on the age classification.

12. The portable medical treatment and guidance apparatus of claim 8, wherein the instructions comprise instructions for treating dull and/or sharp chest pain and the instructions are different depending on whether the patient is an infant, a child, or an adult based on the age classification.

13. The portable medical treatment and guidance apparatus of claim 8, wherein the instructions comprise instructions for treating an allergic reaction and the instructions are different depending on whether the patient is an infant, a child, or an adult based on the age classification.

14. The portable medical treatment and guidance apparatus of claim 13, wherein the instructions for treating the allergic reaction comprise (i) instructions for administering allergy medicine and administering a prescribed rescue inhaler to adult patients based on the age classification and (ii) instructions for administering allergy medicine to children over age 6 and administering a prescribed rescue inhaler to children patients based on the age classification; the instructions for treating the allergic reaction comprise one or more warning screens to warn that the prescribed rescue inhaler is a prescribed medication and the instructions comprise instructions to administer a prescribed number puffs per a rescue inhaler prescription of the patient; and
the one or more warning screens are based on whether the patient is an adult or a child.

15. The portable medical treatment and guidance apparatus of claim 13, wherein the instructions for treating the allergic reaction comprise instructions to administer allergy medicine based on a weight and/or size of the patient according to instructions on a packaging of the allergy medicine.

16. The portable medical treatment and guidance apparatus of claim 8, wherein the instructions comprise instructions for treating a fracture and the instructions are different depending on whether the patient is an infant or an adult based on the age classification; and
the instructions for treating the fracture are based on which body part is fractured.

17. The portable medical treatment and guidance apparatus of claim 16, wherein the instructions comprise instructions for using gauze, a splint, elastic wrap, and ice to treat the patient when experiencing a broken ankle injury and instructions for using gauze, a splint, elastic wrap, ice, and a triangular bandage to treat the patient experiencing a broken elbow injury.

18. The portable medical treatment and guidance apparatus of claim 16, wherein the instructions for treating the fracture comprise positioning instructions based on stored information in memory.

19. The portable medical treatment and guidance apparatus of claim 8, wherein the instructions comprise instructions for treating a diabetic problem and the instructions are different depending on whether the patient is an infant or an adult based on the age classification.

20. The portable medical treatment and guidance apparatus of claim 8, wherein the instructions comprise instructions for treating unconsciousness and the instructions are different depending on whether the patient is an infant, a child, or an adult based on the age classification.

21. The portable medical treatment and guidance apparatus of claim 20, wherein the instructions for treating unconsciousness in adults comprise instructions to retrieve a defibrillator first, followed by instructions to administer hands-only cardiopulmonary resuscitation to the patient after the defibrillator has been retrieved.

22. The portable medical treatment and guidance apparatus of claim 20, wherein the instructions for treating unconsciousness in children comprise instructions to begin cardiopulmonary resuscitation first, followed by instructions to locate a defibrillator after the cardiopulmonary resuscitation has begun.

23. The portable medical treatment and guidance apparatus of claim 20, wherein the instructions for treating unconsciousness in infant patients comprise instructions for administering cardiopulmonary resuscitation to an infant patient that focus on an airway and repositioning of the airway of the infant patient.

24. The portable medical treatment and guidance apparatus of claim 1, wherein the at least one processor and memory is configured to determine the instructions for using the at least one medical supply based on a type and/or brand of the at least one medical supply.

25. The portable medical treatment and guidance apparatus of claim 24, wherein determining the instructions for using the at least one medical supply comprises determining a particular type of tourniquet as the at least one medical supply.

26. The portable medical treatment and guidance apparatus of claim 1, wherein the determined instructions relate to communicative diseases and comprise instructions for applying at least one face mask.

27. The portable medical treatment and guidance apparatus of claim 26, wherein the determined instructions are based on at least one response to at least one inquiry related to shortness of breath and/or a patient cough; and the least one inquiry related to shortness of breath and/or the patient cough is the at least one inquiry according to the second priority medical emergency.

* * * * *